US010035920B2

(12) United States Patent
Omenetto et al.

(10) Patent No.: US 10,035,920 B2
(45) Date of Patent: Jul. 31, 2018

(54) BIOPOLYMER-BASED INKS AND USE THEREOF

(71) Applicant: Tufts University, Medford, MA (US)

(72) Inventors: Fiorenzo Omenetto, Wakefield, MA (US); David Kaplan, Concord, MA (US); Hu Tao, Medford, MA (US); Benedetto Marelli, Somerville, MA (US); Miaomiao Yang, Medford, MA (US)

(73) Assignee: Tufts University, Medford, MA (US)

( * ) Notice: Subject to any disclaimer, the term of this patent is extended or adjusted under 35 U.S.C. 154(b) by 77 days.

(21) Appl. No.: 14/647,470

(22) PCT Filed: Nov. 27, 2013

(86) PCT No.: PCT/US2013/072435
§ 371 (c)(1),
(2) Date: May 27, 2015

(87) PCT Pub. No.: WO2014/085725
PCT Pub. Date: Jun. 5, 2014

(65) Prior Publication Data
US 2015/0307728 A1    Oct. 29, 2015

Related U.S. Application Data

(60) Provisional application No. 61/730,453, filed on Nov. 27, 2012, provisional application No. 61/826,458, filed on May 22, 2013.

(51) Int. Cl.
*C09D 11/04*    (2006.01)
*C09D 11/30*    (2014.01)
(Continued)

(52) U.S. Cl.
CPC .............. *C09D 11/30* (2013.01); *A61K 33/24* (2013.01); *A61K 41/0052* (2013.01);
(Continued)

(58) Field of Classification Search
CPC ......... C09D 11/04; C09D 11/30; C09D 11/38; B41J 2/01; B41J 2/04; B41J 2/135
(Continued)

(56) References Cited

U.S. PATENT DOCUMENTS 2,153,130 A    4/1939 Baxter
4,401,931 A    8/1983 Kulterman et al.
(Continued)

FOREIGN PATENT DOCUMENTS

EP    0 745 651 A1    12/1996
WO    WO-1997/008315 A1    3/1997
(Continued)

OTHER PUBLICATIONS

U.S. Appl. No. 61/883,732, filed Sep. 27, 2013, Kluge et al.
(Continued)

*Primary Examiner* — Helene Klemanski
(74) *Attorney, Agent, or Firm* — Quarles & Brady, LLP

(57) ABSTRACT

The present application discloses biopolymer-based ink formulations that are useful for inkjet printing and other applications. Related methods are also disclosed.

24 Claims, 38 Drawing Sheets

(51) Int. Cl.

| | |
|---|---|
| C09D 11/38 | (2014.01) |
| B41J 2/01 | (2006.01) |
| B41J 2/04 | (2006.01) |
| B41J 2/135 | (2006.01) |
| A61K 33/24 | (2006.01) |
| A61K 41/00 | (2006.01) |
| A61K 47/42 | (2017.01) |
| C08K 5/1535 | (2006.01) |
| G01N 33/543 | (2006.01) |

(52) U.S. Cl.
CPC ............ *A61K 47/42* (2013.01); *C08K 5/1535* (2013.01); *C09D 11/04* (2013.01); *C09D 11/38* (2013.01); *G01N 33/54386* (2013.01)

(58) Field of Classification Search
USPC ................... 106/31.94, 31.53, 31.56, 31.82
See application file for complete search history.

(56) References Cited

U.S. PATENT DOCUMENTS

| | | | | |
|---|---|---|---|---|
| 4,532,276 | A * | 7/1985 | Knable | C09D 11/16 523/161 |
| 4,585,815 | A * | 4/1986 | Ono | C09D 11/0235 106/31.68 |
| 4,648,905 | A * | 3/1987 | Peck | C09D 11/06 106/31.66 |
| 5,245,012 | A | 9/1993 | Lombari et al. | |
| 6,939,576 | B2 | 9/2005 | Deshpande et al. | |
| 2003/0175410 | A1* | 9/2003 | Campbell | A61L 27/38 427/2.24 |
| 2006/0124028 | A1* | 6/2006 | Huang | C09D 11/324 106/31.92 |
| 2009/0117087 | A1* | 5/2009 | Carroll | A61L 27/38 424/93.7 |
| 2009/0291214 | A1* | 11/2009 | Lei | C07K 17/14 106/31.13 |
| 2010/0063404 | A1 | 3/2010 | Kaplan et al. | |
| 2010/0178304 | A1 | 7/2010 | Wang et al. | |
| 2010/0178604 | A1 | 7/2010 | Lee et al. | |
| 2010/0196447 | A1 | 8/2010 | Kaplan et al. | |
| 2011/0021964 | A1* | 1/2011 | Larsen | A61L 26/0066 602/47 |
| 2011/0171239 | A1 | 7/2011 | Kaplan et al. | |
| 2015/0183841 | A1* | 7/2015 | Lo | A61L 27/56 424/402 |
| 2016/0046679 | A1* | 2/2016 | Kluge | A61L 27/3604 435/6.1 |
| 2017/0218228 | A1 | 8/2017 | Jose et al. | |

FOREIGN PATENT DOCUMENTS

| | | |
|---|---|---|
| WO | WO-2004/080346 A2 | 9/2004 |
| WO | WO-2005/012606 A2 | 2/2005 |
| WO | WO-2005/123114 A2 | 12/2005 |
| WO | WO-2006/120227 A1 | 11/2006 |
| WO | WO-2007/016524 A2 | 2/2007 |
| WO | WO-2007/120840 A2 | 10/2007 |
| WO | WO-2008/118133 A2 | 10/2008 |
| WO | WO-2008/150861 A1 | 12/2008 |
| WO | WO-2009/011709 A1 | 1/2009 |
| WO | WO-2011/005381 A2 | 1/2011 |
| WO | WO-2011/109691 A2 | 9/2011 |
| WO | WO-2011/130335 A2 | 10/2011 |
| WO | WO-2014/085725 A1 | 6/2014 |
| WO | WO-2016/019078 A1 | 2/2016 |

OTHER PUBLICATIONS

Acharya, C. et al., Performance evaluation of a silk protein-based matrix for the enzymatic conversion of tyrosine to $_L$-DOPA, Biotechnol. J., 3:226-233 (2008).

Altman, G.H. et al., Silk-based biomaterials, Biomaterials, 24:401-416 (2003).

Ang, T. et al., Fabrication of 3D Chitosan-Hydroxyapatite Scaffolds using a Robotic Dispensing System, 20 Materials Science and Engineering C, 35-42 (2002).

Bayraktar, O. et al., Silk fibroin as a novel coating material for controlled release of theophylline, European Journal of Pharmaceutics and Biopharmaceutics, 60:373-381 (2005).

Boland, T. et al, Application of Inkjet Printing to Tissue Engineering, J. Biotechnology, 1(9):910-7 (2006).

Campbell, P.G. et al.,Tissue Engineering with the Aid of Inkjet Printers, Expert Opinion on Biological Ther., 7(8):1123-7 (2007).

Cao, Y. And Wang, B., Biodegradation of silk biomaterials, Int. J. Mol. Sci., 10(4):1514-24 (2009).

Castilho, M. et al., Direct 3D Powder Printing of Biphasic Calcium Phosphate Scaffolds for Substitution of Complex Bone Defects, Biofabrication, 6(1):015006 (2014).

Chen, G. et al., Gradient Micropattern Immobilization of EGF to Investigate the Effect of Artificial Juxtacrine Stimulation, Biomaterials, 22(18): 2453-2457 (2001).

Demura, M. and Asakura, T., Immobilization of glucose oxidase with Bombyx mori silk fibroin by only stretching treatment and its application to glucose sensor, Biotechnol. Bioeng., 33(5):598-603 (1989).

Derby, B., Bioprinting: inkjet printing proteins and hybrid cell-containing materials and structures, Journal of Materials Chemistry, 18:5717-21 (2008).

Dewair, M. et al., Use of immunoblot technique for detection of human IgE and IgG antibodies to individual silk proteins, J. Allergy Clin. Immunol., 76(4):537-42 (1985).

Extended European Search Report, Application No. 13858553.4, 14 pages, dated Sep. 12, 2016.

Falconnet, D. et al., A Novel Approach to Produce Protein Nanopatterns by Combining Nanoimprint Lithography and Self-Assembly, Nano Letters, 4(10):1909-1914 (2004).

Fuchs, E. and Green, H., Multiple keratins of cultured human epidermal cells are translated from different mRNA molecules, Cell, 17:573-582 (1979).

Galazka, A. et al., Thermostability of vaccines, Global Programme for Vaccines and Immunization, World Health Organization, Geneva, 64 pages (1998).

Ghosh, S. et al., Direct-Write Assembly of Microperiodic Silk Fibroin Scaffolds for Tissue Engineering Applications, Advanced Functional Materials, 18(13):1883-1889 (2008).

Gross, B. C. et al., Evaluation of 3D Printing and its Potential Impact on Biotechnology and the Chemical Sciences, Analytical Chemistry 86(7):3240-3253 (2014).

Hanukoglu, I. and Fuchs, E.,The cDNA sequence of type II cytoskeletal keratin reveals constant and variable structural domains among keratins, Cell, 33:915-924 (1983).

Hoffman, S. et al., Silk Fibroin as an Organic Polymer for Controlled Drug Delivery, Journal of Controlled Release, 111:219-227 (2006).

Hu, X. et al., Regulation of Silk Material Structure by Temperature-Controlled Water Vapor Annealing, Biomacromolecules, 12:1686-1696 (2011).

Hutmacher, D.W. et al., Scaffold-Based Tissue Engineering: Rationale for Computer-Aided Design and Solid Free-Form Fabrication Systems, Trends in Biotechnology, 22(7): 354-362 (2004).

International Search Report for PCT/US2013/072435, 4 pages (dated Mar. 21, 2014).

International Search Report for PCT/US2015/042764, 3 pages (dated Dec. 17, 2015).

Ito, Y. et al., Micropatterned Immobilization of Epidermal Growth Factor to Regulate Cell Function, Bioconjugate Chemistry, 9(2): 277-282 (1998).

Jeon, K. H. et al., Development of an Automated Freeform Construction System and its Construction Materials, In Proceedings of the 30th International Symposium on Automation and Robotics in Construction and Mining; International Association for Automation and Robotics in Construction: Montreal, Canada, 1359-1365 (2013).

(56) References Cited

OTHER PUBLICATIONS

Jin, H.J. et al., Human bone marrow stromal cell responses on electrospun silk fibroin mats, Biomaterials, 25(6):1039-47 (2004).
Jin, I.J. et al., Water-Stable Silk Films with Reduced Beta-Sheet Content, Adv. Funct. Mater., 15:1241-1247 (2005).
Jin,H-J et al., Electrospinning Bombyx mori Silk with Poly(ethylene oxide), Biomarcromolecules, American Chemical Society, 3(6):1233-1239 (2002).
Jordan, S. C. et al., Design Considerations for Micro- and Nanopositioning: Leveraging the Latest for Biophysical Applications, Current Pharmaceutical Biotechnology, 10(5): 515-521 (2009).
Kaji, K. and Kudo, A., The Mechanism of Sperm-Oocyte Fusion in Mammals, Reproduction, 127(4): 423-29 (2004).
Kaplan, D., Bioengineering of Materials, Protein Based Materials, McGrath & Kaplan, eds., Birkhauser, Boston, MA, pp. 103-131 (1998).
Kaplan, D.L. et al., Self-organization (assembly) in biosynthesis of silk fibers—a hierarchical problem, Hierarchically Structured Materials, Materials Res. Symp. Proc., 255:19-29 (1992).
Kaplan, et al., Silk: Biology, Structure, Properties, and Genetics, ACS Symposium Series, 554:2-16 (1993).
Kikuchi, Y. et al., Structure of the Bombyx mori fibroin light-chain-encoding gene: upstream sequence elements common to the light and heavy chain, Gene, 110(2):151-8 (1992).
Lewis, J. A., Novel Inks for Direct-Write Assembly of 3-D Periodic Structures, Material Matters, 3(1): 4-7 (2008).
Lu, S. et al., Insoluble and Flexible Silk Films Containing Glycerol, Biomacromolecules, 11(1):143-150 (2010).
Lu, S. et al., Stabilization of Enzymes in Silk Films, Biomacromolecules, 10:1032-1042 (2009).
Lucas, F. et al., The silk fibroins, Advances in Protein Chemistry, 13:107-242 (1958).
Marga, F. et al., Toward Engineering Functional Organ Modules by Additive Manufacturing, Biofabrication, 4(2):022001 (2012).
Mironov, V. et al., Bioprinting: A Beginning,Tissue Engineering, 12(4): 631-634 (2006).
Miyairi, S. and Sugiura, M., Properties of β-Glucosidase Immobilized in Sericin Membrane, J. Germent. Technol., 56(4):303-308 (1978).
Moll, R. et al, The catalog of human cytokeratins: patterns of expression in normal epithelia, tumors and cultured cells, Cell 31(1): 11-24 (1982).
Moy, R.L. et al., Commonly used suture materials in skin surgery, Am. Fam. Physician, 44(6):2123-8 (1991).
Myers, EW. and Miller, W., Optimal alignments in linear space, Comput. Appl. Biosci., 4:11-17 (1988).
Nakamura, M. et al., Biocompatible Inkjet Printing Technique for Designed Seeding of Individual Living Cells, Tissue Engineering, 11(11-12):1658-66 (2005).
Nishiyama, Y. et al., Development of a Three-Dimensional Bioprinter: Construction of Cell Supporting Structures using Hydrogel and State-of-the-Art Inkjet Technology, J. Biomechanical Engineering, 131(3): 035001 (2009).
Omenetto, F.G. and Kaplan, D.L., New Opportunities for an Ancient Material, Science, 329:528-531 (2010).
Otsuka, J., Nanometer Level Positioning Using Three Kinds of Lead Screws, Nanotechnology, 3(1): 29-36 (1992).
Partial Supplementary European Search Report for EP 13858553.4, 9 pages (dated May 31, 2016).
Peetermans, J. et al., Stability of freeze-dried rubella virus vaccine (Cendehill strain) at various temperatures, J. Biological Standardization, 1:179-185 (1973).
Peleg, H. et al., An experimental comparison of suture materials for tracheal and bronchial anastomoses, Thorac. Cardiovasc. Surg., 34(6):384-8 (1986).
Peltola, S. et al., Review of Rapid Prototyping Techniques for Tissue Engineering Purposes, Annals of Internal Medicine, 40(4): 268-280 (2008).

Phillippi, I.A. et al., Microenvironments Engineered by Inkjet Bioprinting Subpopulations, Stem Spatially Direct Adult Stem Cells Toward Muscle- and Bone-Like Cells, Stem Cells, 26(1): 127-34 (2008).
Rida, A., Conductive inkjet printed antennas on flexible low-cost paper-based substrates for RFID and WSN applications, IEEE Antennas and Propagation Magazine, 51(3):13-23 (2009).
Rockwood, D.N. et al., Materials Fabrication from Bombyx mori Silk Fibroin, Nature Protocols 6(10):1612-1631 (2011).
Rossitch Jr., E. et al., Delayed foreign-body reaction to silk sutures in pediatric neurosurgical patients, Childs Nerv. Syst., 3(6):375-8 (1987).
Sakabe, T. et al., In vivo blood compatibility of regenerated silk fibroin, Gen-I Gakkaishi, 45(11):487-90 (1989).
Santin et al. In vitro Evaluation of the Inflammatory Potential of the Silk Fibroin, J. Biomed. Mater. Res. 46:382-389 (1999).
Sashina, E.S., et al., Structure and solubility of natural silk fibroin, Russ. J. Appl. Chem., 79(6): 869-876 (2006).
Saunders, R.E. et al., Delivery of Human Fibroblast Cells by Piezoelectric Drop-on-Demand Inkjet Printing, Biomaterials, 29(2): 193-203 (2008).
Shaker, G. et al., Inkjet printing of ultrawideband (UWB) antennas on paper-based substrates, IEEE Antennas and Wireless Propagation Letters, 10:111-114 (2011).
Sinha, S. K., Automating Facing Operation on a CNC Machining Centre, International J. Engineering Science and Technology, 2(12): 7616-7618 (2010).
Smith, C.M. et al, Characterizing Environmental Factors that Impact the Viability of Tissue-Engineered Constructs Fabricated by a Direct-Write Bioassembly Tool, Tissue Engineering, 13(2): 373-83 (2007).
Smith, C.M. et al., Three-Dimensional Bioassembly Tool for Generating Viable Tissue-Engineered Constructs, Tissue Engineering, 10(9-10): 1566-76 (2004).
Sun, L. et al., Direct-write assembly of 3D silk/hydroxyapatite scaffolds for bone co-cultures, Adv. Healthc. Mater., 1(6):729-35 (2012).
Takahashi, K. et al., Induction of Pluripotent Stem Cells form Adult Human Fibroblasts by Defined Factors, Cell 131:861-872 (2007).
Takei, F. et al., Further evidence for importance of the subunit combination of silk fibroin in its efficient secretion from the posterior silk gland cells, Journal of Cellular Biology, 105(1):175-180 (1987).
Tanaka, K. et al., Determination of the site of disulfide linkage between heavy and light chains of silk fibroin produced by Bombyx mori, Biochimica et Biophysica Acta, 1432:92-103 (1999).
Tanaka, K. et al., Immunological identification of the major disulfide-linked light component of silk fibroin, Journal of Biochemistry, 114(1):1-4 (1993).
Tao, H. et al., Silk-based conformal, adhesive, edible food sensors, Adv. Mater., 24(8):1067-72 (2012).
Tasoglu, S. and Demirci, U. et al., Bioprinting for Stem Cell Research, Trends in Biotechnology, 31(1): 10-19 (2013).
Vepari, C. et al., Silk as a Biomaterial, Prog. Polym. Sci., 32(8-9): 991-1007 (2007).
Watanabe, K. et al., Growth Factor Array Fabrication Using a Color Ink Jet Printer, Zoological Science, 20(4): 429-434 (2003).
Wen, C.M., et al., Silk-induced asthma in children: a report of 64 cases, Ann. Allergy, 65(5):375-8 (1990).
Whitesides, G.M. et al., Soft Lithography in Biology and Biochemistry, Annual Review Biomedical Engineering, 3:335-373 (2001).
Wray, L.S., et. al., Effect of processing on silk-based biomaterials: Reproducibility and biocompatibility, J. Biomedical Materials Res. Part B, 99B:89-101 (2011).
Written Opinion for PCT/US2013/072435, 7 pages (dated Mar. 21, 2014).
Written Opinion for PCT/US2015/042764, 5 pages (dated Dec. 17, 2015).
Xu, T. et al, Viability and Electrophysiology of Neural Cell Structures Generated by the Inkjet Printing Method, Biomaterials, 27(19): 3580-8 (2006).
Xu, T., et al, Inkjet Printing of Viable Mammalian Cells, Biomaterials, 26(1): 93-9 (2005).

(56) References Cited

OTHER PUBLICATIONS

Yamazoe, H. and Tanabe, T., Cell Micropatterning on an Albumin-Based Substrate using an Inkjet Printing Technique, J. Biomedical Materials Research A, 91(4): 1202-9 (2009).

Yu, J. et al., Induced Pluripotent Stem Cell Lines Derived from Human Somatic Cells, Science 318:1917-1920 (2007).

Zaugg, F. and Wagner, P. et al., Drop-on-Demand Printing of Protein Biochip Arrays, MRS Bulletin, 837-842 (2003).

* cited by examiner

3D Porous Scaffolds
Options - porogen leaching, lyophilization, gas evolution, gas foaming

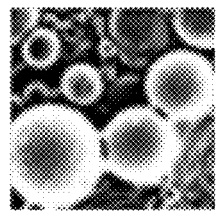

Particles and vesicles
(nano and microscale)
Options - copolymer assembly, lipid templating, salting out

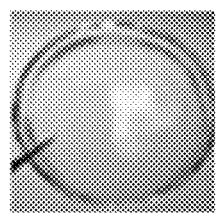

Films and Coatings
Options - dip coating, layer-by-layer, spray, casting

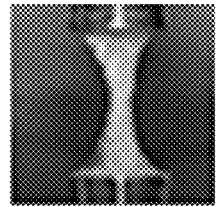

Adhesives
Options - electrogelation

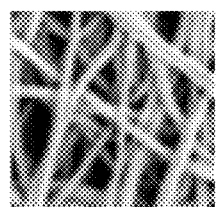

Fibers, Ropes
Options - printing electrospinning, microfluidics spinning, extrusion, gel spinning, textile engineering

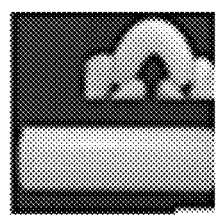

Hydrogels
Options - self-assembly, sonication, vortexing, electric fields

FIG. 2

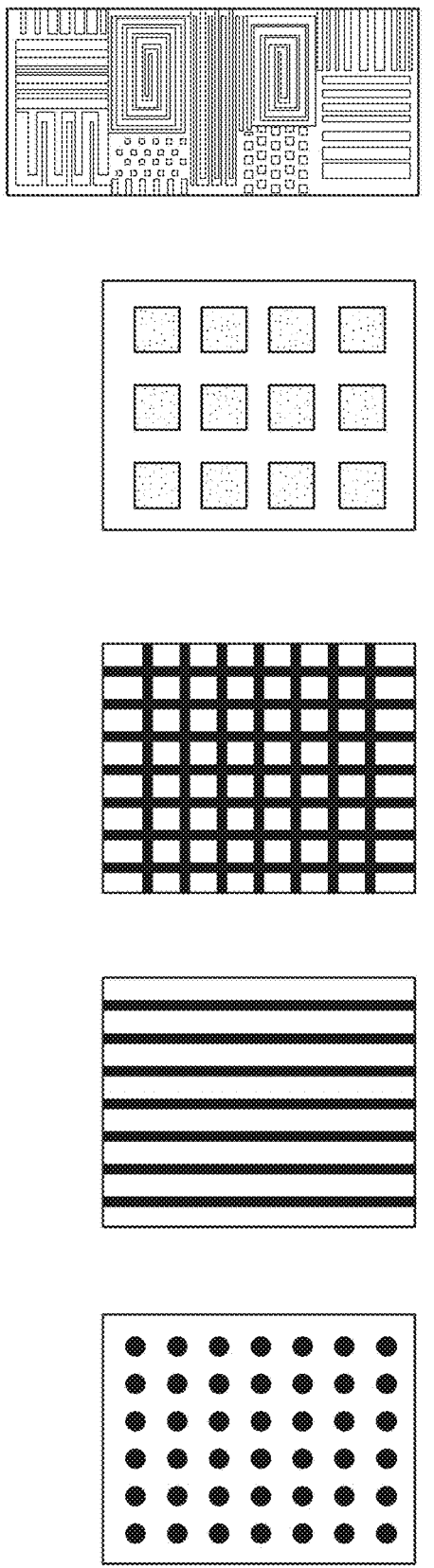
FIG. 12
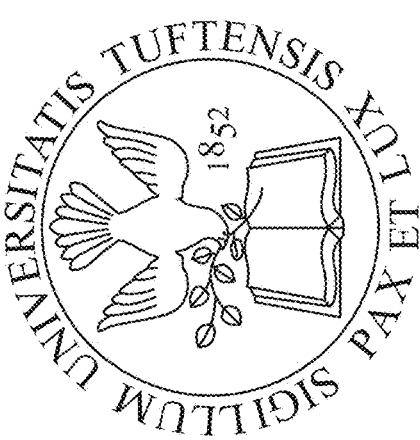
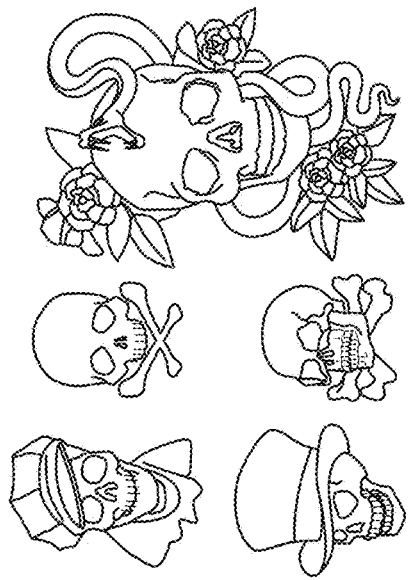
FIG. 13

HRP: Horseradish peroxidase; TMB:3,3',5,5,5'-Tetramethylbenzidine

SEQUENCE LISTING

<160> NUMBER OF SEQ ID NOS: 22

<210> SEQ ID NO 1
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (7)..(90)
<223> OTHER INFORMATION: Wherein any of residues 7-90 may be missing.

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser
                85                  90

<210> SEQ ID NO 2
<211> LENGTH: 30
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is V, I or A.
<220> FEATURE:
<221> NAME/KEY: MISC_FEATURE
<222> LOCATION: (3)..(30)
<223> OTHER INFORMATION: Wherein any of residues 3-30 may be missing
<220> FEATURE:
<221> NAME/KEY: MISC_FEATURE
<222> LOCATION: (4)..(4)
<223> OTHER INFORMATION: Wherein X is V, I or A.
<220> FEATURE:
<221> NAME/KEY: MISC_FEATURE
<222> LOCATION: (6)..(6)
<223> OTHER INFORMATION: Wherein X is V, I or A.
<220> FEATURE:
<221> NAME/KEY: MISC_FEATURE
<222> LOCATION: (8)..(8)
<223> OTHER INFORMATION: Wherein X is V, I or A.
<220> FEATURE:
<221> NAME/KEY: MISC_FEATURE
<222> LOCATION: (10)..(10)
<223> OTHER INFORMATION: Wherein X is V, I or A.
<220> FEATURE:
<221> NAME/KEY: MISC_FEATURE
<222> LOCATION: (12)..(12)
<223> OTHER INFORMATION: Wherein X is V, I or A.
<220> FEATURE:
<221> NAME/KEY: MISC_FEATURE
<222> LOCATION: (14)..(14)
<223> OTHER INFORMATION: Wherein X is V, I or A.
<220> FEATURE:
<221> NAME/KEY: MISC_FEATURE
<222> LOCATION: (16)..(16)
<223> OTHER INFORMATION: Wherein X is V, I or A.
<220> FEATURE:
<221> NAME/KEY: MISC_FEATURE

```
<222> LOCATION: (18)..(18)
<223> OTHER INFORMATION: Wherein X is V, I or A.
<220> FEATURE:
<221> NAME/KEY: MISC_FEATURE
<222> LOCATION: (20)..(20)
<223> OTHER INFORMATION: Wherein X is V, I or A.
<220> FEATURE:
<221> NAME/KEY: MISC_FEATURE
<222> LOCATION: (22)..(22)
<223> OTHER INFORMATION: Wherein X is V, I or A.
<220> FEATURE:
<221> NAME/KEY: MISC_FEATURE
<222> LOCATION: (24)..(24)
<223> OTHER INFORMATION: Wherein X is V, I or A.
<220> FEATURE:
<221> NAME/KEY: MISC_FEATURE
<222> LOCATION: (26)..(26)
<223> OTHER INFORMATION: Wherein X is V, I or A.
<220> FEATURE:
<221> NAME/KEY: MISC_FEATURE
<222> LOCATION: (28)..(28)
<223> OTHER INFORMATION: Wherein X is V, I or A.
<220> FEATURE:
<221> NAME/KEY: MISC_FEATURE
<222> LOCATION: (30)..(30)
<223> OTHER INFORMATION: Wherein X is V, I or A.

<400> SEQUENCE: 2

Gly Xaa Gly Xaa Gly Xaa Gly Xaa Gly Xaa Gly Xaa Gly Xaa Gly Xaa
1               5                   10                  15

Gly Xaa Gly Xaa Gly Xaa Gly Xaa Gly Xaa Gly Xaa Gly Xaa
            20                  25                  30

<210> SEQ ID NO 3
<211> LENGTH: 4
<212> TYPE: PRT
<213> ORGANISM: Bombyx mori

<400> SEQUENCE: 3

Gly Ala Ala Ser
1

<210> SEQ ID NO 4
<211> LENGTH: 15
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (14)..(15)
<223> OTHER INFORMATION: Wherein any of residues 14-15 may be missing

<400> SEQUENCE: 4

Ser Ser Ala Ala Ala Ala Ala Ala Ala Ala Ala Ala Ala Ala Ala
1               5                   10                  15

<210> SEQ ID NO 5
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(5)
<223> OTHER INFORMATION: Wherein any of residues 2-5 may be missing
<220> FEATURE:
```

```
<221> NAME/KEY: MISC_FEATURE
<222> LOCATION: (2)..(2)
<223> OTHER INFORMATION: Wherein X is any residue
<220> FEATURE:
<221> NAME/KEY: MISC_FEATURE
<222> LOCATION: (3)..(3)
<223> OTHER INFORMATION: Wherein X is any residue
<220> FEATURE:
<221> NAME/KEY: MISC_FEATURE
<222> LOCATION: (4)..(4)
<223> OTHER INFORMATION: Wherein X is any residue
<220> FEATURE:
<221> NAME/KEY: MISC_FEATURE
<222> LOCATION: (5)..(5)
<223> OTHER INFORMATION: Wherein X is any residue
<220> FEATURE:
<221> NAME/KEY: MISC_FEATURE
<222> LOCATION: (8)..(8)
<223> OTHER INFORMATION: Wherein X is any residue

<400> SEQUENCE: 5

Gly Xaa Xaa Xaa Xaa Gly Gly Xaa
1               5

<210> SEQ ID NO 6
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Wherein X is A, S, Y, R, D, V or W

<400> SEQUENCE: 6

Gly Gly Gly Xaa
1

<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (4)..(6)
<223> OTHER INFORMATION: Wherein any residues 4-6 may be missing

<400> SEQUENCE: 7

Ser Ser Ala Ala Ala Ala Ser Ser Ala Ala Ala Ala
1               5                   10

<210> SEQ ID NO 8
<211> LENGTH: 6
<212> TYPE: PRT
<213> ORGANISM: Galleria mellonella

<400> SEQUENCE: 8

Gly Leu Gly Gly Leu Gly
1               5

<210> SEQ ID NO 9
<211> LENGTH: 6
<212> TYPE: PRT
<213> ORGANISM: Artificial sequence
```

-continued

```
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is L, I, V or P
<220> FEATURE:
<221> NAME/KEY: MISC_FEATURE
<222> LOCATION: (5)..(5)
<223> OTHER INFORMATION: Wherein X is L, I, V or P

<400> SEQUENCE: 9

Gly Xaa Gly Gly Xaa Gly
1               5

<210> SEQ ID NO 10
<211> LENGTH: 21
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Wherein X is Y, V, S or A
<220> FEATURE:
<221> NAME/KEY: MISC_FEATURE
<222> LOCATION: (6)..(20)
<223> OTHER INFORMATION: Wherein any of 6-20 may be missing
<220> FEATURE:
<221> NAME/KEY: MISC_FEATURE
<222> LOCATION: (10)..(10)
<223> OTHER INFORMATION: Wherein X is Y, V, S or A
<220> FEATURE:
<221> NAME/KEY: MISC_FEATURE
<222> LOCATION: (15)..(15)
<223> OTHER INFORMATION: Wherein X is Y, V, S or A
<220> FEATURE:
<221> NAME/KEY: MISC_FEATURE
<222> LOCATION: (20)..(20)
<223> OTHER INFORMATION: Wherein X is Y, V, S or A

<400> SEQUENCE: 10

Gly Pro Gly Gly Xaa Gly Pro Gly Gly Xaa Gly Pro Gly Gly Xaa Gly
1               5                   10                  15
Pro Gly Gly Xaa Tyr
            20

<210> SEQ ID NO 11
<211> LENGTH: 5
<212> TYPE: PRT
<213> ORGANISM: Argiope trifasciata

<400> SEQUENCE: 11

Gly Arg Gly Gly Ala
1               5

<210> SEQ ID NO 12
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(10)
<223> OTHER INFORMATION: Wherein any of 5-10 may be missing

<400> SEQUENCE: 12

Gly Ala Gly Ala Ala Ala Ala Ala Ala Ala Gly Gly Ala
1               5                   10
```

<210> SEQ ID NO 13
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Wherein X is Q, Y, L, A, S or R
<220> FEATURE:
<221> NAME/KEY: MISC_FEATURE
<222> LOCATION: (5)..(5)
<223> OTHER INFORMATION: Wherein X is Q, Y, L, A, S or R
<220> FEATURE:
<221> NAME/KEY: MISC_FEATURE
<222> LOCATION: (7)..(7)
<223> OTHER INFORMATION: Wherein X is Q, Y, L, A, S or R
<220> FEATURE:
<221> NAME/KEY: MISC_FEATURE
<222> LOCATION: (8)..(8)
<223> OTHER INFORMATION: Wherein X is Q, Y, L, A, S or R

<400> SEQUENCE: 13

Gly Gly Xaa Gly Xaa Gly Xaa Xaa
1               5

<210> SEQ ID NO 14
<211> LENGTH: 16
<212> TYPE: PRT
<213> ORGANISM: Bombyx mori

<400> SEQUENCE: 14

Thr Gly Ser Ser Gly Phe Gly Pro Tyr Val Asn Gly Gly Tyr Ser Gly
1               5                   10                  15

<210> SEQ ID NO 15
<211> LENGTH: 8
<212> TYPE: PRT
<213> ORGANISM: Bombyx mandarina

<400> SEQUENCE: 15

Tyr Glu Tyr Ala Trp Ser Ser Glu
1               5

<210> SEQ ID NO 16
<211> LENGTH: 7
<212> TYPE: PRT
<213> ORGANISM: Antheraea mylitta

<400> SEQUENCE: 16

Ser Asp Phe Gly Thr Gly Ser
1               5

<210> SEQ ID NO 17
<211> LENGTH: 7
<212> TYPE: PRT
<213> ORGANISM: Antheraea yamamai

<400> SEQUENCE: 17

Arg Arg Ala Gly Tyr Asp Arg
1               5

<210> SEQ ID NO 18
<211> LENGTH: 8
<212> TYPE: PRT
<213> ORGANISM: Galleria mellonella

```
<400> SEQUENCE: 18

Glu Val Ile Val Ile Asp Asp Arg
1               5

<210> SEQ ID NO 19
<211> LENGTH: 18
<212> TYPE: PRT
<213> ORGANISM: Nephila madascariensis

<400> SEQUENCE: 19

Thr Thr Ile Ile Glu Asp Leu Asp Ile Thr Ile Asp Gly Ala Asp Gly
1               5                   10                  15

Pro Ile

<210> SEQ ID NO 20
<211> LENGTH: 8
<212> TYPE: PRT
<213> ORGANISM: Nephila clavipes

<400> SEQUENCE: 20

Thr Ile Ser Glu Glu Leu Thr Ile
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 21

Gly Ser Gly Ala Gly Ala
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Wherein X is any residue
<220> FEATURE:
<221> NAME/KEY: MISC_FEATURE
<222> LOCATION: (5)..(5)
<223> OTHER INFORMATION: Wherein X is any residue

<400> SEQUENCE: 22

Gly Pro Gly Xaa Xaa
1               5
```

BIOPOLYMER-BASED INKS AND USE THEREOF

RELATED APPLICATIONS

This patent application is a National Stage Entry of International Patent Application No. PCT/US2013/072435, filed on Nov. 27, 2013; which claims the benefit of and priority to U.S. provisional applications 61/730,453 filed Nov. 27, 2012, entitled "SILK FIBROIN PROTEIN INKS" and 61/826,458 filed May 22, 2013, also entitled "SILK FIBROIN PROTEIN INKS," the entire contents of each of which are incorporated herein by reference.

GOVERNMENT SUPPORT

This invention was made with government support under grants FA9550-14-1-0015 awarded by the United States Air Force and N00014-13-1-0596 awarded by the United States Navy. The government has certain rights in the invention.

BACKGROUND

Inkjet printing is a type of computer-based printing that creates a digital image by propelling droplets of ink onto a substrate, typically paper. The concept of inkjet printing has been around for over a century but was made readily accessible to consumers in the latter half of the 20th century. Inkjet printing can be also employed for direct material deposition, which is an emerging manufacturing technique today.

The field of computer-assisted printing has seen vast technological advancement in recent years, including the 3D printing technology used to fabricate computer-designed objects by so-called "additive manufacturing." Typically, the process of 3D printing involves serial printing (i.e., layering) of particles or 3D dots comprised of materials, such as thermoplastics, metal alloys, and plasters.

The inkjet technology as applied to biological materials, however, generally faces a number of technical obstacles.

SUMMARY OF THE INVENTION

Among other things, the present application provides the use of certain biopolymers for preparing printable liquids, i.e., "biopolymer-based inks" or "bio-inks." In particular, the present invention encompasses the recognition that certain polypeptides have material and chemical features that are suitable to be formulated into such inks.

More specifically, the present invention includes the finding that certain polypeptides of structural proteins in origin are especially suited for fabricating micro- and nano-scale (i.e., sub-micron) printed structures. Such structures include two-dimensional (2D) structures and three-dimensional (3D) structures.

Furthermore, unique material features of biopolymer-based inks allow incorporation of a variety of additives (e.g., agents or dopants) for functionalization, which can be stabilized within the ink. In some embodiments, provided bio-ink compositions may further contain other additives, such as excipients, chelating agents, defoamers, etc., among others.

The invention is useful for a wide range of applications, including but not limited to, optoelectonics, photonics, therapeutics, tissue engineering such as intelligent implants, synthetic biology, and a variety of consumer products.

Accordingly, in one aspect, the invention provides aqueous (i.e., water-based) biopolymer inks. In some embodiments, described biopolymer inks comprise a structural protein. In some embodiments, described biopolymer inks comprise a structural protein having a specified range or ranges of molecular weights (e.g., fragments). In some embodiments, the specified range includes between about 3.5 kDa and 120 kDa. In some embodiments, described biopolymer inks are substantially free of protein fragments exceeding a specified molecular weight. For example, in some embodiments, described biopolymer inks are substantially free of protein fragments over 200 kDa. "Substantially free" means that it is absent or present at a concentration below detection measured by any art-accepted means, such that it is considered negligible.

According to the invention, described biopolymer inks have a viscosity of between about 1-20 centipoise (cP), where 1 cP=1 mPa·s=0.001 Pa·s, as measured at room temperature of between about 18-26° C. In some embodiments, described biopolymer inks further comprise one or more suitable viscosity-modifying agents (i.e., viscosity modifiers or viscosity adjusters).

Biopolymer ink compositions in accordance with the present invention may also contain one or more added agents, or additives, such as dopants. In some embodiments, such added agents are stabilized by the ink composition. In some embodiments, such added agents are stabilized by the biopolymer (e.g., structural protein) present in the ink composition.

In another aspect, the present invention provides a small volume unit of an aqueous composition comprising a low molecular weight structural protein. Such a unit is an liquid droplet of between about 0.1-100 pL. In some embodiments, such an aqueous unit composition contains the low molecular weight structural protein at a concentration of about 0.1-10.0%. In some embodiments, such an aqueous unit composition has a viscosity of between about 1-20 centipoise or 1-20 mPa·s.

In a further aspect, the invention provides an array of printed units, which may be a semi-solid or solid form.

According to the invention, a printed array may comprise a substrate, upon which a plurality of dot units is deposited, wherein each dot unit comprises a low molecular weight structural protein. Each dot unit is typically between about 0.1-250 µm in diameter. Such dot units may be deposited upon the substrate in a predetermined spatial pattern, including regular and irregular patterns. Printed structures as described herein may be a 2D or a 3D structure.

In some embodiments, described printed arrays have a resolution of between about 50-20,000 dpi, depending on a variety of parameters as further described herein.

In any of the embodiments, such printed structures, which are made of dot units as described, may be deposited on a suitable substrate.

In yet a further aspect, the invention provides methods for printing a structure. The described methods involve providing a protein-based ink comprising a low molecular weight structural protein of suitable characteristics and depositing the protein-based ink onto a substrate in a predetermined spatial pattern. According to the invention, each liquid droplet has a volume of between about 0.1-100 pL.

The invention also includes methods for manufacturing biopolymer-based ink compositions (i.e., "bio-inks"). In some embodiments, provided manufacturing methods include providing an aqueous solution comprising a low molecular weight structural protein (or fragment thereof), and confirming or adjusting the aqueous solution so as to achieve a suitable parameter(s), such as viscosity, surface tension, density (specific gravity), pH, etc.

BRIEF DESCRIPTION OF DRAWING

FIG. 2 shows materials formed with regenerated silk fibroin.

FIG. 12 shows patterns for a pattern editor.

FIG. 13 shows patterns for a pattern editor.

DETAILED DESCRIPTION OF CERTAIN EMBODIMENTS

Inkjet Printing Technology

Figure 1:
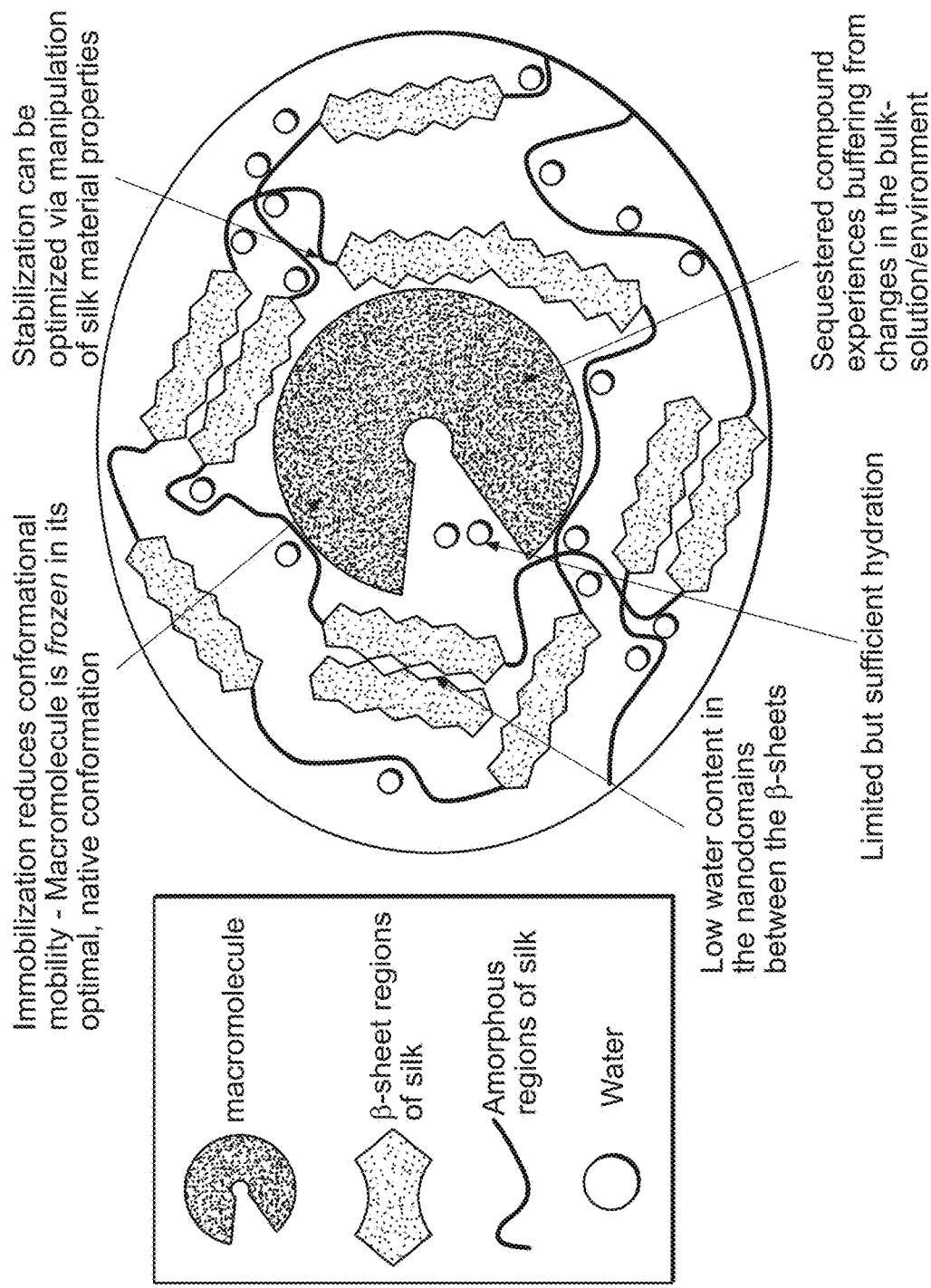
FIG. 1 shows a summary of silk fibroin stabilization effects on immobilized compounds.
Figure 3:
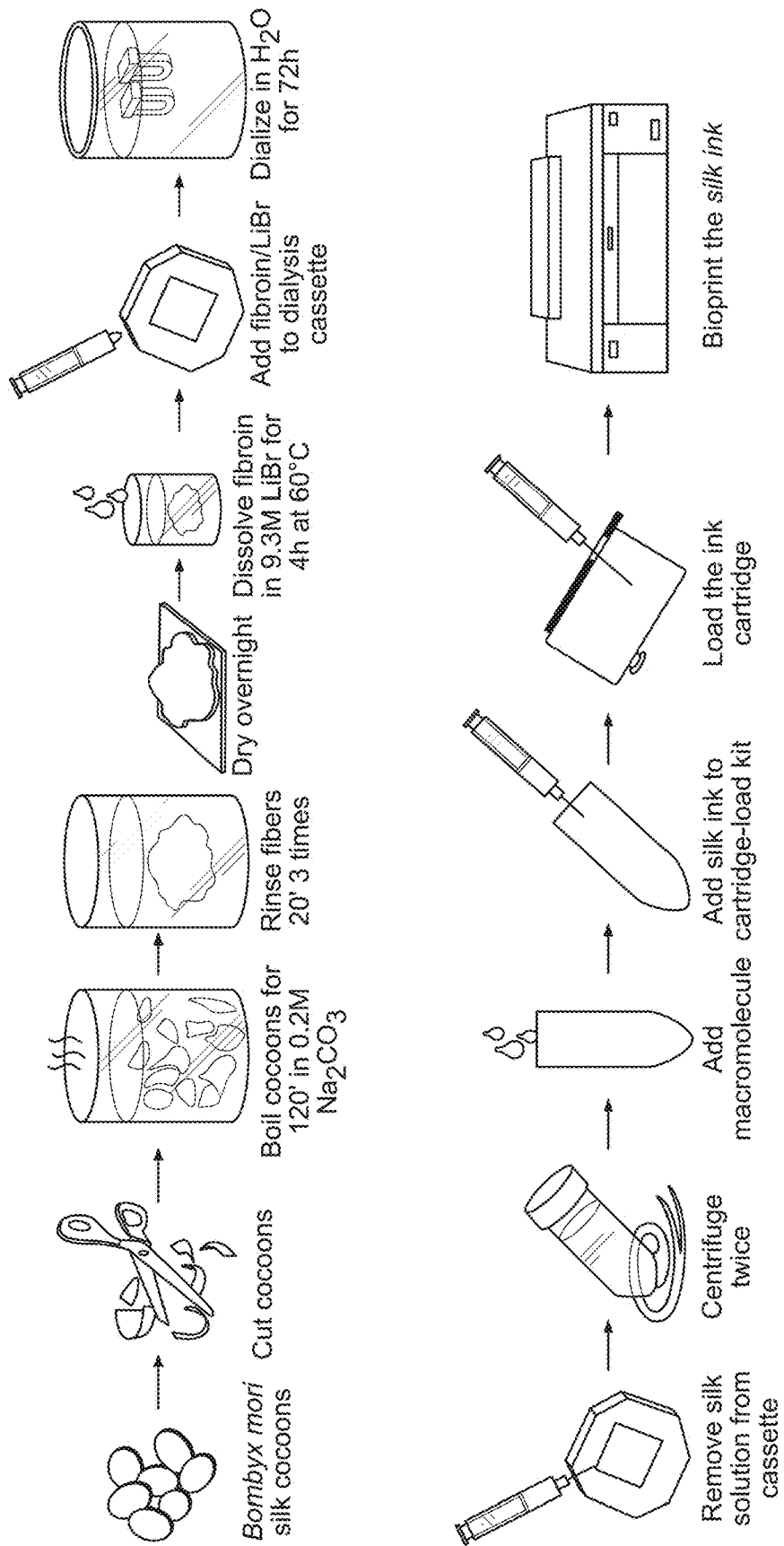
FIG. 3 shows a protocol to obtain printable silk inks from raw cocoon.
Figure 4A:
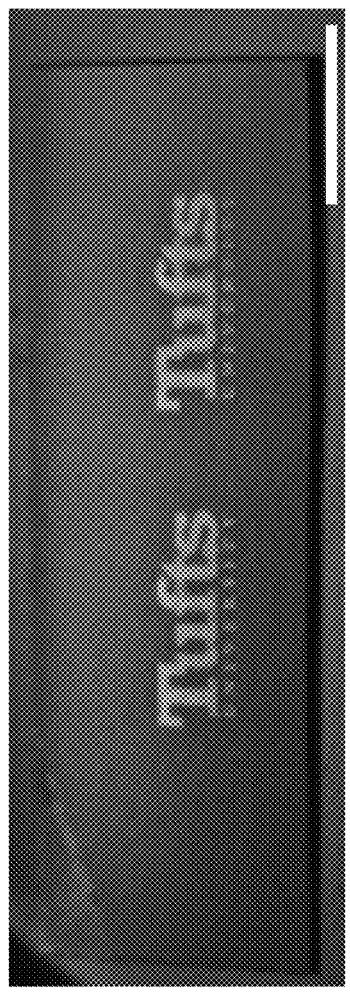
FIG. 4 shows inkjet printing of biopolymer inks on different substrates.
Figure 4B:
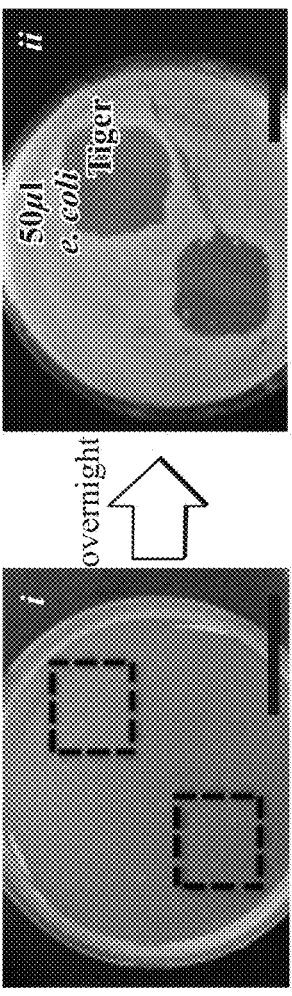
Figure 4C:
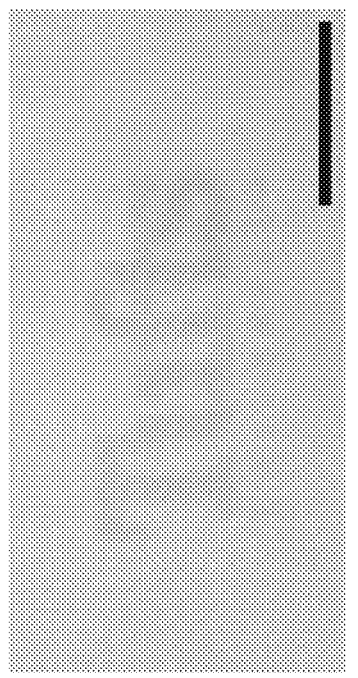
Figure 4D:
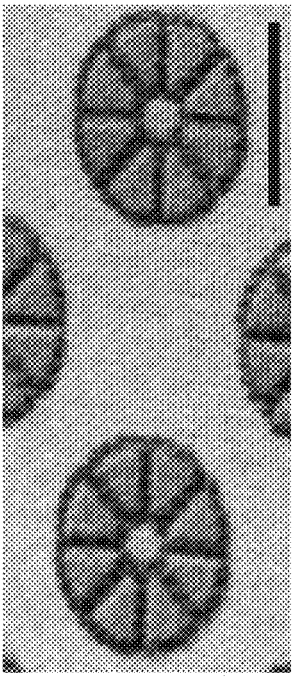

Inkjet printing (IJP) is an easy, inexpensive and widely accessible technology spread around the world for several decades. The fortune of IJP is tied to the pervasiveness of personal computing, as for the last two decades it has represented one of the fundamental accessories for any PC workstation.

IJP is based on the use of electrical actuators to eject picoliter (pL) volumes of liquid from micrometer-wide nozzles onto a substrate in a defined pattern. IJP has gained extensive acceptance in microfabrication for basic patterning and rapid fabrication. While the most popular purpose of IJP technology remains printing paper documents, it has also been applied in organic electronics, chemical synthesis, sensor fabrication, combinatorial chemistry and biology.

Inkjet printing can be divided into two categories: (1) drop-on-demand (DoD) or impulse inkjet, where droplets are generated when required; and (2) continuous inkjet, in which droplets are deflected from a continuous stream to a substrate when needed.

Inkjet printing can be further subdivided according to the specific means of generating droplets, such as piezoelectric, thermal and electrostatic. Each of these techniques has specific ranges of operation that limit their applicability. Such variables include: operating temperature range, material throughput, reproducibility of droplets, precision of deposition, range of printable viscosities, range of shear forces within the nozzle, reservoir volume and the number of fluids that may be printed during at the same time. Droplet size involves, typically, volumes ranging from 1.5 pL to 5 nL at a rate of 0-25 kHz for drop-on-demand printers (and up to 1 MHz for continuous printheads).

Alternative Printing Methods

Electrohydrodynamic jet printing (EHJP) can produce features as small as 1 μm wide lines, which is typically an order of magnitude smaller than inkjet printing. Naturally, the droplets produced by this technique are also smaller, being in the femto-liter region. Such small droplet sizes are of interest since this means that less material can be dispensed with more spatial control, which couples with the ongoing miniaturization seen in many applications. An open question to be addressed is whether the EHJP droplet ejection method affects the material contained within the ink. Whereas inkjet printers eject their droplets from within the nozzle, EHJ printers eject their droplets from outside the nozzle. The ink in an EHJ printer forms a droplet that is attached to the nozzle. This dome of ink is charged by a wire contained within the nozzle using voltages up to 200 V, which is necessary to overcome the surface tension and causes a Taylor cone to form. The droplets are ejected from the tip of the cone. This process likely makes protein susceptible to electrical breakdown and droplet deflection during application of inks to substrates. Furthermore, the EHJP process is still in its infancy and it has not yet been applied to the full range of applications that inkjet printing has. In addition, EHJP is based on electrostatic forces; meaning that the substrate must be conductive, which is also a limitation. Finally, the cost of the technique is another factor to consider.

Bio-Printing

Bio-printing is defined as the process of inkjet printing biomaterials. The field of bio-printing originated in the mid-1990s, with an expansion after the turn in the new millennium. Several factors contributed to this increase: by 1985 functional materials for sensing biological matter (e.g. for glucose and urea) were spatially disposed to form multi-analyte arrays. In 1987 the first patent for an inkjet-printed enzyme-based biosensor was filed. The robustness and versatility of inkjet printing enabled researchers to modify the technique to meet their needs. In particular, the mild conditions afforded by the IJP process make it particularly suited for handling biological materials. Minimal sample contamination and waste together with the accurate control and placement of pre-determined quantities of material are also highly appealing features. The possibility to integrate biomaterials with IJP technology is convenient because it combines ease, low-cost and robustness. In particular, the use of IJP to deposit proteins is of particular appeal given that the impossibility to apply conventional polymer processing techniques to proteins is one of the major hindrance to their applications as biomaterials.

Limitations to Protein Printing

During the course of research that led to the invention disclosed herein, several fundamental issues and technical obstacles related to the methods employed were addressed. While inkjet printing of proteins has been employed successfully with certain materials, it is not without limitations. In particular, shear stress-induced denaturation and non-specific protein adsorption on the inner surfaces of the printer have been previously reported as problems to be addressed during the process set up. Prior to dealing with any protein-specific considerations, the first and foremost limitation to drop-on-demand inkjet printing of any material is its feasibility: whether or not the material can be formulated into an ink that is printable (i.e., stable, repeatable droplets are able to be ejected from the nozzle, with uniform velocities and volumes). Generally, some of the most important intrinsic physical properties determining printability of given ink include: viscosity ($\eta$), density ($\rho$), surface tension ($\gamma$), and nozzle diameter ($\alpha$). Using a modified form of the Navier-Stokes equation, originally proposed by Fromm, a dimensionless number Z based on the aforementioned physical properties can be used to estimate whether or not the right balance between the capillary force, inertial force, and viscous force may be achieved for stable droplet formation by the following equation:

$$Z = \frac{\alpha \rho \gamma^{1/2}}{\eta}$$

The mathematics involved in describing the theoretical printability of fluids based on their calculated Z number has been outlined elsewhere in greater detail by other authors, and in this review, it is sufficient to say that a solution is theoretically printable when $1<Z<10$. In most instances, any protein solution under consideration for printing may be dilute and aqueous, and thus have a density that is already pre-determined; for a given nozzle, the printability of a given protein solution is strongly affected at least by surface tension and viscosity.

Surface Tension

Proteins formulated as bio-inks are inkjet-printed in aqueous solutions. The composition of the solution influences its surface tension. For high values of surface tension, the applied force that stretches and eventually causes the ejection of the drop is lower than the cohesive counter-force. Indeed, the droplet resists to the external force, resulting in the lack of ejection.

Viscosity

Proteins are by nature macromolecules, and consequently the viscosity of their solutions is often dramatically affected by changes in concentration. At higher concentrations, the capillary force is insufficient to break the filament of the droplet during the ejection, and the droplet retracts back into the nozzle. For polymers, the micro-rheological explanation for this behavior is that the coiled and folded polymer chains are elongated in the direction of flow into a stretched state, which is accompanied by a strong increase of the hydrodynamic drag. However, most proteins, unlike synthetic linear polymers, are not randomly coiled chains; rather, most proteins tend to be carefully folded into organized structures in their native state, and the degree to which proteins are either globular or fibrous plays an important role in their intrinsic viscosity, which, consequently affects the maximum concentration of a printable solution. This implies a relative facility in the printing of globular protein such as enzymes, messenger/signaling, and transport proteins, while structural fibrous protein, such as keratin, collagen, and elastin are impossible to print at relevant concentrations or in mild conditions (e.g., neutral pH, aqueous solution). This has a significant impact on the concentration limitation of printable solutions of specific categories of important proteins, e.g., structural proteins. As an example, globular proteins may be easily printable in concentrations of 10 wt % or more with common dampened nozzles, but type I collagen solutions, for example, in concentrations even as low as 0.3-0.5 wt % (a range commonly used for biomedical applications) are unprintable with the same devices. While a common technique for improving the printability of viscous inks is to raise the printing temperature, there are practical restrictions which further limit the printability of structural proteins.

Bioprinting processes involve shear rates in the range of $2 \times 10^4$ to $2 \times 10^6$ s$^{-1}$; while such shear rates pose no foreseeable problems for small, globular proteins, they are sufficiently high to compromise the structural integrity of some of their more fragile, larger, counterparts (e.g. structural proteins). Another hindrance in bioprinting structural proteins is the high compression rates used to generate droplets, which may result in the loss of both structural and biological properties, particularly in the absence of stabilizing additives.

Indeed, the highly organized nature of structural protein (collagen, elastin, keratin, fibrin, etc.) results in high surface tension, viscosity and shear stress, which are some of the main hindrance to the bioprinting process. This aspect is inherited from the tendency of cell-produced monomers in more organized structures to self-assemble when exposed to physiological conditions. Such proteins are engineered by Nature to self-organize in the extracellular space and not in an extrusion process upon exposure specific stimuli.

Composition of Novel, Printable Bio-Inks

Among other things, the present disclosure provides novel, water-based, biopolymer ink compositions ("bio-inks") suitable for high resolution inkjet printing. The techniques described herein opens a door to a new approach of additive printing that enables the fabrication of biocompatible sub-micron and micro-scale structures with good precision and reproducibility.

Non-limiting, exemplary ink formulations as a vehicle, suitable for carrying out various embodiments of the present invention include the following components: water (~60-90%); water-soluble solvent such as humectants for viscosity control (~5-30%); dye or pigments (colorants) (~1-10%); surfactant (~0.1-10%); buffering agent (~0.1-0.5%); and, other additives (~1%), each of which is measured by weight.

Typically, an aqueous bio-ink composition in accordance with the present invention comprises the following three components: (i) a structural protein, (ii) a viscosity-modifying agent (i.e., viscosity modifier or viscosity adjuster), such as an amphiphilic agent, and (iii) water.

Structural Proteins

The present disclosure encompasses the recognition that it is possible to control certain parameters of an aqueous biopolymer composition, thereby making it possible to be prepared and used as a liquid ink composition that can be readily printed on a substrate. In accordance with the invention, upon disposition or printing, such ink compositions can then form semi-solid or solid forms, which allows the fabrication of even sub-micron structures.

In some embodiments, a structural protein (such as silk fibroin and keratin) is present in a bio-ink composition at a final concentration of about 0.1-10% by weight, e.g., about 0.1%, about 0.2%, about 0.3%, about 0.4%, about 0.5%, about 0.6%, about 0.7%, about 0.8%, about 0.9%, about 1%, about 1.5%, about 2%, about 3%, about 4%, about 5%, about 6%, about 7%, about 8%, about 9%, about 10%, or greater.

In some embodiments, structural proteins (e.g., families and subfamilies of such proteins) suitable for carrying out the present invention include the following: fibroins, actins, collagens, catenins, claudins, coilins, elastins, elaunins, extensins, fibrillins, lamins, laminins, keratins, tublins, viral structural proteins, zein proteins (seed storage protein) and any combinations thereof.

In some embodiments, it is particularly advantageous to use or select protein fragments of certain molecular weight ranges. The inventors of the present invention have determined that bio-inks made from a structural protein of molecular weights ranging between about 3.5 kDa and about 120 kDa are particularly useful. In some embodiments, therefore, provided bio-inks of the invention predominantly contain structural protein fragments ranging between about 3.5 kDa and about 120 kDa, e.g., about 3.5 kDa and about 100 kDa, about 5 kDa and about 100 kDa, about 3.5-90 kDa, about 3.5-80 kDa, about 3.5-70 kDa, about 3.5-60 kDa, about 3.5-50 kDa, about 3.5-40 kDa, about 3.5-35 kDa, about 3.5-30 kDa, about 3.5-25 kDa, about 3.5-20 kDa, about 50-120 kDa, about 60-120 kDa, about 70-120 kDa, about 80-120 kDa, about 90-120 kDa.

Where such fragments correspond to reduced size, relative to the naturally occurring full-length counterpart, such polypeptide fragments are broadly herein referred to as "low molecular weight" protein.

In some embodiments, polypeptide fragments corresponding to at least a portion of any one of the structural proteins listed above may be used to make a bio-ink described herein. Such polypeptides suitable for practicing the present invention may be produced from various sources, including a regenerated (e.g., purified) protein from natural sources, recombinant proteins produced in heterologous systems, synthetic or chemically produced peptides, or combination of these.

In some embodiments, described bio-inks may be prepared from a polypeptide corresponding to any one of the list provided above, with or without one or more sequence variations, as compared to the native or wild type counterpart. For example, in some embodiments, such variants may show at least 85% overall sequence identity as compared to a wild type sequence, e.g., at least 86%, 87%, 88%, 89%, 90%, 91%, 92%, 93%, 94%, 95%, 96%, 97%, 98%, 99% overall sequence identity.

In some embodiments, bio-ink compositions of the present invention comprise silk fibroin, keratin, or combination thereof.

Silk Fibroin

Interestingly, silk fibroin has a different nature, being extruded from a living organism and changing its structure from globular to highly crystalline during such process. The scope of this work therefore included mimicking the natural silk fibroin extrusion process by inkjet printing regenerated silk solution, pioneering a new way to process this ancient material and providing unprecedented functions to fibroin-based biomaterials.

Silk fibroin-based solutions may be formulated as "silk inks" for use in printing. Accordingly, the invention includes silk fibroin-based ink compositions and methods for manufacturing the same.

In some embodiments where silk fibroin polypeptides are used to prepare peptide-based aerogels in accordance with the present invention, such silk fibroin polypeptide may be a low molecular weight silk fibroin polypeptide, ranging between about 3.5 kDa and about 120 kDa. Low molecular weight silk fibroin is described in detail in U.S. provisional application 61/883,732, entitled "LOW MOLECULAR WEIGHT SILK FIBROIN AND USES THEREOF," the entire contents of which are incorporated herein by reference.

In particular, such silk inks are suitable for use in conjunction with commercially available inkjet printers. As described herein, in a relatively inexpensive, streamlined fashion, inkjet printing can be employed for the fabrication of a wide range of nanostructures, using silk inks as a medium. These include two-dimensional (2D) and three-dimensional (3D) nanostructures. Unique material features of silk fibroin allow incorporation of a variety of agents or dopants for functionalization, which are stabilized within the silk ink. The invention is applicable to an array of technologies, including but not limited to, optoelectonic, photonics, and therapeutics.

As used herein, the term "silk fibroin" useful for carrying out the present invention includes silkworm fibroin and insect or spider silk protein. See e.g., Lucas et al., 13 Adv. Protein Chem. 107 (1958). For example, silk fibroin useful for the present invention may be that produced by a number of species, including, without limitation: *Antheraea mylitta; Antheraea pernyi; Antheraea yamamai; Galleria mellonella; Bombyx mori; Bombyx mandarins; Galleria mellonella; Nephila clavipes; Nephila senegalensis; Gasterancantha mammosa; Argiope aurantia; Araneus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata*; and *Nephila madagascariensis*.

In general, silk for use in accordance with the present invention may be produced by any such organism, or may be prepared through an artificial process, for example, involving genetic engineering of cells or organisms to produce a recombinant silk fibroin polypeptide and/or chemical synthesis. In some embodiments of the present invention, silk is produced by the silkworm, *Bombyx mori*.

As is known in the art, silks are modular in design, with large internal repeats flanked by shorter (~100 amino acid) terminal domains (N and C termini). Naturally occurring silk fibroin polypeptides have high molecular weight (200 to 350 kDa or higher) with transcripts of 10,000 base pairs and higher and >3000 amino acids (reviewed in Omenatto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules. An exemplary list of silk-producing species and corresponding silk proteins may be found in International Patent Publication Number WO 2011/130335, the entire contents of which are incorporated herein by reference.

Cocoon silk produced by the silkworm, *Bombyx mori*, is of particular interest because it offers low-cost, bulk-scale production suitable for a number of commercial applications, such as textile. Silkworm cocoon silk contains two structural proteins, the fibroin heavy chain (~350 k Da) and the fibroin light chain (~25 k Da), which are associated with a family of nonstructural proteins termed sericin, which glue the fibroin brings together in forming the cocoon. The heavy and light chains of fibroin are linked by a disulfide bond at the C-terminus of the two subunits (Takei, F., Kikuchi, Y., Kikuchi, A., Mizuno, S. and Shimura, K. (1987) J. Cell Biol., 105, 175-180; Tanaka, K., Mori, K. and Mizuno, S. (1993) J. Biochem. (Tokyo), 114, 1-4; Tanaka, K., Kajiyama, N., Ishikura, K., Waga, S., Kikuchi, A., Ohtomo, K., Takagi, T. and Mizuno, S. (1999) Biochim. Biophys. Acta, 1432, 92-103; Y Kikuchi, K Mori, S Suzuki, K Yamaguchi and S Mizuno, Structure of the *Bombyx mori* fibroin light-chain-encoding gene: upstream sequence elements common to the light and heavy chain, Gene 110 (1992), pp. 151-158). The sericins are a high molecular weight, soluble glycoprotein constituent of silk which gives the stickiness to the material. These glycoproteins are hydrophilic and can be easily removed from cocoons by boiling in water. This process is often referred to as "degumming."

As used herein, the term "silk fibroin" embraces silk fibroin protein, whether produced by silkworm, spider, or other insect, or otherwise generated (Lucas et al., Adv. Protein Chem., 13: 107-242 (1958)). In some embodiments, silk fibroin is obtained from a solution containing a dissolved silkworm silk or spider silk. For example, in some embodiments, silkworm silk fibroins are obtained, from the cocoon of *Bombyx mori*. In some embodiments, spider silk fibroins are obtained, for example, from *Nephila clavipes*. In the alternative, in some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

Thus, in some embodiments, a silk solution is used to fabricate compositions of the present invention contain fibroin proteins, essentially free of sericins. Provided silk fibroin particles contemplated herein are essentially free of sericins, unless otherwise explicitly specified. "Essentially free of sericins" means that such compositions contain no (e.g., undetectable) or little (i.e., trace amount) sericin such that one of ordinary skill in the pertinent art will consider negligible for a particular use.

In some embodiments, silk solutions used to fabricate various compositions of the present invention contain the heavy chain of fibroin, but are essentially free of other proteins. In other embodiments, silk solutions used to fabricate various compositions of the present invention contain both the heavy and light chains of fibroin, but are essentially free of other proteins. In certain embodiments, silk solutions used to fabricate various compositions of the present invention comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds.

Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Ala-rich" hydrophobic blocks are typically separated by segments of amino acids with bulky side-groups (e.g., hydrophilic spacers).

In some embodiments, core repeat sequences of the hydrophobic blocks of fibroin are represented by the following amino acid sequences and/or formulae:

(GAGAGS)$_{5-15}$; (SEQ ID NO: 1)

(GX)$_{5-15}$ (X = V, I, A); (SEQ ID NO: 2)

GAAS; (SEQ ID NO: 3)

(S$_{1-2}$A$_{11-13}$); (SEQ ID NO: 4)

GX$_{1-4}$ GGX; (SEQ ID NO: 5)

GGGX (X = A, S, Y, R, D V, W, R, D); (SEQ ID NO: 6)

(S1-2A1-4)$_{1-2}$; (SEQ ID NO: 7)

GLGGLG; (SEQ ID NO: 8)

GXGGXG (X = L, I, V, P); (SEQ ID NO: 9)

GPX (X = L, Y, I);

(GP(GGX)$_{1-4}$ Y)n (X = Y, V, S, A); (SEQ ID NO: 10)

GRGGAn; (SEQ ID NO: 11)

GGXn (X = A, T, V, S);

GAG(A)$_{6-7}$GGA;
and (SEQ ID NO: 12)

GGX GX GXX (X = Q, Y, L, A, S, R). (SEQ ID NO: 13)

In some embodiments, a fibroin peptide contains multiple hydrophobic blocks, e.g., 3, 4, 5, 6, 7, 8, 9, 10, 11, 12, 13, 14, 15, 16, 17, 18, 19 and 20 hydrophobic blocks within the peptide. In some embodiments, a fibroin peptide contains between 4-17 hydrophobic blocks. In some embodiments of the invention, a fibroin peptide comprises at least one hydrophilic spacer sequence ("hydrophilic block") that is about 4-50 amino acids in length. Non-limiting examples of the hydrophilic spacer sequences include:

TGSSGFGPYVNGGYSG; (SEQ ID NO: 14)

YEYAWSSE; (SEQ ID NO: 15)

SDFGTGS; (SEQ ID NO: 16)

RRAGYDR; (SEQ ID NO: 17)

EVIVIDDR; (SEQ ID NO: 18)

TTIIEDLDITIDGADGPI
and (SEQ ID NO: 19)

TISEELTI. (SEQ ID NO: 20)

In certain embodiments, a fibroin peptide contains a hydrophilic spacer sequence that is a derivative of any one of the representative spacer sequences listed above. Such derivatives are at least 75%, at least 80%, at least 85%, at least 90%, or at least 95% identical to any one of the hydrophilic spacer sequences.

In some embodiments, a fibroin peptide suitable for the present invention contains no spacer.

As noted, silks are fibrous proteins and are characterized by modular units linked together to form high molecular weight, highly repetitive proteins. These modular units or domains, each with specific amino acid sequences and chemistries, are thought to provide specific functions. For example, sequence motifs such as poly-alanine (polyA) and polyalanine-glycine (poly-AG) are inclined to be beta-sheet-forming; GXX motifs contribute to 31-helix formation; GXG motifs provide stiffness; and, GPGXX (SEQ ID NO: 22) contributes to beta-spiral formation. These are examples of key components in various silk structures whose positioning and arrangement are intimately tied with the end material properties of silk-based materials (reviewed in Omenetto and Kaplan (2010) Science 329: 528-531).

It has been observed that the beta-sheets of fibroin proteins stack to form crystals, whereas the other segments form amorphous domains. It is the interplay between the hard crystalline segments, and the strained elastic semi amorphous regions, that gives silk its extraordinary properties. Non-limiting examples of repeat sequences and spacer sequences from various silk-producing species are provided in An exemplary list of hydrophobic and hydrophilic components of fibroin sequences may be found in International Patent Publication Number WO 2011/130335, the entire contents of which are incorporated herein by reference.

In any of the embodiments contemplated herein, silk fibroin polypeptides of various molecular weights (e.g., fragments) may be used. In some embodiments, for example, provided silk fibroin hydrogel comprises silk fibroin polypeptides having an average molecular weight of between about 3.5 kDa and about 350 kDa. Non-limiting examples of suitable ranges of silk fibroin fragments include, but are not limited to: silk fibroin polypeptides have an average molecular weight of between about 3.5 kDa and about 200 kDa; silk fibroin polypeptides have an average molecular weight of between about 3.5 kDa and about 200 kDa; silk fibroin polypeptides have an average molecular weight of between about 3.5 kDa and about 120 kDa; silk fibroin polypeptides have an average molecular weight of between about 25 kDa and about 200 kDa, and so on. Silk fibroin polypeptides that are "reduced" in size, for instance, smaller than the original or wild type counterpart, may be referred to as "low molecular weight silk fibroin."

In some embodiments, provided silk fibroin particles are prepared from composition comprising a population of silk fibroin fragments having a range of molecular weights, characterized in that: no more than 15% of total weight of the silk fibroin fragments in the population has a molecular weight exceeding 200 kDa, and at least 50% of the total weight of the silk fibroin fragments in the population has a molecular weight within a specified range, wherein the specified range is between about 3.5 kDa and about 120 kDa.

For more details related to low molecular weight silk fibroins, see: U.S. provisional application 61/883,732, entitled "LOW MOLECULAR WEIGHT SILK FIBROIN AND USES THEREOF," the entire contents of which are incorporated herein by reference.

Keratins

Keratin is a large family of fibrous structural proteins. Keratin is the key structural material making up the outer layer of human skin. It is also the key structural component of hair and nails. Keratin monomers assemble into bundles to form intermediate filaments, which are tough and insoluble and form strong unmineralized tissues found in reptiles, birds, amphibians, and mammals. The only other biological matter known to approximate the toughness of keratinized tissue is chitin.

Viscosity-Modifying Agents

As stated, biopolymer-based ink formulations described herein typically contain at least one viscosity-modifying agent, also referred to as viscosity modifiers or viscosity adjusters. As described in detail herein, having the optimal range of viscosity is important for ensuing high quality, reproducible inkjet printing. As such, one or more of any suitable viscosity modifiers maybe used to adjust the viscosity of a bio-ink. It should be noted, however, that certain ink formulations may not require addition of any such viscosity modifiers, so long as the viscosity of the ink composition is already at or near a recommended range.

Typically, aqueous bio-ink compositions of the present invention contain between about 0.1-35 vol % of viscosity modifying agent or agents in the formulation. In a broad sense, a viscosity modifying agent suitable for use in water-based inks is a water-soluble solvent that regulates or contributes to viscosity control in the liquid ink. In some embodiments, the provided bio-ink compositions contain between about 0.5-30%, about 1.0-25%, about 5-20% of viscosity modifying agent agents (measured by volume). In some embodiments, the provided bio-ink compositions contain about 0.5%, about 1.0%, about 2.0%, about 3.0%, about 4.0%, about 5.0%, about 6.0%, about 7.0%, about 8.0%, about 9.0%, about 10%, about 11%, about 12%, about 13%, about 14%, about 15%, about 16%, about 17%, about 18%, about 18%, about 20%, about 21%, about 22%, about 23%, about 24%, about 25%, about 26%, about 27%, about 28%, about 29%, about 30%, about 31%, about 32%, about 33%, about 34%, about 35%, of viscosity modifying agent agents (measured by volume).

Aqueous bio-ink compositions disclosed described herein may include a viscosity modifier to modulate the final viscosity of the ink formulation. As already stated, any viscosity modifier known and used in the pertinent art can be included in the bio-ink formulations provided herein.

In some embodiments, humectants may function as viscosity modifiers for the bio-ink composition of the invention. Generally, a humectant is a water soluble solvent and any one of a group of hygroscopic substances with hydrating properties, i.e., used to keep things moist. They often are a molecule with several hydrophilic groups, most often hydroxyl groups; however, amines and carboxyl groups, sometimes esterified, can be encountered as well (its affinity to form hydrogen bonds with molecules of water, is the crucial trait).

Non-limiting examples of some humectants include: propylene glycol (E1520), hexylene glycol, and butylene glycol; glyceryl triacetate (E1518); vinyl alcohol; neoagarobiose; Sugar alcohols/sugar polyols: glycerol/glycerin, sorbitol (E420), xylitol, maltitol (E965); polymeric polyols (e.g., polydextrose (E1200)); quillaia (E999); urea; aloe vera gel; MP Diol; alpha hydroxy acids (e.g., lactic acid); and, honey. The chemical compound lithium chloride is an excellent (but toxic) humectant, as well. Typically, humectants such as glycerol and ethylene glycol are used in water-based inks to prevent the nozzle from clogging.

Examples of other viscosity modifiers that may be included in the inks include, but are not limited to: acrylate esters, acrylic esters, acrylic monomer, aliphatic mono acrylate, aliphatic mono methacrylate, alkoxylated lauryl acrylate, alkoxylated phenol acrylate, alkoxylated tetrahydrofurfuryl acrylate, $C_{12}$-$C_{14}$ alkyl methacrylate, aromatic acrylate monomer, aromatic methacrylate monomer, caprolactone acrylate, cyclic trimethylol-propane formal acrylate, cycloaliphatic acrylate monomer, dicyclopentadienyl methacrylate, diethylene glycol methyl ether methacrylate, epoxidized soybean fatty acid esters, epoxidized linseed fatty acid esters, epoxy acrylate, epoxy (meth)acrylate, 2-(2-ethoxyethoxy) ethyl acrylate, ethoxylated (4) nonyl phenol acrylate, ethoxylated (4) nonyl phenol methacrylate, ethoxylated nonyl phenol acrylate, glucose, fructose, corn syrup, gum syrup, hydroxy-terminated epoxidized 1,3-polybutadiene, isobornyl acrylate, isobornyl methacrylate, isodecyl acrylate, isodecyl methacrylate, isooctyl acrylate, isooctyl methacrylate, lauryl acrylate, lauryl methacrylate, methoxy polyethylene glycol (350) monoacrylate, methoxy polyethylene glycol (350) monomethacrylate, methoxy polyethylene glycol (550) monoacrylate, methoxy polyethylene glycol (550) mono-methacrylate, nonyl-phenyl polyoxyethylene acrylate, octyldecyl acrylate, 2-phenoxyethyl acrylate, 2-phenoxyethyl methacrylate, polybutadiene polymer, polyester acrylate, polyester methacrylate, polyether acrylate, polyether methacrylate, polysorbates, stearyl acrylate, stearyl methacrylate, syrups, tetrahydrofurfuryl acrylate, tetrahydrofurfuryl methacrylate, triethylene glycol ethyl ether methacrylate, 3,3,5-trimethylcyclohexyl methacrylate, urethane acrylate and urethane methacrylate and combinations thereof.

Surfactants

In some embodiments, provided aqueous bio-ink compositions may contain a surfactant agent which works as a wetting and/or penetrating agent. Use of surfactants in water-based inks is, in some embodiments, crucial because even a relatively small amount of a surfactant can significantly modify or affect the surface tension of an aqueous solution (e.g., water or buffers). In some embodiments, a surfactant agent is present at concentrations ranging between about 0.05-20%, e.g., between about 0.1-10% (either by volume or by weight) of an ink composition.

Relative Ratios of Ink Components

These components are present in predetermined ratios.

To illustrate: in some embodiments, where a 6.25% silk fibroin solution is used as the starting component (i), silk fibroin solution, an amphiphilic agent (such as a polysorbate) and water are present in a volume ratio of about 17:2:1. In some embodiments, silk fibroin solution, an amphiphilic agent and water are present in a volume ratio of about 17:1.5:1.5. In some embodiments, silk fibroin solution, an amphiphilic agent and water are present in a volume ratio of about 18:1.5:0.5. In some embodiments, silk fibroin solution, an amphiphilic agent and water are present in a volume ratio of about 16:2:2. In some embodiments, silk fibroin solution, an amphiphilic agent and water are present in a volume ratio of about 16:1.5:2.5. In some embodiments, silk fibroin solution, an amphiphilic agent and water are present in a volume ratio of about 16:2.5:1.5. In some embodiments, silk fibroin solution, an amphiphilic agent and water are present in a volume ratio of about 16:3:1. In some embodiments, silk fibroin solution, an amphiphilic agent and water are present in a volume ratio of about 15:3:2. In some embodiments, silk fibroin solution, an amphiphilic agent and water are present in a volume ratio of about 15:2.5:2.5. In some embodiments, silk fibroin solution, an amphiphilic agent and water are present in a volume ratio of about 15:2:3. Of course, these ratios should be appropriately adjusted when as silk fibroin solution used as the starting component (i) contains different silk fibroin concentrations, such as 5%, 6%, 7%, 8%, 9% and 10%.

In some embodiments, silk fibroin solutions used to prepare silk inks are substantially free of sericin (i.e., degummed). In some embodiments, silk fibroin useful for the preparation of silk inks described herein are extracted from cocoons (i.e., natural source of silk fibers). In some embodiments, silk fibroin useful for the preparation of silk inks described herein are recombinantly produced. In some embodiments, silk fibroin useful for the preparation of silk inks described herein are low molecular weight silk fibroin.

Amphiphilic agents useful for preparing silk fibroin-based inks include surfactants. In some embodiment, non-ionic detergents are used as an amphiphilic agent for this purpose. In some embodiments, silk fibroin-based inks (i.e., silk inks) comprise at least one polysorbate. Non-limiting examples of polysorbates include but are not limited to: polysorbate 20, polysorbate 40, polysorbate 60, polysorbate 80, or any combinations thereof.

Additives, Dopants, and Biologically Active Agents

In any of the embodiments described herein, bio-ink compositions of the present invention may further include one or more agent(s) (e.g., dopants and additives) suitable for intended purposes, including therapeutics (e.g., biologically active agents) and biological samples. Typically, addition of such agents (or dopants) are said to "functionalize" the ink composition by providing added functionality. To prepare functional bio-inks by adding appropriate dopants, suitable dopants (one dopant or a combination of compatible dopants) may be mixed in with an ink (or to a component of such ink). Non-limiting examples of suitable agents (or dopants) to be added for functionalization of bio-inks include but are not limited to: conductive or metallic particles; inorganic particles; dyes/pigments; drugs (e.g., antibiotics, small molecules or low molecular weight organic compounds); proteins and fragments or complexes thereof (e.g., enzymes, antigens, antibodies and antigen-binding fragments thereof); cells and fractions thereof (viruses and viral particles; prokaryotic cells such as bacteria; eukaryotic cells such as mammalian cells and plant cells; fungi).

In some embodiments, the additive is a biologically active agent. The term "biologically active agent" as used herein refers to any molecule which exerts at least one biological effect in vivo. For example, the biologically active agent can be a therapeutic agent to treat or prevent a disease state or condition in a subject. Biologically active agents include, without limitation, organic molecules, inorganic materials, proteins, peptides, nucleic acids (e.g., genes, gene fragments, gene regulatory sequences, and antisense molecules), nucleoproteins, polysaccharides, glycoproteins, and lipoproteins. Classes of biologically active compounds that can be incorporated into the composition described herein include, without limitation, anticancer agents, antibiotics, analgesics, anti-inflammatory agents, immunosuppressants, enzyme inhibitors, antihistamines, anti-convulsants, hormones, muscle relaxants, antispasmodics, ophthalmic agents, prostaglandins, anti-depressants, anti-psychotic substances, trophic factors, osteoinductive proteins, growth factors, and vaccines.

In some embodiments, the additive is a therapeutic agent. As used herein, the term "therapeutic agent" means a molecule, group of molecules, complex or substance administered to an organism for diagnostic, therapeutic, preventative medical, or veterinary purposes. As used herein, the term "therapeutic agent" includes a "drug" or a "vaccine." This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term can also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a therapeutic effect, for example deoxyribonucleic acid (DNA), ribonucleic acid (RNA), nucleic acid analogues (e.g., locked nucleic acid (LNA), peptide nucleic acid (PNA), xeno nucleic acid (XNA)), or mixtures or combinations thereof, including, for example, DNA nanoplexes, siRNA, microRNA, shRNA, aptamers, ribozymes, decoy nucleic acids, antisense nucleic acids, RNA activators, and the like. Generally, any therapeutic agent can be included in the composition described herein.

The term "therapeutic agent" also includes an agent that is capable of providing a local or systemic biological, physiological, or therapeutic effect in the biological system to which it is applied. For example, the therapeutic agent can act to control infection or inflammation, enhance cell growth and tissue regeneration, control tumor growth, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism. Additionally, a silk-based drug delivery composition can contain one therapeutic agent or combinations of two or more therapeutic agents.

A therapeutic agent can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon—carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary therapeutic agents include, but are not limited to, those found in Harrison's Principles of Internal Medicine, 13th Edition, Eds. T. R. Harrison et al. McGraw-Hill N.Y., N.Y.; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990, the complete contents of all of which are incorporated herein by reference.

Therapeutic agents include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an antiinflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifungal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyl-transferase inhibitors, pump inhibitors, histone acetyltransferase inhibitors, metalloproteinase inhibitors, ribonucleoside reductase inhibitors, TNF alpha agonists/antagonists, endothelinA receptor antagonists, retinoic acid receptor agonists, immuno-modulators, hormonal and anti-hormonal agents, photodynamic agents, and tyrosine kinase inhibitors.

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillinV, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramiisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N°-monomethyl-Larginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-amino glutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, non-steroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenybutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, norbinaltorphimine, buprenorphine, chlomaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof Prostaglandins are art recognized and are a class of naturally occurring chemically related long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. trophic factors include, without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, and transforming growth factors (beta), including beta-1, beta-2, beta-3, inhibin, and activin.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g., testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

In some embodiments, the additive is an agent that stimulates tissue formation, and/or healing and regrowth of natural tissues, and any combinations thereof. Agents that increase formation of new tissues and/or stimulates healing or regrowth of native tissue at the site of injection can include, but are not limited to, fibroblast growth factor (FGF), transforming growth factor-beta (TGF-beta, platelet-derived growth factor (PDGF), epidermal growth factors (EGFs), connective tissue activated peptides (CTAPs), osteogenic factors including bone morphogenic proteins, heparin, angiotensin II (A-II) and fragments thereof, insulin-like growth factors, tumor necrosis factors, interleukins, colony stimulating factors, erythropoietin, nerve growth factors, interferons, biologically active analogs, fragments, and derivatives of such growth factors, and any combinations thereof.

In some embodiments, the silk composition can further comprise at least one additional material for soft tissue augmentation, e.g., dermal filler materials, including, but not limited to, poly(methyl methacrylate) microspheres, hydroxylapatite, poly(L-lactic acid), collagen, elastin, and glycosaminoglycans, hyaluronic acid, commercial dermal filler products such as BOTOX® (from Allergan), DYSPORT®, COSMODERM®, EVOLENCE®, RADIESSE®, RESTYLANE®, JUVEDERM® (from Allergan), SCULPTRA®, PERLANE®, and CAPTIQUE®, and any combinations thereof.

In some embodiments, the additive is a wound healing agent. As used herein, a "wound healing agent" is a compound or composition that actively promotes wound healing process. Exemplary wound healing agents include, but are not limited to dexpanthenol; growth factors; enzymes, hormones; povidon-iodide; fatty acids; anti-inflammatory agents; antibiotics; antimicrobials; antiseptics; cytokines; thrombin; angalgesics; opioids; aminoxyls; furoxans; nitrosothiols; nitrates and anthocyanins; nucleosides, such as adenosine; and nucleotides, such as adenosine diphosphate (ADP) and adenosine triphosphate (ATP); neutotransmitter/neuromodulators, such as acetylcholine and 5-hydroxytryptamine (serotonin/5-HT); histamine and catecholamines, such as adrenalin and noradrenalin; lipid molecules, such as sphingosine-1-phosphate and lysophosphatidic acid; amino acids, such as arginine and lysine; peptides such as the bradykinins, substance P and calcium gene-related peptide (CGRP); nitric oxide; and any combinations thereof.

In certain embodiments, the active agents described herein are immunogens. In one embodiment, the immunogen is a vaccine. Most vaccines are sensitive to environmental conditions under which they are stored and/or transported. For example, freezing may increase reactogenicity (e.g., capability of causing an immunological reaction) and/or loss of potency for some vaccines (e.g., HepB, and DTaP/IPV/HIB), or cause hairline cracks in the container, leading to contamination. Further, some vaccines (e.g., BCG, Varicella, and MMR) are sensitive to heat. Many vaccines (e.g., BCG, MMR, Varicella, Meningococcal C Conjugate, and most DTaP-containing vaccines) are light sensitive. See, e.g., Galazka et al., Thermostability of vaccines, in Global Programme for Vaccines & Immunization (World Health Organization, Geneva, 1998); Peetermans et al., Stability of freeze-dried rubella virus vaccine (Cendehill strain) at various temperatures, 1 J. Biological Standardization 179 (1973). Thus, the compositions and methods described herein also provide for stabilization of vaccines regardless of the cold chain and/or other environmental conditions.

In some embodiments, the additive is a cell, e.g., a biological cell. Cells useful for incorporation into the composition can come from any source, e.g., mammalian, insect, plant, etc. In some embodiments, the cell can be a human, rat or mouse cell. In general, cells to be used with the compositions described herein can be any types of cells. In general, the cells should be viable when encapsulated within compositions. In some embodiments, cells that can be used with the composition include, but are not limited to, mammalian cells (e.g. human cells, primate cells, mammalian cells, rodent cells, etc.), avian cells, fish cells, insect cells, plant cells, fungal cells, bacterial cells, and hybrid cells. In some embodiments, exemplary cells that can be can be used with the compositions include platelets, activated platelets, stem cells, totipotent cells, pluripotent cells, and/or embryonic stem cells. In some embodiments, exemplary cells that can be encapsulated within compositions include, but are not limited to, primary cells and/or cell lines from any tissue. For example, cardiomyocytes, myocytes, hepatocytes, keratinocytes, melanocytes, neurons, astrocytes, embryonic stem cells, adult stem cells, hematopoietic stem cells, hematopoietic cells (e.g. monocytes, neutrophils, macrophages, etc.), ameloblasts, fibroblasts, chondrocytes, osteoblasts, osteoclasts, neurons, sperm cells, egg cells, liver cells, epithelial cells from lung, epithelial cells from gut, epithelial cells from intestine, liver, epithelial cells from skin, etc, and/or hybrids thereof, can be included in the silk/platelet compositions disclosed herein. Those skilled in the art will recognize that the cells listed herein represent an exemplary, not comprehensive, list of cells. Cells can be obtained from donors (allogenic) or from recipients (autologous). Cells can be obtained, as a non-limiting example, by biopsy or other surgical means known to those skilled in the art.

In some embodiments, the cell can be a genetically modified cell. A cell can be genetically modified to express and secrete a desired compound, e.g. a bioactive agent, a growth factor, differentiation factor, cytokines, and the like. Methods of genetically modifying cells for expressing and secreting compounds of interest are known in the art and easily adaptable by one of skill in the art.

Differentiated cells that have been reprogrammed into stem cells can also be used. For example, human skin cells reprogrammed into embryonic stem cells by the transduction of Oct3/4, Sox2, c-Myc and Klf4 (Junying Yu, et. al., Science, 2007, 318, 1917-1920 and Takahashi K. et. al., Cell, 2007, 131, 1-12).

Pigment/Dye

In some embodiments, bio-ink compositions provided herein can include a colorant, such as a pigment or dye or combination thereof. Any organic and/or inorganic pigments and dyes can be included in the inks. Exemplary pigments suitable for use in the present invention include International Color Index or C.I. Pigment Black Numbers 1, 7, 11 and 31, C.I. Pigment Blue Numbers 15, 15:1, 15:2, 15:3, 15:4, 15:6, 16, 27, 29, 61 and 62, C.I. Pigment Green Numbers 7, 17, 18 and 36, C.I. Pigment Orange Numbers 5, 13, 16, 34 and 36, C.I. Pigment Violet Numbers 3, 19, 23 and 27, C.I. Pigment Red Numbers 3, 17, 22, 23, 48:1, 48:2, 57:1, 81:1, 81:2, 81:3, 81:5, 101, 114, 122, 144, 146, 170, 176, 179, 181, 185, 188, 202, 206, 207, 210 and 249, C.I. Pigment Yellow Numbers 1, 2, 3, 12, 13, 14, 17, 42, 65, 73, 74, 75, 83, 93, 109, 110, 128, 138, 139, 147, 142, 151, 154 and 180, D&C Red No. 7, D&C Red No. 6 and D&C Red No. 34, carbon black pigment (such as Regal 330, Cabot Corporation), quinacridone pigments (Quinacridone Magenta (228-0122), available from Sun Chemical Corporation, Fort Lee, N.J.), diarylide yellow pigment (such as AAOT Yellow (274-1788) available from Sun Chemical Corporation); and phthalocyanine blue pigment (such as Blue 15:3 (294-1298) available from Sun Chemical Corporation). The classes of dyes suitable for use in present invention can be selected from acid dyes, natural dyes, direct dyes (either cationic or anionic), basic dyes, and reactive dyes. The acid dyes, also regarded as anionic dyes, are soluble in water and mainly insoluble in organic solvents and are selected, from yellow acid dyes, orange acid dyes, red acid dyes, violet acid dyes, blue acid dyes, green acid dyes, and black acid dyes. European Patent 0745651, incorporated herein by reference, describes a number of acid dyes that are suitable for use in the present invention. Exemplary yellow acid dyes include Acid Yellow 1 International Color Index or C.I. 10316); Acid Yellow 7 (C.I. 56295); Acid Yellow 17 (C.I. 18965); Acid Yellow 23 (C.I. 19140); Acid Yellow 29 (C.I. 18900); Acid Yellow 36 (C.I. 13065); Acid Yellow 42 (C.I. 22910); Acid Yellow 73 (C.I. 45350); Acid Yellow 99 (C.I. 13908); Acid Yellow 194; and Food Yellow 3 (C.I. 15985). Exemplary orange acid dyes include Acid Orange 1 (C.I. 13090/1); Acid Orange 10 (C.I. 16230).; Acid Orange 20 (C.I. 14603); Acid Orange 76 (C.I. 18870); Acid Orange 142; Food Orange 2 (C.I. 15980); and Orange B.

Exemplary red acid dyes include Acid Red 1. (C.I. 18050); Acid Red 4 (C.I. 14710); Acid Red 18 (C.I. 16255), Acid Red 26 (C.I. 16150); Acid Red 2.7 (C.I. as Acid Red 51 (C.I. 45430, available from BASF Corporation, Mt. Olive, N.J.) Acid Red 52 (C.I. 45100); Acid Red 73 (C.I. 27290); Acid Red 87 (C.I. 45380); Acid Red 94 (C.I. 45440) Acid Red 194; and Food Red 1 (C.I. 14700). Exemplary violet acid dyes include Acid Violet 7 (C.I. 18055); and Acid Violet 49 (C.I. 42640). Exemplary blue acid dyes include Acid Blue 1 (C.I. 42045); Acid Blue 9 (C.I. 42090); Acid Blue 22 (C.I. 42755); Acid Blue 74 (C.I. 73015); Acid Blue 93 (C.I. 42780); and Acid Blue 158A (C.I. 15050). Exemplary green acid dyes include Acid Green 1 (C.I. 10028); Acid Green 3 (C.I. 42085); Acid Green 5 (C.I. 42095); Acid Green 26 (C.I. 44025); and Food Green 3 (C.I. 42053). Exemplary black acid dyes include Acid Black 1 (C.I. 20470); Acid Black 194 (Basantol® X80, available from BASF Corporation, an azo/1:2 CR-complex.

Exemplary direct dyes for use in the present invention include Direct Blue 86 (C.I. 74180); Direct Blue 199; Direct Black 168; Direct Red 253; and Direct Yellow 107/132 (C.I. Not Assigned).

Exemplary natural dyes for use in the present invention include Alkanet (C.I. 75520,75530); Annafto (C.I. 75120); Carotene (C.I. 75130); Chestnut; Cochineal (C.I. 75470); Cutch (C.I. 75250, 75260); Divi-Divi; Fustic (C.I. 75240); Hypernic (C.I. 75280); Logwood (C.I. 75200); Osage Orange (C.I. 75660); Paprika; Quercitron (C.I. 75720); Sanrou (C.I. 75100); Sandal Wood (C.I. 75510, 75540, 75550, 75560); Sumac; and Tumeric (C.I. 75300). Exemplary reactive dyes for use in the present invention include Reactive Yellow 37 (monoazo dye); Reactive Black 31 (disazo dye); Reactive Blue 77 (phthalo cyanine dye) and Reactive Red 180 and Reactive Red 108 dyes. Suitable also are the colorants described in The Printing Ink Manual (5th ed., Leach et al. eds. (2007), pages 289-299. Other organic and inorganic pigments and dyes and combinations thereof can be used to achieve the colors desired.

In addition to or in place of visible colorants, bio-ink compositions described herein can contain UV fluorophores that are excited in the UV range and emit light at a higher wavelength (typically 400 nm and above). Examples of UV fluorophores include but are not limited to materials from the coumarin, benzoxazole, rhodamine, napthalimide, perylene, benzanthrones, benzoxanthones or benzothia-xanthones families. The addition of a UV fluorophore (such as an optical brightener for instance) can help maintain maximum visible light transmission. The amount of colorant, when present, generally is between 0.05% to 5% or between 0.1% and 1% based on the weight of the bio-ink composition.

For non-white inks, the amount of pigment/dye generally is present in an amount of from at or about 0.1 wt % to at or about 20 wt % based on the weight of the ink composition. In some applications, a non-white ink can include 15 wt % or less pigment/dye, or 10 wt % or less pigment/dye or 5 wt % pigment/dye, or 1 wt % pigment/dye based on the weight of the ink composition. In some applications, a non-white ink can include 1 wt % to 10 wt %, or 5 wt % to 15 wt %, or 10 wt % to 20 wt % pigment/dye based on the weight of the ink composition. In some applications, a non-white ink can contain an amount of dye/pigment that is 1 wt %, 2 wt %, 3 wt %, 4 wt %, 5%, 6 wt %, 7 wt %, 8 wt %, 9 wt %, 10 wt %, 11 wt %, 12 wt %, 13 wt %, 14 wt %, 15%, 16 wt %, 17 wt %, 18 wt %, 19 wt % or 20 wt % based on the weight of the ink composition.

For white ink compositions, the amount of white pigment generally is present in an amount of from at or about 1 wt % to at or about 60 wt % based on the weight of the ink composition. In some applications, greater than 60 wt % white pigment can be present. Preferred white pigments include titanium dioxide (anatase and rutile), zinc oxide, lithopone (calcined coprecipitate of barium sulfate and zinc sulfide), zinc sulfide, blanc fixe and alumina hydrate and combinations thereof, although any of these can be combined with calcium carbonate. In some applications, a white ink can include 60 wt % or less white pigment, or 55 wt % or less white pigment, or 50 wt % white pigment, or 45 wt % white pigment, or 40 wt % white pigment, or 35 wt % white pigment, or 30 wt % white pigment, or 25 wt % white pigment, or 20 wt % white pigment, or 15 wt % white pigment, or 10 wt % white pigment, based on the weight of the ink composition. In some applications, a white ink can include 5 wt % to 60 wt %, or 5 wt % to 55 wt %, or 10 wt % to 50 wt %, or 10 wt % to 25 wt %, or 25 wt % to 50 wt %, or 5 wt % to 15 wt %, or 40 wt % to 60 wt % white pigment based on the weight of the ink composition. In some applications, a non-white ink can an amount of dye/pigment that is 5%, 6 wt %, 7 wt %, 8 wt %, 9 wt %, 10 wt %, 11 wt %, 12 wt %, 13 wt %, 14 wt %, 15%, 16 wt %, 17 wt %, 18 wt %, 19 wt %, 20 wt %, 21 wt %, 22 wt %, 23 wt %, 24 wt %, 25%, 26 wt %, 27 wt %, 28 wt %, 29 wt %, 30 wt %, 31 wt %, 32 wt %, 33 wt %, 34 wt %, 35%, 36 wt %, 37 wt %, 38 wt %, 39 wt %, 40 wt %, 41 wt %, 42 wt %, 43 wt %, 44 wt %, 45%, 46 wt %, 47 wt %, 48 wt %, 49 wt %, 50 wt %, 51 wt %, 52 wt %, 53 wt %, 54 wt %, 55%, 56 wt %, 57 wt %, 58 wt %, 59 wt % or 60 wt % based on the weight of the ink composition.

The lifetime (e.g., stability) of provided bio-ink compositions depends on the usage and the storage conditions. In some embodiments, storage in a refrigerator at 4 degree C. when finishing printing is recommended. In some embodiments, provided bio-inks (with our without dopants) may be stored without refrigeration, such as at room temperature (typically between about 18-26° C.) for an extended duration of time without significant loss of function. In some embodiments, provided bio-inks (with our without dopants) may be stored at room temperature (typically between about 18-26° C.) for an extended duration of time, such as at least for 1 week, at least for 2 weeks, at least for 3 weeks, at least for 4 weeks, at least for 6 weeks, at least for 2 months, at least for 3 months, at least for 4 months, at least for 5 months, at least for 6 months, at least for 9 months, at least for 12 months, at least for 15 months, at least for 18 months, and at least for 24 months, or longer, without significant loss of function. In some embodiments, provided bio-inks (with our without dopants) may be stored at elevated temperature (between about 27-40° C.) for at least part of the duration of storage, for an extended duration of time, such as at least for 1 week, at least for 2 weeks, at least for 3 weeks, at least for 4 weeks, at least for 6 weeks, at least for 2 months, at least for 3 months, at least for 4 months, at least for 5 months, at least for 6 months, at least for 9 months, at least for 12 months, at least for 15 months, at least for 18 months, and at least for 24 months, or longer, without significant loss of function.

Properties of Bio-Inks

According to some example embodiments of the present invention, provided bio-ink compositions have suitable properties as measured by surface tension, viscosity and/or pH. In some embodiments, a bio-ink composition of the present disclosure is prepared as described herein, so that the ink composition has, for example, surface tension ranges between about 24-50 dynes/cm at room temperature, between about 28-44 dynes/cm at room temperature, between about 30-38 dynes/cm at room temperature; viscosity of between about 8-10 centipoise at room temperature. In some embodiments, such ink composition has a pH value of between about 5-9, such as between 6-7, between 5.5-7.5. As used herein, "room temperature" is typically between about 18-26° C., and also referred to as "ambient" condition. In some embodiments, therefore, the phrase "room temperature" and "ambient temperature (or condition)" may include temperatures such as about 18° C., about 19° C., about 20° C., about 21° C., about 22° C., about 23° C., about 24° C., about 25° C., about 26° C., and so on, unless otherwise specified.

Preparation of Bio-Inks

Another aspect of the invention provides methods for preparing bio-inks, such as silk fibroin inks. An exemplary protocol for preparing a silk fibroin ink in accordance with the present disclosure is provided below.

Preparation of Low Molecular Weight Structural Proteins

While silk fibroin extraction methods generally have been well documented, the present invention encompasses the recognition that certain structural proteins can be processed further to be made suitable for bio-printing described herein, thereby overcoming previously existed hurdles that had prevented the use of certain structural proteins for printing purposes.

Accordingly, in some embodiments, such methods involve extraction of structural proteins (such as silk fibroin) under high temperature, such as between about 101-135° C., between about 105-130° C., between about 110-130° C., between about 115-125° C., between about 118-123° C., e.g., about 115° C., 116° C., 117° C., 118° C., 119° C., 120° C., 121° C., 122° C., 123° C., 124° C., 125° C.

Additionally or alternatively, provided methods in some embodiments involve extraction of structural proteins (such as silk fibroin) under elevated pressure, such as about 5 psi, 6 psi, 7 psi, 8 psi, 9 psi, 10 psi, 11 psi, 12 psi, 13 psi, 14 psi, 15 psi, 16 psi, 17 psi, 18 psi, 19 psi, 20 psi, 21 psi, 22 psi, 23 psi, 24 psi, 25 psi, 30 psi, 31 psi, 32 psi, 33 psi, 34 psi and 35 psi. In some embodiments, structural proteins (such as silk fibroin) are extracted under high temperature and under elevated pressure, e.g., at about 110-130° C. and about 10-20 psi for a duration suitable to produce a protein solution that would easily go through a 0.2 μm filter. In some embodiments, structural proteins (such as silk fibroin) are extracted under high temperature and under elevated pressure, e.g., at about 110-130° C. and about 10-20 psi for about 60-180 minutes. In some embodiments, structural proteins (such as silk fibroin) are extracted under high temperature and under elevated pressure, e.g., at about 116-126° C. and about 12-20 psi for about 90-150 minutes.

An exemplary protocol is provided below:

In accordance with some examples, the following example process may be performed to obtain ~40 mL of silk solution with a concentration of ~6.25% (wt/vol); if more volumes are needed, the materials can be scaled appropriately.

1) Cut *Bombyx mori* silk cocoons (10 gram) into half-dime-sized pieces and dispose of silkworms;
2) Measure 8.48 gram of sodium carbonate and add it into 4 liter of water in a 5 liter glass beaker (to prepare a 0.02 M solution);
3) Put the beaker into an autoclave and set the autoclave to run at 121 degree C. under the pressure of 16 psi for 120 minutes;
4) Remove the silk fibroin with a strainer and cool it by rinsing in ultrapure cold water for 20 minutes and repeat twice for a total of three rinses;
5) After the third rinse, remove the silk fibroin and squeeze the water;
6) Spread the squeezed silk fibroin, spread it out and let it dry in a fume hood for 12 hours, which results in silk fibroin weighing slightly over 2.5 gram;
7) Dissolve 2.5 gram of silk fibroin into 10 mL of 9.3 M lithium bromide;
8) The silk fibroin should dissolve completely in a few minutes upon stirring;
9) Insert 10 mL of the silk-LiBr solution into a pre-wet 3-12-mL dialysis cassette and dialyze against 1 liter of ultrapure water for 48 hours (change the water every 6 hours);
10) Remove silk from the cassette;
11) Place the silk solution in a centrifuge and spin at 9,000 r.p.m. at 2 degree C. for 60 minutes, and store the centrifuged silk solution (~40 mL of silk solution with a concentration of ~6.25%) in a refrigerator at 4 degree C.

For ~2 mL of silk fibroin protein ink, if more volumes are needed, the materials can be scaled appropriately.

1) Mix the silk solution with surfactant (for example, Tween 20 from Sigma-Aldrich Co.) and water in a volume ratio of 17:2:1 (i.e. 1700 μL of ~6.25% silk fibroin solution, 200 μL of Tween 20 and 100 μL of water);
2) This results in a 2 mL of silk fibroin ink with the following properties:
   Surface tension: 30-38 dynes/cm at room temperature
   Viscosity: 8-10 centipoise at room temperature
   pH value: between 6 and 7.

Note that the ratio of the mixture is optimized for Tween 20 and other biological or chemical surfactant (for example, glycol, ether, and etc.) can be also used with modifications of the mixture ratio. Surface treatment of the printing nozzle(s) can also improve the formation of silk ink drops.

Silk as Biomaterial

Even among structural proteins, silk fibroin (SF) is a fascinating material, extensively investigated for its potential in textile, biomedical, photonic and electronic applications. SF is a structural protein, like collagen, but with a unique feature: it is produced from the extrusion of an amino-acidic solution by a living complex organism (while collagen is produced in the extracellular space by self-assembly of cell-produced monomers). SF properties are derived from its structure, which consists of hydrophobic blocks staggered by hydrophilic, acidic spacers. In its natural state, SF is organized in β-sheet crystals alternated with amorphous regions, which provide strength and resilience to the protein. The multiplicities of forms in which regenerated SF can be process at a high protein concentration and molecular weight make it attractive for several high-tech applications, as recently discovered and described by our group. The degree of crystallinity of the protein can be finely tuned and it influences SF's biological, physical, biochemical and mechanical properties. In addition, the amino-acidic nature of SF brings a diversity of side chain chemistries that allows for the incorporation and stabilization of macromolecules useful in drug delivery applications or in providing cellular instructions. In particular, we have recently showed that dry SF with diverse degrees of crystallinity stabilizes vaccines and antibiotics, eliminating the need for the cold chain. SF is indeed considered a platform technology in biomaterials fabrication as its robustness and qualities bring the assets to add a large portfolio of distinct features (e.g. nanopatterning, biochemical functionalization) to the final construct. Processing of regenerated SF generally involves the partial or total dehydration of a fibroin solution (protein content of 1-15 wt %) to form films, sponges, gels, spheres (micron- to nano-sized) and foams with numerous techniques (e.g. solvent casting, freeze drying, salt leaching, sonication). The rationale beyond these fabrication processes is to manufacture a robust material that combines mechanical strength with biochemical properties.

Liquid Droplet Unit

The present invention provides means for achieving a very small unit volume of a bio-ink composition formed as liquid droplets for carrying out printing. In some embodiments, the present application provides an aqueous unit composition (i.e., a liquid droplet) having a volume of between about 0.1-100 pL. In some embodiments, each droplet has a volume of between about 0.5-50 pL, between about 0.5-25 pL, between about 0.5-20 pL, between about 0.5-15 pL, between about 0.5-10 pL, between about 1.0-40 pL, between about 1.0-30 pL, between about 1.0-25 pL, between about 1.0-20 pL, between about 1.0-15 pL, between about 1.0-10 pL. For example, in some embodiments, a unit volume of a single droplet of a bio-ink described herein is about 0.5 pL, about 1.0 pL, about 1.5 pL, about 2.0 pL, about 3.0 pL, about 4.0 pL, about 5.0 pL, about 6.0 pL, about 7.0 pL, about 8.0 pL, about 9.0 pL, about 10 pL, about 11 pL, about 12 pL, about 13 pL, about 14 pL, about 15 pL, about 16 pL, about 17 pL, about 18 pL, about 19 pL, about 20 pL, about 21 pL, about 22 pL, about 23 pL, about 24 pL, about 25 pL, about 30 pL, about 40 pL, about 50 pL, about 60 pL, about 70 pL, about 80 pL, about 90 pL, or about 100 pL. In some embodiments, for example, each droplet of such a bio-ink has a volume of between 0.1-100 pL, wherein the bio-ink has a viscosity ranging between 8-10 centipoise at room temperature.

Uniformity

The ability to control droplet size distribution (e.g., uniformity) on the micron scale and sub-micron (e.g., nano) scale to ensure reproducible printing quality is important in a number of contexts. For example, for downstream applications involving medical or clinical use, such as drug delivery applications, it is crucial to ensure the uniformity of release kinetics. Generally, monodisperse particles (e.g., droplets) provide greater degree of uniformity in release kinetics than polydisperse particles (e.g., droplets). Similarly, it is of particular interest to have the ability to finely control droplet size and distributions in a number of optical applications involving the use of nano-sized particles, such as the plasmonic resonance of core/shell nanospheres and their tunable, size-dependent, optical properties. Moreover, the use of protein-based materials provides additional utility for these systems, since they can be absorbed by the body with safe degradation.

The process of "break-off" and jetting of the droplet from a nozzle may be at least in part determined by, or otherwise influenced by interplay of a number of factors, including the interfacial tension and the viscosity of the liquid ink, among other factors. This, in conjunction with the nozzle characteristic of the printer, in turn determines the size of the droplets that breaks off and to be deposited onto a substrate. Moreover, interactions between a bio-ink and a substrate (e.g., charge interactions) also affects the behavior.

Accordingly, as a result of extensive experimentation, the inventors of the present application have determined certain desirable sets of conditions and/or parameters by which to produce reproducibly uniform droplet formation and high quality printing, as exemplified below.

As used herein, the term "uniform" or "uniformity" refers to a composition characterized by a plurality of units of similar features with respect to a parameter (such as size, e.g., volume and diameter). The less the degree of deviation with respect to a parameter being measured, the greater the degree of uniformity within the composition.

In some embodiments, for example, dots of a bio-ink described herein are uniform in that liquid ink droplets deposited for printing show a narrow size distribution such that a majority of droplets within a single printing run fall within a specified range of volumes.

In some embodiments, at least 50% of droplets have volumes within a specified range, wherein the specified range may be between about 1.0 pL and 20 pL. In some embodiments, at least 55%, at least 60%, at least 65%, at least 70%, at least 75%, at least 80%, at least 85%, at least 90%, at least 95% or greater number of droplets within a single printing run have volumes within a specified range. The specified range may be between about 10 pL and about 20 pL.

In some embodiments, provided aqueous bio-inks have a useful viscosity range of about 5-15 centipoise at jetting temperature. In some embodiments, provided aqueous bio-inks have a useful viscosity range of about 8-14 centipoise, e.g., about 8-13 centipoise, about 7-13 centipoise, about 6-12 centipoise, about 6-11 centipoise, about 7-12 centipoise, about 9-13 centipoise, about 10-13 centipoise, about 10-12 centipoise, for example, about 5 centipoise, about 6 centipoise, about 7 centipoise, about 8 centipoise, about 9 centipoise, about 10 centipoise, about 11 centipoise, about 12 centipoise, about 13 centipoise, about 14 centipoise, about 15 centipoise at jetting temperature.

It has been further determined that, in any one of the embodiments, provided aqueous bio-inks have a useful surface tension range of about 20-50 dynes/cm at jetting temperature. In some embodiments, provided aqueous bio-inks have a useful surface tension range of about 22-48 dynes/cm, about 23-47 dynes/cm, about 24-46 dynes/cm, about 25-47 dynes/cm, about 26-46 dynes/cm, about 27-45 dynes/cm, 28-44 dynes/cm, for example, about 28 dynes/cm, about 29 dynes/cm, about 30 dynes/cm, about 31 dynes/cm, about 32 dynes/cm, about 33 dynes/cm, about 34 dynes/cm, about 35 dynes/cm, about 36 dynes/cm, about 37 dynes/cm, about 38 dynes/cm, about 39 dynes/cm, about 40 dynes/cm, about 41 dynes/cm, about 42 dynes/cm, about 43 dynes/cm and about 44 dynes/cm at jetting temperature.

In addition, extensive work has revealed that the parameter of viscosity and surface tension are co-dependent, such that relatively higher surface tension may be well combined with relatively lower viscosity to achieve effective printing. For example, a bio-ink having a surface tension greater than 44 can combine well with a viscosity lower than 10 in the context of DMP 2800 printer by way of modifying the waveform.

It has been further determined that, in any one of the embodiments, provided aqueous bio-inks exhibit low volatility, such that such bio-inks preferably have boiling point higher than 100° C., e.g., about 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., 120° C., 121° C., 122° C., 123° C., 124° C., 125° C., 126° C., 127° C., 128° C., 129° C., 130° C., or greater.

Further yet, it has been determined that, in any one of the embodiments, provided aqueous bio-inks have specific gravity greater than 1.0.

It has also been determined that, in any of the embodiments, provided aqueous bio-ink compositions have a useful pH range of between about 4 and 9, e.g., about pH 4.0, about pH 4.5, about pH 5.0, about pH 5.5, about pH 6.0, about pH 6.5, about pH 7.0, about pH 7.5, about pH 8.0, about pH 8.5, about pH 9.0. In some embodiments, a buffer component may be added to such ink compositions to maintain the pH level in the ink. For example, in some embodiments, buffering salt components may optionally comprise between about 0.1-0.5% (by weight) of bio-ink compositions.

Low Molecular Weight Structural Proteins

According to the invention, structural proteins particularly suitable for formulating as a bio-ink are below 200 kDa, preferably below 150 kDa. In some embodiments, structural proteins (or fragments thereof) particularly suitable for formulating as a bio-ink have molecular weight ranging between about 3.5 kDa and about 120 kDa, e.g., about 3.5-110 kDa, about 3.5-100 kDa, about 3.5-90 kDa, about 3.5-80 kDa, about 3.5-70 kDa, about 3.5-60 kDa, about 3.5-50 kDa, about 3.5-40 kDa, about 3.5-35 kDa, about 3.5-30 kDa, about 3.5-25 kDa, about 3.5-20 kDa, about 50-120 kDa, about 60-120 kDa, about 70-120 kDa, about 80-120 kDa, about 90-120 kDa. In some embodiments, such structural protein may be a full-length (e.g., wild type) structural protein having a molecular weight falling within any of the ranges shown above. In other embodiments, such structural protein may be so-called "low molecular weight protein," i.e., corresponding to reduced size fragments of a full-length counterpart, for example fragments of the full-length counterpart.

In some embodiments, where silk fibroin is used as a structural protein for a bio-ink, no more than 15% of the total number of silk fibroin fragments in a silk fibroin ink composition has a molecular weight exceeding 200 kDa, and at least 50% of the total number of the silk fibroin fragments in the population has a molecular weight within a specified range, wherein the specified range is between about 3.5 kDa and about 120 kDa. Low molecular weight silk fibroin is described in detail in U.S. provisional application 61/883,732, entitled "LOW MOLECULAR WEIGHT SILK FIBROIN AND USES THEREOF," the entire contents of which are incorporated herein by reference.

In some embodiments, consistency of a bio-ink may be further enhanced by selectively enriching certain range or ranges of fragment size (molecular weight) in a preparation.

In some embodiments, therefore, a step of filtration may be included during the preparation of such an ink composition. For instance, filters with a known cut-off range (such as 0.2 µm) may be used to remove any fragments or aggregates (e.g., contamination) that are larger than the pore size. Alternatively or additionally, in some embodiments, protein solution may be further processed, including extended heating and/or high pressure treatment, in order to promote fragmentation of large structural proteins.

In some embodiments, an aqueous protein ink solution described herein may be heated (such as by boiling at atmospheric pressure) during the process of protein preparation for a period of time, e.g., for about 10 minutes, about 15 minutes, about 20 minutes, about 30 minutes, about 40 minutes, about 45 minutes, about 50 minutes, about 60 minutes, about 70 minutes, about 80 minutes, about 90 minutes, about 100 minutes, about 110 minutes, about 120 minutes, or longer.

Alternatively or additionally, in some embodiments, such protein solution may be heated or boiled at an elevated temperature. For example, in some embodiments, the protein solution can be heated or boiled at about 101.0° C., at about 101.5° C., at about 102.0° C., at about 102.5° C., at about 103.0° C., at about 103.5° C., at about 104.0° C., at about 104.5° C., at about 105.0° C., at about 105.5° C., at about 106.0° C., at about 106.5° C., at about 107.0° C., at about 107.5° C., at about 108.0° C., at about 108.5° C., at about 109.0° C., at about 109.5° C., at about 110.0° C., at about 110.5° C., at about 111.0° C., at about 111.5° C., at about 112.0° C., at about 112.5° C., at about 113.0° C., 113.5° C., at about 114.0° C., at about 114.5° C., at about 115.0° C., at about 115.5° C., at about 116.0° C., at about 116.5° C., at about 117.0° C., at about 117.5° C., at about 118.0° C., at about 118.5° C., at about 119.0° C., at about 119.5° C., at about 120.0° C., or higher.

In some embodiments, such elevated temperature can be achieved by carrying out at least portion of the heating process (e.g., boiling process) under pressure. For example, suitable pressure under which protein fragments described herein can be produced are typically between about 10-40 psi, e.g., about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, or about 40 psi.

Alternatively or additionally, in some embodiments, protein solution may be further processed, including centrifugation.

In some embodiments, provided aqueous bio-inks have low dissolved gas contents. In some embodiments, a step of degassing may be optionally performed prior to printing in order to enhance printing quality.

It should be noted that certain structural proteins, including silk fibroin, exhibit an inherent self-assembly property. In some embodiments, this process involves the formation of beta-sheet secondary structure within a structural protein (or fragments). As such, bio-inks comprising a structural protein described herein may contain a range of degrees/levels of beta-sheet crystallinity. For example, provided protein ink compositions may contain a beta-sheet content ranging between about 5% and 70%, e.g., about 5%, about 10%, about 15%, about 20%, about 25%, about 30%, about 35%, about 40%, about 45%, about 50%, about 55%, about 60%, about 65% or about 75%.

Printed Arrays

One aspect of the invention relates to printed forms of biopolymer-based inks (bio-inks) Typically, such prints are made by the use of at least one bio-ink described herein and include an array of unit dots formed from ink droplets, deposited upon a substrate. Thus, in some embodiments, a printed array comprises a substrate; and a plurality of dot units, wherein the plurality of dot units has a semi-solid or solid form, wherein each dot unit comprises a low molecular weight structural protein. Typically, each dot unit on the substrate is between about 0.1-250 µm in diameter. According to the invention, a plurality of dot units is deposited upon a substrate in a predetermined spatial pattern to form a structure, e.g., 2D structures and 3D structures.

Thus, inkjet printers such as those described herein may be used to print biopolymer patterns, such as, for example, dots, signal line, and 2D patterns, on both hydrophilic and hydrophobic substrates. The resolution of printing is affected by viscosity and surface tension of the biopolymer ink. Also, the resolution of pattern may depend on the roughness of the substrate and nozzle size of the printer. An example printer that provides a 10 pl size nozzle to make patterns produces a drop size around 25 µm and the width of a printed line which is around 40 um on the hydrophilic substrates. A signal layer line will give the interface between dots, and a 2D pattern presents interface between lines.

Parameter Setting for Biopolymer Ink

Voltage

Figure 21:
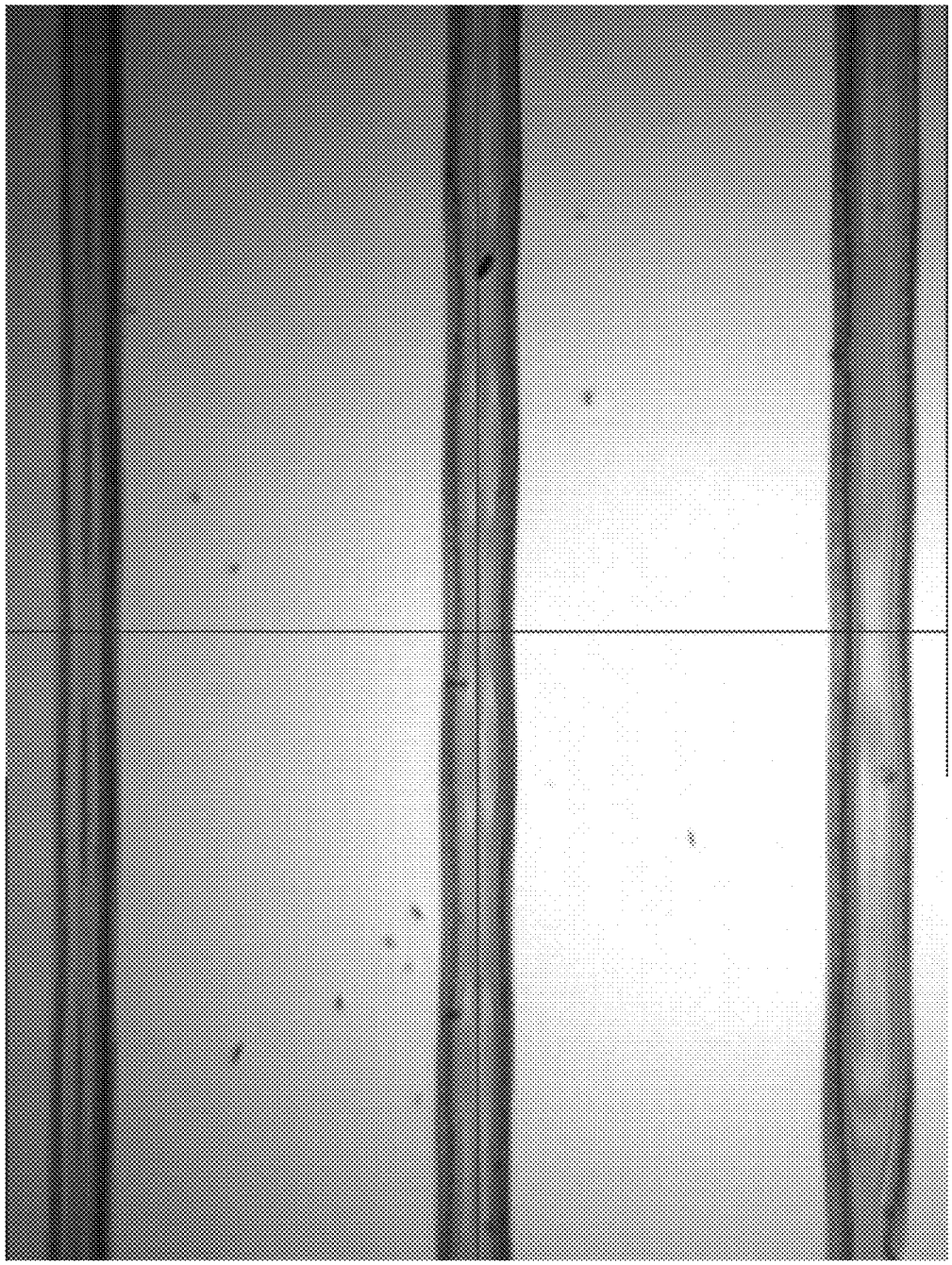
FIG. 21 shows biopolymer lines printed under different voltage: 1) 15 v voltage, 65 um; 2) 20 v voltage, 100 um; and 3) 25 v voltage, 110 um.

The voltage is a function of drop size and drop velocity. So the voltage setting depends on the desired height level of the nozzle above the substrate and the desired drop size to be printed. However, with insufficient voltage (in some examples, voltage level below 15 V), the biopolymer ink will not come out due to the surface tension of biopolymer ink. Higher voltage settings, on the other hand, increase the volume of the drop. FIG. 21 shows biopolymer lines on a silicon wafer under 15 v, 20V and 25 v voltage printing, with the width of the biopolymer lines being 65 µm, 100 µm, and 110 µm. As shown, high voltage printing gives greater-width lines due to increasing the drop volume.

Cleaning Cycle

Figure 22:
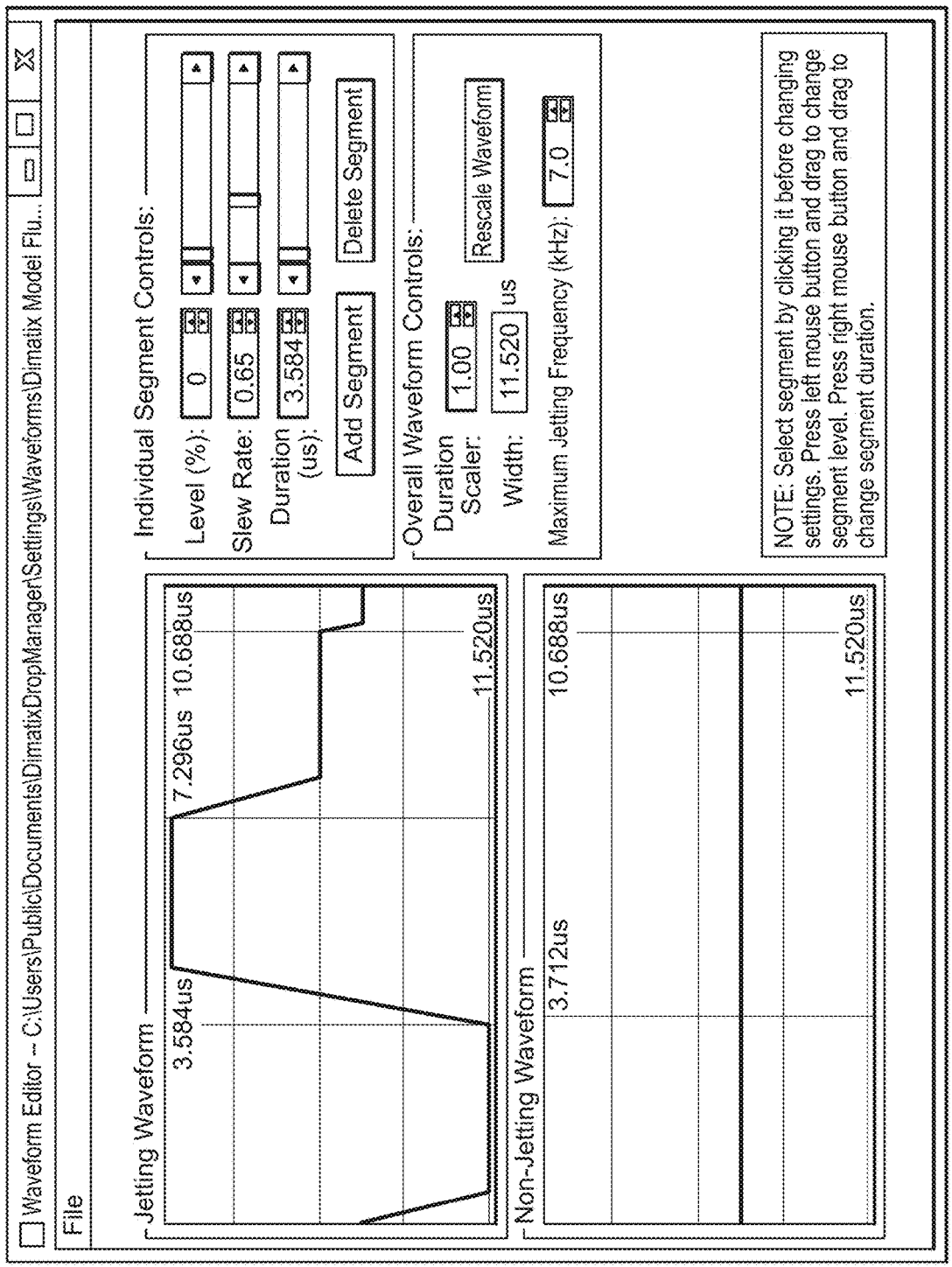
FIG. 22 shows a waveform for biopolymer ink printing.

Before printing, a purging process may be performed, which applies air pressure to the outside of a fluid bag to force fluid through the entire fluid path and out all nozzles, as shown in the waveform of FIG. 22. After the purging process, air in the chamber is forced out of the nozzles, and ensures ink wets the nozzle to start printing.

During printing, a blotting process may be provided to absorb biopolymer ink in close proximity to the nozzle plate. After the blotting process, the excess biopolymer ink, which may cause misdirected firing, is removed.

After printing, a spitting process may protect the nozzle from clogging. The spitting process provides for ejection of some drops ink from the chamber. This allows the fresh biopolymer drops to reach the meniscus to replace the previous one from the prior drop.

Nozzle Number

Figure 23:
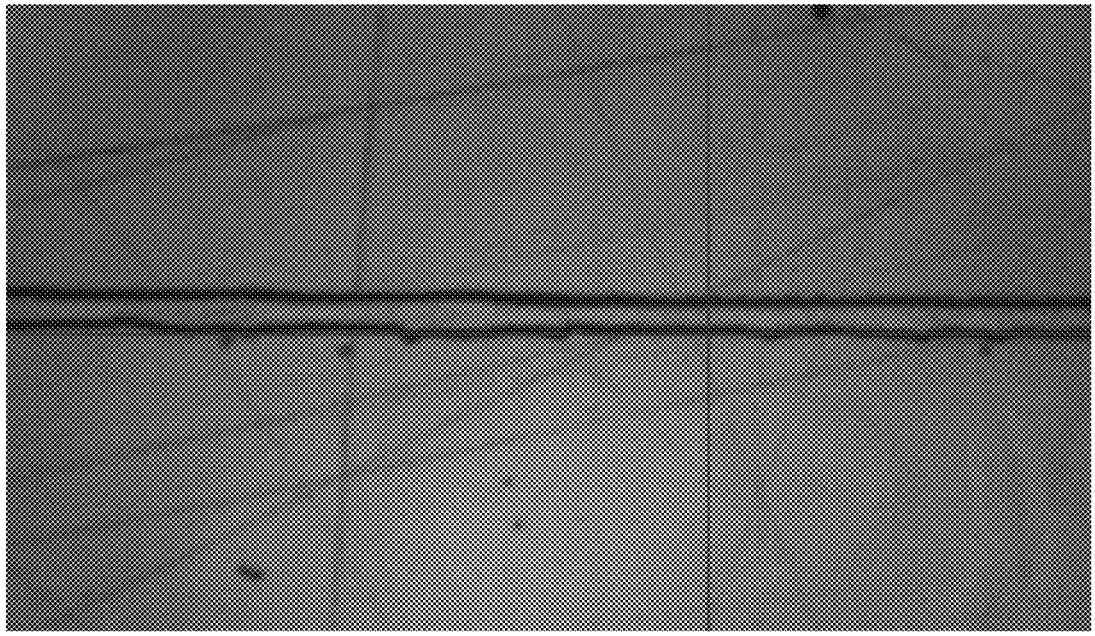
FIG. 23 shows a one-nozzle printing with a 20 µm line width.
Figure 24:
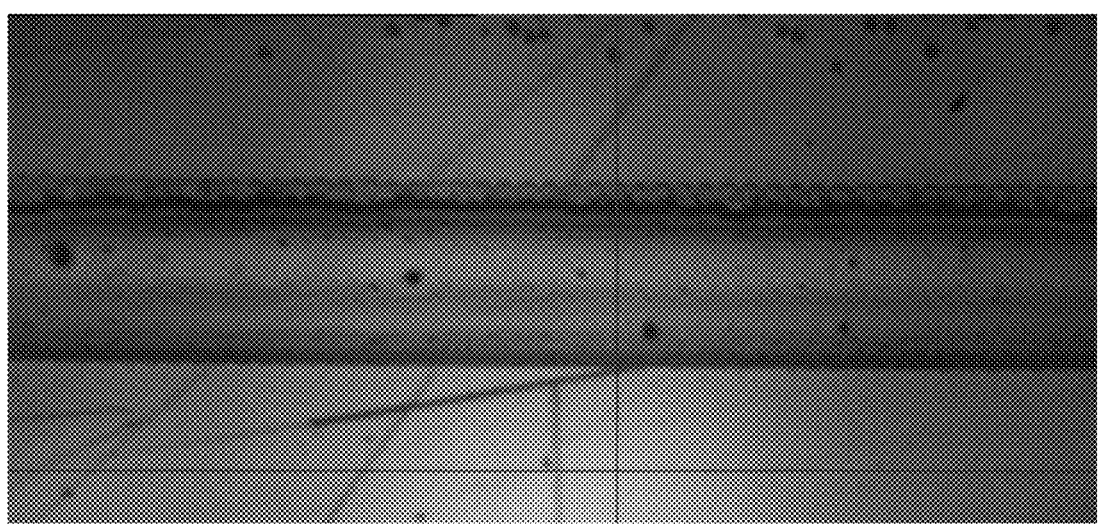
FIG. 24 shows a multi-nozzle printing with a 240 µm line width.

The number of nozzle may also affect the printing patterns. FIG. 23 shows a biopolymer line on acrylic with 25 v and one nozzle printing, and provides a 40 µm width biopolymer line. FIG. 24 shows a biopolymer line with a 240 µm—although still under 25 v printing, the width of the line is substantially increased in comparison to the pattern of FIG. 23, because of printing by seven nozzles as opposed to one.

Biopolymer Drops from Nozzle

Figure 25:
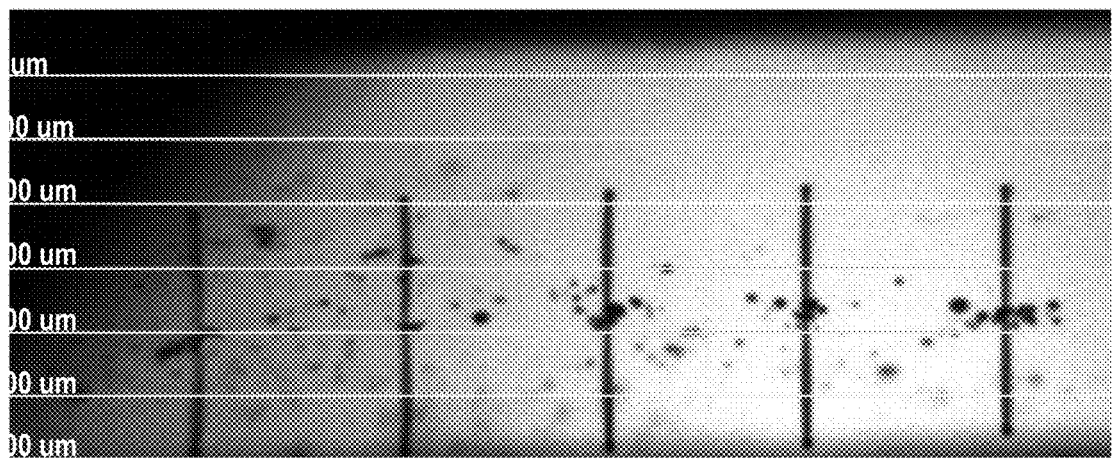
FIG. 25 shows biopolymer drops.

FIG. 25 shows the drops from 10 pL nozzles, and the voltage value set at 23V, with jetting frequency at 5 KHz.

The uniform drops from the nozzle show stable performance. There are no misdirected nozzles which means that biopolymer solution jetting smooth without bubbles under the high frequency oscillating system. All of the sixteen nozzles in this example work well for at least 8 hours which means the high temperature biopolymer will not clog the 20 µm diameter nozzle.

Various Biopolymer Patterns Using Direct Inkjet Printing Technique

Dots

Figure 26:
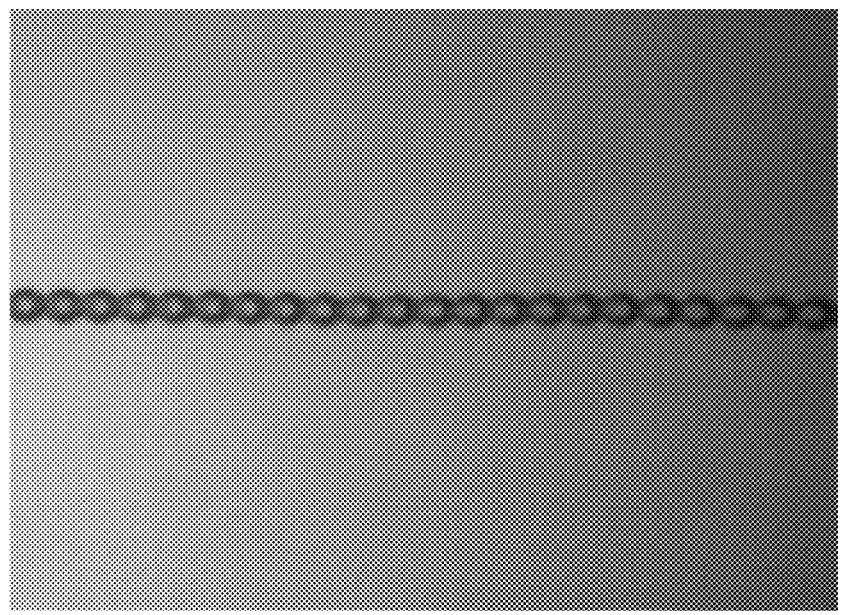
FIG. 26 shows biopolymer dots printed on a silicon wafer.
Figure 27:
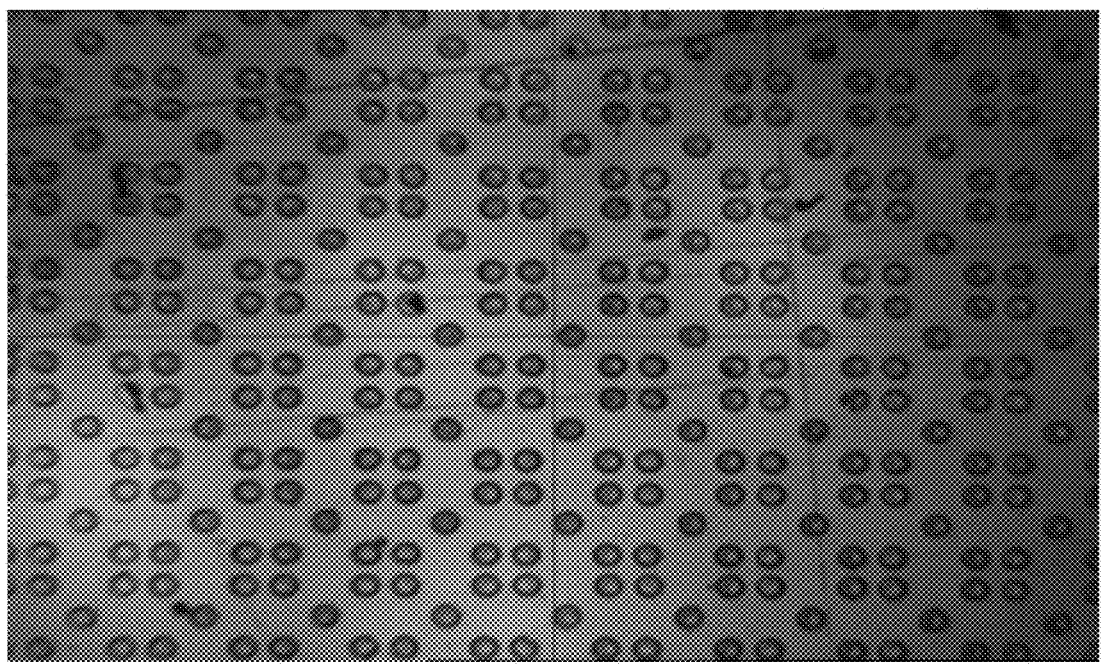
FIG. 27 shows biopolymer dots printed on acrylic.

FIG. 26 and FIG. 27 show biopolymer dots printed on silicon wafer and acrylic, respectively. This example utilizes 1 nozzle and 1-layer printing, the voltage value is 15 v and the jetting frequency is 1 KHz. The size of dots is 40 µm on silicon wafer (FIG. 26) and 30 µm on acrylic (FIG. 27).

Lines

Multiple Layers Printing

Figure 28:
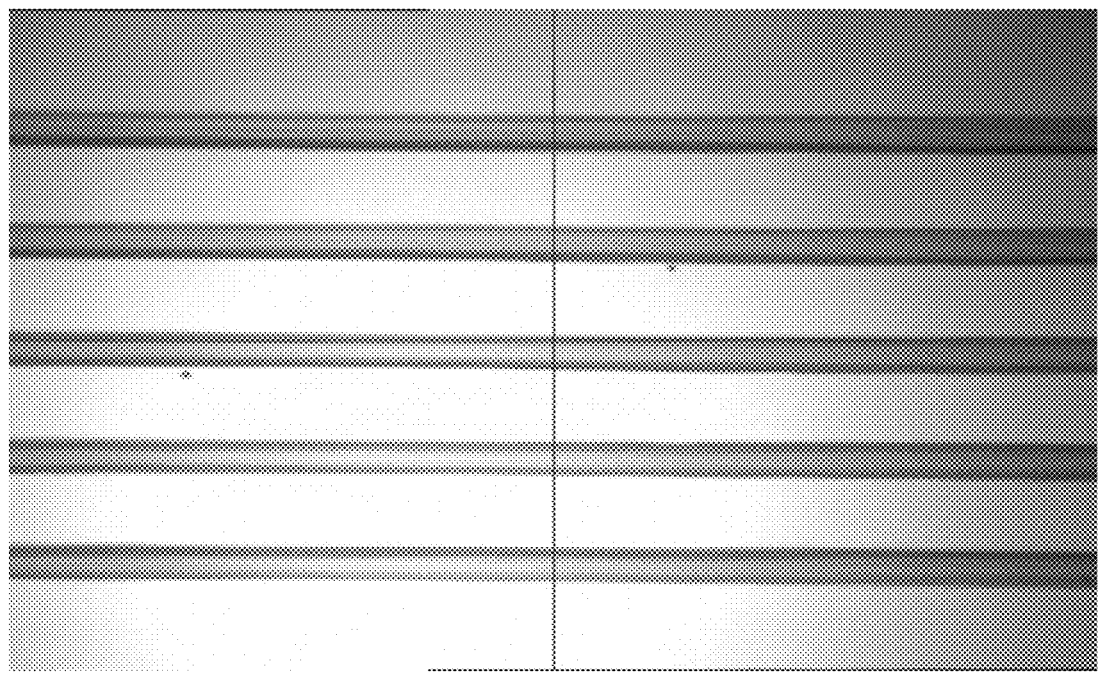
FIG. 28 shows a one-layer biopolymer pattern on a silicon wafer.
Figure 29:
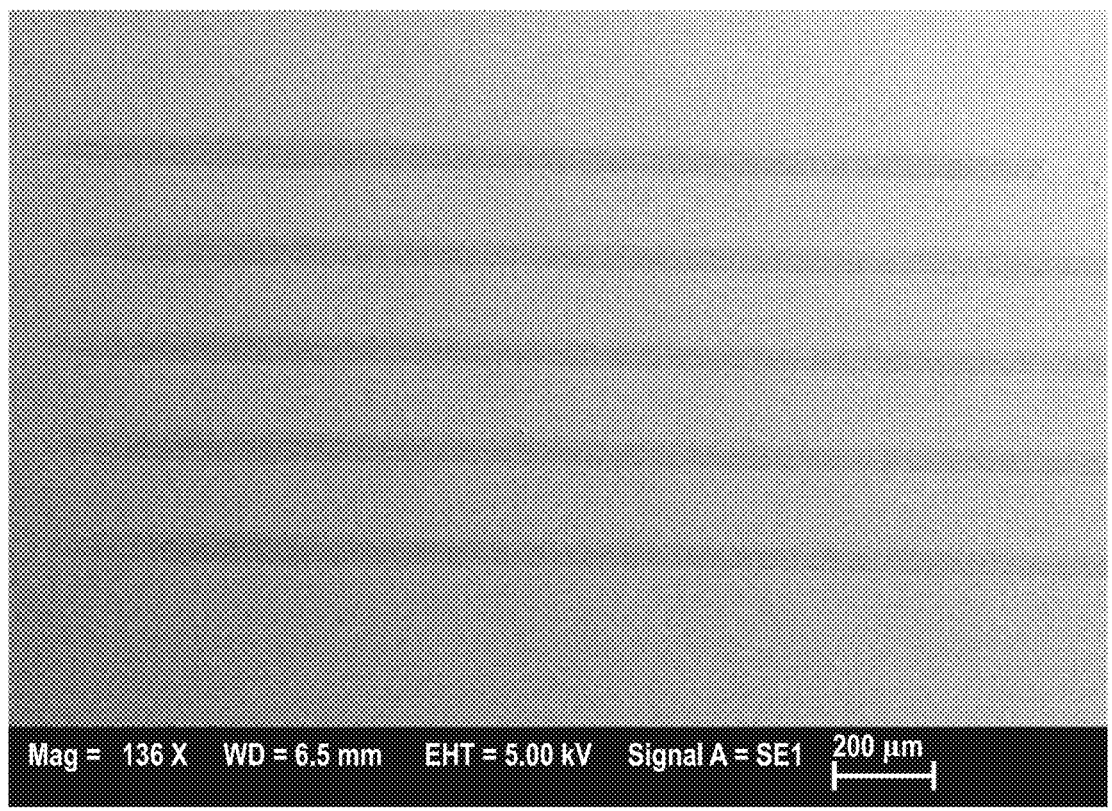
FIG. 29 shows one-layer lines.
Figure 30:
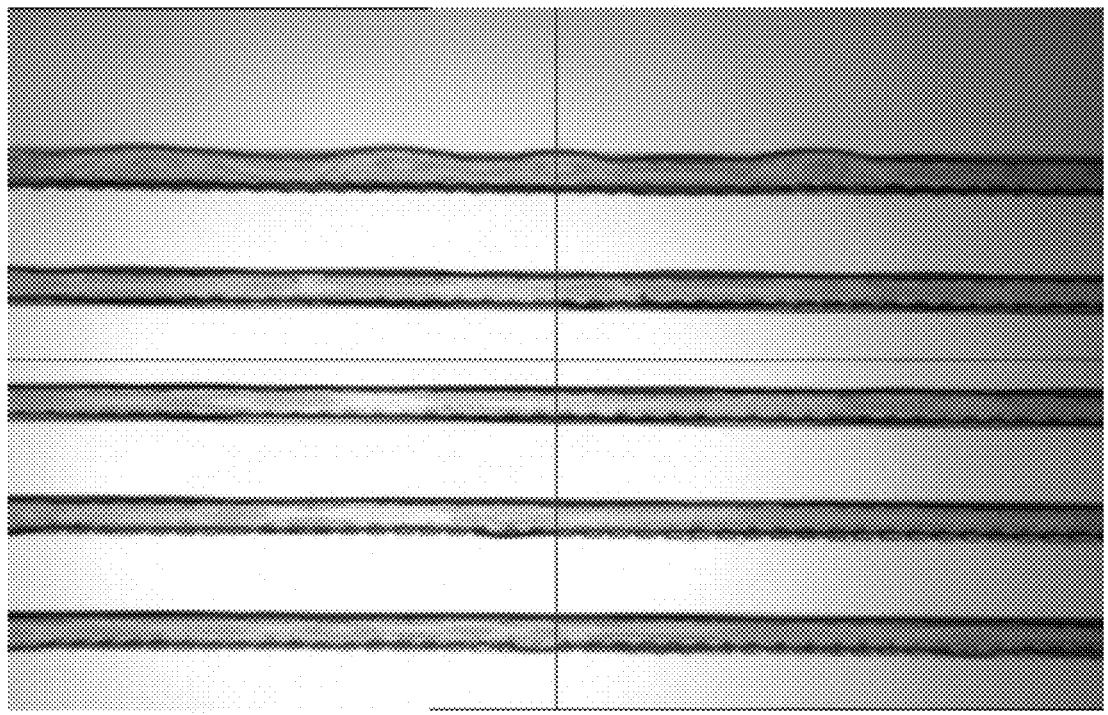
FIG. 30 shows a three-layer biopolymer pattern on a silicon wafer.
Figure 31:
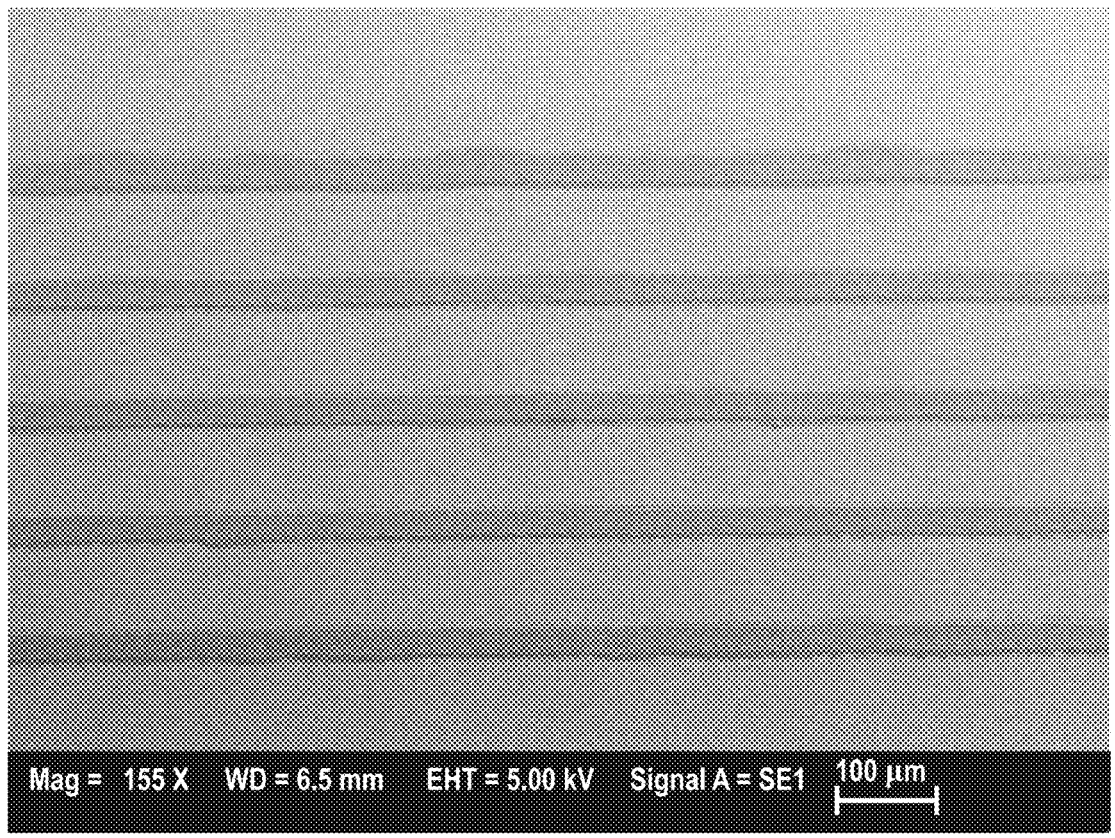
FIG. 31 shows three-layer lines.
Figure 32:
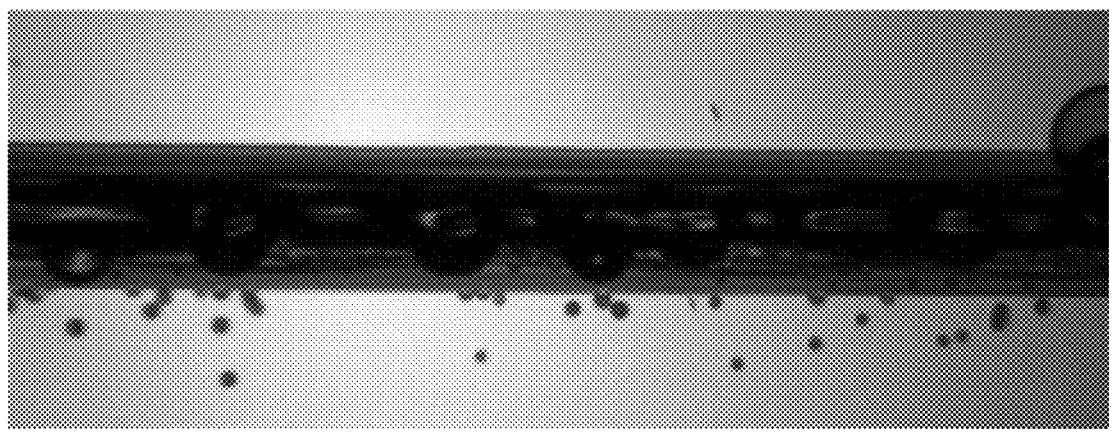
FIG. 32 shows a twenty-layer biopolymer pattern on a silicon wafer.

FIG. 28 shows biopolymer lines which are printed with one nozzle and 15 v on the silicon wafer. FIG. 29 shows the SEM image of this one-layer printing. One-layer printing is clear without any interface between drops. Comparing one-layer printing with three-layer printing, one-layer patterns are more uniform and the edge of line is cleaner. A rough edge is present in this example on three-layers printing (FIG. 30), because the upper layer fluid causes capillary instability when the upper layers of biopolymer are printed. FIG. 31 shows the first line as being wider than the other four lines, because the alignment of first line is not as good as the other four lines. FIG. 32 shows serious capillary instability in a twenty-layer pattern, so multiple-layer printing may be best suited, in some examples, for low resolution patterns.

Cross Lines Printing

Figure 33:
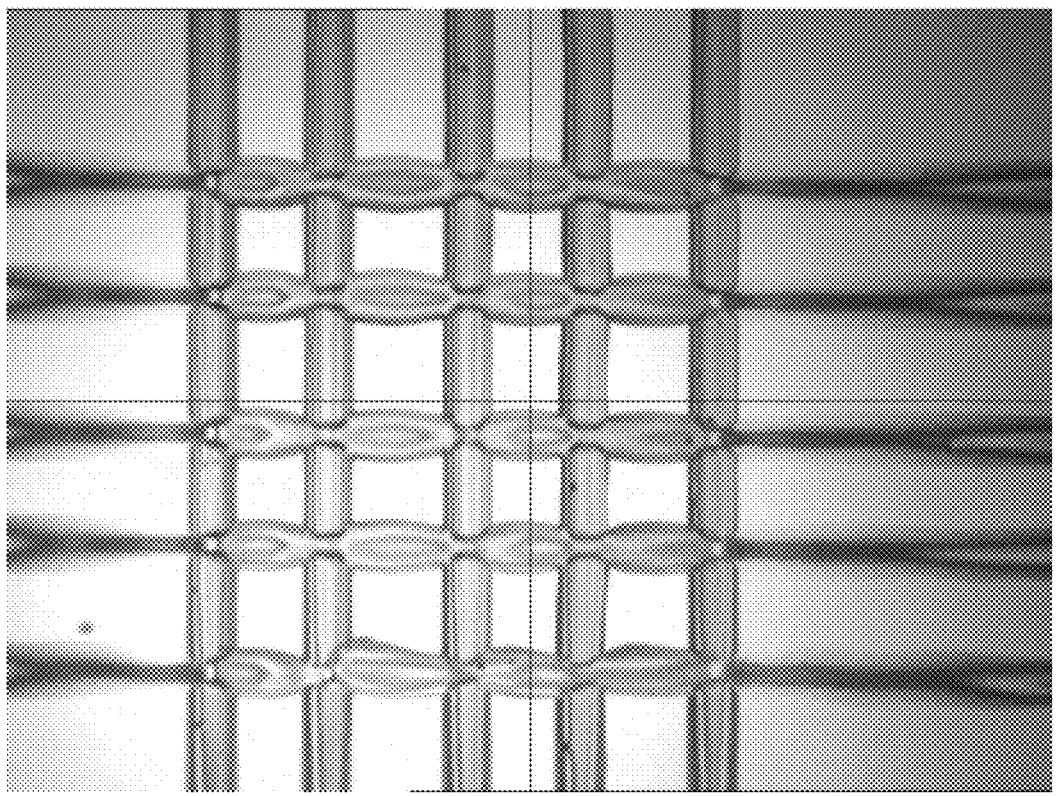
FIG. 33 shows a cross biopolymer line pattern.
Figure 34:
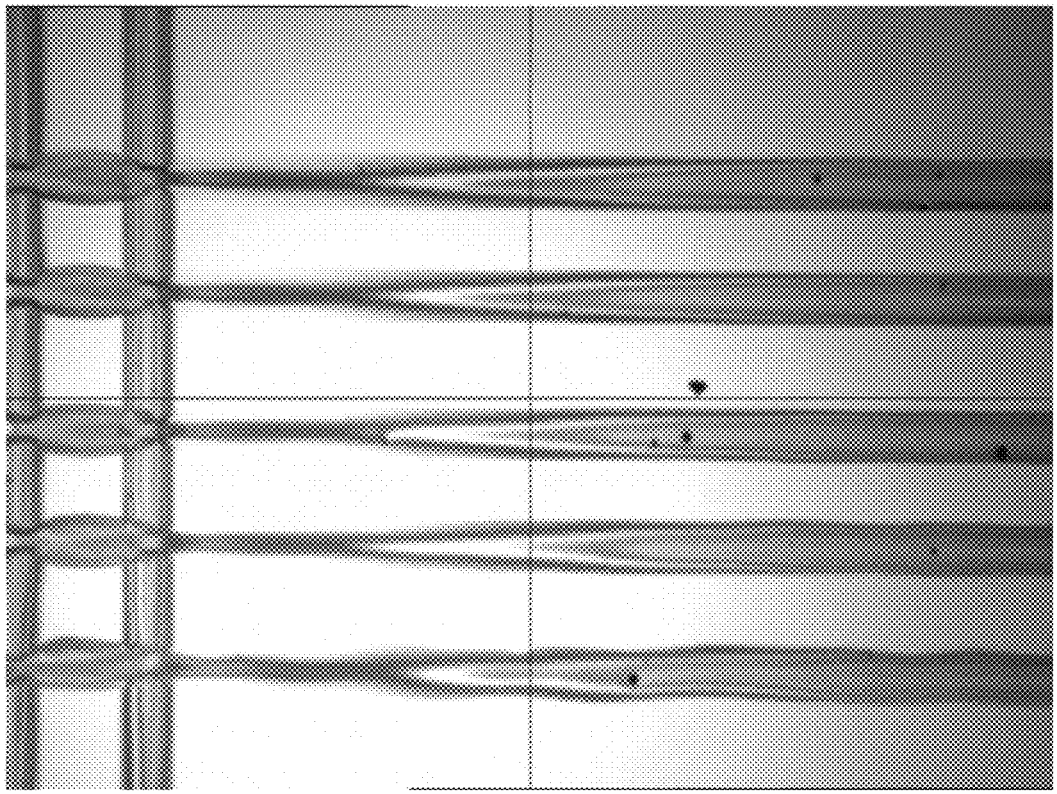
FIG. 34 shows a cross biopolymer line pattern with capillary instability.
Figure 35:
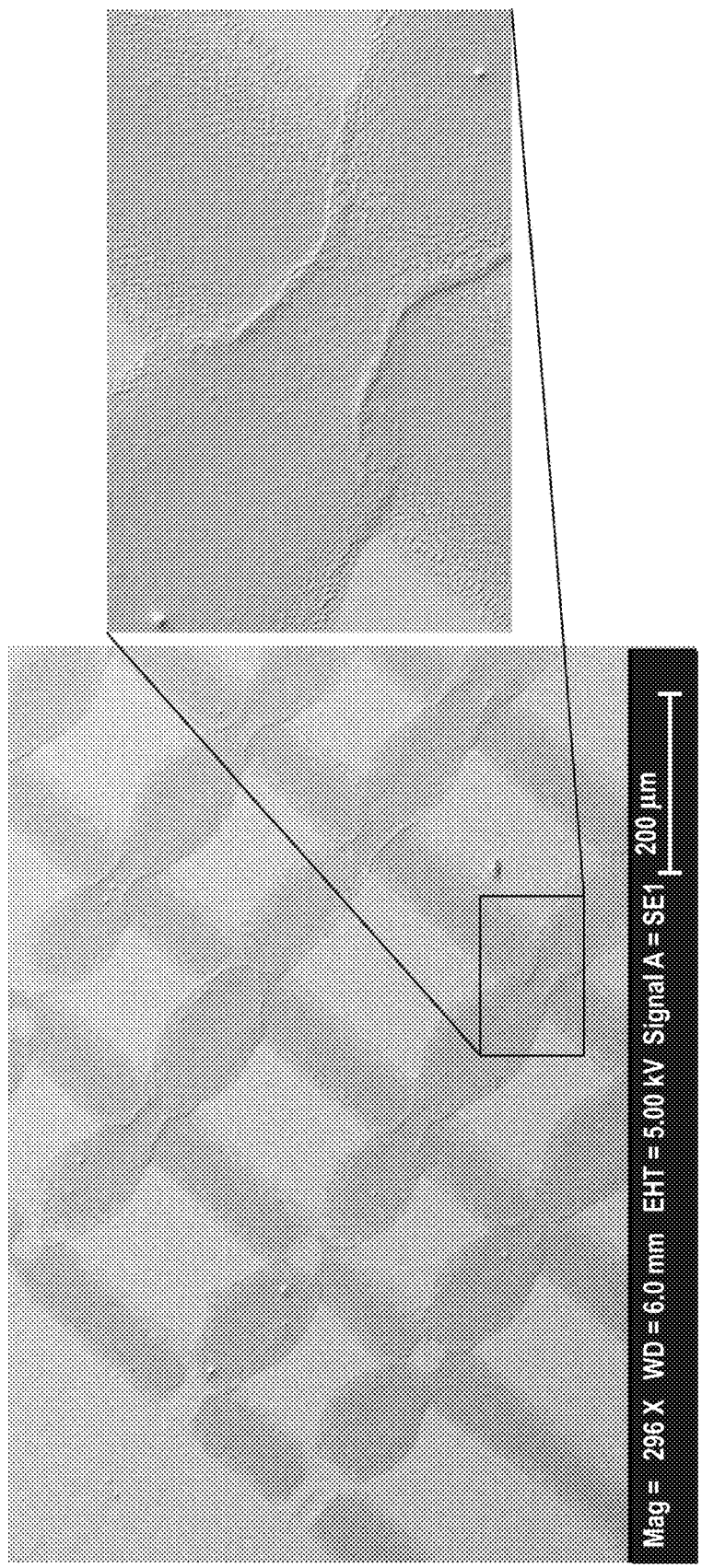
FIG. 35 shows a cross silk line patter with capillary instability, with an enlarged inset view.

In accordance with example embodiments, the method for printing multiple layer lines and cross lines is different. For multiple layer lines, the substrate is fixed during printing and the direction of printing among multiple layer lines is the same. For the cross lines printing, the substrate is rotated by 90 degree C. after first layer printing, and then the second layer printing is performed. As such, the direction of the two layers is different. FIGS. 33 to 35 indicate capillary instability between two layers, and the edge of pattern shows a clean gradual capillary instability process.

Two Dimension Printing

Figure 36:
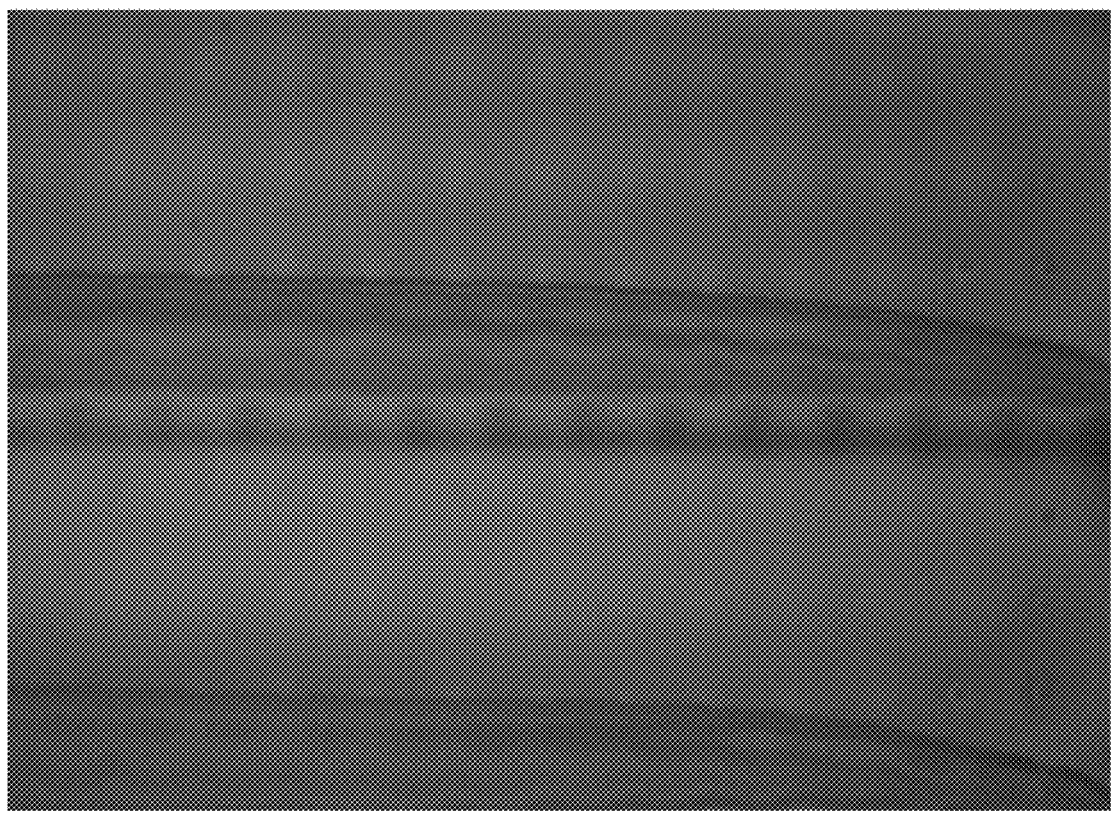
FIG. 36 shows one-layer 2D biopolymer patterns.
Figure 37:
FIG. 37 shows one-layer 2D patterns showing diffraction grating patterns.
Figure 38:
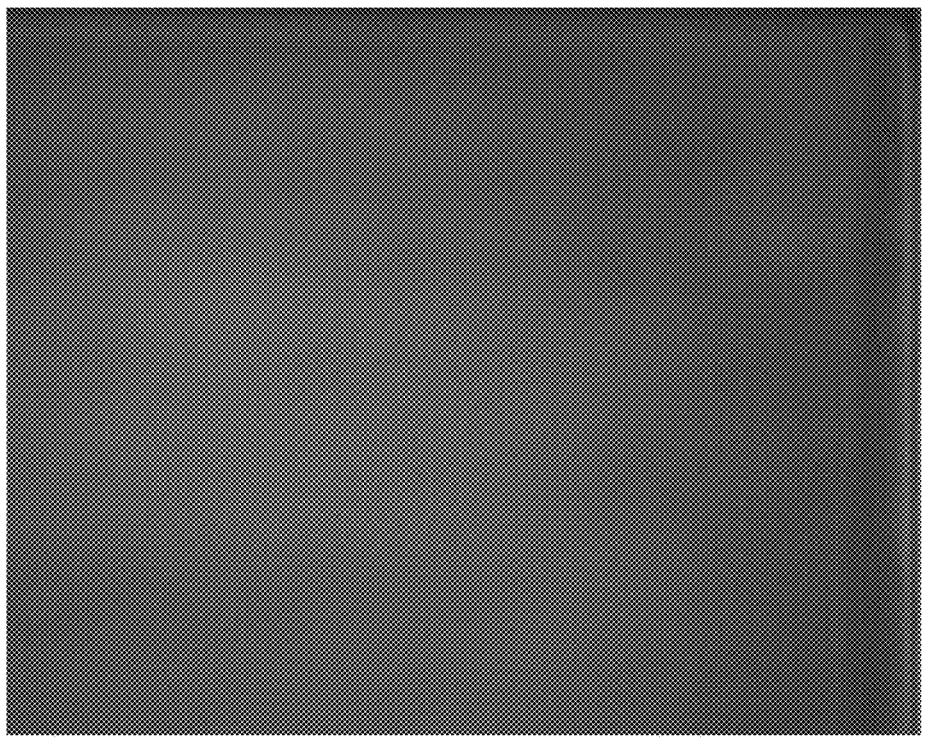
FIG. 38 shows multi-layer 2D patterns.
Figure 39:
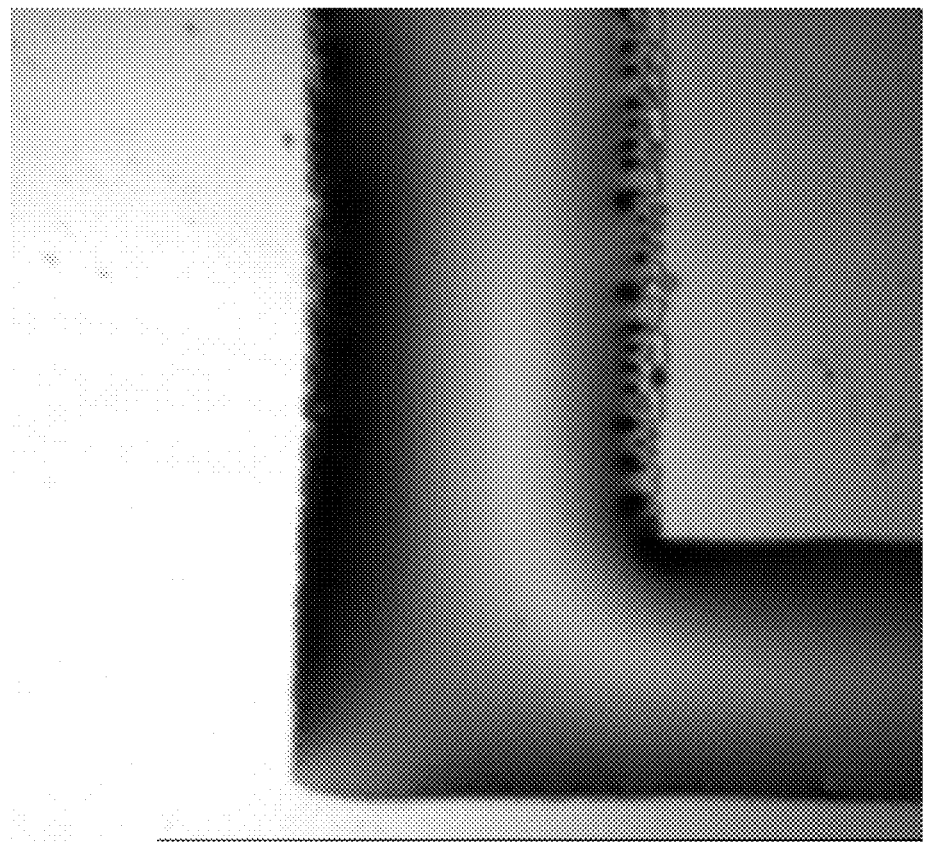
FIG. 39 shows an enlarged partial view of the multi-layer 2D pattern of FIG. 38.

A one-layer square pattern shows an interface between lines. As shown in the example of FIG. 36, there is less than 1 µm width overlap between two lines. After applying a laser point to the pattern, a diffraction grating pattern shows on the wall due to the 1 µm overlap, as shown in FIG. 37. However, the overlap part of the pattern disappears after printing the second layer pattern. As such, the multiple layers give a smooth finish pattern (FIGS. 38 and 39).

Biopolymer Patterns after Alcohol Annealing Treatments

Figure 40:
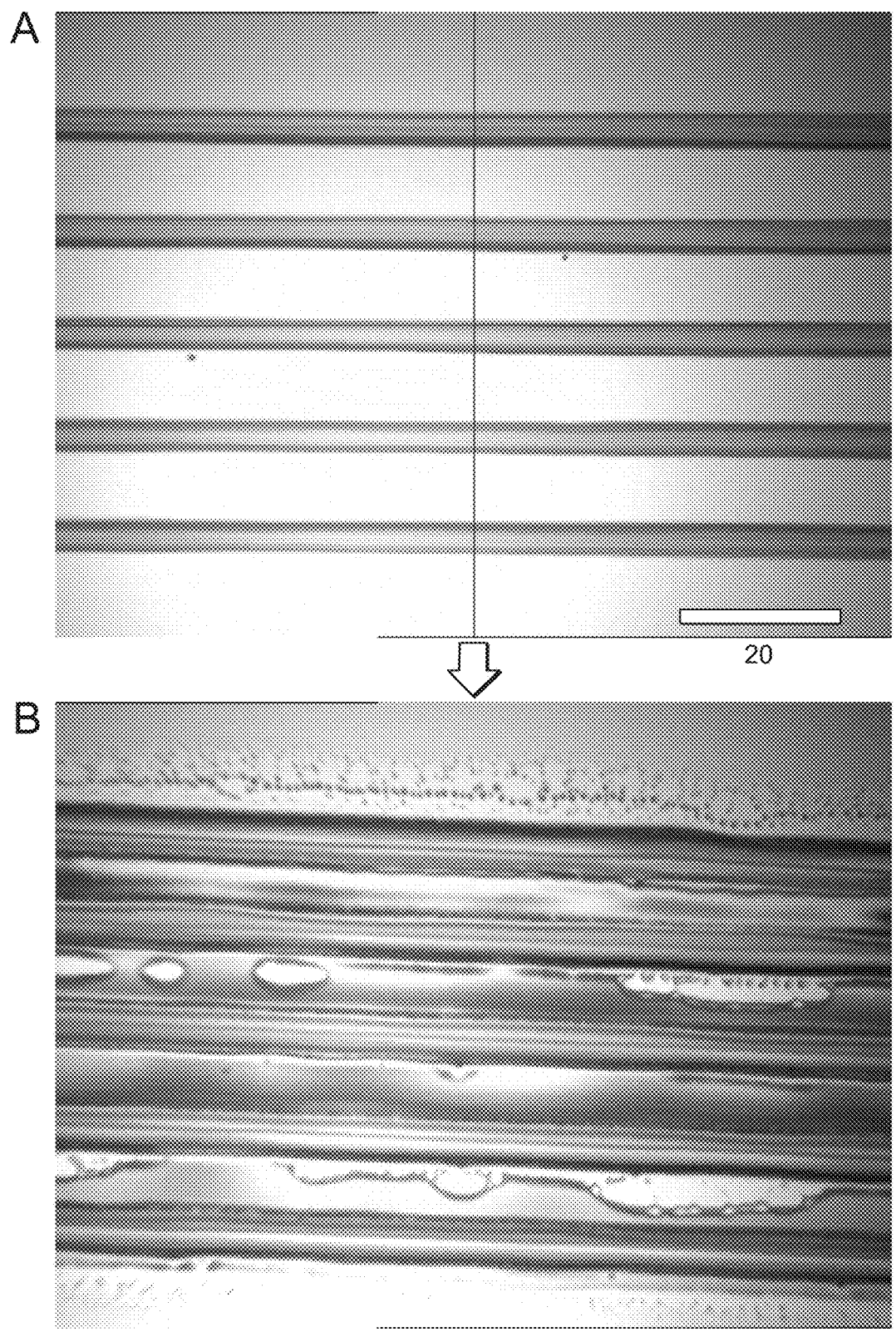
FIG. 40 shows a) a silk pattern before annealing and b) the silk pattern after annealing.

Biopolymer film is easily dissolved in water. However it will not dissolve after alcohol annealing due to the formation of β sheet. A printer may be used to make a β sheet pattern. To do so, the printing pattern is set to do a 2-hour vacuum annealing. It turns out that, in some examples, the patterns tend to spread out, as shown in FIG. 40, which shows the biopolymer pattern before annealing and after annealing.

Thickness of Biopolymer Pattern

Figure 41:
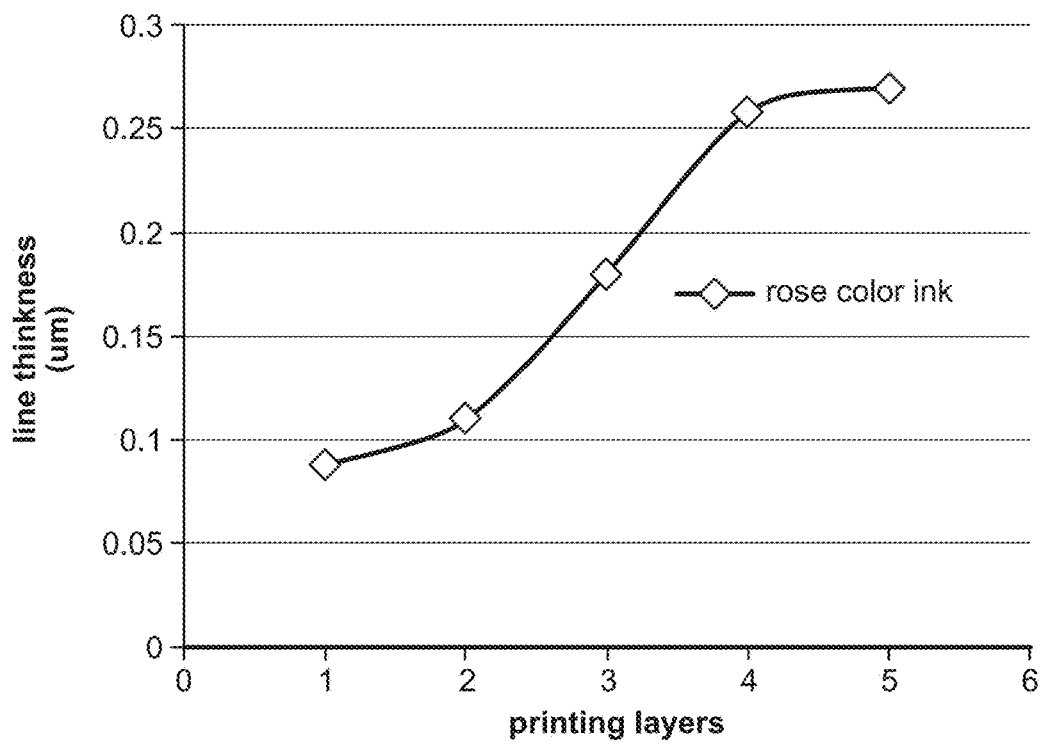
FIG. 41 shows printing layers vs. thickness of food color biopolymer patterns.
Figure 42:
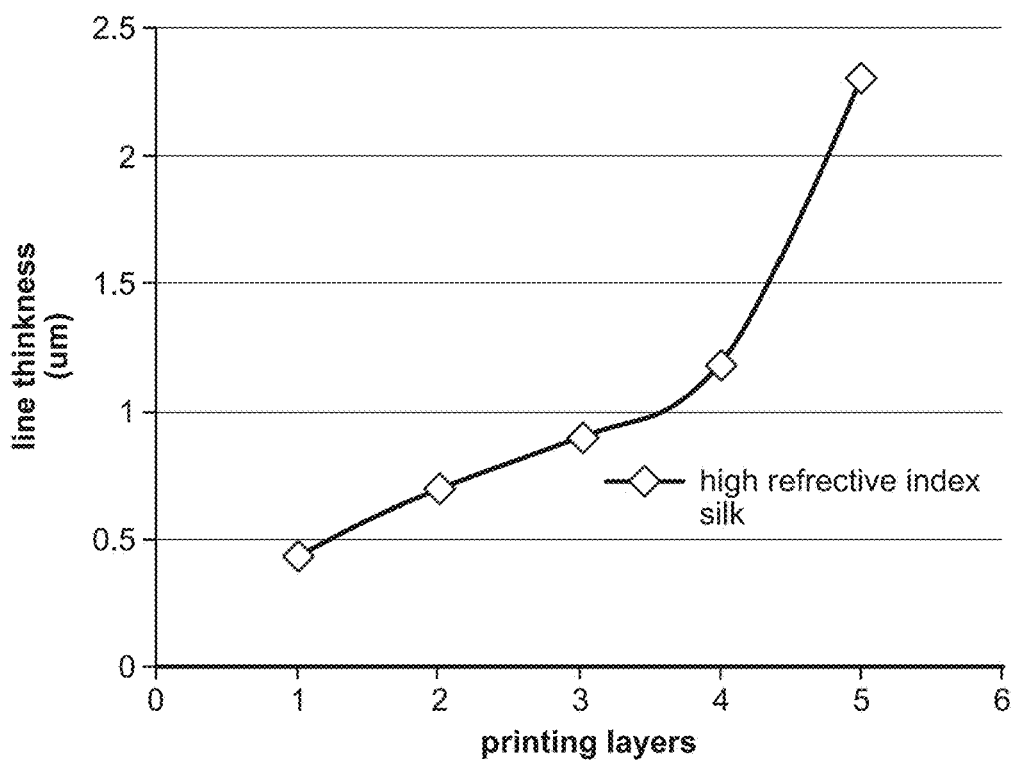
FIG. 42 shows printing layers vs. thickness of high refractive index biopolymer patterns.
Figure 43:
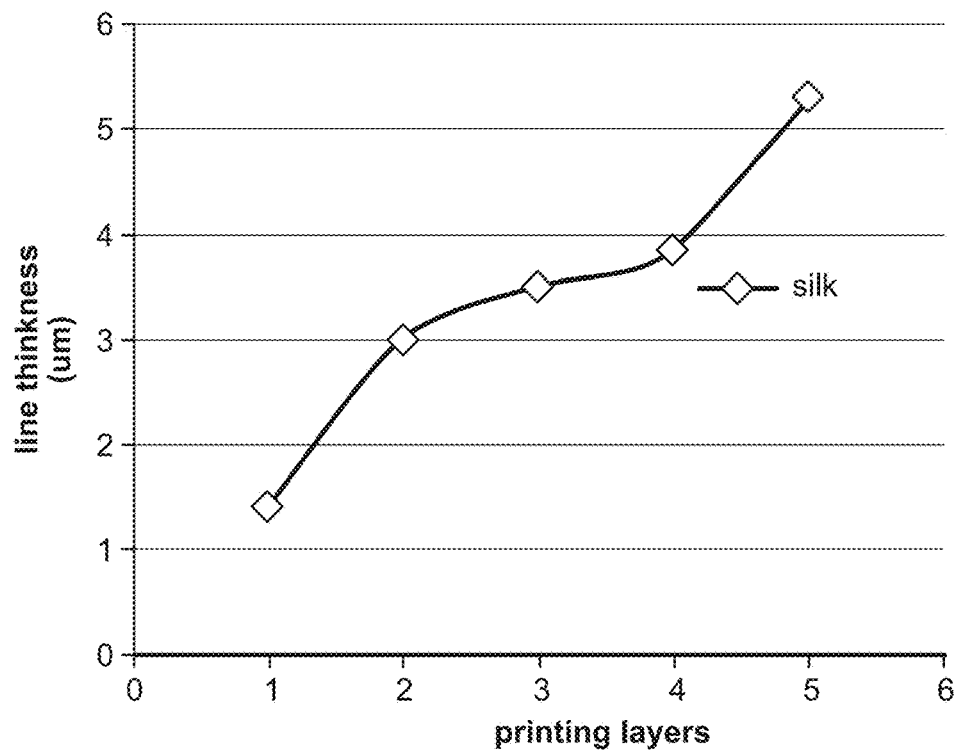
FIG. 43 shows printing layers vs. thickness of biopolymer patterns.
Figure 44:
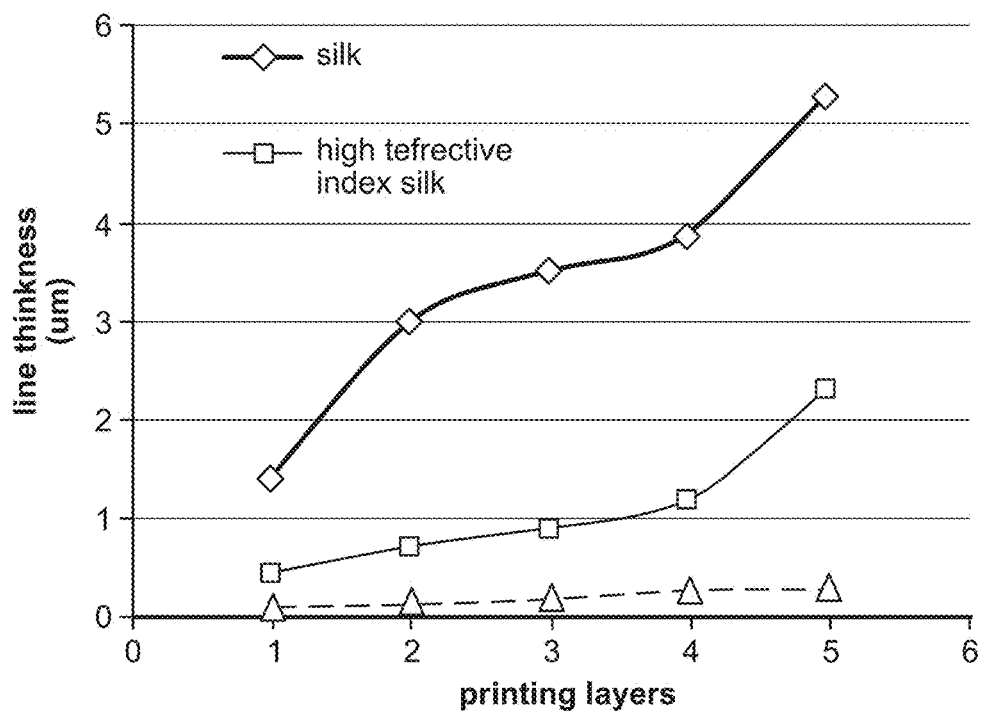
FIG. 44 shows a comparison of printing layers vs. thickness of different silk inks.

Biopolymers, such as, for example, silk, provide a biologically favorable environment allowing them to entrain various biological and chemical dopants and maintain their functionality. Mixing different chemical solutions with biopolymer solution gives different viscosity and surface tension which affect the thickness of pattern. As is clear, the number of printing layers is another important element that affects the thickness of pattern. In an example implementation, three kinds of biopolymer solution are prepared and include food color biopolymer, high refractive index biopolymer, and pure biopolymer (e.g., pure silk), and then printed with a number of nozzles. FIGS. 41 to 43 show the thickness of patterns are increased by the number printing layer. The thinnest pattern in this example is less than 100 nm created by a one-layer food color biopolymer pattern. According to FIG. 44, the thickest pattern is pure biopolymer pattern due to highest percentage biopolymer in the solution.

Biopolymer Patterns on Various Substrates

Figure 45:
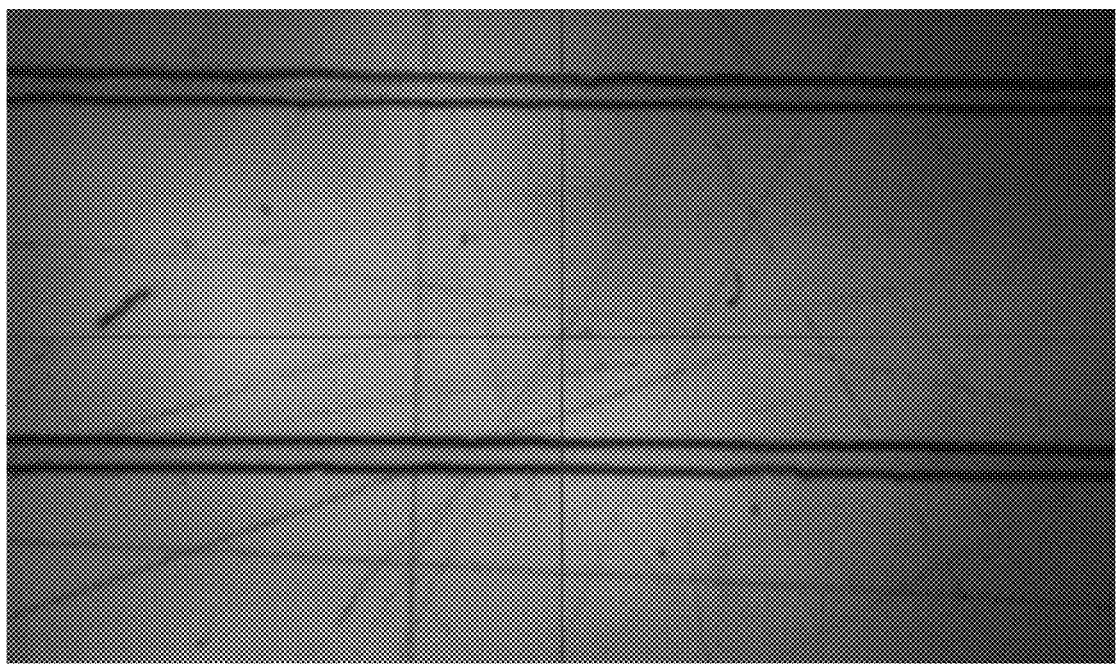
FIG. 45 shows one-layer biopolymer patterns on acrylic.
Figure 46:
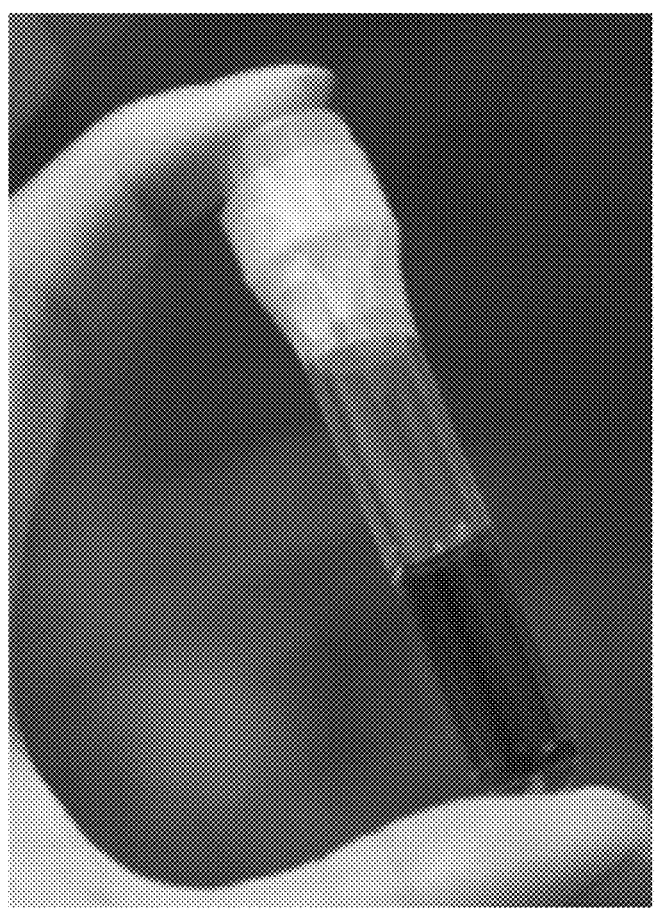
FIG. 46 shows gold nanoparticle doped silk ink in a tube.

The printable substrates for biopolymer ink may include, for example, paper, glass, silicon, metals, cloth textiles, and plastics. Such substrates can be divided into two groups which are hydrophobic substrates and hydrophilic substrates. The drop size on hydrophobic substrate is smaller due to high surface energy. The width of biopolymer lines from FIG. 28 is similar with respect to the biopolymer lines from FIG. 45. However, the two patterns are supplied by different voltages. Biopolymer patterns on silicon have slightly larger voltage values.

Direct Printing of Functional Biopolymer Devices Using Doped Biopolymer Solution as the Ink A biopolymer such as, for example, Silk fibroin is shown to be effective material and matrix that can maintain the functionalities of dopants. Therefore, choosing the appropriate dopants (including both physical dopants, e.g. metallic nanoparticles, laser dyes, quantum dots, etc., and biochemical dopants, e.g., cells, enzymes, bacterium, etc.) and mixing them into silk fibroin solution or other biopolymer solution as the ink is an advantageous way to directly print functional devices using an inkjet printer. In the following section, a series of functional biopolymer devices (with different dopants) are described as examples.

Inkjet Printing of Gold Nanoparticle Doped Biopolymer Patterns

As mentioned above, biopolymers provide a biologically favorable environment allowing them to entrain various biological and chemical dopants and maintain their functionality. Proteins and enzymes have been doped into various biopolymer material formats, especially biopolymer films. Biopolymer films have been doped with gold nanoparticles such that they resonantly absorb incident light and convert the light to heat, which may used as, for example, a biocompatible thermal therapy for in vivo medical applications such as killing of tumor tissue and bacteria.

The preparation of gold nanoparticle biopolymer ink includes the production of the print grade biopolymer film (e.g., silk fibroin solution) and synthesis of gold nanoparticles, followed by a simple mixing of the two in solution with a certain ratio that is determined by application. Where silk fibroin solution is utilized, pre-cut Bombyx mori cocoon pieces are boiled in a 0.02 M $Na_2CO_3$ solution for 2 hours to remove sericin, and boiled silk fibers are dried overnight and then dissolved in a 9.3 M LiBr at 60 degree C. for 4 hours. The lithium bromide salt is then removed from the silk solution through a water-based dialysis process. The gold nanoparticle solution is prepared by adding 20 mL 1% $Na_3C_6H_5O_7$ into 200 mL boiled 1.0 mM $HAuCl_4$, followed by continuously heating for 10 minutes until the solution has turned deep red. Then the gold nanoparticle solution is carefully added into the silk solution with gentle agitation for uniform dispersion and is ready for printing after being filtered, e.g., against a 0.2 micron filter.

Figure 47:
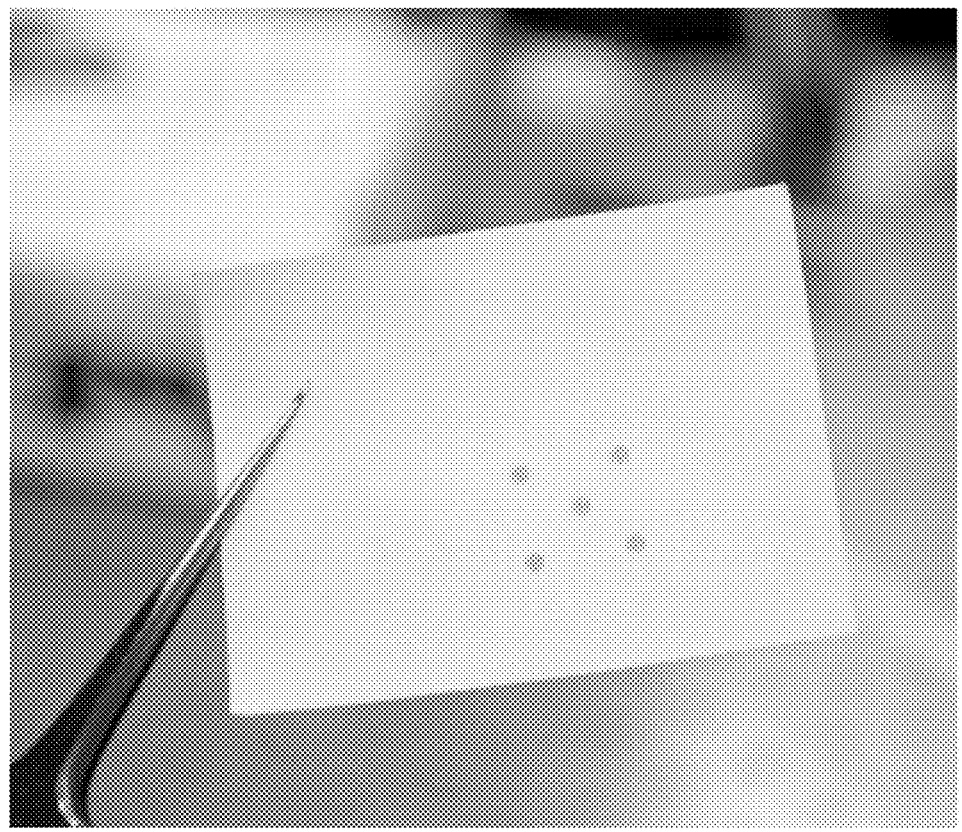
FIG. 47 shows a gold nanoparticle doped silk dot pattern on paper.

Table 5.1 provides the main parameters for printing and the printing result is shown in FIG. 47.

Figure 48:
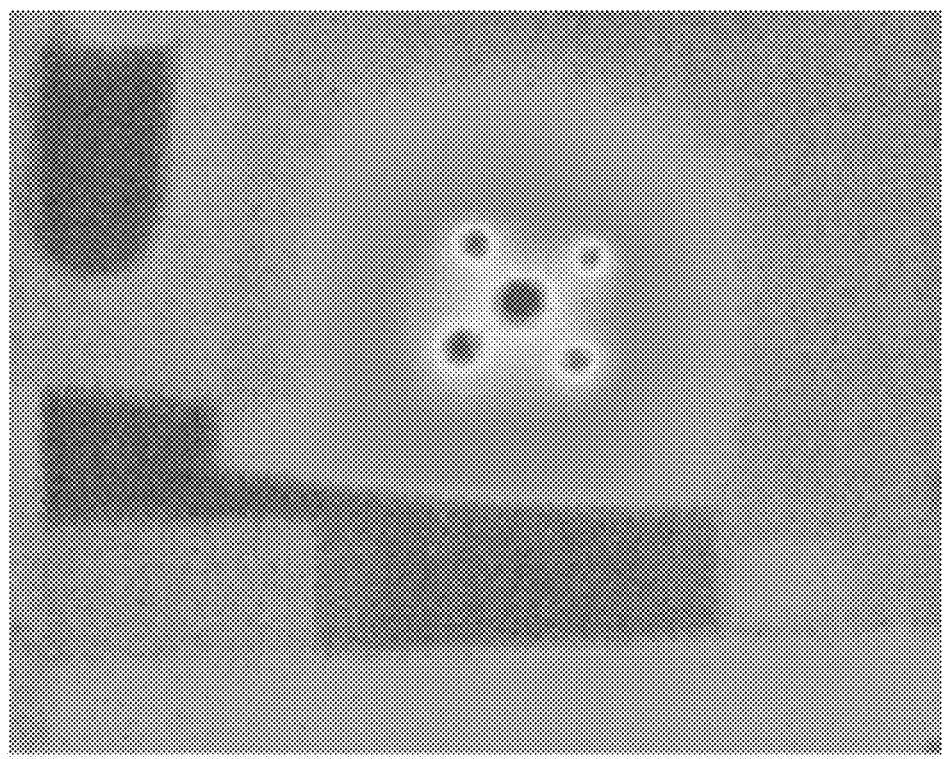
FIG. 48 shows an infrared view of the pattern of FIG. 47 when exposed to green light radiation.

The printed Au-NPs doped biopolymer device shows enhanced plasmatic absorption of green light (FIG. 48), resulting in a temperature increase of ~15 degree s with an irradiance of ~0.25 W/cm². The heating effects could be further improved and optimized by adjusting the Au-NPs concentration and layers of the printed structures, which could be potentially used for light-mediated patterned heating treatments.

TABLE 5.1

Printing Permanents for Gold Nanoparticle Biopolymer Ink

| | |
|---|---|
| Voltage | 25 v |
| Nozzle Number | 4 |
| Drop Spacing | 25 µm |
| Printing Layer | 5 |
| Firing Frequency | 2 KHz |

Inkjet Printing of Enzyme Doped Biopolymer Patterns

Figure 49:
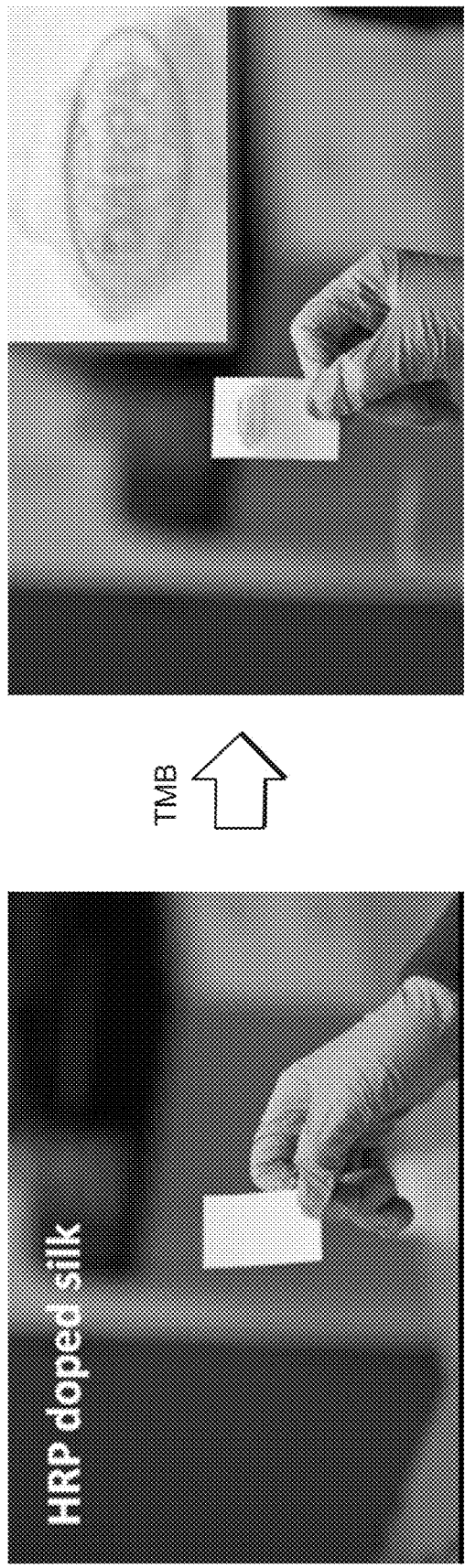
FIG. 49 shows printed HRP doped biopolymer changing color to blue when sprayed with a tetramehtylbenzidine (TMB) solution.

In addition to printing gold nanoparticle doped biopolymer, it is also possible to directly print enzyme-doped biopolymer for biomedical applications such as enzyme-linked immuosorbent assay test (i.e. ELISA). ELISA is a widely used test to identify certain substances using antibodies and the colorimetric change as the sensing/diagnostic mechanism. Usually, the enzymes used in ELISA tests need to be stored at low temperature for maintaining the bioactivities. It has been shown that biopolymer can help to maintain the functionalities of the doped enzyme at room temperatures without fridge-storage. Therefore, directly printing of enzyme-doped biopolymer patterns (in a precise way) is an advantageous mechanism for applications such as, for example, rapid and low volume screening tests, food allergens, and toxicology applications, as shown in FIG. 49.

Inkjet Printing of Antibiotics Doped Biopolymer Patterns

The use of antibiotics is important for effective infectious disease containment and curing. However, most, if not all, current antibiotics need to be maintained within a specific refrigeration temperature range due to their temperature sensitivity. Silk fibroin, as an example, has been proven to be a biologically friendly protein polymer. Recently, researchers found that silk was capable of stabilizing labile antibiotics (in the form of films) even at temperatures up to 60 degree C. over more than 6 months. Direct inkjet printing of antibiotics-doped biopolymer by mixing penicillin solution of various concentration levels with purified biopolymer solution prepared as previously described may be provided. Compared to antibiotics-doped biopolymer films, direct printing of antibiotics-doped biopolymer has the advantages of precise control of the antibiotic distribution and potential multilayer and multi-drugs printing that may benefit, for example, more sophisticated cases where fine control and micro-manipulation of the antibiotic drug are needed.

Figure 50:
FIG. 50 shows two clean bacterial inhibition zones in a bacterial growth petri dish.

To obtain a clear pattern on bacterial growth area, first we use method one, below, to print a pattern before bacterial growth. The result shows that two clean squares without any clean pattern in the Petri dish after 5 hours incubation, as shown in FIG. 50.

Figure 51:
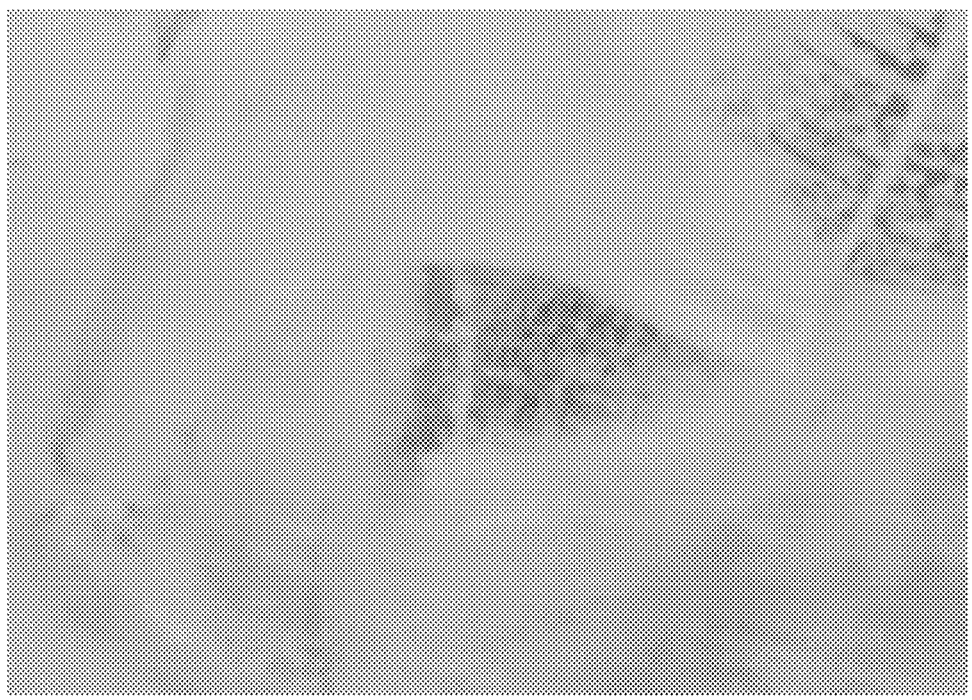
FIG. 51 shows a bacterial growth inhibition zone in the shape of an arrow.

Method One:
1) Culture 50 ul bacterial on agar
2) Print 1 layer an arrow and text pattern on bacterial, with drop gap 50 um
3) Take 5 hours culture in 37 degree C. incubator To improve the method, the pattern is printed after bacterial overnight growth, as provided by method two, below. There is an arrow in the in the Petri dish after 9 hours incubation (FIG. 51).

Method Two:
1) Culture bacterial on agar
2) Take overnight culture in 37 degree C. incubator
3) Print 2 layers an arrow and 25 um drop gap on bacterial
4) Take 9 hours culture in 37 degree C. incubator Inkjet Printing of Colored Biopolymer Patterns In accordance with example embodiments, in addition to biomedical applications (e.g., implantable biomedical applications), biopolymers are used to construct edible food sensors as a green and edible material that is extracted and purified from domesticated silkworm cocoons. Plain biopolymer solution (i.e. non-doped biopolymer solution) is a water-like highly transparent protein solution that is colorless.

Food coloring, alternatively called color additive, imparts color when added to food or drink, and is used widely both in commercial food production and in domestic cooking Commercially available food dyes (considered as safe) may be mixed with biopolymer solution to make colored biopolymer inks, e.g., for direct inkjet printing. Further, patterns may be printed on textile silk which carries a basic color (light yellow).

Figure 52:
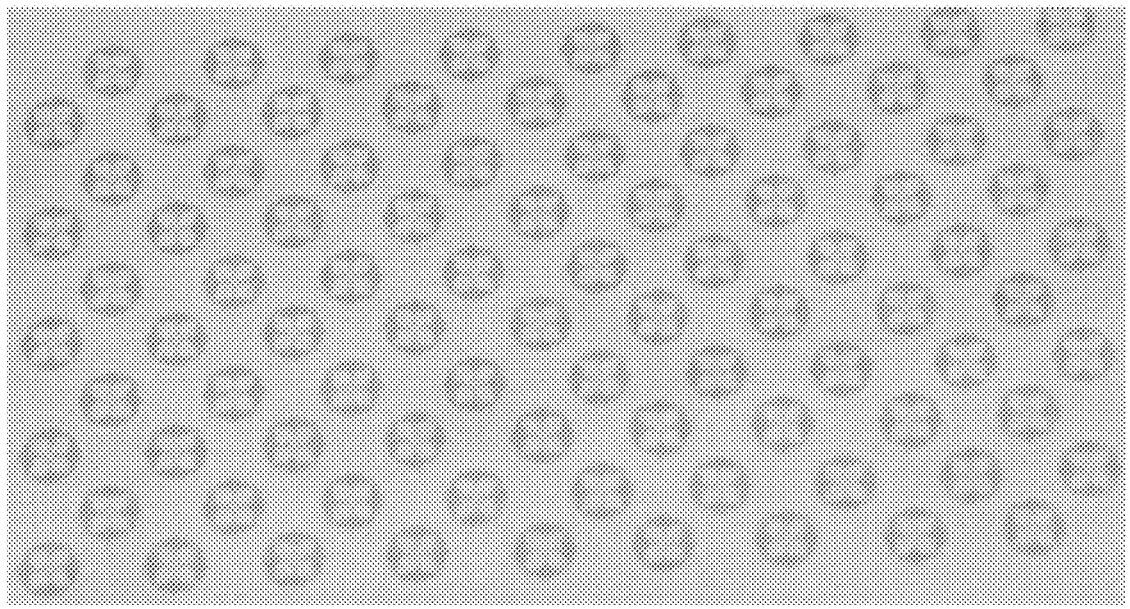
FIG. 52 shows a single color biopolymer pattern on silk textile.

To achieve a clear pattern on textile silk, multiple-layer printing may be beneficial, because the color of textile silk is darker than a blank paper. After seven layers of printing, the pattern is clear and beautiful, as shown in FIG. 52.

Figure 53:
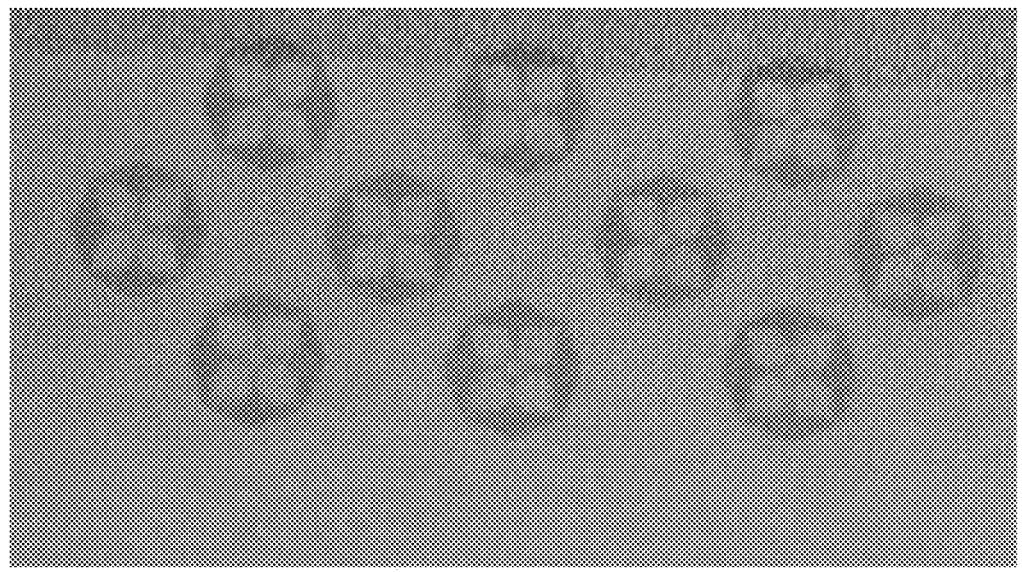
FIG. 53 shows a single color biopolymer pattern on silk textile after dry cleaning.

The colored silk patterns remain in their original patterns after 2 hours of vacuum annealing. The patterns also survive a dry cleaning process, as shown in FIG. 53.

Figure 54:
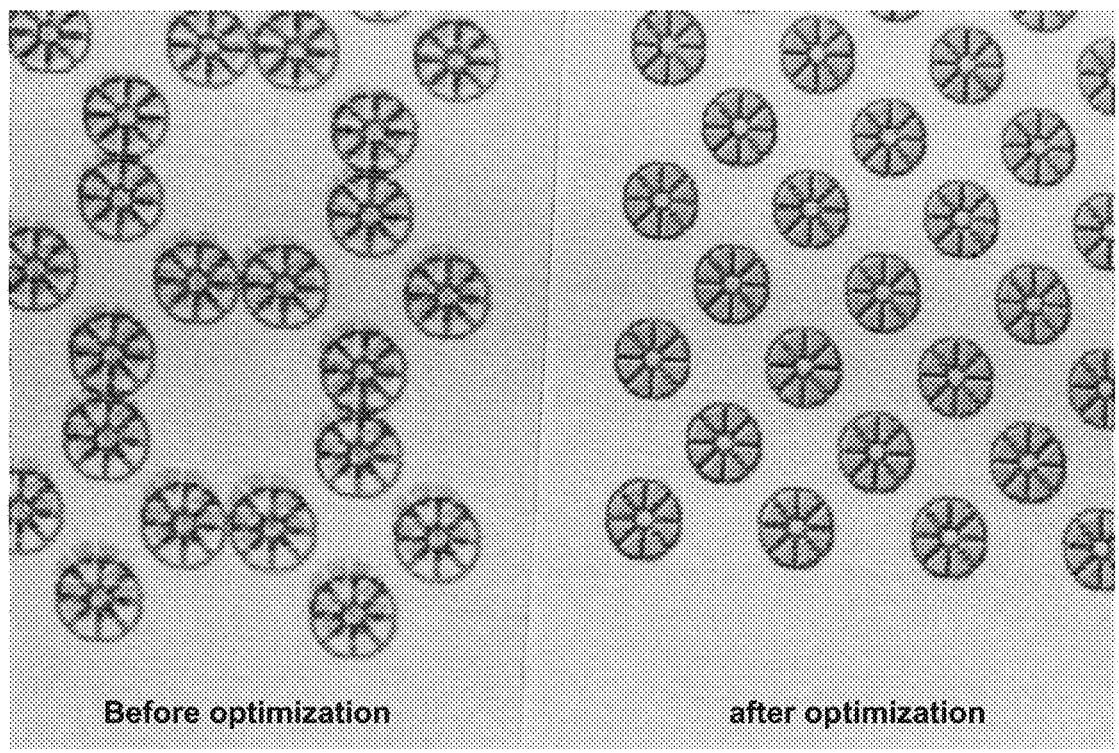
FIG. 54 shows multiple-color silk pattern on silk textile before and after alignment optimization.
Figure 55:
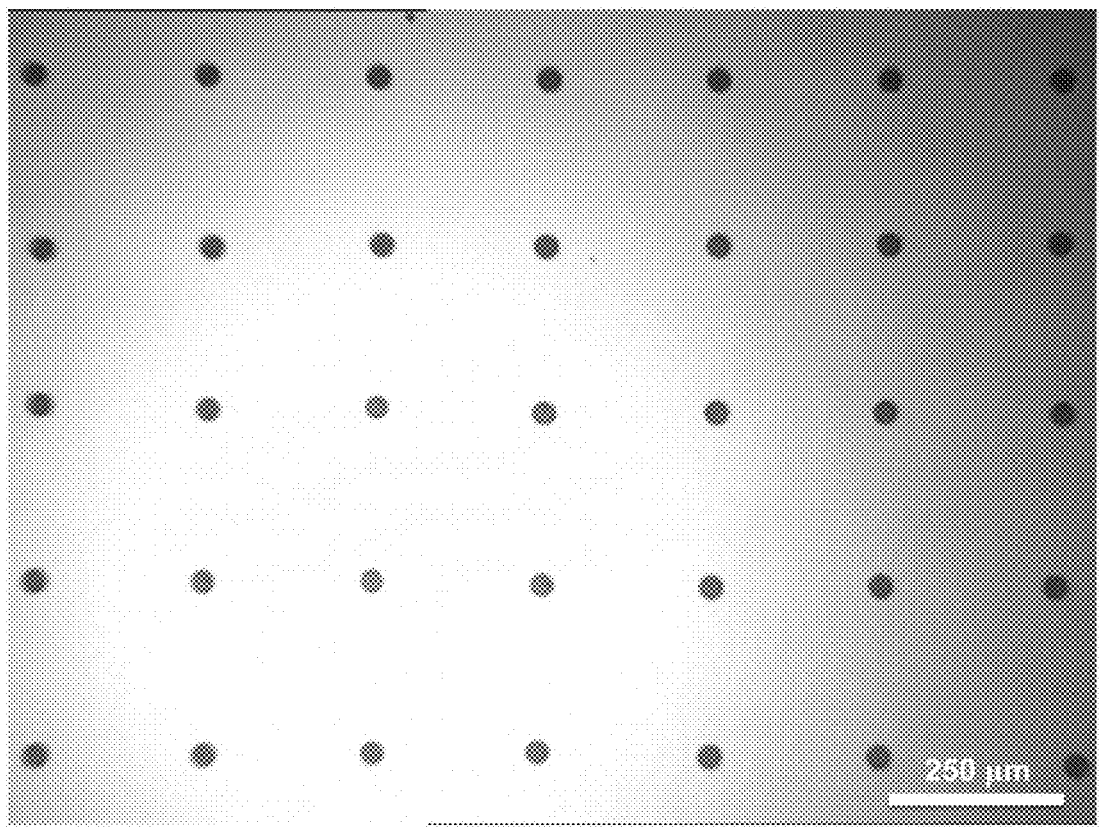
FIG. 55 shows cashmere (keratin) ink in the form of dots on a silicon substrate.
Figure 56:
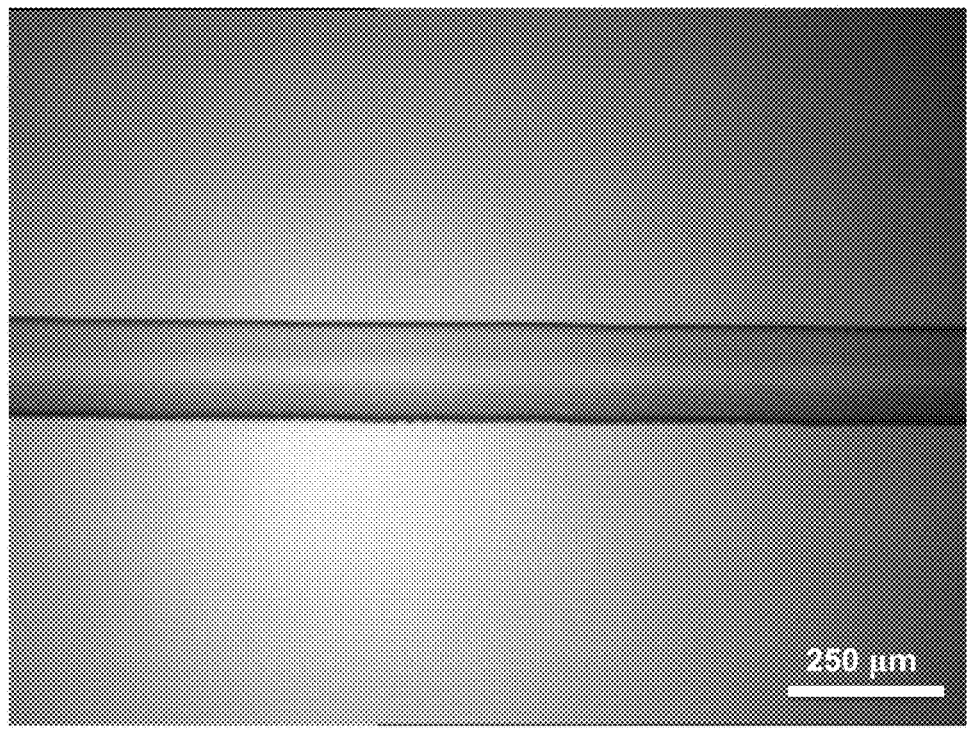
FIG. 56 shows cashmere (keratin) ink in the form of a line on a silicon substrate.
Figure 57:
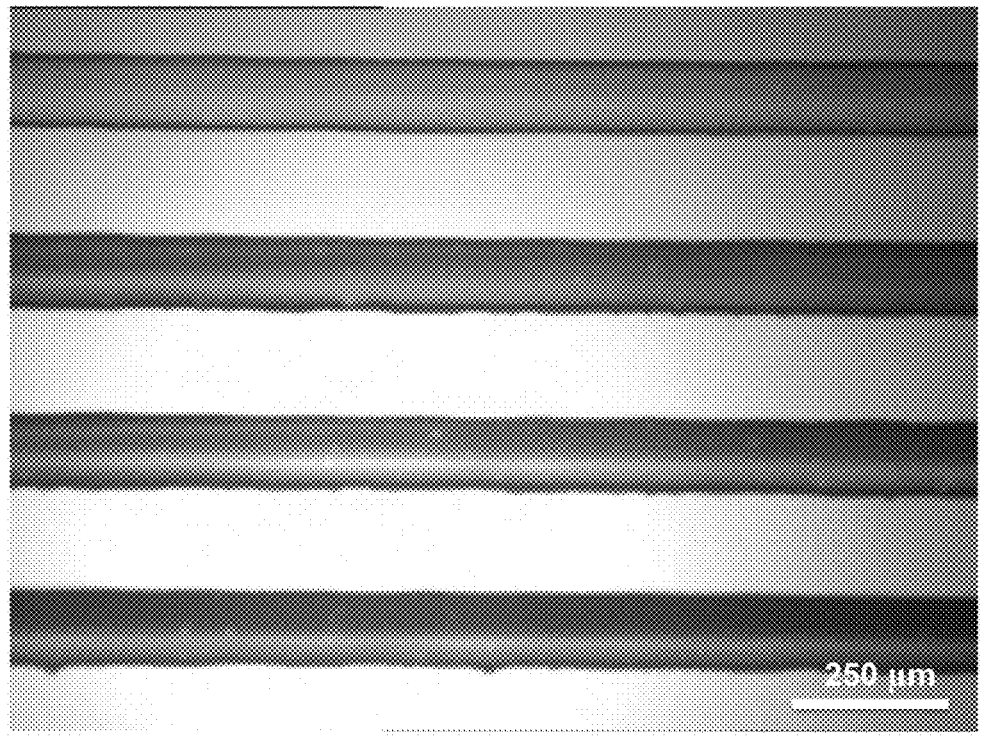
FIG. 57 shows cashmere (keratin) ink in the form of lines on a silicon substrate.
Figure 58:
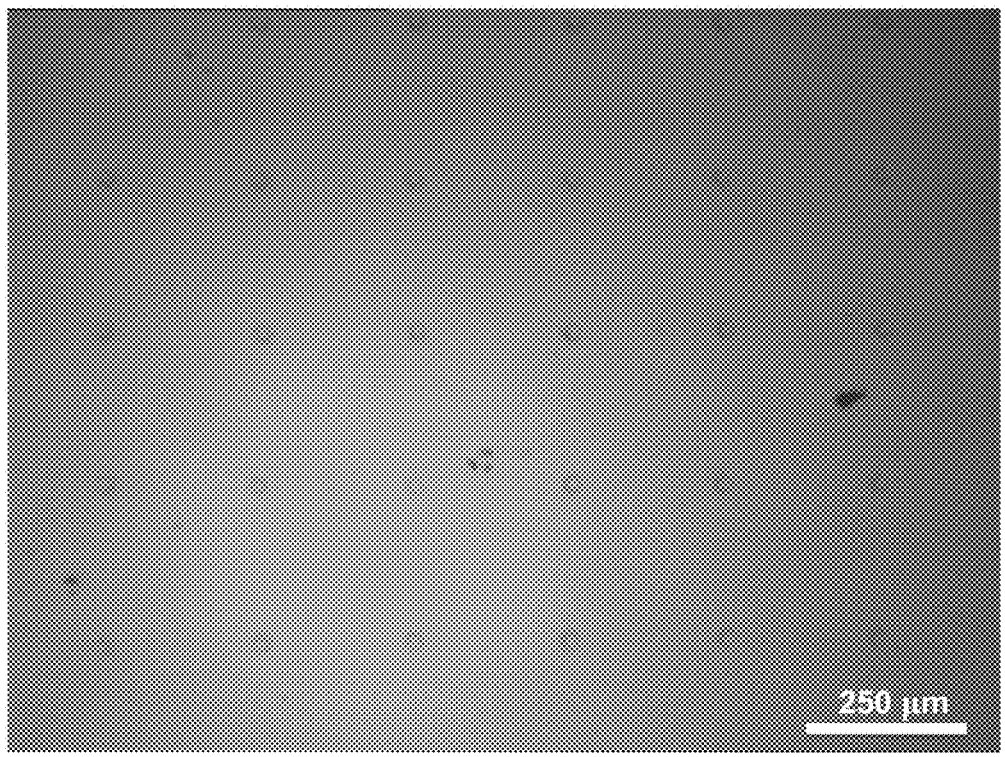
FIG. 58 shows cashmere (keratin) ink in the form of dots on a glass substrate.
Figure 59:
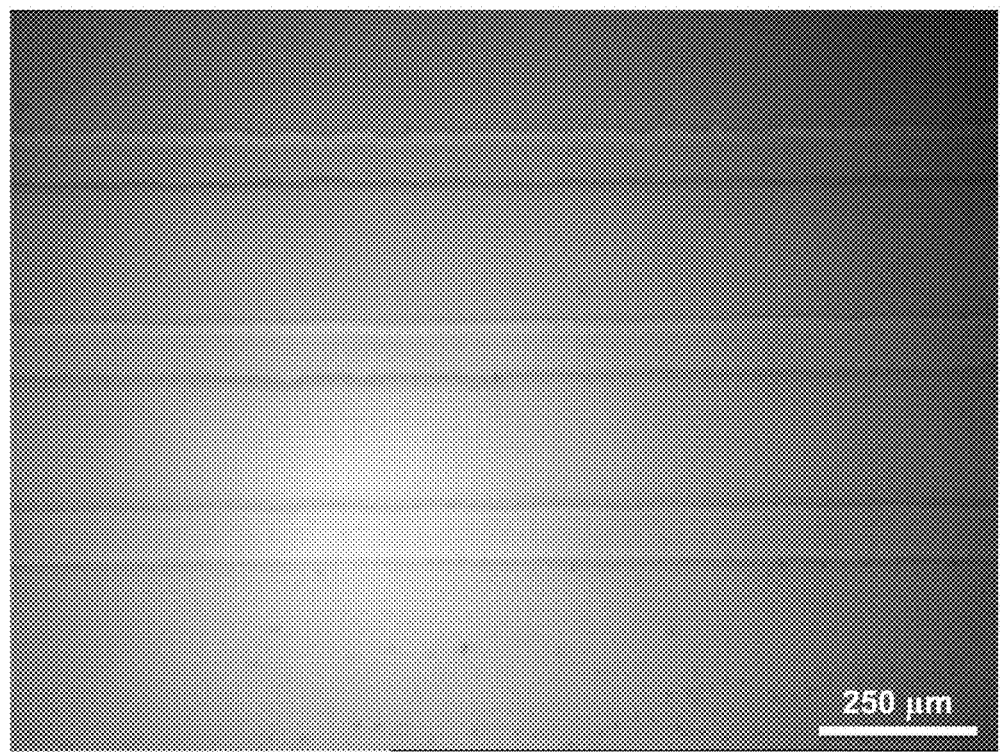
FIG. 59 shows cashmere (keratin) ink in the form of lines on a glass substrate.

Multiple-color biopolymer printing may benefit from an alignment process, because the printer in accordance with some examples, loads one cartridge with one color at a time, as shown in FIG. 54. In some examples, there are four steps of alignment including multiple-layer alignment, cartridge, voltage alignment, and nozzle alignment.

Multilayer alignment: one color for each layer of printing;
Cartridge alignment: set drop offset before every layer printing;
Voltage alignment: different color inks have slight change in viscosity;
Nozzle alignment: using the same nozzles for every layer printing (number of nozzles determines line width).

Direct printing of silk fibroin protein based inks using a inkjet printers (e.g., commercially available inkjet printers) has been shown and described. Various types of biopolymer inks may be prepared by choosing appropriate dopants and mixing with the biopolymer solution (e.g., purified silk fibroin solution), and printed. A set of operating parameters may be optimized for each individual biopolymer ink (including, for example, gold nanoparticle biopolymer ink, enzyme-doped biopolymer ink, high refractive index biopolymer ink, and antibacterial biopolymer ink) to improve the performance for specific applications. Both single layer and multiple-layer printing may be carried out, with advantageous resolutions (e.g., a resolution of 25 microns).

Resolution

One aspect of the invention relates to printed forms of biopolymer-based inks (bio-inks) Typically, such prints made by the use of at least one bio-inks described herein include an array of unit dots formed from ink droplets, deposited upon a substrate. Thus, in some embodiments, a printed array comprises a substrate; and a plurality of dot units, wherein the plurality of dot units has a semi-solid or solid form, wherein each dot unit comprises a low molecular weight structural protein. Typically, each dot unit on the substrate is between about 0.1-250 µm in diameter. According to the invention, a plurality of dot units is deposited upon a substrate in a predetermined spatial pattern to form a structure, e.g., 2D structures and 3D structures. Typically, printed forms of biopolymer-based inks prepared in accordance with the disclosure of the present application have a resolution of between about 50-20,000 dpi, e.g., about 100 dpi, about 200 dpi, about 300 dpi, about 400 dpi, about 500 dpi, about 600 dpi, about 700 dpi, about 800 dpi, about 900 dpi, about 1000 dpi, about 1100 dpi, about 1200 dpi, about 1500 dpi, about 2000 dpi, about 2500 dpi, about 3000 dpi, about 3500 dpi, about 4000 dpi, about 4500 dpi, about 5000 dpi, about 5500 dpi, about 6000 dpi, about 6500 dpi, about 7000 dpi, about 7500 dpi, about 8000 dpi, about 8500 dpi, about 9000 dpi, about 9500 dpi, about 10000 dpi, about 11000 dpi, about 12000 dpi, about 13000 dpi, about 14000 dpi, about 15000 dpi, about 16000 dpi, about 17000 dpi, about 18000 dpi, about 19000 dpi, and about 20000 dpi.

Substrates

A variety of substrates may be suitable for use in printing a bio-ink described herein. Such printable substrates using bio-inks are limitless, simply depending on the available inkjet printers. Non-limiting examples of useful substrates include, but are not limited to: papers, polyimide, polyethylene, natural fabric, synthetic fabric, metals, liquid crystal polymer, palladium, glass and other insulators, silicon and other semiconductors, metals, cloth textiles and fabrics, plastics, biological substrates, such as cells and tissues, protein- or biopolymer-based substrates (e.g., agarose, collagen, gelatin, etc.), and any combinations thereof.

In some embodiments of the invention, provided bio-inks can be printed on substrates that generally are of a flexible material, such as a flexible polymer film or paper, such as wax paper or non-wax substrates. In some embodiments, suitable substrates include releasable substrates, such as a label release grade or other polymer coated paper, as is known in the art (e.g., see U.S. Pat. No. 6,939,576). Such substrate also can be or include a non-silicone release layer. Such substrate also can be a plastic or polymer film, such as any one of an acrylic-based film, a polyamide-based film, a polyester-based film, a polyolefin-based film such as polyethylene and polypropylene, a polyethylene naphthylene-based film, a polyethylene terephthalate-based film, a polyurethane-based film or a PVC-based film, or a combination thereof.

Printable Patterns and Structures

In some embodiments, inkjet printing can be employed for printing patterns of bio-inks, such as silk fibroin inks (with or without dopants). The printable patterns (e.g., structures) using bio-inks are limitless, simply depending on the available inkjet printers. The printable patterns (e.g., structures) include, but are not limited to regular and irregular patterns, such as lines, curves, dots, solids, and any combinations thereof.

Each pattern or structure to be printed is formed from a plurality of small "dots" each of which is generated from a liquid droplet of a bio-ink deposited onto the substrate.

Such patterns can be either one layer of dot prints or multilayer of prints (e.g., serial printing), depending on the intended applications. Each layer in the multilayer prints can be overlapping on top of each other for thicker patterns or cross with other layers for complicated patterns. In some embodiments, serial printing can be performed to fabricate a 3D structure.

Annealing and/or Crosslinking

As already mentioned, certain structural proteins, including silk fibroin, exhibit an inherent self-assembly property. In some embodiments, this process involves the formation of beta-sheet secondary structure within a structural protein (or fragments). As such, bio-inks comprising a structural protein described herein may contain a range of degrees/levels of beta-sheet crystallinity. For example, provided protein ink compositions may contain a beta-sheet content ranging between about 5% and 70%, e.g., about 5%, about 10%, about 15%, about 20%, about 25%, about 30%, about 35%, about 40%, about 45%, about 50%, about 55%, about 60%, about 65% or about 75%.

Depending on the applications in some embodiment, a conformational change can be induced in such structural protein or low molecular weight fragments thereof to control or tune the solubility of the protein-based structure printed on a substrate. In some embodiments, the conformational change can induce the protein at least partially insoluble. Without wishing to be bound by a theory, the induced conformational change alters the crystallinity of the protein, e.g., beta-sheet crystallinity. In some embodiments, including with silk fibroin-based inkjet prints, the conformational change may be induced by any methods known in the art, including, but not limited to, alcohol immersion (e.g., ethanol, methanol), water annealing, shear stress, ultrasound (e.g., by sonication), pH reduction (e.g., pH titration and/or exposure to an electric field) and any combinations thereof. For example, the conformational change can be induced by one or more methods, including but not limited to, controlled slow drying (Lu et al., Biomacromolecules 2009, 10, 1032); water annealing (Jin et al., 15 Adv. Funct. Mats. 2005, 15, 1241; Hu et al., Biomacromolecules 2011, 12, 1686); stretching (Demura & Asakura, Biotech & Bioengin. 1989, 33, 598); compressing; solvent immersion, including methanol (Hofmann et al., J Control Release. 2006, 111, 219), ethanol (Miyairi et al., J. Fermen. Tech. 1978, 56, 303), glutaraldehyde (Acharya et al., Biotechnol J. 2008, 3, 226), and 1-ethyl-3-(3-dimethyl aminopropyl) carbodiimide (EDC) (Bayraktar et al., Eur J Pharm Biopharm. 2005, 60, 373); pH adjustment, e.g., pH titration and/or exposure to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304 and International App. No. WO2008/150861); and any combinations thereof. Contents of all of the references listed above are incorporated herein by reference in their entireties.

In some embodiments, the conformation of certain structural proteins in a bio-ink, including silk fibroin, may be altered by water annealing. Without wishing to be bound by a theory, it is believed that physical temperature-controlled water vapor annealing (TCWVA) provides a simple and effective method to obtain refined control of the molecular structure of biomaterials. To illustrate a non-limiting example, in the case of silk fibroin, the relative degree of crystallinity can be controlled, ranging from a low beta-sheet content using conditions at 4° C. (α helix dominated silk I structure), to higher beta-sheet content of 60% crystallinity at 100° C. (β-sheet dominated silk II structure). Water or water vapor annealing is described, for example, in PCT application no. PCT/US2004/011199, filed Apr. 12, 2004 and no. PCT/US2005/020844, filed Jun. 13, 2005; and Jin et al., Adv. Funct. Mats. 2005, 15: 1241 and Hu et al., Biomacromolecules, 2011, 12(5): 1686-1696, contents of all of which are incorporated herein by reference in their entireties.

Alternatively or additionally, in some embodiments, alteration in the conformation of certain structural proteins, such as silk fibroin, may be induced by immersing in alcohol or organic solvent, e.g., methanol, ethanol, propanol, acetone, etc. The alcohol concentration can be at least 10%, at least 20%, at least 30%, at least 40%, at least 50%, at least 60%, at least 70%, at least 80%, at least 90% or 100%. In some embodiment, alcohol concentration is 100%. If the alteration in the conformation is by immersing in a solvent, the protein composition can be washed, e.g., with solvent/water gradient to remove any of the residual solvent that is used for the immersion. The washing step can be repeated one, e.g., one, two, three, four, five, or more times.

Alternatively or additionally, the alteration in the conformation of certain structural proteins, such as silk fibroin, can be induced with shear stress. The shear stress can be applied, for example, by passing a structural protein composition through a needle. Other methods of inducing conformational changes include applying an electric field, applying pressure, and/or changing the salt concentration.

The treatment time for inducing the conformational change can be any period of time to provide a desired degree of beta-sheet crystallinity content. In some embodiments, the treatment time can range from about 1 hour to about 12 hours, from about 1 hour to about 6 hours, from about 1 hour to about 5 hours, from about 1 hour to about 4 hours, or from about 1 hour to about 3 hours. In some embodiments, the sintering time can range from about 2 hours to about 4 hours or from 2.5 hours to about 3.5 hours.

When inducing the conformational change is by solvent immersion, treatment time can range from minutes to hours. For example, immersion in the solvent can be for a period of at least about 15 minutes, at least about 30 minutes, at least about 1 hour, at least about 2 hours, at least 3 hours, at least about 6 hours, at least about 18 hours, at least about 12 hours, at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, or at least about 14 days. In some embodiments, immersion in the solvent can be for a period of about 12 hours to about seven days, about 1 day to about 6 days, about 2 to about 5 days, or about 3 to about 4 days.

After the treatment to induce the conformational change, structural proteins, such as silk fibroin, may comprise a beta-sheet crystallinity content of at least about 5%, at least about 10%, at least about 20%, at least about 30%, at least about 40%, at least about 50%, at least about 60%, at least about 70%, at least about 80%, or at least about 90%.

Device (e.g., Printers)

It is desired, in accordance with example embodiments, to turn a biopolymer solution into the "ink" for directly printing biopolymer devices using a suitable printer. It is very challenging though since there are certain requirements for the biopolymer to function as ink. Inkjet printers have grown in popularity and performance—actually, inkjet printers are by far the most popular since their introduction in the latter half of the 1980s. Compared to laser printers (which use dry ink, also known as toner, static electricity, and heat to print), inkjet printers use liquid inks and nozzles (usually multiple nozzles needed) to spray drops of ink directly onto the substrates.

A typical inkjet printer includes: a) print head—that contains a series of nozzles that are used to spray the ink drops; b) ink cartridge—that contains the ink; c) stepper motor—that moves the print head back and forth across the substrate.

It is noted most inkjet printers use piezoelectric nozzle techniques for precision printing. Such techniques use piezo crystals that vibrate when they receive a very small electric charge. When the crystal vibrates inward and outward, it pulls and forces a tiny amount of ink and sprays it out of the nozzle.

Figure 6:
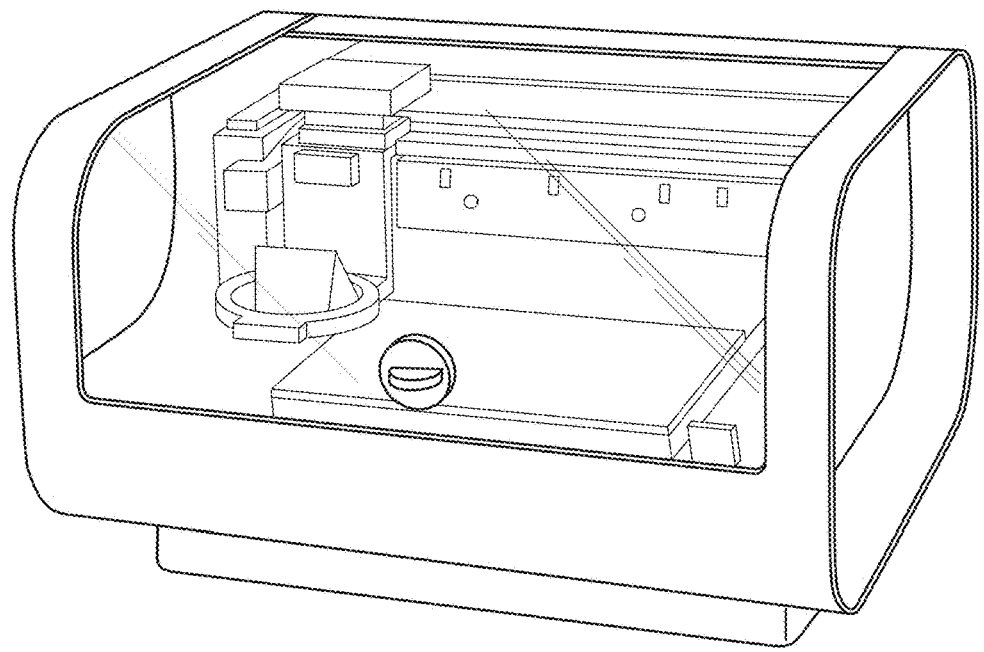
FIG. 6 shows an inkjet materials printer.
Figure 7:
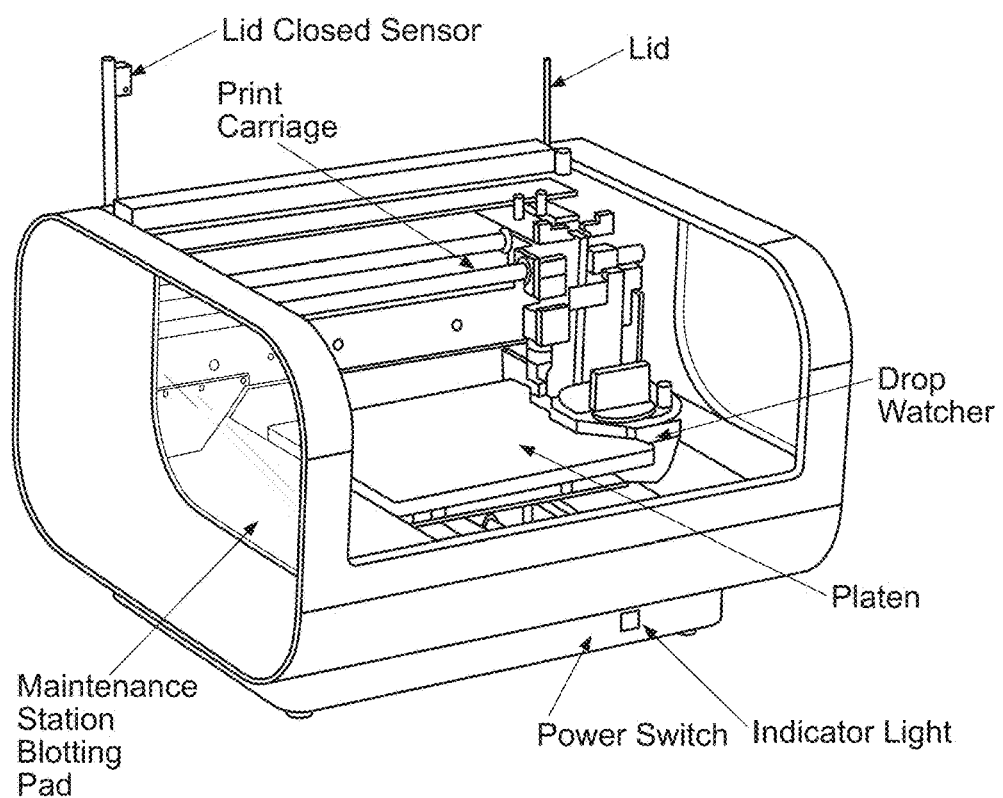
FIG. 7 shows a schematic of components of the inkjet printer of FIG. 6.

Referring to FIGS. 6 and 7 an inkjet printer is provided. The inkjet printer may be, for example, a commercial inkjet printer, e.g., a FUJIFILM Dimatix Materials Printer DMP-2800. The illustrated printer uses piezoelectric inkjet technology and MEMS fabrication processes (for cartridges, nozzles and etc.).

Referring to FIG. 2, the printer includes a base, a print cartridge, a maintenance station blotting pad, a platen, a drop watcher, and a lid.

As shown in FIG. 2, the printer works, in this example, with a maximum printable area of A4 size substrate (8×11 inch) with a disposable (but reusable with certain modifications/tweaks) piezo inkjet cartridge. The maximum height of printable substrate is up to 25 mm in the illustrated example. The printer also has the ability to heat up the substrate up to 60 degrees C. In addition, there is a fiducially camera available allowing real time watching the formation of the drop as it is ejected from the nozzle.

The printer may serve as a convenient laboratory tool that enables users (e.g., students, researchers, and engineers) to evaluate the use of specific inks (e.g., silk fibroin solution in accordance with example embodiments) for new and proof of principle technology development with extensive flexibilities to optimize process parameters for user oriented applications.

Following are some example applications using the printer and listins of various types of functional materials and printable inks.

Printer-compatible substrates may include, for example: paper, Kapton (i.e. polyimide), poyethylene (PET), fabrics (such as, for example, cotton, nylon, polyester), metals (such as, for example, aluminum foil, copper foil, stainless steel foil and etc.), liquid crystal polymer, palladium, and glass.

Printer-compatible fluids/inks may include, for example: conductive silvers, conductive inorganics (e.g., non silver ink, such as ITO inks), conductive organics (such as OLED), single wall carbon nanotubes (SWCNTs), insulators, polyimides, photoresists, resins, and UV curable inks.

Among different types of conductive inks, a wide range of ink properties including viscosity, density, surface tension, and dispersion stability may be observed. Therefore, it may be necessary to optimize the printer parameters such as the volume of the jetted ink, the gap distance between droplets, the printing frequency, temperatures of the jetted ink and the substrate, and/or the sintering/curing mechanism performed after printing. A popular application of using inkjet printer for conductive printing is rapid printing of RFID tags. However, this is a rather challenging endeavor since precise control of the desired conductivity and pattern designs (on non-perfect substrates, for example, on non-glossy rough papers).

Unlike the traditional photolithograph and etching PCB fabrication process (which is a subtractive method by removing undesired metal from the substrate surface), conductive inkjet printing for RF applications jets the single conductive ink droplet from the nozzle to a predefined position (usually controlled by, for example computer and a precise motor stepper). Accordingly, no harsh chemicals as the etching waste are created, which results in an economical and ecological fabrication solution. Silver nano-particle inks are selected and commonly used for good metal conductivity. As mentioned above, a sintering process either by applying heat or UV exposure (to remove excess solvent and to remove material impurities) is usually needed, which also enhance the bond strength between the ink and the as-printed substrate. It should be noted that an immediate sintering process may be essential, because the biopolymer ink may begin to oxidize, which would reduce the efficiency of conductivity of the metallic patterns.

Figure 8:
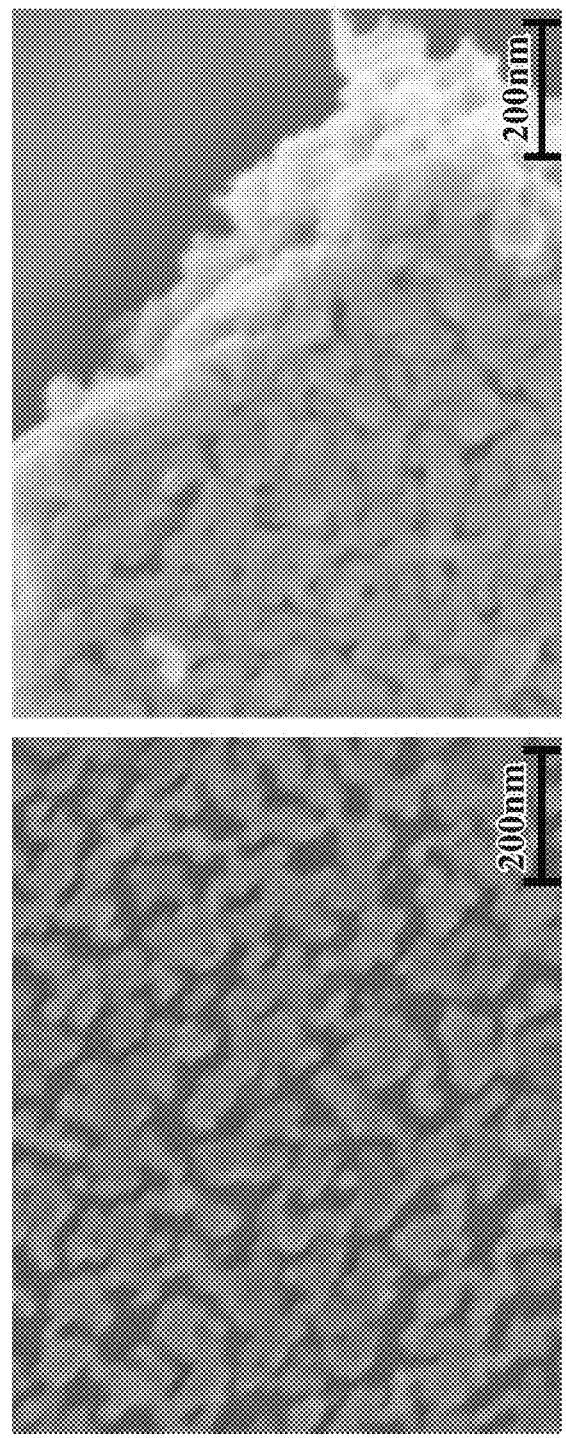
FIG. 8 shows scanning electron microscope (SEM) images of inkjet-printed silver nanoparticle ink before and after sintering at 100 degrees C. for 15 minutes.
Figure 9:
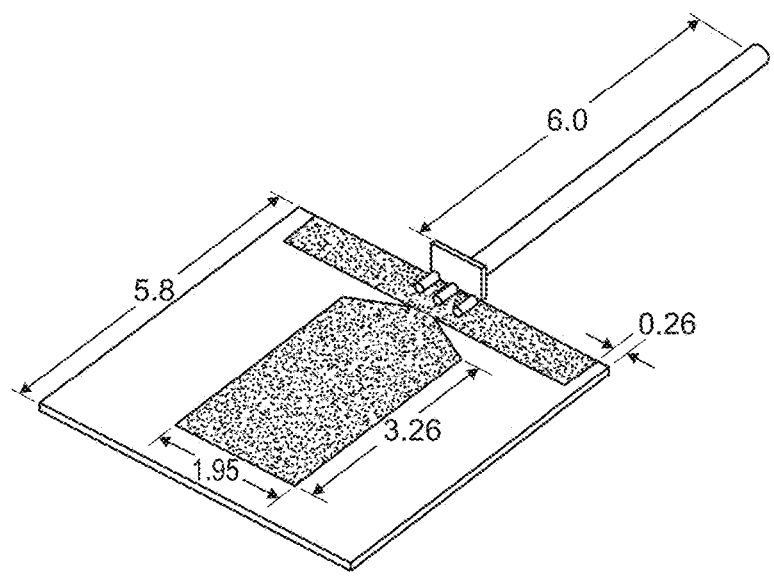
FIG. 9 shows an inkjet printed RFID tag.
Figure 10:
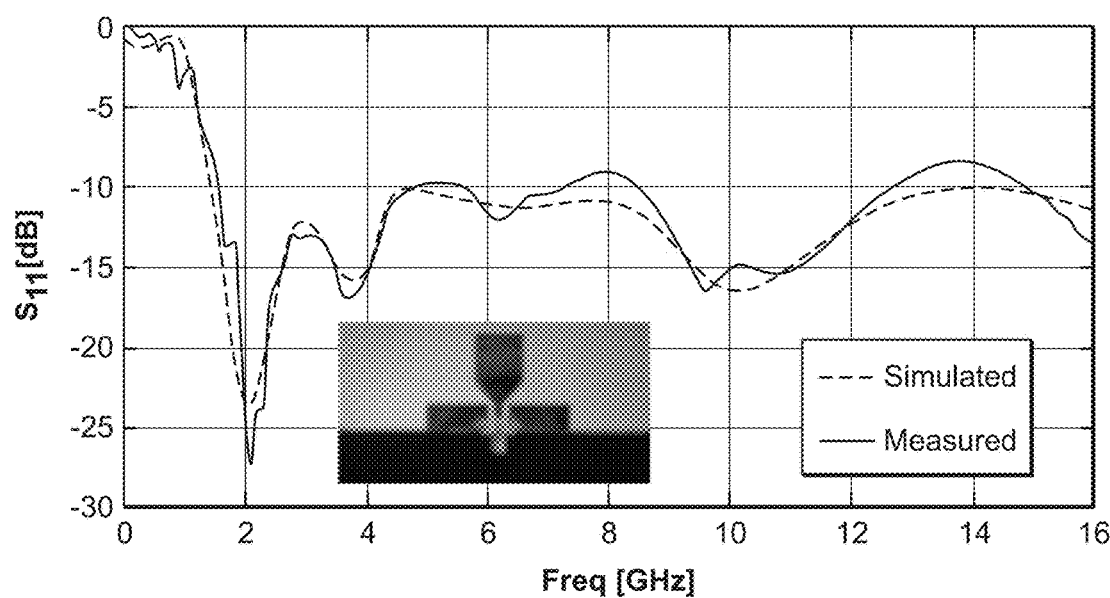
FIG. 10 illustrates simulated and measured intensity over frequency of the inkjet-printed RFID tag of FIG. 9.

As shown in FIG. 8, there are, in the illustrated structure, gaps between printed silver nanoparticles after printing, resulting in a poor connection and therefore lack of sufficient conductivity. After a period, e.g., 15 minutes, of a heating/curing process, the particles begin to aggregate and gaps start to diminish, which forms a continuous metal film and guarantees a good conductor, which determines the performance of printed electric devices such as, for example, an RFID tag as shown in FIG. 9. The simulated and measured intensity over frequency of an example embodiment in accordance with FIG. 9 is shown in FIG. 10. As shown in the graph, this example has a working frequency of 2 GHz, although example embodiments may be configured to have any suitable frequency range.

Figure 11:
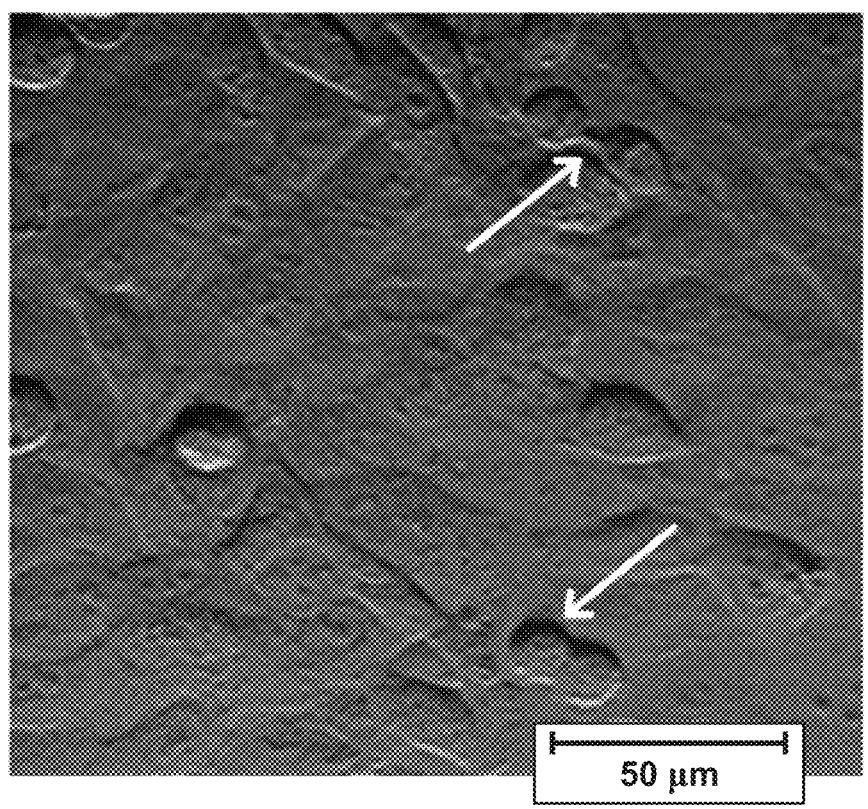
FIG. 11 shows an SEM image of human fibrosarcoma cells after inkjet printing.

One potential aspect of inkjet printing techniques is "bioprinting", which requires micro-level, and in many cases, nano-level, liquid manipulation. Typical applications may include, for example, micro-dosing, biochemical surface patterning and modification, tissue engineering and importantly the direct placement of living cells, DNA arrays, and proteomics. Questions have been raised on the influence of mechanical forces and relatively intense electric field during the inkjet process on cells and some research reports show that although some cell death may occur, surviving cells recover rapidly and seem to behave normally, as shown in FIG. 11.

Working Principle of Materials Printer

In accordance with example embodiments, materials printers (e.g., the DMP-2800 inkjet printer from FUJIFILM Dimatix, Inc.) are used to directly print regenerated silk fibroin protein. The printers may be able, in some implementations, to create patterns and load BMP patterns over any suitable area (e.g., an area of about 200×300 mm). The printers may allow substrates having any suitable dimensions, (e.g., substrates up to 25 mm thick or much thicker or thinner substrates) and may have an adjustable Z height.

The materials printers may have any suitable number of jetting nozzles, e.g., piezo-based jetting nozzles. For example, a materials printer may have a single nozzle or a plurality of any desired number of nozzles. In some embodiments, between 8 and 32 nozzles are provided. For example, some embodiments have 16 jetting nozzles. Where a plurality of such nozzles are provided, the nozzles may be arranged with any suitable spacing, which may be regular or irregular. For example, the nozzles may be spaced from each at a spacing that is between 30 μm and 500 μm, between 50 μm and 400 μm, between 150 μm and 350 μm, or between 200 μm and 300 μm, e.g., at 254 μm spacing. The nozzle or nozzles may be provided in connection with a fillable cartridge.

In some embodiments, a method is provided in which the biopolymer base (e.g., silk fibroin protein) is regenerated as the ink to match specific fluid requirement of the printer. The printed biopolymer (e.g., silk protein) may be biocompatible and can be further functionalized by mixing the biopolymer ink with appropriate dopants (including, for example, organic and/or inorganic dopants) for specific applications.

Printer Operation

The printer may serve, for example, as a powerful laboratory tool, and may have capabilities to allow users to optimize process parameters, such as, for example, nozzle voltage, substrate height, and wave form. The printer may, in some embodiments, provide multi-layer printing and allow an alignment process when using multiple cartridges and matching the origin point on the substrate. In some example embodiments, the printer operates according to a method including creating a pattern, loading ink, and setting printing permanents.

As indicated above, a printer may be utilized in an example method that includes creating a pattern, loading ink, and setting printing permanents. The printer, in some implementations, may include a processor running software and that accepts pattern files and/or provides a pattern creation and editing software interface to allow users to create and/or edit patterns. The pattern creation and editing software allows the user to modify a pattern of drops for printing, which may be useful for some fine and small scale patterns, for example, patterns illustrated in FIG. 12. However, creating a complex structure pattern for printing may be very time consuming. For patterns such as illustrated in FIG. 13, a transformation to a pattern design file format may first be required, followed by importation into the pattern design software.

In some example embodiments, to print fine patterns, a user may first make a high resolution original file before transforming the file into the file format of the pattern design and editing software, because some such software only allows importation of monochrome Bitmap files which can be a low resolution file. After creating a Bitmap pattern, a user may select an option titled Pattern Editor (Bitmap images) from the main software window and choose a drop space size which depends on the ink and substrate before importing the Bitmap file. It may be beneficial for the user to double check the final size of the pattern to minimize the risk of error. If the final size is not in accordance with the user's expectation, the user may adjust the final size by changing the pattern size in the Bitmap file, then reloading the pattern. The pattern may be repeated by controlling a placement number.

For a user to create his or her own pattern, the user may select an option in the software, e.g., in a main windows of the software, and select an option indicated as Pattern Edition. This allows the user to create a pattern by entering dimensions in a Pattern Block Drop Positions field. Alternatively, the user may draw a feature through a corresponding software window. Before creating the pattern, the user may wish to choose the size of drop spacing which is the center to center distance from one drop to the next. For a normal biopolymer drop (e.g., a silk drop) the drop spacing may be, for example, about 25 μm on a hydrophilic surface, such as, for example, a silicon wafer.

To load the cartridge, the ink used to fill into the cartridge may need go through a filter first. For example, for a 26 μm nozzle and a drop volume of 10 pL, the ink may pass through a 0.22 μm filter first. In this example, the nozzle may easy be clogged by particle sizes larger than 0.22 μm.

After loading a new cartridge onto the printer, the user may change the clean pad for new ink to avoid contamination by other chemicals. After loading the cartridge, the user may select the pattern the use wishes to print from the software. The system may automatically calculate the cartridge mounting angle determined by drop spacing specified in the pattern. Table 2.1 shows the relation of saber angle, resolution, and drop spacing.

TABLE 2.1

Resolutions relationships

| Resolution [dpi] | Saber angle [°] | Drop spacing [μm] |
|---|---|---|
| 5080.00 | 1.1 | 5 |
| 2540 | 2.3 | 10 |
| 1693.33 | 3.4 | 15 |
| 1270.00 | 4.5 | 20 |
| 1016.00 | 5.6 | 25 |
| 846.67 | 6.8 | 30 |
| 725.71 | 7.9 | 35 |
| 635.00 | 9.1 | 40 |
| 564.44 | 10.2 | 45 |
| 508.00 | 11.4 | 50 |
| 461.82 | 12.5 | 55 |
| 423.33 | 13.7 | 60 |
| 390.77 | 14.8 | 65 |
| 362.86 | 16.0 | 70 |
| 338.67 | 17.2 | 75 |
| 317.50 | 18.4 | 80 |
| 298.82 | 19.6 | 85 |
| 282.22 | 20.8 | 90 |
| 267.37 | 22.0 | 95 |
| 254.00 | 23.2 | 100 |
| 241.90 | 24.4 | 105 |
| 230.91 | 25.7 | 110 |
| 220.87 | 26.9 | 115 |
| 211.67 | 28.2 | 120 |
| 203.20 | 29.5 | 125 |
| 195.38 | 30.8 | 130 |
| 188.15 | 32.1 | 135 |
| 181..43 | 33.4 | 140 |
| 175.17 | 34.8 | 145 |
| 169.33 | 36.2 | 150 |
| 163.87 | 37.6 | 155 |
| 158.75 | 39.0 | 160 |
| 153.94 | 40.5 | 165 |
| 149.41 | 42.0 | 170 |
| 145.41 | 43.5 | 175 |
| 141.11 | 45.1 | 180 |
| 137.30 | 46.7 | 185 |
| 133.68 | 48.4 | 190 |
| 130.26 | 50.1 | 195 |
| 127.00 | 51.9 | 200 |
| 123.90 | 53.8 | 205 |
| 120.95 | 55.8 | 210 |
| 118.14 | 57.8 | 215 |
| 115.45 | 60.0 | 220 |
| 112.89 | 62.4 | 225 |
| 110.43 | 64.9 | 230 |
| 108.09 | 67.7 | 235 |
| 105.83 | 70.9 | 240 |
| 103.67 | 74.7 | 245 |
| 101.60 | 79.8 | 250 |
| 100.00 | 90 | 254 |

In some example embodiments, to set printing parameters, the user may select a drop watch button and the system may move the cartridge to the right side of the platen, positioning the nozzles over the drop watcher camera system. The user may first select the range of nozzles the user wishes to jet the pattern. Second, the user may modify the nozzles to uniform performance by adjusting voltage of those nozzle as being monitored by camera. Another potentially important parameter the user may wish to set up carefully is the cartridge print height according to the substrate thickness. If the substrate thickness is, for example, less than 0.5 mm, the printable range may be 210 mm*315 mm. If the substrate thickness is, for example, from 0.5 mm to 25 mm, the printable range may be 210 mm*260 mm. The repeatability distance may be, for example, ±25 μm. The last step before printing may be an alignment process through a fiducial camera tool, e.g., via a tools menu in the software window. First, the user may calibrate the position of a new cartridge or head angle by setting the drop offset to automatic or manual, e.g., from the tools menu. Second, the user may set the printing origin point and reference point for multiple-layer printing.

Setting Cartridge Parameters

In some implementations, to optimize drop performance, there are some parameters that may need be set up precisely. The main parameters may include, for example, nozzle voltage, nozzle temperature, meniscus set point, cleaning cycles, and waveform.

Figure 14:
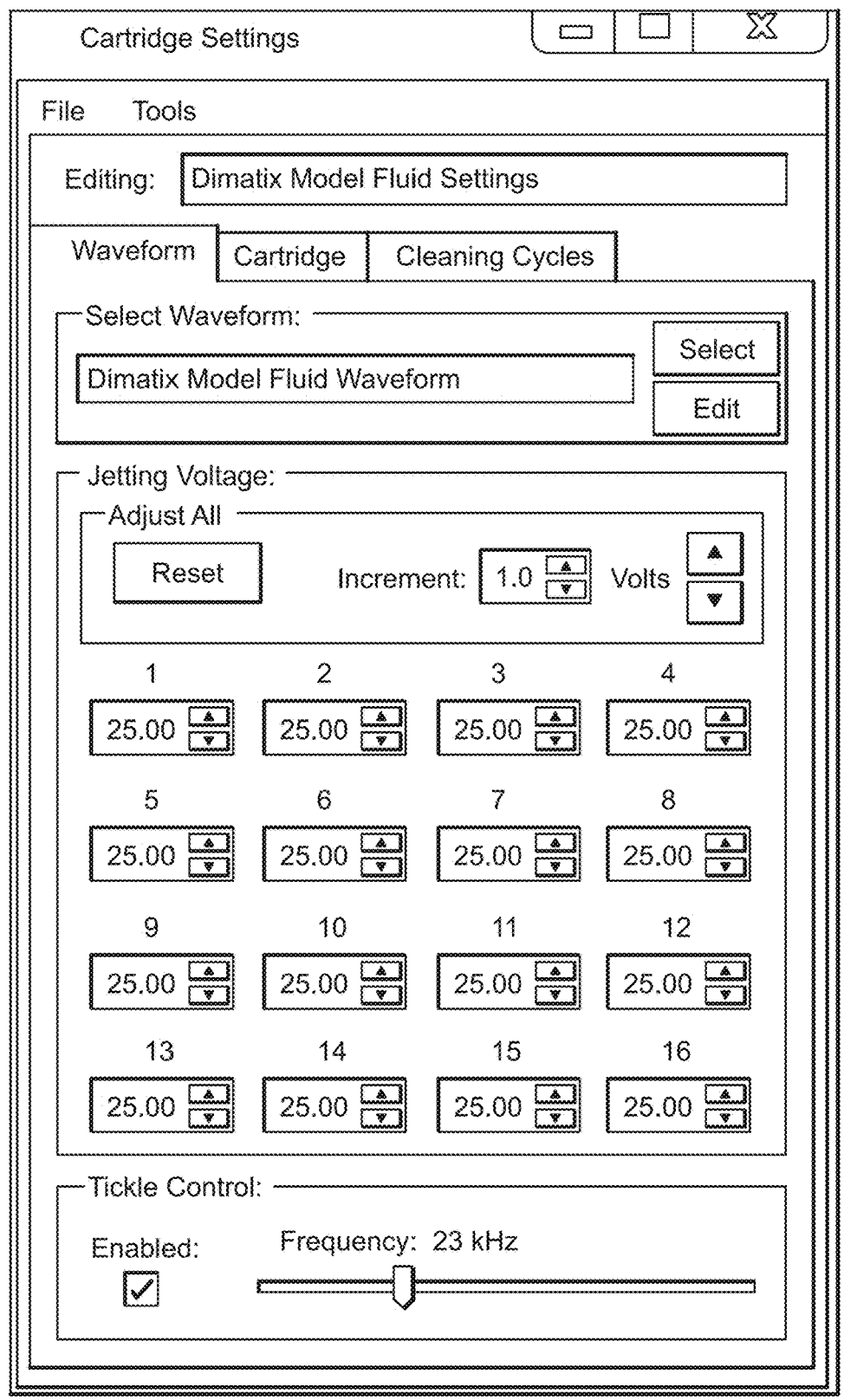
FIG. 14 shows a cartridge settings interface with voltage settings.

To adjust nozzle voltage, the user may click on an edition button the cartridge setting box of the software. In some examples, the voltage of each nozzle may be individually adjusted, as shown in FIG. 14. Increasing voltage increases drop volume and jetting velocity. A suitable velocity to be set is, for example, 7-9 m/sec.

To adjust nozzle temperature, meniscus set point, nozzle number, and print height, the user may make a selection in the cartridge settings of the software.

Figure 15:
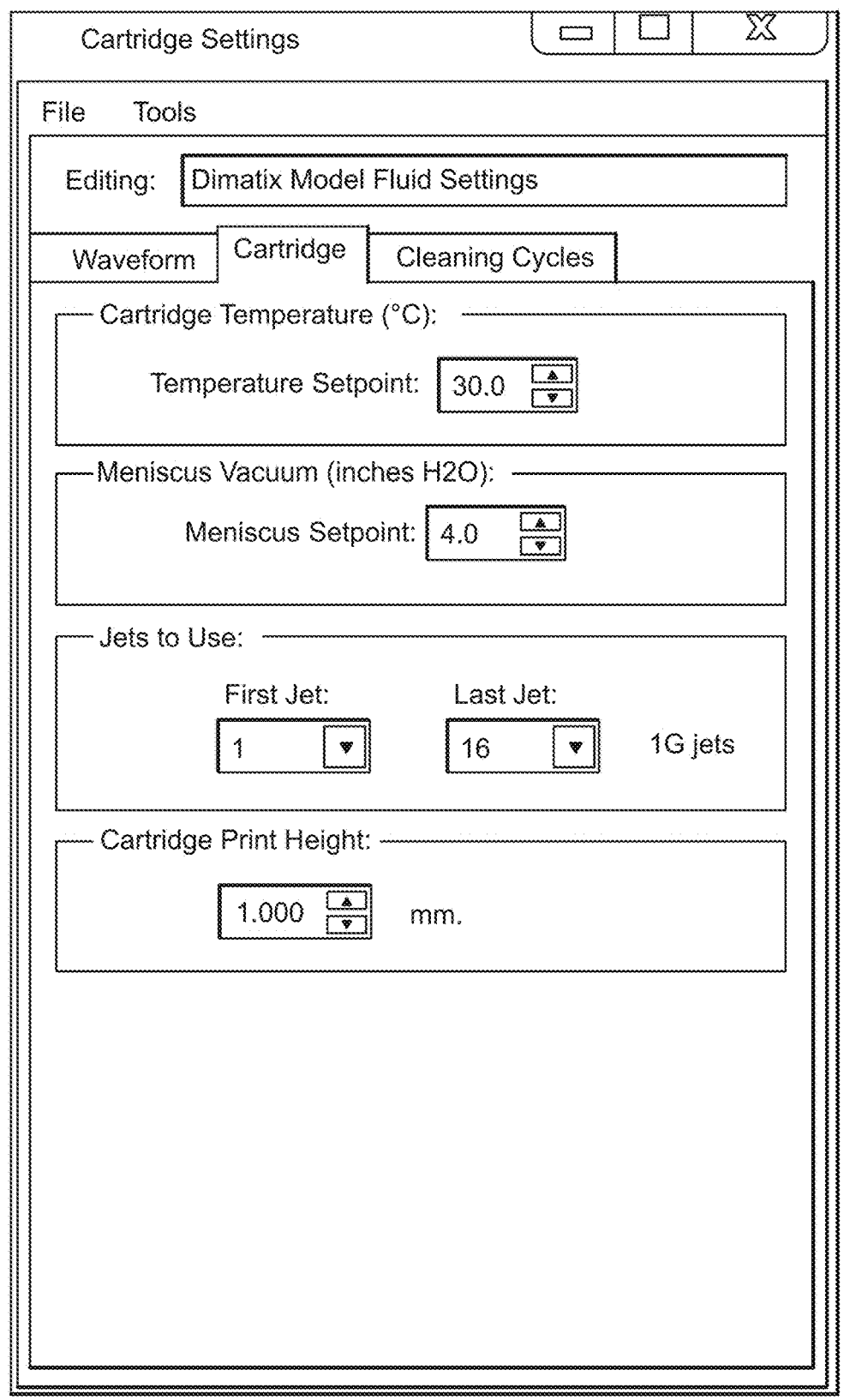
FIG. 15 shows a cartridge tab of the cartridge settings interface of FIG. 14.

The user may lower the ink viscosity and surface tension by increasing nozzle temperature. The printer may allow the user to adjust nozzle temperature in a range from, for example, 28 degree C. to 70 degree C., as shown in FIG. 15. A good viscosity of printing ink is 10-12 centipoises and a good surface tension of printing ink is 28-44 dynes/cm, although other viscosities and surface tensions may be provided in example embodiments.

Meniscus vacuum is a negative pressure for keeping the meniscus at the edge of nozzle. The user may change the value of meniscus vacuum depending on the viscosity and surface tension of the ink. The typical meniscus vacuum value of water is 4 inches. If the meniscus vacuum number is not correct, the performance of ink may be affected with high frequency.

The user may choose the number of nozzles from which to print, and the system may automatically compensate for the number of nozzles used but the nozzles selected may only be one series of adjacent nozzles. In some implementations, the printer has a drop watch camera which allows the user to monitor, in real time, the drop performance. In this way, the camera may assist the user to ensure that the nozzles chosen performance uniformly.

Cleaning Cycles

Figure 16:
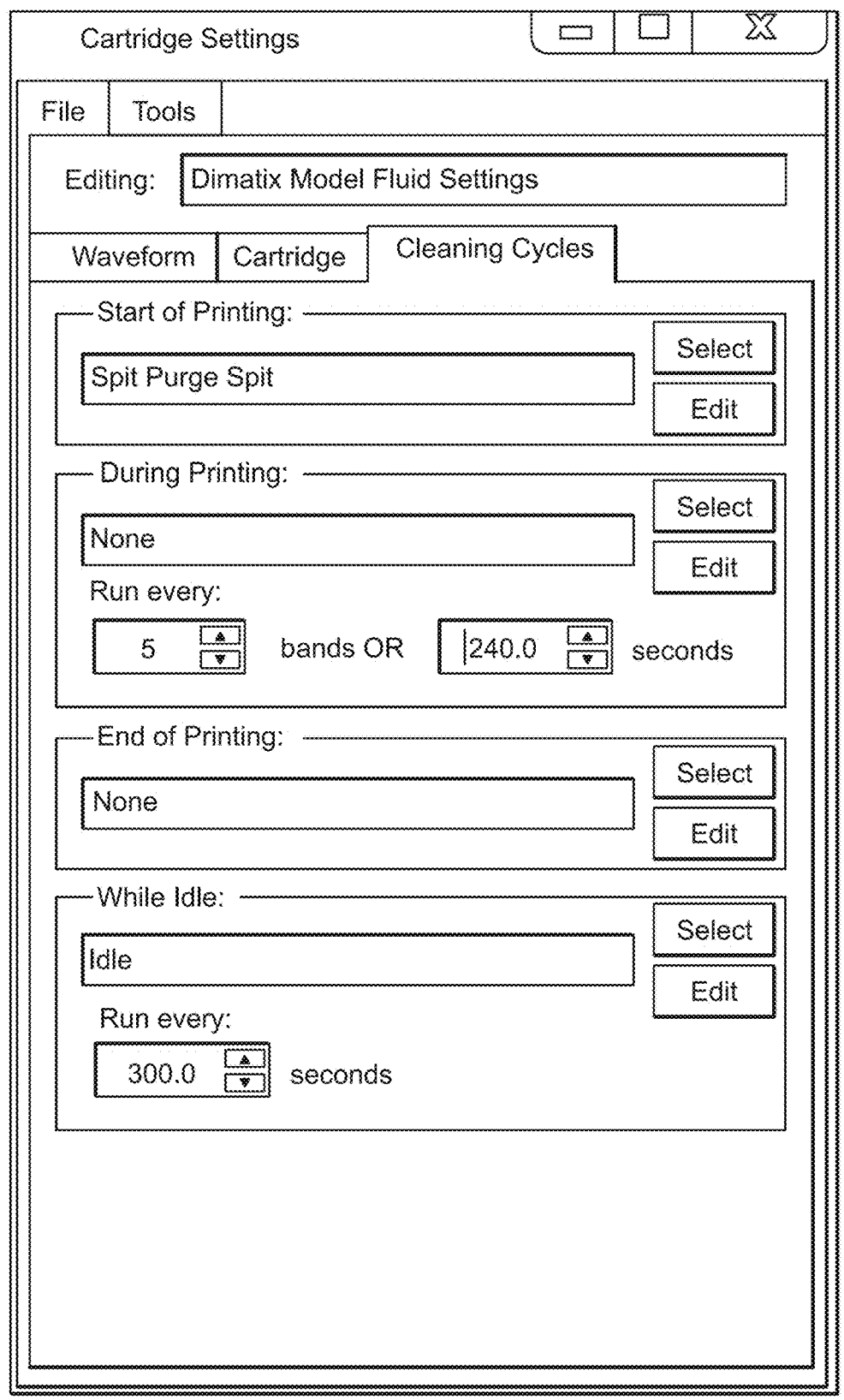
FIG. 16 shows a cleaning cycles tab of the cartridge settings interface of FIG. 14.

In some examples, a cleaning cycle table allows the user to set nozzle cleaning processes before, during, and after printing. Setting cleaning cycle before printing may give a uniform start for every running of the printer. Cleaning cycle may be especially important for some high viscosity applications, because setting cleaning cycle during printing may prevent the high viscosity ink from clogging. Setting the cleaning cycle after printing may facilitate maintenance of the nozzles, as shown in FIG. 16.

Waveform

The printer software may have any suitable wavefore, for example, a standard 4-step waveform which is good for normal ink (e.g., ink having a viscosity of 11-12 centipoises and a surface tension of 28-32 dynes/cm. The 4 steps may include start, phase 1, phase 2, and phase 3. The basic concept for these 4 steps is use a bias voltage to control piezo actuation to suck a drop of ink and jet it with a controlled velocity.

Waveform Start

Figure 17:
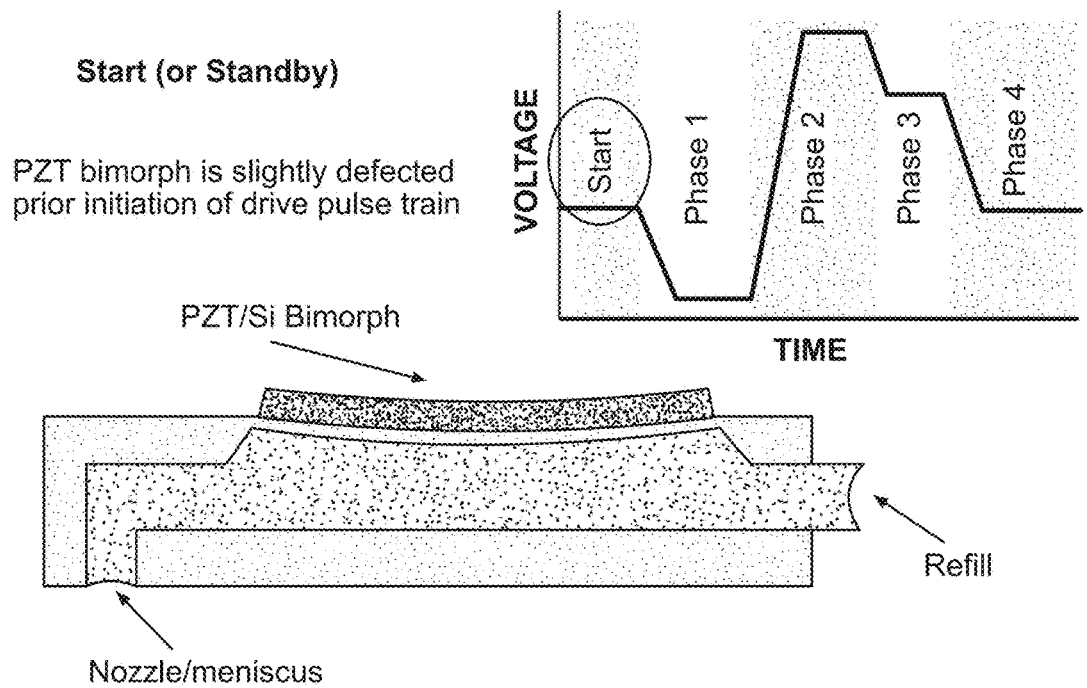
FIG. 17 shows a piezo actuated nozzle unit of an inkjet printer when a waveform begins.

In some examples, at a standby point, the nozzle voltage is set to a 40% level and is held for 1 μs. Under this condition, the channel which is piezo basic slightly deflected and sucks some ink from cartridge starting to eject, as shown in FIG. 17.

Waveform Phase 1

Figure 18:
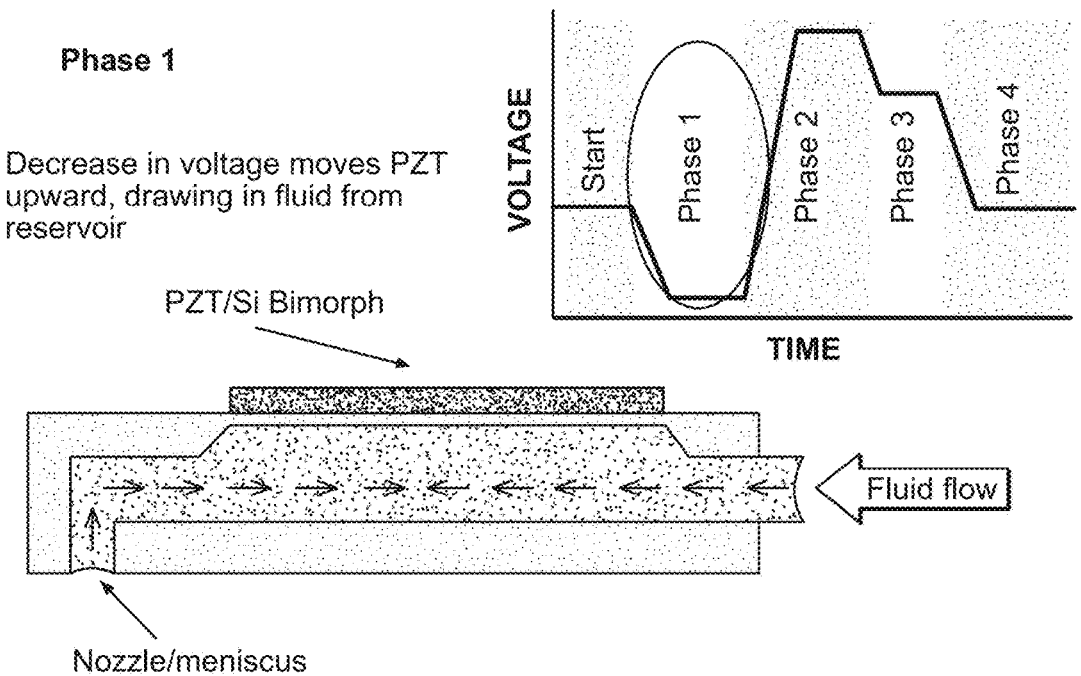
FIG. 18 shows the piezo actuated nozzle unit of FIG. 17 in a first waveform phase.

At phase 1, the voltage level may be set to 0 and held for, e.g., 3.584 μs or any other suitable period, e.g., a period in a range from 3 μs to 4 μs. The voltage brings the piezo back to a neutral straight position with the chamber at its maximum volume. In this phase, the fluid is filled into chamber. FIG. 18 shows the meniscus at the nozzle edge.

Waveform Phase 2

Figure 19:
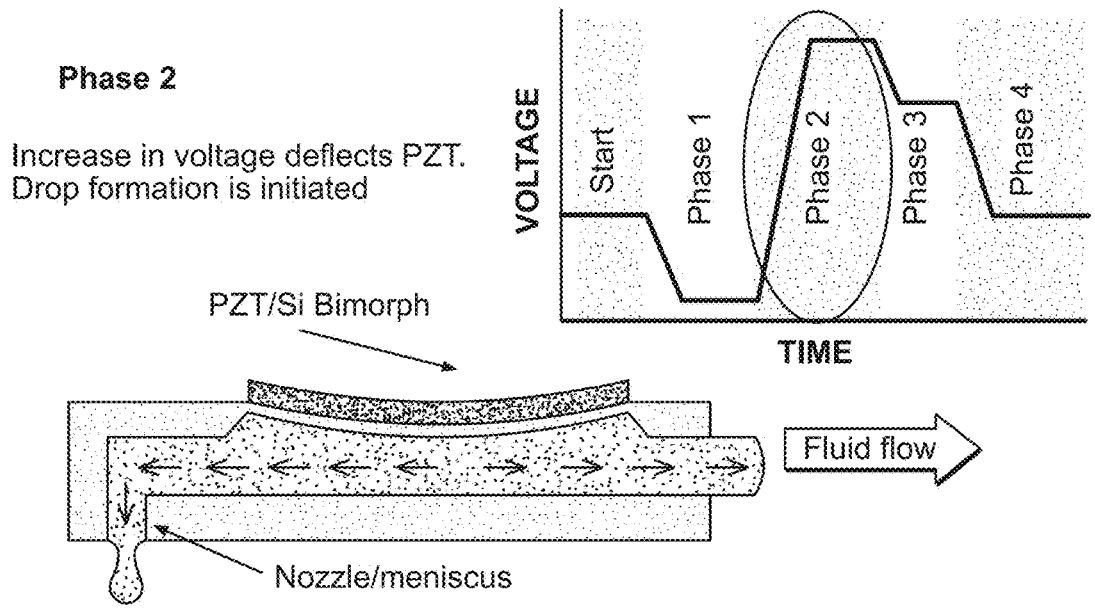
FIG. 19 shows the piezo actuated nozzle unit of FIG. 17 in a second waveform phase.

Phase 2 is a firing pulse, as shown in FIG. 19. The steepness of the slope provides the energy for initial ejection and it is followed by a hold period. On the hold period, the voltage increases to 100% level and is held for, e.g., 3.712 μs or any other suitable period, e.g., a period in a range from 3 μs to 4.5 μs. A this point, the chamber starts to jet a drop of ink. According to the hold time and voltage volume, the velocity of a drop can be calculated.

Waveform Phase 3

Figure 20:
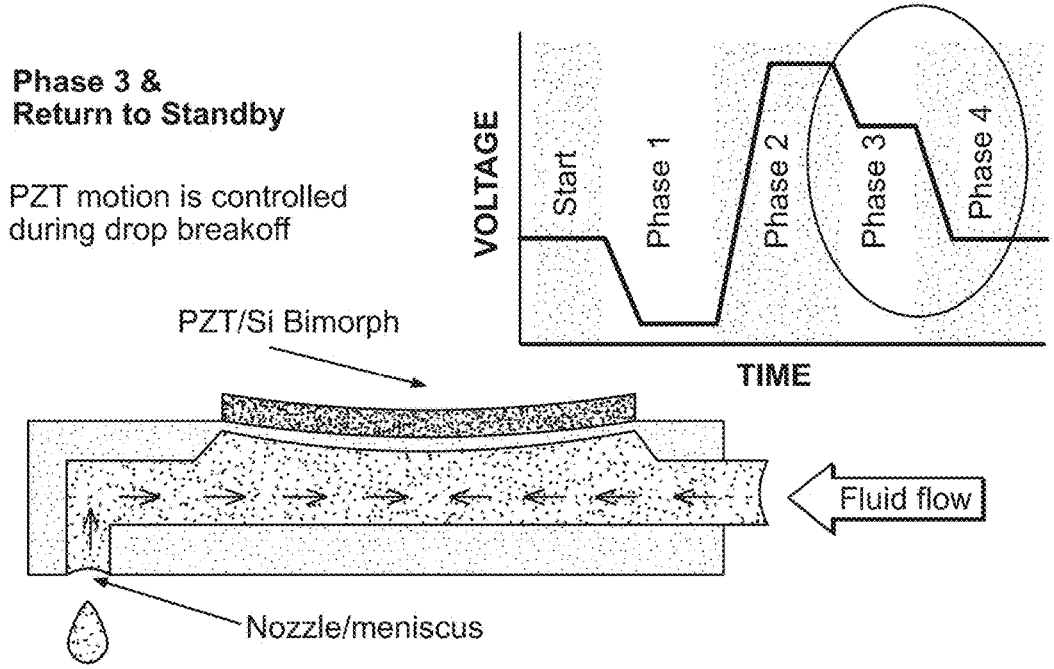
FIG. 20 shows the piezo actuated nozzle unit of FIG. 17 in a third waveform phase.

Phase 3, the last phase of the waveform, is a return to standby, as shown in FIG. 20. First, the voltage level decreases to 70% and is hold it for, e.g., 3.392 μs (or any other suitable period, e.g., a period in a range from 3 μs to 4 μs), which is intended to prevent the printed head from sucking air back in. Second, the voltage level is brought to 40% level and chamber back to the standby position.

Those parameters mentioned above may play an important role during printing. They may advantageously be checked every printing running according to the ink and material of substrate. Also ink condition may slightly change according to room temperature and humidity level.

In further aspect of the invention, methods for printing of silk fibroin inks using a inkjet printer are provided.

The prepared silk fibroin inks (functionalized or non-functionalized) can be filled into any types of liquid-refillable based cartridge for commercial inkjet printers. The lifetime of the inks depends on the usage and the storage conditions. In some embodiments, storage in a refrigerator at 4 degree C. when finishing printing is recommended. In some embodiments, silk inks (with our without dopants) may be stored without refrigeration, such as at room temperature (between about 18-26° C.) for an extended duration of time without significant loss of function. High resolution (depending on the specific model of the printer) can be achieved for printers with fine nozzle size and the access to control the nozzle operating performance (for example, firing voltage and waveform, cleaning cycle, printing temperature and etc.)

Applications

The social benefits and commercial opportunities associated with these and other systems define an important set of broader impacts. The sustainable manufacturing approaches, the associated reduction in resource consumption and the decreased risk associated with chemical and drug transport and handling constitute additional features with global significance.

The development of every new generation of biomaterials has incorporated efforts for the material properties to have an increasing degree of interaction with the biological environment. Biomaterials have evolved from inert, monolithic matter, into "bio-instructive", hybrid systems, with specific functionalities that are defined by correspondingly specific applications [1]. This approach limits the possibility to apply a single biomaterial widely by favoring the functionality dictated to meet stringent therapeutic requirements. Regulations that enforce the clinical use of biomaterials (e.g., FDA approval is not given to the biomaterial per se but to its specific application) have also contributed to the current high specialization of biomaterials. Under this approach, biomaterials are conceptualized as bio-high-tech materials, which are provided to the end-user in their refined state, as "ready-for-use" products. The present application challenges this viewpoint by developing the scientific underpinnings of a technology that provides the end-user with a unified "base biomaterial" or platform material, whose final utility can be easily and controllably defined at the end-users' site.

In some embodiments of the invention described herein, the use of inkjet printing (e.g., with personal printers) is provided. In some embodiments, inkjet printing of bio-inks (such as inks comprising a structural protein, e.g., silk fibroin and keratin) is provided as a platform. In some embodiments, inkjet printing of bio-inks, such as silk fibroin inks, can enable the fabrication of custom printable biomaterials for a variety of applications. In some embodiments, such platform is useful for optics, photonics, electronics, as well as therapeutics and sensing applications. Non-limiting examples of enabled applications range from drug-doped printable inks that can preserve heat-sensitive biomacromolecules without refrigeration (elimination of the cold-chain), to functionalized silk ink libraries to be used for printable drug formulation or activation (elimination of user-induced error in drug reconstitution). Another concept involves biological and environmental analysis on orthogonal printing of 'sensing' silk ink libraries.

Work described in this application develops a scientific and engineering base of knowledge on the design of structural protein-based inks, bulk and surface properties, material-substrate interface, and manufacturing strategies. An emphasis has been placed on the fundamental development of the working examples of particular types of bio-inks, including silk fibroin-based inkjet printing technology, as well as keratin based inkjet printing technology. The targets in performance, reliability in operation and scalability are comparable to those established in commercial inks for personal printers. As described in more detail herein, the present application provides working models of structural protein-based liquid compositions suitable for use as ink (e.g., paint, marker, and the like), including silk fibroin inks and keratin inks that are suitable for use in conjunction with an inkjet printer. The work is a culmination of research and development efforts involving a deep and wide characterization of the effect of the printing process on the biomaterials conducted, including the analysis of the fundamentals of phase transformation incurred by the biomacromolecular inks during their phase transformation in the printing process.

A set of device designs to address applications ranging from drug delivery to biochemical analysis described herein is based at least on the following: (1) development of bio-inks, such as silk inks, that stabilize vaccines and integrate the vaccine reconstitution within the printing process; (2) bio-inks that topographically control the release of antibiotics; (3) bio-inks that allows for basic biochemical analysis of biological samples, including human tissues (e.g. blood, urine); and, (4) bio-inks that spatially control stem cell fate by a controlled release of custom-printed growth factors.

Resorbable Silk-based Electronics

The development of every new class of electronics has historically involved efforts to achieve operation in forms that undergo negligible change with time. More recently, with an opposite goal, novel silk-based electronics systems that physically disappear into the surrounding environment at prescribed times and rates have been described. The core idea exploits transient electronics devices, which can be dissolved on demand, upon the exposure to a specific stimulus. This research yielded to the first biocompatible and bioresorbable electronic device designed, manufactured and implanted in vivo, which maintained its functionality before being degraded by the body fluids. Here, the design of silk fibroin materials as substrate for the deposition of electronic circuits plays a role as prominent as that in a fibroin-based tissue engineered construct, where the control of scaffold degradation while exploiting its function is the main design criterion. The unique properties of silk fibroin, in fact, guarantee a broad processability portfolio together with a fine-tuning of degradation kinetic both in vivo and in vitro. The amino-acidic structure of fibroin well suites the possibility to be flexible, robust and well interfaced with materials such as metals, without negative phenomena such as delamination. These properties make the resorbable electronic concept presently impossible to achieve using any other material. With this background, silk fibroin ink compositions and related methods described herein can be effectively employed in conjunction with the development and manufacture of transient electronic device described above.

Thus, example embodiments of the invention described herein combine diverse, but highly complementary, technology that will generate foundational knowledge for both material design and material processing. New insights may be given in silk fibroin polymorphism, providing new approaches for fibroin processing, fibroin phase transformation and fibroin interaction with several classes of biofunctional macromolecules. A new approach is needed for biomaterial design to enable a versatile technology that starts uses a common production platform (e.g., inkjet printing) yet covers a broad range of outcomes and applications. For this purpose, the standard processes of fibroin regeneration has to be re-invented and tuned to achieve useful operation; new processing approaches are essential for use with practical inkjet systems through personal printers; new ways to stabilize fibroin solution are required to achieve useful operation.

Incorporating inkjet printing, bioinstructive biomacromolecules and biomaterials into a single technology that offers high performance and robust operational characteristics has the potential to be a game-changer in the current biomaterials scenario. Many of the underlying inventive concepts have applicability beyond the application exemplified in this application. For example, the inkjet printing of functionalized silk fibroin-based inks will open the door to biomaterial-based applications in energetics (printed silk-based batteries) and electronics (printed conductive silk). Indeed, the deep and extensive design, development and characterization of silk-based ink for inkjet printing proposed in this program provides the route to robustly develop the aforementioned technology.

The stabilization of biomacromolecules in inkjet-printed biomaterials is an appealing concept that allows for the creation of structural protein-based ink libraries to print a variety of agents, such as therapeutics, sensing, and bioinstructive molecules. Interestingly, the combination of the libraries may be left to the end-user, providing several degrees of freedom and a wide flexibility in the use of the technology described herein. Feedback from the end user will also increase the portfolio of biomacromolecules incorporated and stored within the bio-inks, opening the possibility of applications such as a printable pharmacy or biochemical lab. This has become possible, with the development of a robust standard "biomaterial ink" for inkjet printing technology as described herein.

Particularly compelling is the possibility to print stabilized biological agents, such as vaccines and antibiotics, by taking advantage of (a) the ability of silk to stabilize and preserve biological, and (b) the controllable transiency of fibroin and the consequent controlled release of such therapeutics. The former possibility addresses two problem of increasing urgency, driven by the high mortality in the developing world from infectious diseases. In the recent years, the World Health Organization has underlined the urgency of addressing two priorities: the cold chain system and the possible adverse event following immunization (AEFI).

Cold Chain System

More than 17 million people die every year from infectious diseases, particularly in the developing world. Vaccines and antibiotics are important components of an effective infectious disease containment strategy; antibiotics represent a rescue measure while vaccination can be a primary mode of disease prevention. Unfortunately, the use of vaccines and antibiotics is severely limited in the poorest countries where infectious diseases account for more than half of all deaths. Due to temperature sensitivity, vaccine and antibiotic formulations must be maintained within a specific refrigeration temperature range. Because ambient temperatures in the developing world deviate significantly from refrigeration temperatures, the successful delivery of active vaccines and antibiotics depends on the cold chain system, a distribution network to maintain optimal cold temperatures during transport, storage, and handling. Cold chain requirements represent a major economic and logistical burden, particularly in lower resource settings, where refrigeration and electricity can be limited. The cold chain alone can account for 80% of the financial cost of vaccination and is estimated to cost vaccine programs $200-300 million per year. Deficiencies in the process frequently occur even in industrialized countries. For temperature sensitive compounds like vaccines and antibiotics, maintaining the cold chain is critical for adequate bioactivity. Failures in the cold chain result in costly waste and the loss of nearly half of all global vaccines. Such failures can also result in the delivery of ineffective, sub-therapeutic doses. For antibiotics, this problem can be associated with the development of antibiotic-resistant strains, a major public health concern.

Adverse Event Following Immunization

An AEFI is any adverse event that follows immunization that is believed to be caused by the immunization. Immunization can produce adverse events from the inherent properties of the vaccine (vaccine reaction), or some errors in the immunization process (programme error). Although rare in the developed countries, program errors are more frequent in the developing world, where non-sufficient structures limit and negatively influence the use of recommended immunization practices. Generally, these errors results from mistakes and/or accidents in vaccine preparation, handling, or administration and results from the poor conditions in which immunization is practiced. Examples of the common mistakes are inadequate shaking of the vaccine before use, errors in the reconstitution of vaccines before they are administered, contamination of vaccine or injection equipment, use of a drug instead of a vaccine or diluent, superficial injection, and use of frozen vaccine.

Current Applications of Bioprinting

Bio-printing allows for the dispensation of pico-sized quantities of biomaterial solutions (such as protein solution, nucleic acid solution, etc.) to designated sample space with minimal waste, both of which are highly sought features in processing biological materials. What follows is a summary of exemplary applications, in which bio-printing is explored.

Biosensors and Immunoassay Tests

From a life sciences/microelectromechanical systems (MEMS) standpoint, the ability to array proteins with good precision in uniform quantities is a useful feature both for the preparation of analytical samples, as well as for the fabrication of devices. Protein microarrays allow for the study of specific interactions between immobilized individual proteins and other biological systems. This ability translates directly into applications such as point-of-care clinical diagnostics and biosensors. A biosensor is an analytical device that uses antibodies, enzymes, nucleic acids, microorganisms, isolated cells, or other biologically derived systems as a sensing element. In terms of cost, very small quantities of material are required to make sensors, and inkjet deposition lends itself well to mass production, allowing for sensors in many applications to be treated as disposable. The inherently small size of the detectors involved implies the need for only small quantities of material for analysis, resulting in greater sensitivity. Also, the need for a smaller amount of analyte offers faster detector response times, since less time is required for the substrate to interact with the analyte before a signal is detected. The use of enzymes and antibodies as transducers also results in unmatchable specificity for bioactive compounds. The limited stability of the many biologically active materials involved lower limit the number of macromolecules that can be used to fabricate inkjet-printed biosensors. From a commercial standpoint, the areas where inkjet-printed biosensors have gained the most interest has been disposable, point-of-care diagnostic products, such as glucose sensors, ELISA kits, analysis of biomarkers (particularly for detecting or monitoring cancers).

Inkjet Printing of Antibiotics and Growth Factors

Spatial control of bioactive molecule distribution in therapeutics and cell-stimulant molecules is highly sought. The ability to use IJP to control the topographical distribution of therapeutics may in fact lead to more effective and customized control of biofilm colonies formation, particularly in healing burns and in implantable prostheses. The application of patterned growth factors on a cell-culture substrate (two- and three-dimensional) may lead to effective co-culture of cells minimizing the problems of culture medium incompatibilities while providing bioinstructive persistent patterns. This would lead to the functional organization of multiple tissues types, addressing one of the major bottlenecks in the engineering of the tissue-tissue interfaces (e.g. osteo-chondral and ligament-bone interface).

EXEMPLIFICATION

Although the present invention has been described with reference to particular examples and embodiments, it should be understood that the present invention is not limited to those examples and embodiments. Moreover, the features of the particular examples and embodiments may be used in any combination. The present invention therefore includes variations from the various examples and embodiments described herein, as will be apparent to one of skill in the art.

Example 1: Silk Fibroin Ink

Feasibility Demonstrations

Silk fibroin polymorphism overturns the general concept that structural protein with high molecular weight cannot be printed at high concentration. Under certain conditions, regenerated silk fibroin possesses the unique property of having a globular form. This allows for the on-demand extrusion of the solution through nozzle with a sub-micrometric diameter, mimicking the natural extrusion of silk solution. Unpublished work within our laboratory has developed a protocol to obtain printable silk inks to establish a set of functional silk-based inks.

The following components has been used to explore the biomaterial parameter space and investigate the feasibility of a fibroin-based bioprinting technology:

Printer

Dedicated (FujiFilm Dimatix Materials Printer DMP-2800) and personal (e.g. Epson Artisan 1430 and Epson WorkForce 30) printers have been used to print functionalized fibroin-based inks. The dedicated printer has been used to prove the concept of printing fibroin-based inks and to assess the different condition (e.g. process type, drop size) of the inkjet printing process. After a first screening, the piezoelectric driven ejection of the drop has been preferred to the thermal one. To obtain a robust method valid for different fibroin-based inks, a droplet size in the range of 6-20 pl has been chosen. Within this range, in fact, it was possible to successfully print all the fibroin-based inks investigated. Spurred by the results obtained with the dedicated printer, personal printers with specifications similar to the aforementioned values have been used for IJP of silk inks Epson is the only commercial brand to offer piezoelectric inkjet technology. In addition, Epson printers have a Variable Size Droplet Technology®, that allows to choose between five pre-determined drop sizes (1.5 to 15 pl). CUPS drivers offered in Linux environment can be used to control the droplet size through a 3 bit signal.

Substrate

The substrate is part and parcel of the IJP fibroin-based biomaterials. In accordance with the definition of hybrid and composite materials, the ink-substrate system may be considered either a hybrid (no separate interfaces between ink and substrate) or a composite (separate interfaces). This distinction may strongly influence the structural, functional, mechanical and biological properties of the deposited proteins. In addition, different choices of substrates may tailor the properties of the end product. Several materials are currently under investigation in our laboratories as silk-based IJP substrates. Plain paper is used both as a 'standard' substrate and as a substrate for colorimetric sensing applications. Silk-based electrospun matrices are used for tissue engineering and therapeutics applications. Silicon wafers have been tested for microelectronics and biological assays applications. Tissue culture plastics are used for biological applications. Microneedle-Silk-sheets may be used for vaccine delivery.

Silk Ink

We have established a robust protocol to print SF solution, by controlling the molecular weight (MW) of the protein through the fine regulation of the fibroin boil time (e.g. longer dissolution time corresponds to a decrease in MW). A basic functional silk-based ink library has been explored by hybridizing regenerated silk solutions with different dyes (a-c), antibiotics (e.g. penicillin), vaccines (e.g. Merck MMR II), photochromatic salt (e.g. AgCl, $CuSO_4$, $CoCl_2$), hygroscopic salts ($MgCl_2$), enzymes (e.g. glucose oxidase, pesin, Alcalase®, α-chymotrypsin). The functionality of inkjet-printed fibroin-penicillin hybrid has been recently tested and the antimicrobial efficacy of the antibiotic silk ink has been successfully assessed in preliminary results (d).

Research on Bio Printing of Functional Silk-Based Inks

We have developed an unprecedentedly versatile, inkjet printable, SF-based biomaterial. The possibility to ink-jet print SF may accompany the SF-induced preservation, stabilization, and controlled-release of biomacromolecules with the possibility to obtain a programmable topographic control of their release in the micro-scale. In addition, SF may be successfully implemented to immobilize and stabilize sensing molecules and to drive their interface with electronics device. SF has been preferred to other abundant biopolymers (e.g. collagen, chitosan and keratin) due to the properties of the solvated protein. Whereas it is possible to regenerate SF in neutral aqueous solution at physiologically relevant protein densities (1-15 wt %), soluble collagen is only obtainable at pH <4.0 (in the form of tropocollagen dimers or trimers) and at low densities (<0.5 wt %), chitosan can only be solubilized in acidic conditions, and keratin is expensively obtained in aqueous solution only at low concentration (<0.5 wt %). Alternative candidates as polycaprolactone, poly-hydroxyalkanoates, poly(lactic acid) (PLA), poly(glycolic acid) (PGA) and their co-polymer (PLGA) do not offer the polypeptidic nature of proteins, which highlights the opportunity offered by the unique properties of the silk biomaterial. Research involves an extensive characterization of neat and hybrid silk solutions (silk inks) to evaluate the interfaces between silk-silk and silk-allo macromolecules, necessary both to fully understand the hybridization process and to control the IJP process. In addition, the project may be focused on protein characterization, IJP processing design and stability of ink jet printed macromolecules. The envisioned outcomes include a deep knowledge on the polymorphism of SF in the presence of other macromolecules, both in liquid and solid phase. This fundamental material characterization will not only cope with the technological challenges involved in the IJP process of stable macromolecules, but it will also open the door to their stabilization in silk solutions. This is a step towards therapeutic inkjet printing technology.

Silk Ink Design

Research on fibroin solution as a robust, printable biomaterial is crucial to develop the SF-IJP technology proposed here. Several parameters influence the rheological and biochemical properties of SF solutions, impacting the IJP process. In particular, a main focus of our efforts has been to maximize the stability of the inks, without compromising the achievement of a printable solution (i.e. particle size <200 nm, surface tension <65 mN/m, viscosity <10 mPa/s, pH=4-10). Although the project may leverage previous studies as a starting point, a new set of parameters other than MW may be used to control and tailor the viscosity and the surface tension of the SF solution. pH, ionic strength, protein and salts concentration may be considered in order to tailor the viscosity and the surface tension of the silk solutions. In general, pH plays the major role in controlling the silk solution's viscosity. A decrease in pH corresponds to a higher interaction between the SF chains, particularly at values close to the isoelectric point (pH=4.8). In addition, for pH<3.5, the chains are reversibly aggregating in crystalline β-sheet crystals, forming a gel structure. On the other end, for strongly alkaline pH values (pH>9.5), SF chains irreversibly degrade in small polypeptides. An optimum pH range between 6-8 may be therefore targeted in the design of the silk-based inks Increasing salt concentration in the SF solution increases its surface tension, which is also dependent on the pH. The addition of small organic molecules may be used to decrease the surface tension of the SF solution. Unpublished ICP-MS measurements conducted on regenerated SF has shown the presence of several cations, such as calcium, magnesium, iron(II) and copper(II). However, such ions are bound to the protein and are present only in traces. This is however an indication of the strong affinity of SF to divalent cations, which are been reported to have a strong stabilization effect on the molecules, with a consequent increase of viscosity at concentrations≥50 mM. Although the use of chelators to reduce the free divalent cations is possible, it has to be considered that multicarboxyl acids (e.g. EDTA, citric acids) are also reported to cross-link SF chains, producing an increase in the viscosity and in the particle size. The combined effects of these parameters on the micellar and liquid crystalline form of SF chains in liquid phase may be therefore investigated. The morphological analysis of the SF solution may be accomplished with CryoTEM. The use of this technique to analyze regenerated silk solutions may provide a snapshot of the chain conformation and aggregation within the solution in the different conditions proposed. Circular dichroism (CD), dynamic light scattering (DLS), Raman spectroscopy and attenuated total reflectance Fourier transform infrared (ATR-FTIR) spectroscopy may be used to monitor the effects of the aforementioned parameters on SF chain distribution, profile, orientation and structure. Although some studies already described the effect of pH, ionic strength and salt concentration on SF regenerated solution properties, there is a lack of knowledge of the combined effects of these three parameters and their mutual interdependence. Viscosity and surface tension measurements may evaluate the efficacy of the proposed changes. With the exception of CryoTEM, all the instruments necessary to achieve a deep characterization of SF solution are available in house. Transmission electron microscopy may be carried out at the NSF-funded Harvard Center for Nanoscale System (CNS), as for previous studies.

Device Design

The above-described fundamental characterization and optimization of fibroin solution for IJP may build the necessary know-how to cope with the difficulties that occur during hybridization of SF with biofunctional macromolecules to be used as therapeutics (i.e., antibiotics, vaccines) or sensors (glucose oxidase, hemoglobin). Although the incorporation of a large variety of macromolecules in SF solution has been previously reported, little is known on silk-biomacromolecule interactions. The latter may affect the therapeutic compound's stability and functionality, silk structure, and rheological properties of the solution. Indeed these aspects are crucial for the scope of the work and may be investigated during the course of this work.

Based on our previous work, we are able to pursue hybridized silk inks with antibiotics (e.g., penicillin, neomycin, gentamycin, streptomycin, and tetracycline), vaccines (e.g., Merck® M-M-R® II—Measles, Mumps, and Rubella Virus Vaccine), enzymes (glucose oxidase) and growth factors (to control human mesenchymal stem cells (h-MSCs) fate toward osteogenic (ascorbic acid, β-glycerolphosphate and dexamethasone) and chondrogenic (IGF-1, TGF-β) lineages. Such hybridized silk inks may be characterized at three different levels by evaluating the effects of the hybridization on (1) rheological properties of the solution (2) SF chains structure and aggregation, and (3) preservation and functionality of the biofunctional macromolecules incorporated. Successful hybridization may satisfy the criteria of printability while preserving the functionality of the macromolecules incorporated.

The problem may be approached by hybridizing different amounts of any of the above mentioned macromolecule with the current fibroin standard solution for printing. The analysis of the rheological properties of the solution together with the measurement of the particle size may then provide an indication of the printability of the hybrid inks. If the requirements to obtain a printable solution are not met (particularly due to the aggregation of SF chain in the solution to form particles >200 nm), strategies such as the use of additives (e.g., divalent cations), changes in pH, or a reduction in SF concentration may be used, in accordance with the know-how acquired during silk ink development (Paragraph 6.1). The effects of hybridization on the structure of SF in solution may also be characterized with the previously described techniques (FTIR and Raman spectroscopy, CD, DLS). Specific assays may be used to evaluate the stability of the different biofunctional macromolecules in the aqueous SF environment before bio-printing, in accordance with previously developed and adopted protocols. More specifically:

Vaccines:

Two distinct studies have been conducted. i) Stabilization of vaccine in SF solution—This is a fundamental study to investigate the SF chains-vaccine interaction in solution over a prolonged exposure time. The study is preparatory for device-oriented application. SF solution hybridized with increasing amount of reconstituted vaccine may be stored at 4° C., 25° C., and 37° C. for 1, 3, and 7, 14 and 28 days. The stabilization of the trivalent vaccine investigated may be accomplished as regulated by the World Health Organization (WHO): 1) the vaccine should retain at least 1,000 live virus particles in each human dose after incubation at 37° C. for 7 days and 2) virus titer should not decrease by more than 1 $\log_{10}$ during storage. Viral infectivity assay may be used to evaluate vaccine stabilization, by employing RT-PCR, as recently published. As made, printed trivalent vaccine solutions with and without SF may be used as positive controls. ii) printed silk inks that stabilize vaccines and integrate the vaccine reconstitution within the printing process. This is a device-oriented study. As made SF-vaccine solutions with increasing concentrations of vaccine may be printed on different substrates (e.g. plain paper, TCP, and microneedle-silk substrates). The so formed biomaterials may be exposed to increasing temperatures (4° C., 25° C., and 37° C. for 1, 3, and 7, 14 and 28 days). Upon exposure to these conditions, a vaccine-reconstitution ink will then be printed on top of the printed silk-vaccine layers and the aforementioned viral infectivity assay may then be used to evaluate vaccine stabilization. This experiment may cover an interesting future scenario given that the molecules that compose the reconstitution ink are stable in water and may therefore be shipped included in a commercially available inkjet cartridge compatible with most of personal printers and may be subsequently used in situ to reconstitute pre-printed vaccines.

Sensor:

Glucose oxidase, a flavin adenine dinucleotide dependent enzyme (GOD-FAD), may be used to manufacture silk-based glucose sensors. The enzyme shows high substrate specificity for β-d-glucose oxidation with molecular oxygen:

$$\beta\text{-}d\text{-glucose}+\text{GOD-FAD}\rightleftharpoons\text{GOD-FAD}\cdot H_2+\delta\text{-}d\text{-gluconolactone}\ \text{GOD-FAD}\cdot H_2\rightarrow\text{GOD-FAD}+H_2O_2$$

β-d-glucose is oxidized to δ-gluconolactone with concomitant reduction of GOD-FAD. The reduced form of GOD-FAD is regenerated to its oxidized form by molecular oxygen to produce hydrogen peroxide.

Two different sensors have been investigated by exposing the printed biomaterials to known concentration of glucose. First, different concentrations of glucose oxidase (derived from *Aspergillus niger*) can be incorporated in SF solutions and printed on electrodes built on silicon wafers to form sensor arrays. SF has already shown to provide a structural and functional role in interfacing the biological milieu with electrodes and may also serve to immobilize the enzyme. The electric signal generated from the reaction can be monitored by any suitable means.

Secondly, two inks can be used simultaneously. SF-glucose oxidase ink may be co-printed with a silk ink hybridized with peroxidase and a chromogenic system (3,5-dichloro-2-hydroxybenzenesulfonic acid/4-aminoantipyrine). After exposure to glucose, the hydrogen peroxide generated from glucose oxidase reduction may react with the chromogenic system (reaction catalyzed by peroxidase), to generate a pink colorimetric response (intensity as a function of glucose concentration), with an peak absorption at λ=514 nm. The stability of the proposed hybrid solutions may be evaluated as made and after storing them for 1, 3 and 7 days at 4° C. and 22° C. A commercial colorimetric glucose sensor may be used as control.

Antibiotics:

SF solution hybridized with increasing amount of antibiotics may be stored at 4° C., 25° C., 37° C. and 45° C. for 0, 1, 3, 7, 14 and 28 days (tetracyclines may be protected for the whole time from light exposure). Stabilization may be evaluated by printing a pattern with a gradient of antibiotics on tissue culture plastic (TCP) with previously cultured bacteria strains (e.g., *E. Coli* ATCC 25922 and *S. Aureus* ATCC 2593-cultured for 18-24 hours, to an optical density (OD600) between 0.8 and 1 or equivalent to 107-108 CFU/ml). Effectiveness in control of the topographical-selective destruction of bacterial culture may be evaluated by measuring zones of clearance, when compared with positive controls (inkjet-printed fresh antibiotic hybrid inks and antibiotic solutions (without SF) with known concentration of active therapeutic). In addition, as made SF solution hybridized with antibiotics may be printed with a controlled pattern and a biological gradient on gauzes, while bacteria strains may be cultured on a TCP as previously described. The printed gauzes may be then applied to the bacterial cultures and the effectiveness of antibacterial activity may be evaluated by measuring the zones of clearance, when compared to a positive controls (antibiotic solution inkjet printed on gauzes).

Growth Factors:

Different concentrations of osteogenic and chondrogenic growth factors (GFs) were incorporated in SF solution and printed on TCP and on an electrospun silk fibroin (ES-SF) matrices. The printed silk-based biomaterial is water annealed for 6, 12 and 24 hours to induce an increased amount of crystallinity in SF, which corresponds to a slower release of GFs. As preliminary study, the release of GFs in cell culture medium in the presence of physiologically relevant concentration of MMPs were evaluated with specific immunoassays. h-MSCs response to GFs release may be evaluated at days 7, 14 and 21 with RT-PCR. In particular, the total RNA may be extracted from h-MSC-seeded scaffolds with TRIzol® (Invitrogen, Carlsbad, Calif., USA) following the manufacturer's instructions. After RNA separation, nucleic acid concentration and integrity may be determined with an Eppendorf BioPhotometer Plus (Eppendorf, Hamburg, Germany). 250 ng of total RNA may be mixed with 0.25 ng of random hexamers (Invitrogen, Carlsbad, Calif., USA) and reverse-transcribed into complementary DNA (cDNA) with 200 U of Superscript Reverse Transcriptase II (Invitrogen, Carlsbad, Calif.) and RNasin (Promega). Quantitative RT-PCR may be performed with an ABI Prism 7900 HT 139 (Applied Biosystems). Each PCR reaction may contain 9 μl of cDNA, 0.5 μl of both forward and reverse primers (10 μM), and 10 μl of SYBR Green (Applied Biosystems). The cycling conditions may be, for example: 50° C. for 2 minutes, initial denaturation at 95° C. for 10 minutes, and 45 cycles of 15 seconds at 95° C. and 1 minute at 60° C. Relative quantification of target gene expression may be achieved first normalizing to an endogenous reference gene (housekeeping gene GAPDH) to correct different amounts of input RNA, and then relating the expression of the target genes to a reference sample (h-MSCs extracted from relative control without GFs) using the −2ΔΔCt method. h-MSC cultured with standard procedures on TCP may be used as control.

Silk Ink-Substrate Interfaces

As previously stated, the substrate is a vital component of IJP fibroin-based biomaterials. The deposition of silk inks on the substrate may be affected by adsorption, which affects the structural, functional, mechanical and biological properties of the deposited proteins. In addition, different choices of substrate may influence the properties of the biomaterials, bringing unique features to the end product. Several materials are currently under further investigation as silk-based IJP substrates in our laboratory. Among these, are plain paper (used both as a 'standard' substrate and for colorimetric sensing applications), silk-microneedle sheets (for therapeutic and vaccine delivery), silk-based electrospun mats (used for tissue engineering and therapeutics applications), silicon wafers (for microelectronics and biological assays applications), and TCP (for biological applications).

The morphology of the ink-substrate interfaces for all the aforementioned substrates (diagnostics are available in-house) prepared in accordance with the present application can be evaluated using suitable techniques, such as through scanning electron microscopy (SEM), and atomic force microscopy (AFM). In addition, detachment force measurements at the silk ink/substrate interface for different crystallinity of SF-based inks may be investigated through AFM measurements, as previously reported. Characterization of the printed fibroin structure on different substrates may be studied with FTIR and Raman spectroscopy for both neat SF and hybrid silk inks.

Example 2: Keratin Ink

Referring to FIGS. 55 to 59, a keratin-based ink was prepared using wool as a starting material. To prepare delipided wool, the following protocol was used.

Australian Merino 64's top wool (30 g) was rinse in distilled water (6 liters, 30° C.) for 30 minutes (three water changes every 10 minutes), blotted and dried under vacuum for 6 hours. Lipid extraction was then performed with 100% acetone for 24 hours to remove remaining unbound surface lipids. The fibers were then washed (3×) with distilled water (6 liters, 30° C.) for 3 hours (three water changes every 45 min) and air-dried.

The delipided wool fibers were then cut into short fibers, 3 mm long.

A mixture of 7M urea (500 ml), 2-mercaptoethanol (50 ml) and 0.5M thiolurea (50 ml), was used to solubilized 30 g of keratin at room temperature for 24 h. The solution was then filtered through a stainless steel sieve (#200) and dialyzed in dialysis cassettes (3,500 MW cut-off) against distilled water (8 liters) for 72 hours (changed every 6 hours). The so obtained keratin solution was then centrifuged twice (5° C., 9000 rpm, 20 min per cycle). The regenerated keratin solution was then concentrated to 7 wt % (70 mg/ml) through centrifugation in vacuum.

The so obtained regenerated ink was then used for ink jet printing as described before with silk fibroin.

It was observed that the solution of keratin at 6 wt % has substantially the same rheological properties of the one of silk fibroin at the same concentration. The MW of the so obtained keratin is around 40-60 kDa with a second band at 15-20 kDa.

Example 3: Demonstration and Characterization of Silk Fibroin Ink and its Utility in Inkjet Printing (The accompanying document describing this portion of work is incorporated herein by reference in its entirety.)

Project Report: Directly Printing of Silk Fibroin Based Patterns and Devices Using a Commercial Inkjet Printer Fujifilm Dimatix™ DMP 2800 Printer Miaomiao Yang, Biomedical Engineering, Tufts University

1 Introduction and background

Silk is generally considered as a protein polymer that are usually synthesized within specialized glands and then spun into fibers by some Lepidoptera larvae such as spiders, silkworms, mites and flies [1-3]. Silks generated by different species differ widely in composition, structure and their mechanical and chemical properties. In this work, efforts will be focused on the silk generated from the domesticated silkworm, i.e. *Bombyx mori*, partially due to the convenience to the silk source and the extensive experience and knowledge that the Department of Biomedical Engineering at Tufts University has gained in the past two decades.

It is worth mentioning that each of the different silks has a different amino acid composition that further determines the mechanical properties for their specific functions and the forms of the end product such as reproduction as silk cocoons, silk webs, and etc. Even within the "same" type of larvae – for example *Bombyx mori* silkworms - the silkworms from different locations slightly differ. In this work, we mainly discuss the silk fibroin regenerated from the silk cocoons from Japan.

The first use of the silkworm silk for biomedical purposes can be chased back to centuries ago (mainly for silk sutures for wound closure). However, it was found raw silk fibers cause an inflammatory response that was later found to be due to the sericin (a "glue"-like protein that holds silk fibroins to form the cocoon). After careful removal of the sericin [4], the purified silk proteins have been used in many biomedical applications and have proven to be effective in many clinical applications [5].

1.1 Biocompatibility of silk

Silkworm silk fibers have been used in biomedical applications, particularly as sutures for wound ligation. However, some biological responses to the protein were found, which raised questions about the biocompatibility of the protein [6-8]. There have been some difficulties in identifying the exact source that causes the biological responses due to the lack of detailed characterization of the silk fibers prepared under different conditions. The silk from *Bombyx mori* silkworms contains at least two main silk fibroin proteins (i.e. light and heavy chains with the molecular weight of ~ 25 and 325 kDa, respectively) that are encased in a coat of sericin. Later on, it is clear that – based on many studies [9-10] –the sericin glue-like proteins are the major cause of adverse reactions while the core silk fibroin fibers appear to be quite biocompatible and to be comparable to most other commonly used biomaterials [11]. The biocompatibility was evaluated for human mesenchymal stem cells (hMSC) and the inflammatory responses were considerably lower in cells cultured on silk fibroin films as compared to collagen and poly(lactic acid) films [12].

1.2 Structure and properties of silk

A continuous silk thread (with a length over 1 kilometer) can be drawn from a single silk cocoon. The fibroin is a huge molecule consisting of both amorphous region (~1/3, commonly termed as Silk I) and crystalline portion (~2/3, Silk II), as shown in Figure 1.1. Silk I is a water-soluble structure while Silk II excludes waters and is therefore insoluble in water and some other mild acid and alkaline solutions [13].

| | *Bombyx mori* silk worm | | | |
|---|---|---|---|---|
| Silk fiber | Silk fibroin (72-81%) | | | Silk sericin (19-58%) |
| | H chain | L chain | P 25 glycoprotein | a glue-like protein |
| Molecular Weight | 325 kDa | 25 kDa | 25 kDa | ~300 kDa |
| Polarity | Hydrophobic | | | Hydrophilic |
| Structure | silk I(random-coil or unordered structure) silk II(crystalline structure) silk III (unstable structure) | | | non-crystalline structure |
| Function | the structure protein of fibers filament core protein | | | binds two fibroins together coating protein |

Figure 1.1: Structure of silk fibers [13].

The crystalline portion contains repetitive amino acids along its sequence (-Gly-Al-Gly-Ala-Gly-Ser-), resulting in an antiparallel beta sheet. And it is this beta sheet structure that leads to the extraordinary stability and mechanical properties of the fiber such as remarkable strength and toughness. The toughness of silk fibers is found to be even greater than the best synthetic materials, including Kevlar [14]. And in terms of strength, silk is significantly superior to most of commonly used polymeric biodegradable biomaterials such as collagen. A comparison of the mechanical properties of silk and other biodegradable materials is shown in Figure 1.2.

| Source of biomaterial | UTS (MPa) | Modulus (GPa) | Strain (%) at breakage |
|---|---|---|---|
| *Bombyx mori* silk (with sericin) | 500 | 5-12 | 19 |
| *Bombyx mori* silk (without sericin) | 610-690 | 15-17 | 4-16 |
| *Bombyx mori* silk | 740 | 10 | 20 |
| Collagen | 0.9-7.4 | 0.0018-0.046 | 24-68 |
| Cross-linked collagen | 47-72 | 0.4-0.8 | 12-16 |
| Polylactic acid | 28-50 | 1.2-3.0 | 2-6 |

Figure 1.2: Mechanical properties of biodegradable materials [13].

1.3 Regeneration of silk protein from *Bombyx mori* silk fibers

Silk has been processed to a range of biomaterials such as films, gels, fibers and sponges. The starting point of those silk-based materials is the regeneration (alternatively called extraction) of silk fibroin protein from silk fibers. In this section, the regeneration of silk protein (for printable silk ink grade) from *Bombyx mori* silk fibers/cocoons is shown in Figure 1.3 and briefly described as followings:

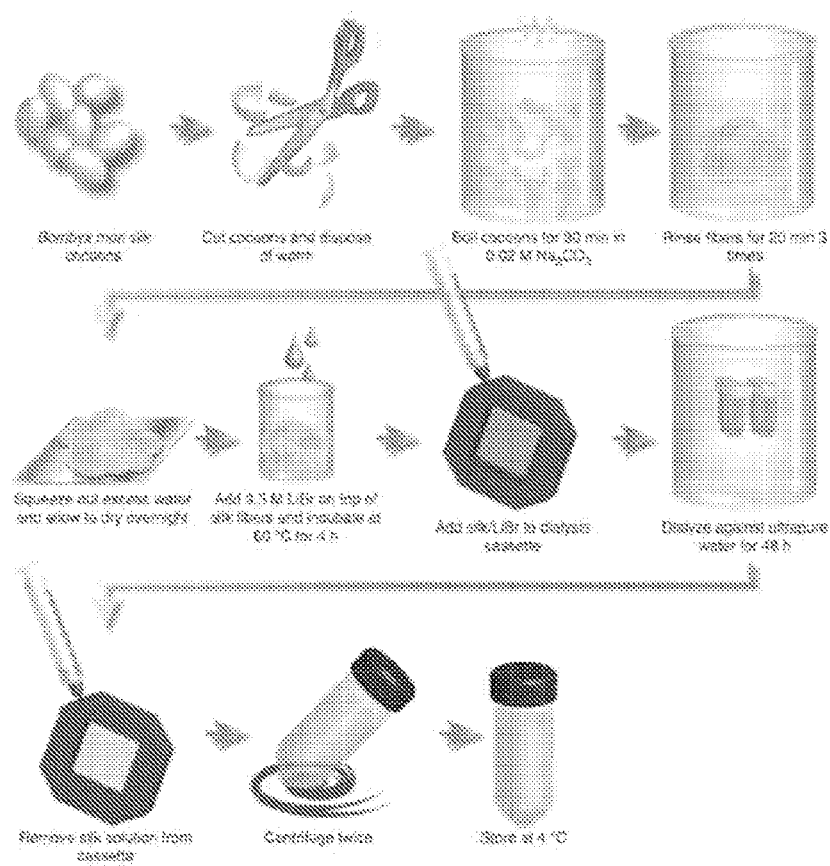

Figure 1.3: Schematic of the silk fibroin extraction procedure [15].

1. Fill a 2 liter glass beaker filled with 2 liters of ultrapure water and heat until boiling;
2. Weigh 4.24 grams of sodium carbonate ($Na_2CO_3$) and add it into 2 liters of ultrapure water prepared in Step 1 (to prepare a 0.02 M solution);
3. Prepare and weigh 5 grams of silk fiber or pre-cut silk cocoon pieces and add it into the boiled $Na_2CO_3$ solution;
4. Boil for 120 min with occasionally stirring;
5. Remove the silk fibroin with a colander and rinse it in ultrapure cold water;
6. Rinse the fibroin in ultrapure water for 20 min;
7. Change the water and repeat step 6 for twice (for a total of three rinses);
8. Remove the silk and then spread it out to dry in a fume hood for 24 hours;
9. Prepare a 9.3 M lithium bromide (LiBr) solution (the volume of LiBr solution equals four times of the weight of the dried silk in gram). For example, for 1 gram of dry silk processed by Step 1-8, prepare 4 mL LiBr solution;
10. Pack silk fibroin tightly into a glass beaker and add the required amount of LiBr solution calculated in Step 9 on top;
11. Put the beaker in an oven at 60 degree C for at least 4 hour;
12. Insert the dissolved silk (in LiBr solution) solution into dialysis cassette for 48 hours. Change the water every 8 hours (for a total of 6 changes);
13. Centrifuge to remove impurities. Spin rate: 9,000 r.p.m. (i.e. ~ 12,700g) at 4 degree C for 1 hour;
14. Store the purified silk solution in a fridge at 4 degree C.

The entire extraction process takes about 4 days. The resulted silk solution can be used for printing as it is or can be doped with appropriate dopants for specific applications.

1.4 Material formats and fabrication methods of silk fibroin protein

The extracted silk fibroin can be further processed into different material formats for a range of potential applications, as shown in Figure 1.4 & 1.5.

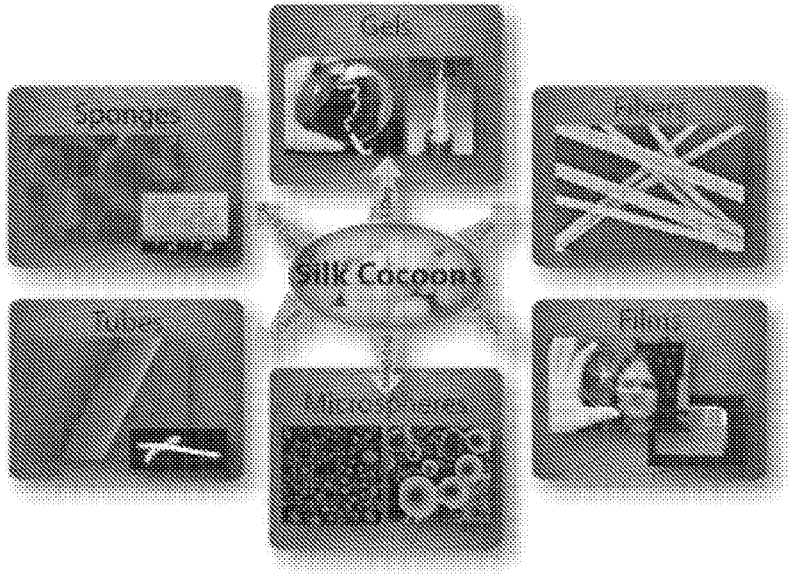

Figure 1.4: Some of the popular material formats that can be processed from extracted silk fibroin [15].

The fabrication methods of some popular silk materials are briefly listed as followings [1]:

Silk gels: One important material option for silk-based biomaterials is the formation of hydrogels. Silk hydrogels can be formed through vortexing (without needing to contact the solution with a probe), sonication (a simple method to produce silk gels), and the application of electrical current (the gelation process is reversible by reversing the polarity of the control voltage).

Silk films: Among those material forms, silk films are of particular interest for bio-optics and bio-photonics applications due to their outstanding transparency and surface smoothness. Silk films can be readily fabricated using both spin-coating process (for extremely thin films with the thickness ranging from a few nanometers to submicron; the thickness can be controlled by adjusting the concentration of the silk solution and spin-coating rate.) and soft-lithograph-like casting process (for films with the thickness of a few microns to hundreds of microns).Furthermore, pouring the silk fibroin solution on to a pre-patterned substrate can reproduce silk films that replicate the patterns on the substrate.

| Application | Tissue type | Material format |
|---|---|---|
| Tissue engineering | | |
| | Bone | HFIP sponges[1,2,3] |
| | | Aqueous sponges[1,2,3] |
| | | Electrospun fibers[b] |
| | Cartilage | HFIP sponges[c] |
| | | Aqueous sponges[a,b] |
| | | Electrospun fibers[a] |
| | Soft tissue | HFIP sponges[a] |
| | | Aqueous sponges[a] |
| | | Hydrogels[a] |
| | Corneal | Patterned silk films[a,b] |
| | Vascular tissues | Tubes[a] |
| | | Electrospun fibers[a,b] |
| | Cervical tissue | Aqueous sponges[a] |
| | Skin | Electrospun fibers[a,b] |
| Disease models | | |
| | Breast cancer | HFIP sponges[a] |
| | | Aqueous sponges[a,b] |
| | Autosomal dominant polycystic kidney disease | Aqueous sponges[a] |
| Implant devices | | |
| | Anterior cruciate ligament | Fibers[a,b] |
| | Femur defects | HFIP sponges[a] |
| | Mandibular defects | Aqueous sponges[a,b] |
| Drug delivery | | |
| | Drug delivery | Spheres[a,b,c] |
| | Growth factor delivery | Spheres[a] |
| | Small molecule | Spheres[a] |

Figure 1.5: Biomedical applications of various silk material formats [15].

Silk sponges: Biomaterials play a key role in tissue engineering. Silk sponges (as a versatile 3D porous scaffolding material) allow cells seeded within or on the matrix and have the advantage of being able to degrade into biocompatible fragments afterwards. Silk fibroin offers versatility in terms of matrix design for a number of tissue engineering needs. Aqueous based porous silk sponges can be fabricated using variable size salt crystals as porogen and manipulating the concentration of silk solution and the salt size.

Silk fibers: Silk fibers (for silk mats) are of particular interest as biomaterials due to the increased surface area and rougher topography that facilitate cell attachment. Silk fibers can be prepared by directly drawing the fibers from silk solution or by electrospinning. Silk fibers can be produced in a wide range of diameters (ranging from a few nanometers to tens of microns).

1.5 Inkjet printing technique and FUJIFILM DMP series printers

It is almost a "no-brainer" to come up with the idea of turning the silk solution into the "ink" for directly printing silk devices using a suitable printer. It is very challenging though since there are certain requirements on the silk as ink. Inkjet printers have grown in popularity and performance – actually, inkjet printers are by far the most popular – since their introduction in the latter half of the 1980s. Compared to laser printers (that use dry ink, also known as toner, static electricity and heat to print), inkjet printers use liquid inks and nozzles (usually multiple nozzles needed) to spray drops of ink directly onto the substrates.

A typical inkjet printer includes: a) print head – that contains a series of nozzles that are used to spray the ink drops; b) ink cartridge – that contains the ink; c) stepper motor – that moves the print head back and forth across the substrate.

It is worth mentioning that nowadays most inkjet printers use piezoelectric nozzle technique for precision printing, which use piezo crystals that vibrate when receive a tiny electric charge. When the crystal vibrates inward and outward, it pulls and forces a tiny amount of ink and sprays it out of the nozzle.

In this work, we use a commercial inkjet printer from FUJIFILM, Dimatix Materials Printer DMP-2800, as shown in Figure 1.6. It uses piezoelectric inkjet technology and MEMS fabrication processes (for cartridges, nozzles and etc.).
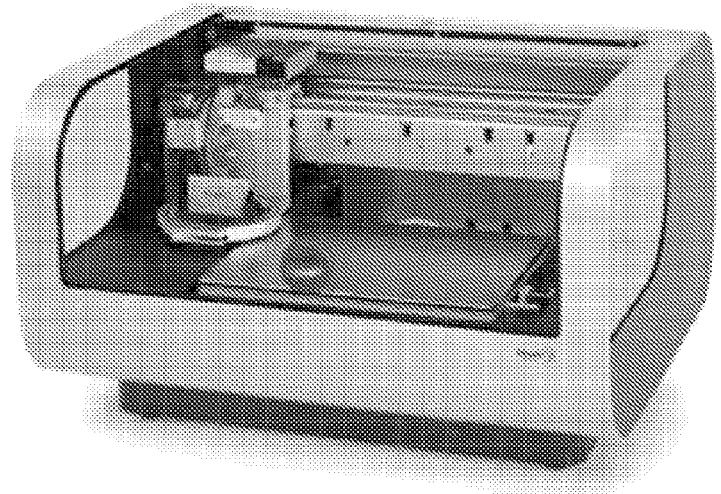
Figure 1.6: FUJIFILM Dimatix Materials Printer DPM-2800 [16].
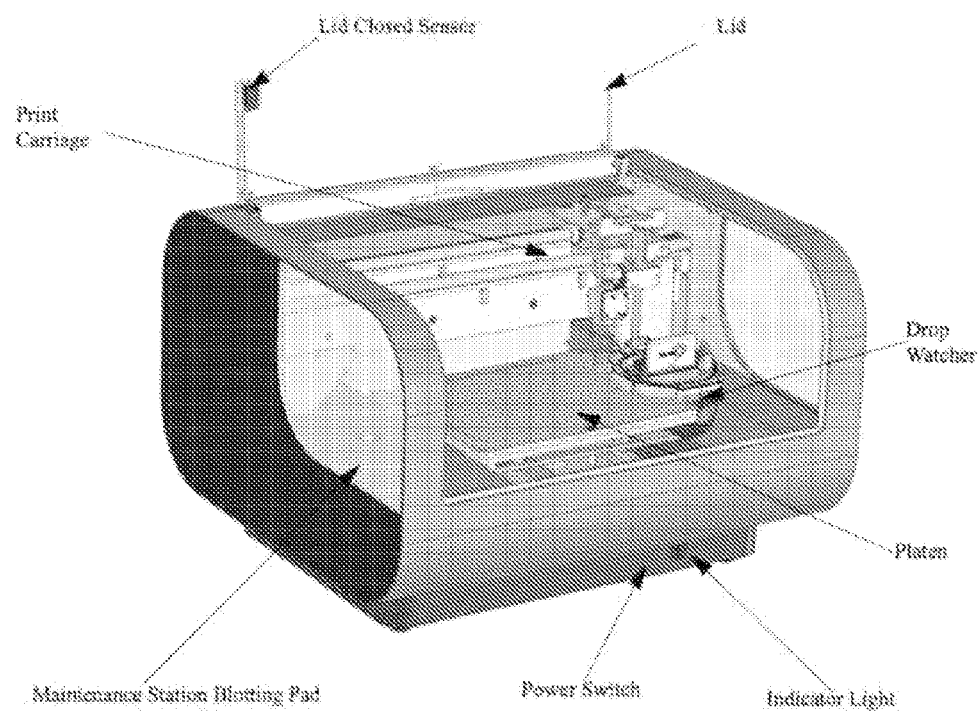
Figure 1.7: The schematic of the key components of DMP 2800 inkjet printer [16].

As shown in Figure 1.7, the DMP-2800 series printer works with a maximum printable area of A4 size substrate (8×11 inch) with a disposable (but reusable with certain modifications/tweaks) piezo inkjet cartridge. The maximum height of printable substrate is up to 25 mm. It also has the ability to heat up the substrate up to 60 degree C. In addition, there is a fiducially camera available allowing real time watching the formation of the drop as it is ejected from the nozzle.

The Dimatix Materials Desktop Printer DMP 2800 is a convenient laboratory tool that enables users (i.e. students, researchers and engineers) to evaluate the use of specific ink (i.e. silk fibroin solution in our case) for new and proof of principle technology development with extensive flexibilities to optimize process parameters for user oriented applications.

In the rest of this section, several typical applications of using DMP 2800 and various types of functional materials and printable inks will be listed.

Printer-compatible substrates:

Paper, Kapton (i.e. polyimide), poyethylene (PET), fabrics (such as cotton, nylon, polyester), metals (such as aluminum foil, copper foil, stainless steel foil and etc.), liquid crystal polymer, palladium, and glass.

Printer-compatible fluids/inks:

Conductive silvers, conductive inorganics (non silver ink, such as ITO inks), conductive organics (such as OLED), single wall carbon nanotubes (SWCNTs), insulators, polyimides, photoresists, resins, and UV curable inks.

For different types of conductive inks, they usually have a wide range of ink properties including viscosity, density, surface tension, and dispersion stability. Therefore, it is necessary to optimize the printer parameters such as the volume of the jetted ink, the gap distance between droplets, the printing frequency, temperatures of the jetted ink and the substrate, and the sintering/curing mechanism performed after printing. One of the most popular applications of using inkjet printer for conductive printing is rapid printing of RFID tags. However, it is a rather challenging endeavor since precise control of the desired conductivity and pattern designs (on non-perfect substrates, for example, on non-glossy rough papers).

Unlike the traditional photolithograph and etching PCB fabrication process (which is a subtractive method by removing undesired metal from the substrate surface), conductive inkjet printing for RF applications jets the single conductive ink droplet from the nozzle to pre-defined position (usually controlled by computer and a precise motor stepper) – therefore, no harsh chemicals as the etching waste created –resulting in an economical and ecological fabrication solution. Silver nano-particle inks are and usually selected and commonly used for good metal conductivity. As mentioned above, a sintering process either by applying heat or UV exposure (to remove excess solvent and to remove material impurities) is usually needed, which also enhance the bond strength between the ink and the as-printed substrate. Note that an immediate sintering process is essential, because the silk ink begins to oxidize that would render the conductivity of efficiency of the metallic patterns.

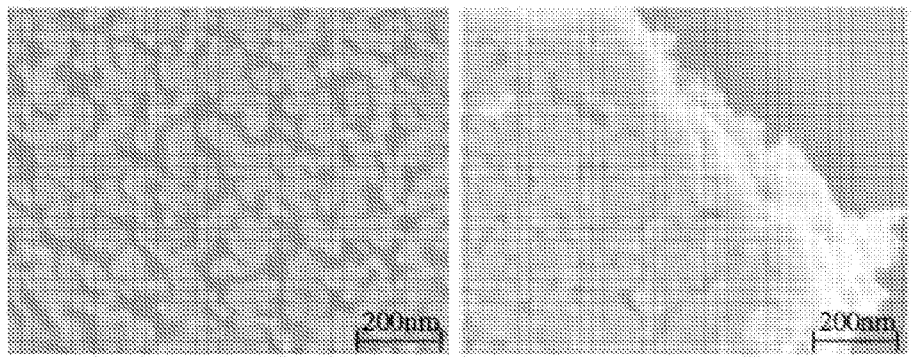

Figure 1.8: SEM images of inkjet printed silver nanoparticle ink before and after sintering at 100 degree C for 15 minutes [17].

As shown in Figure 1.8, there are gaps between printed silver nanoparticles after printing, resulting in a poor connection and therefore not conductive. After 15 minutes of heating/curing process, the particles begin to aggregate and gaps start to diminish, which forms a continuous metal film and guarantees a good conductor, which determines the performance of the printed electric devices (e.g. RFID tags, as shown in Figure 1.9).

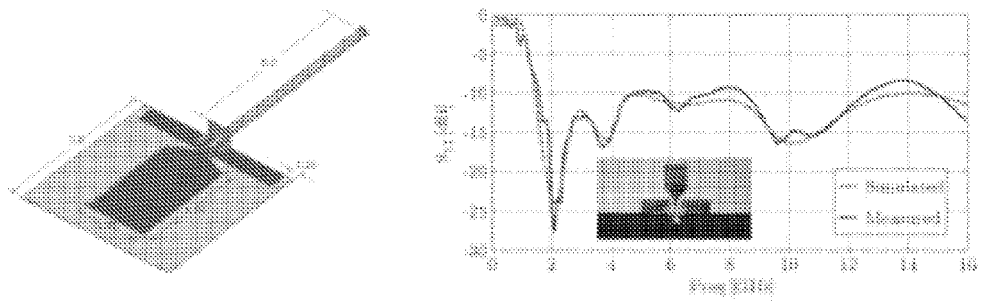

Figure 1.9: An example of inkjet printed RFID tag with a working frequency at 2GHz [18].

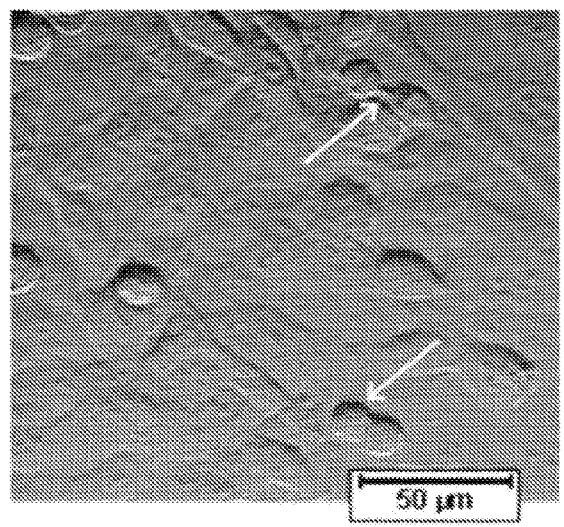

Figure 1.10: SEM image showing human fibrosarcoma cells after inkjet printing [19].

Another arena of inkjet printing technique is so called "bioprinting", which requires micro level (and in many cases, nano level) liquid manipulation. The typical applications include micro-dosing, biochemical surface patterning and modification, tissue engineering and importantly the direct placement of living cells, DNA arrays, and proteomics [19]. Questions have been raised on the influence of mechanical forces and relatively intense electric field during the inkjet process on the cells and some research reports showed that although some cell death may occur, surviving cells recover rapidly and seem to behave normally, as shown in Figure 1.10.

2 Working principle of Dimatix Materials Printer

We use DMP-2800 inkjet printer from FUJIFILM Dimatix, Inc to directly print regenerated silk fibroin protein. The DMP-2800 printer can create your own patterns and load BMP patterns over an area of about 200*300mm. The printer allows the substrates up to 25mm thick with an adjustable Z height. It also includes 16 piezo-based jetting nozzles at 254 μm spacing and a fillable cartridge. In this way, we invent a method to regenerate silk fibroin protein as the ink to match specific fluid requirement of this printer. The printed silk protein is biocompatible and can be further functionalized by mixing the silk ink with appropriate dopants (including both organic and inorganic ones) for specific applications.

2.1 Dimatix Materials Printer 2800 Operation

The DMP-2800 is a powerful laboratory tool which has capabilities to allow user to optimize process parameters, like nozzle voltage, substrate height, and wave form. Different from other commercial printer, DMP-2800 provides multi-layer printing and allows alignment process when using multiple cartridges and matching the origin point on the substrate. To brief introduce the operation of the printer, the process includes creating pattern, loading ink, setting printing permanents.

2.1.1 Create pattern

The DMP software only accepts DMP files or let you create patterns using Pattern Editor. Pattern Editor allows you to modify pattern of drops for printing, so it is good for some fine and small scale patterns, for example, patterns from Figure 2.1. However, it takes a long time to create a complex structure pattern for printing. Patterns like Figure 2.2, you need transform to BMP file first, and then import them to DMP software.

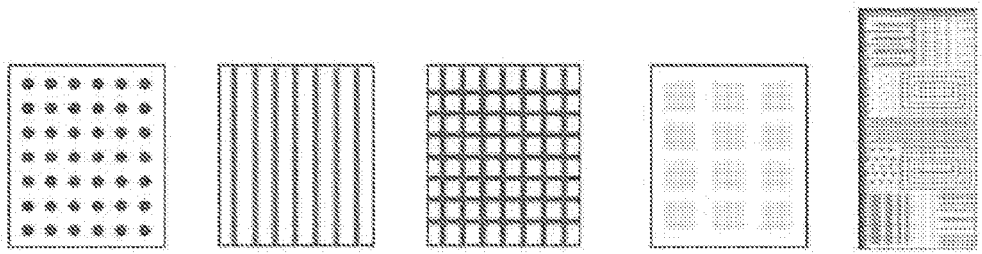

Figure 2.1: patterns for Pattern Editor [19].

2.1.1.1 BMP pattern import

To print a fine pattern, first make a high resolution original file before you transform it to BMP file, because the DMP soft ware only allow you import an monochrome Bitmap file which is quite low resolution file. After creating Bitmap pattern, selecting Pattern Editor (Bitmap images) from the DDM main window and choosing a drop space size which depends on your ink and substrate before importing the Bitmap file. Double check the final size of the pattern. If the final size is not your exception, you can adjust the final size by changing the pattern size in Bitmap file, then reloading your pattern. And repeat your pattern by controlling the placement number.

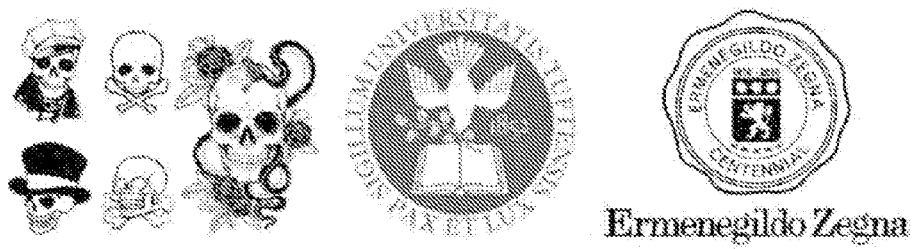

Figure 2.2: Patterns for BMP pattern editor.

2.1.1.2 Create user's own patterns

Select Tools on the DDM main window, click Pattern Edition. It will allows you to create your pattern by enter dimension on Pattern Block Drop Positions. On the other way, you can draw a feature through Preview Drops Window. Before you create your pattern, you still need choose the size of Drop Spacing which is the center to center distance from one drop to the next. For a normal silk drop is about 25μm on hydrophilic surface, like silicon wafer.

2.1.2 Loading Cartridge

The ink which you fill into the cartridge need go through 0.22 μm filter first, because the size of a nozzle is 26 μm and the volume of a drop is 10pL. It means the nozzle is easy clogged by particle size larger than 0.22 μm. After loading new cartridge onto the printer, change the clean pad for new ink due to not contaminating by other chemicals. After loading your cartridge, select the pattern you want to print from the Select Pattern. The system will automatic calculate the Cartridge Mounting Angle determined by drop spacing specified in the pattern. Here is a table (Table 2.1) to compare the relation of saber angle, resolution, and drop spacing.

2.1.3 Setting parameter for printing

Click the Drop Watch button, the system will move the cartridge to the right side of the platen, positioning the nozzles over the drop watcher camera system. First, select the range of nozzles you wish to jet your pattern. Second, modify the nozzles to performance uniform by adjusting voltage of those nozzle monitored by camera. Another important parameter should be set up carefully is the cartridge print height according to the substrate thickness. If the substrate thickness is less than 0.5mm, the printable range is 210mm*315mm. If the substrate thickness is between 0.5mm to 25mm, the printable range is 210mm*260mm. And the repeatability distance is ±25μm. The last step before printing is alignment process through Fiducial Camera from the tools menu on the DDM window. First, calibrate the position of a new cartridge or head angle by setting the Drop Offset automatic or manual from tools menu. Second, set the printing origin point and reference point for multiple layers printing.

Table 2.1 Resolutions relationships

| Resolution [dpi] | Saber angle [°] | Drop spacing [µm] | Resolution [dpi] | Saber angle [°] | Drop spacing [µm] |
|---|---|---|---|---|---|
| 5080.00 | 1.1 | 5 | 188.15 | 32.1 | 135 |
| 2540 | 2.3 | 10 | 181.43 | 33.4 | 140 |
| 1693.33 | 3.4 | 15 | 175.17 | 34.8 | 145 |
| 1270.00 | 4.5 | 20 | 169.33 | 36.2 | 150 |
| 1016.00 | 5.6 | 25 | 163.87 | 37.6 | 155 |
| 846.67 | 6.8 | 30 | 158.75 | 39.0 | 160 |
| 725.71 | 7.9 | 35 | 153.94 | 40.5 | 165 |
| 635.00 | 9.1 | 40 | 149.41 | 42.0 | 170 |
| 564.44 | 10.2 | 45 | 145.41 | 43.5 | 175 |
| 508.00 | 11.4 | 50 | 141.11 | 45.1 | 180 |
| 461.82 | 12.5 | 55 | 137.30 | 46.7 | 185 |
| 423.33 | 13.7 | 60 | 133.68 | 48.4 | 190 |
| 390.77 | 14.8 | 65 | 130.26 | 50.1 | 195 |
| 362.86 | 16.0 | 70 | 127.00 | 51.9 | 200 |
| 338.67 | 17.2 | 75 | 123.90 | 53.8 | 205 |
| 317.50 | 18.4 | 80 | 120.95 | 55.8 | 210 |
| 298.82 | 19.6 | 85 | 118.14 | 57.8 | 215 |
| 282.22 | 20.8 | 90 | 115.45 | 60.0 | 220 |
| 267.37 | 22.0 | 95 | 112.89 | 62.4 | 225 |
| 254.00 | 23.2 | 100 | 110.43 | 64.9 | 230 |
| 241.90 | 24.4 | 105 | 108.09 | 67.7 | 235 |
| 230.91 | 25.7 | 110 | 105.83 | 70.9 | 240 |
| 220.87 | 26.9 | 115 | 103.67 | 74.7 | 245 |
| 211.67 | 28.2 | 120 | 101.60 | 79.8 | 250 |
| 203.20 | 29.5 | 125 | 100.00 | 90 | 254 |
| 195.38 | 30.8 | 130 | | | |

2.2 Cartridge Parameter Setting

To optimize drop performance, there are some parameters need be set up precisely. The main parameter includes nozzles voltage, nozzle temperature, meniscus set point, cleaning cycles, and waveform.

2.2.1 Nozzles Voltage

Clicking on the Edition button the cartridge setting box, the follow screen displays. The voltage of each nozzle can be individual adjusted, as shown in Figure 2.3. Increasing voltage will increase drop volume and jetting velocity. And a good velocity to be set is 7-9m/sec.

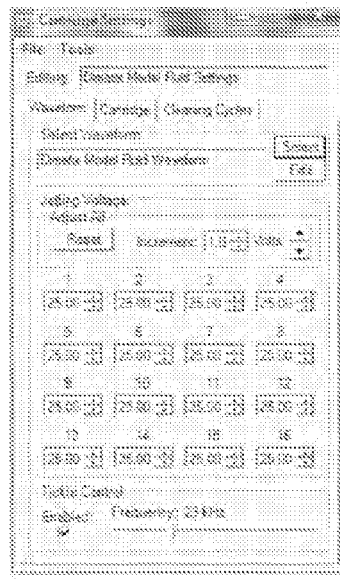

Figure 2.3: Cartridge setting screen- voltages setting.

2.2.2 Nozzles Temperature, Meniscus Set point, Nozzle Number, Print Height

Clicking on the cartridge tab in the Cartridge Settings, you can adjust nozzles temperature, meniscus set point, nozzle number and print height.

We can lower the ink viscosity and surface tension by increasing nozzle temperature. The printer allows you to adjust nozzle temperature from 28 degree C to 70 degree C, as shown in Figure 2.4. A good viscosity of printing ink is 10-12 centipoises and a good surface tension of printing ink is 28-44 dynes/cm.

Meniscus Vacuum is a negative pressure for keeping the meniscus at the edge of nozzle. Change the value of meniscus vacuum depends on the viscosity and surface tension of the ink. The typical meniscus vacuum value of water is 4 inches. If the meniscus vacuum number is not correct, it would affect the performance of ink with high frequency.

Choose the number of nozzles to print, and the system will automatically compensates for the number of nozzles used but the nozzles selected can only be one series of adjacent nozzles. The printer has drop watch camera which allows you to real time monitor drop performance. In this way, the camera will help you to make sure the nozzles you choose performance uniform.

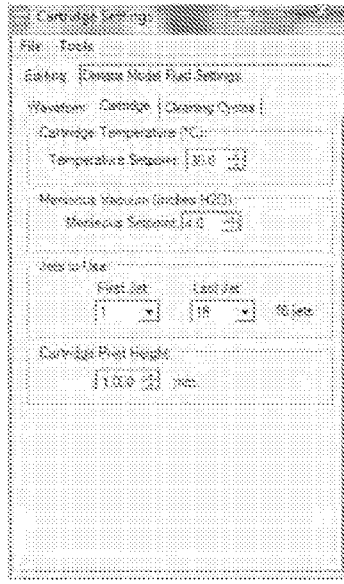

Figure 2.4: Cartridge Settings Cartridge Tab.

2.2.3 Cleaning Cycles

The cleaning cycle table lets you setting nozzles cleaning process before, during and after printing. Setting cleaning cycle before printing gives a uniform start every running. Cleaning cycle is very import for some high viscosity, because setting cleaning cycle during printing prevents the ink from clogging. And Setting cleaning cycle after printing help you maintenance nozzles, as shown in Figure 2.5.

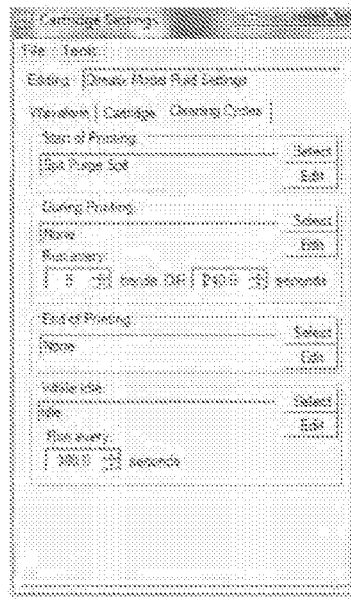

Figure 2.5: Cartridge Settings Cleaning Cycles Tab.

2.2.4 Waveform

The DDM software has a standard 4 steps waveform which is good for normal ink (viscosity: 11-12 centipoises; surface tension: 28-32 dynes/cm). The 4 steps include start, phase 1, phase 2, and phase 3. The basic idea for those 4 steps is use a bias voltage to control piezo to suck a drop of ink and jet it with a controlled velocity.

2.2.4.1 Waveform Start

At standby point, the voltage of nozzle sets to 40% level and holds it for 1μs. Under this condition, the channel which is piezo basic slightly deflected and sucks some ink from cartridge starting to eject, as shown in Figure 2.6.

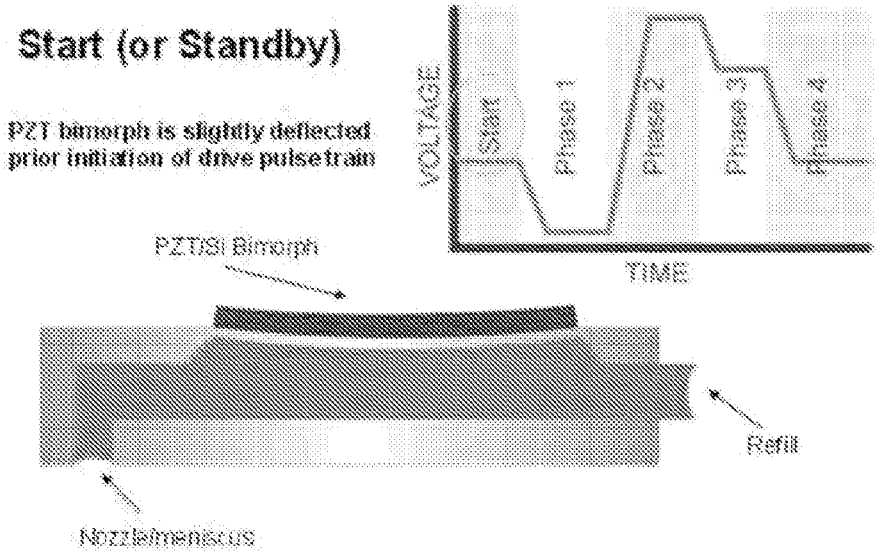
Figure 2.6: Waveform-starts.
2.2.4.2 Waveform Phase 1
At the phase 1, set the voltage level to 0 and hold it for 3.584µs. The voltage brings the piezo back to a neutral straight position with chamber at its maximum volume. In this phase, the fluid is filled into chamber. From the Figure 2.7, it shows meniscus at the nozzle edge.
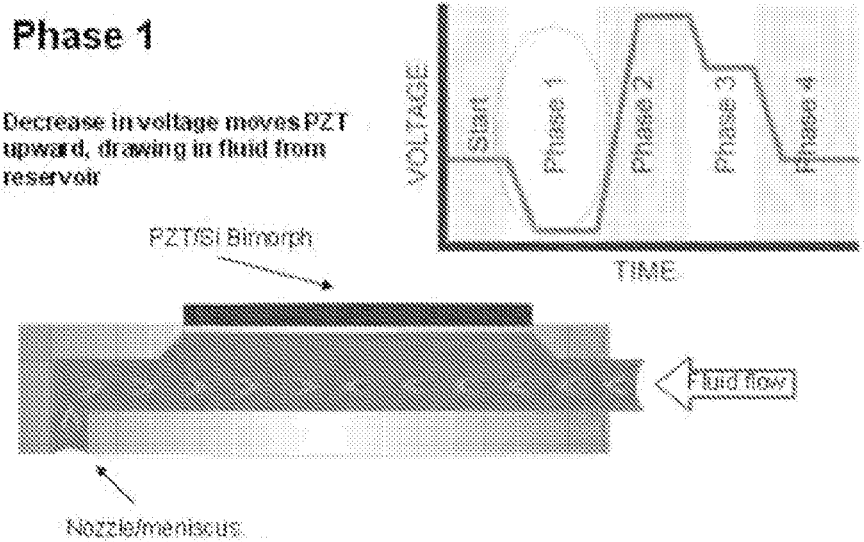
Figure 2.7: Waveform- Phase 1.

2.2.4.3 Waveform Phase 2

The phase 2 is firing pulse, as shown in Figure 2.8. The steepness of the slope provides the energy for initial ejection and it is followed by a hold period. On the hold period, the voltage increases to 100% level and holds it for 3.712μs. A this point, the chamber starts to jet a drop of ink. According to the hold time and voltage volume, the velocity of a drop can be calculated.

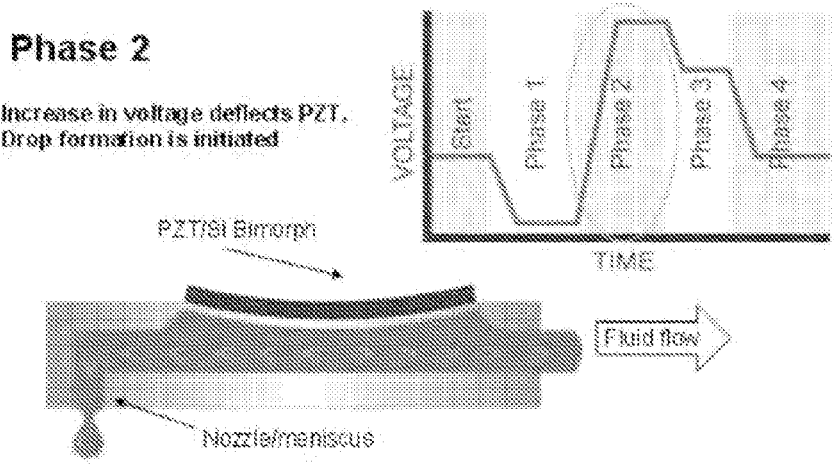

Figure 2.8: Waveform- Phase 2.

2.2.4.4 Waveform Phase 3

The last phase of the waveform is return to standby, as shown in Figure 2.9. First, the voltage level decreases to 70% and hold it for 3.392 μs that is designed for prevent the printed head from sucking air back in. Second, the voltage level brings to 40% level and chamber back to the standby position.

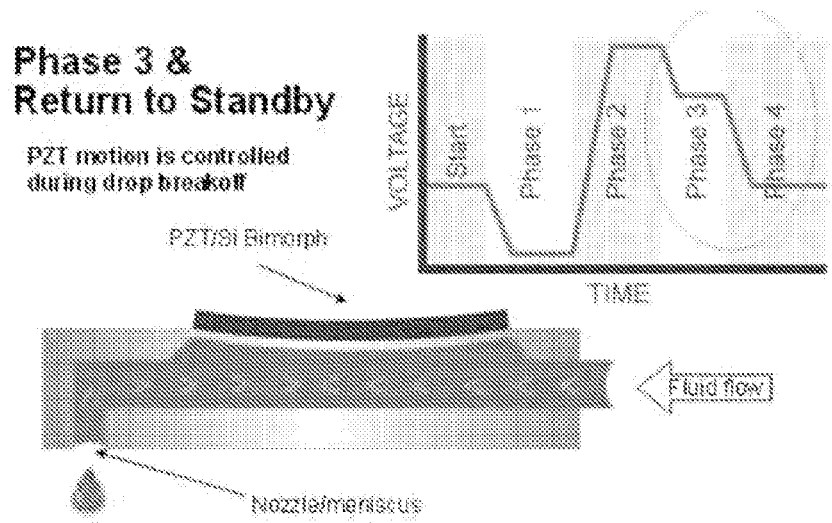
Figure 2.9: Waveform-Phases 3.
2.3 Conclusion
Those parameters what have be mentioned above play an important role during printing. They should be checked every printing running according to the ink material of substrate. Also ink condition has been slight changed according to room temperature and humidity level.

3 Silk inks

There are two kinds of ink including solvent based ink and water based ink. Solvent based ink usually contains some poisonous chemical material. And silk is processed in an all water-based, room temperature, neutral pH environment, is mechanically stable, edible, biocompatible, and implantable in the human body. Given the favorable material properties, the use of silk-based inks can be important for a variety of controlled chemical and biological material fabrication on the micro-and nano- scale.

3.1 Water based inks

The majority of inkjet printers use water based inks. While every manufacturer has its own ink formulations with specific chemical constituents, the main components in water based inks are similar. The table below describes the components that comprise water-based ink.

Table 3.1 Components in water based ink [20]

| Component | Function | Concentration, % |
|---|---|---|
| water | Aqueous carrier medium | 60 - 90 |
| Water soluble solvent | Humectants, viscosity control | 5 - 30 |
| Dye or pigment | Provides color | 1 - 10 |
| Surfactant | Wetting, penetrating | 0.1 - 10 |
| Buffer | Controls the pH of ink | 0.1 - 0.5 |
| Other additives | Chelating agent, defoamer | >1 |

3.1.1 Humectants

The role of the humectants is to preserve the water content in ink, so that it does not clog and dry out print head nozzles. People usually use glycerol, ethylene glycol as the humectants in the water based ink.

3.1.2 Surfactant

Surface tension is the main parameter for water based ink, because distilled water has a very high surface tension (70 dynes/cm). But the ideal value of surface tension for inkjet printer to print is 28-44 dynes/cm. A high surface tension ink will not wet the nozzle, so that the ink will not travel through the nozzle. Under this condition, the ink will clop the nozzle. Furthermore, high surface tension will cause the ink not wet the substrate and result in uneven patterns on the substrate. But the low surface tension ink also causes some problem. Low surface tension induces fluid leaking from the nozzles. Surface tension of the liquid drives the fluid into a spherical shape in order to reach minimum surface area, minimum energy state. The higher the surface tension, the faster the fluid changes to a sphere. Adding just 1.34% of a surfactant, P103 (BASF, USA) decreases the surface tension of water from 69.5 dynes/cm to 33 dynes/cm at 20°C [21]. Increasing the surfactant to 5% has no effect on surface tension; the measured value was still 33 dynes/cm [21].

3.1.3 Viscosity adjuster

Viscosity is a physical property that is often manipulated to make jet-able fluids. Viscosity is the reciprocal of fluidity and indicates resistance to flow. The flow speed decreases as viscosity increases. Temperature increases fluid flow in Newtonian fluids. When a force is applied to a volume of material, then displacement (deformation; i.e. flow) occurs. In ambient pressure, low temperatures push fluids towards their ordered state, and as fluids become more ordered, they also increase in viscosity. On the other hand, heat can be applied to decrease apparent viscosity (increase fluidity), and the DMP ink jet print head contains a heater thereby increasing the jettability window for viscous fluids. The ideal viscosity for inkjet printer to print is 11 centpoises and the viscosity of water at room temperature is 1 centipoises. Polyvinyl alcohol and glycerol add to water based ink as the viscosity to increase the viscosity. Viscosity adjuster keeps ink at proper thickness so that it can be jetted smoothly and stabile.

3.1.4 Buffer

The role of the buffer is to maintain the PH level in the ink.

3.2 Fluid Requirement for Dimatix Materials Printer

Some ink physical characteristics to achieve optimum performance are [19]:

* Viscosity – 10-12 centipoises at jetting temperature
* Surface Tension – 28-44 dynes/cm at jetting temperature
* Low Volatility – Boiling points higher than 100° C are preferred
* Density – Specific gravity greater than 1 is beneficial
* Degassing – Additionally the fluid may need to be degassed to remove any dissolve gas which inhibits jetting. Typical degassing can be done with a vacuum (A negative pressure of 2 psi for 1-2 hours maybe sufficient or up to only 50mbar).
* Filtration – If particle size allows, it is recommended to filter all fluids to 0.2µm.
* Acidity or Alkalinity – A pH-value between 4 and 9 is recommended.

Note: The parameter of viscosity and surface tension is a pair of combine parameter. Fluid with surface tension higher than 44 combines with viscosity lower than 10 also works for DMP 2800 printer by modifying the waveform.

3.3 Silk fibroin ink

In order to go through the 0.2µm filter, we developed a new method to make a low molecular weight silk solution which can easy go through 0.2µm filter.

3.3.1 Method for Manufacturing High Temperature, High pressure Silk

Example: for ~ 40 mL of silk solution with a concentration of ~ 6.25 % (wt/vol), if more volumes are needed, the materials can be scaled appropriately.

1) Cut *Bombyx mori* silk cocoons (10 gram) into half-dime-sized pieces and dispose of silkworms;

2) Measure 8.48 gram of sodium carbonate and add it into 4 liter of water in a 5 liter glass beaker (to prepare a 0.02 M solution);

3) Put the beaker into an autoclave and set the autoclave to run at 121 degree C under the pressure of 16 psi for 120 minutes;

4) Remove the silk fibroin with a strainer and cool it by rinsing in ultrapure cold water for 20 minutes and repeat twice for a total of three rinses;

5) After the third rinse, remove the silk fibroin and squeeze the water;

6) Spread the squeezed silk fibroin, spread it out and let it dry in a fume hood for 12 hours, which results in silk fibroin weighing slightly over 2.5 gram;

7) Dissolve 2.5 gram of silk fibroin into 10 mL of 9.3 M lithium bromide;

8) The silk fibroin should dissolve completely in a few minutes upon stirring;

9) Insert 10 mL of the silk-LiBr solution into a pre-wet 3-12-mL dialysis cassette and dialyze against 1 liter of ultrapure water for 48 hours (change the water every 6 hours);

10) Remove silk from the cassette;

11) Place the silk solution in a centrifuge and spin at 9,000 r.p.m. at 2 degree C for 60 minutes, and store the centrifuged silk solution (~ 40 mL of silk solution with a concentration of ~ 6.25 %) in a refrigerator at 4 degree C.

3.3.2 Silk Ink Preparation

One important property Silk solution is that silk is easy getting β sheet when it is mixed with surfactant and viscosity adjuster. So, we just add surfactant, like Tween 20, to silk solution. To increase the viscosity, adjust the waveform to compensate the viscosity.

Example: for ~ 2 mL of silk fibroin protein ink, if more volumes are needed, the materials can be scaled appropriately.

Mix the silk solution with surfactant (for example, Tween 20 from Sigma-Aldrich Co.) and water in a volume ratio of 17:2:1 (i.e. 1700 μL of ~ 6.25% silk fibroin solution, 200 μL of Tween 20 and 100 μL of water);

Note that the ratio of the mixture is optimized for Tween 20 and other biological or chemical surfactant (for example, glycol, ether, and etc.) can be also used with modifications of the mixture ratio. Surface treatment of the printing nozzle(s) can also improve the formation of silk ink drops.

3.3.3 Surface Tension Measurement

Here are two tables for surface tension measurement of pure high temperature silk solution and it mixed with surfactant.

Table 3.2 Surface Tension of Pure high temperature Silk Solution

| No. | Time | Gamma | Beta | R0 | Area | Volume | Theta | Height | Width |
|---|---|---|---|---|---|---|---|---|---|
| 1 | 0.0 | 46.83 | 0.261 | 1.118 | 19.67 | 8.20 | 109.48 | 3.014 | 2.350 | 2 |
| 2 | 0.1 | 46.81 | 0.261 | 1.118 | 19.67 | 8.20 | 109.45 | 3.015 | 2.349 | 2 |
| 3 | 0.2 | 46.80 | 0.262 | 1.119 | 19.68 | 8.20 | 109.36 | 3.016 | 2.350 | 2 |
| 4 | 0.3 | 46.80 | 0.262 | 1.119 | 19.68 | 8.20 | 109.29 | 3.018 | 2.350 | 2 |
| 5 | 0.4 | 46.78 | 0.262 | 1.119 | 19.68 | 8.21 | 109.23 | 3.018 | 2.350 | 2 |
| 6 | 0.4 | 46.79 | 0.262 | 1.119 | 19.69 | 8.21 | 109.16 | 3.019 | 2.350 | 2 |
| 7 | 0.6 | 46.78 | 0.262 | 1.119 | 19.69 | 8.21 | 109.09 | 3.020 | 2.351 | 2 |
| 8 | 0.6 | 46.76 | 0.262 | 1.119 | 19.70 | 8.21 | 109.03 | 3.021 | 2.351 | 2 |
| 9 | 0.8 | 46.77 | 0.262 | 1.119 | 19.70 | 8.21 | 108.93 | 3.022 | 2.351 | 2 |
| 10 | 0.8 | 46.75 | 0.262 | 1.119 | 19.71 | 8.22 | 108.84 | 3.023 | 2.351 | 2 |
| 11 | 0.9 | 46.78 | 0.262 | 1.119 | 19.71 | 8.22 | 108.92 | 3.023 | 2.351 | 2 |
| 12 | 1.0 | 46.75 | 0.262 | 1.119 | 19.71 | 8.22 | 108.79 | 3.024 | 2.351 | 2 |
| 13 | 1.1 | 46.74 | 0.262 | 1.119 | 19.71 | 8.22 | 108.76 | 3.025 | 2.351 | 2 |
| 14 | 1.3 | 46.71 | 0.262 | 1.119 | 19.71 | 8.22 | 108.66 | 3.026 | 2.351 | 2 |
| 15 | 1.3 | 46.69 | 0.262 | 1.119 | 19.72 | 8.22 | 108.58 | 3.027 | 2.351 | 2 |
| 16 | 1.4 | 46.67 | 0.262 | 1.119 | 19.72 | 8.22 | 108.54 | 3.028 | 2.351 | 2 |
| 17 | 1.6 | 46.67 | 0.262 | 1.119 | 19.72 | 8.22 | 108.52 | 3.028 | 2.351 | 2 |
| 18 | 1.6 | 46.65 | 0.262 | 1.118 | 19.72 | 8.22 | 108.44 | 3.029 | 2.351 | 2 |
| 19 | 1.8 | 46.66 | 0.262 | 1.119 | 19.72 | 8.22 | 108.45 | 3.029 | 2.351 | 2 |
| 20 | 1.9 | 46.63 | 0.262 | 1.119 | 19.72 | 8.22 | 108.33 | 3.031 | 2.351 | 2 |
| 21 | 2.0 | 46.65 | 0.262 | 1.119 | 19.73 | 8.22 | 108.35 | 3.030 | 2.351 | 2 |
| 22 | 2.1 | 46.62 | 0.263 | 1.119 | 19.73 | 8.22 | 108.28 | 3.031 | 2.351 | 2 |

Opt Messages

| | | | | | | | | | | |
|---|---|---|---|---|---|---|---|---|---|---|
| 23 | 2.1 | 46.64 | 0.262 | 1.119 | 19.73 | 8.22 | 108.19 | 3.032 | 2.351 | 2 |
| 24 | 2.3 | 46.54 | 0.263 | 1.118 | 19.73 | 8.22 | 108.02 | 3.034 | 2.350 | 2 |
| 25 | 2.3 | 46.61 | 0.263 | 1.119 | 19.73 | 8.22 | 108.13 | 3.032 | 2.351 | 2 |
| 26 | 2.4 | 46.58 | 0.263 | 1.118 | 19.73 | 8.22 | 108.06 | 3.034 | 2.350 | 2 |
| 27 | 2.5 | 46.59 | 0.263 | 1.118 | 19.74 | 8.22 | 108.01 | 3.034 | 2.351 | 2 |
| 28 | 2.7 | 46.57 | 0.263 | 1.118 | 19.74 | 8.23 | 107.98 | 3.035 | 2.350 | 2 |
| 29 | 2.8 | 46.55 | 0.263 | 1.118 | 19.74 | 8.22 | 107.91 | 3.036 | 2.350 | 2 |
| 30 | 2.8 | 46.54 | 0.263 | 1.118 | 19.74 | 8.22 | 107.86 | 3.036 | 2.350 | 2 |
| 31 | 2.9 | 46.53 | 0.263 | 1.118 | 19.74 | 8.23 | 107.86 | 3.036 | 2.351 | 2 |
| 32 | 3.1 | 46.56 | 0.263 | 1.118 | 19.74 | 8.23 | 107.84 | 3.037 | 2.350 | 2 |
| 33 | 3.2 | 46.51 | 0.263 | 1.118 | 19.75 | 8.23 | 107.76 | 3.038 | 2.351 | 2 |
| 34 | 3.3 | 46.56 | 0.263 | 1.119 | 19.75 | 8.23 | 107.82 | 3.037 | 2.351 | 2 |
| 35 | 3.3 | 46.52 | 0.263 | 1.118 | 19.75 | 8.23 | 107.68 | 3.039 | 2.351 | 2 |
| 36 | 3.5 | 46.53 | 0.263 | 1.118 | 19.75 | 8.23 | 107.71 | 3.039 | 2.351 | 2 |
| 37 | 3.5 | 46.51 | 0.263 | 1.118 | 19.75 | 8.23 | 107.66 | 3.039 | 2.351 | 2 |
| 38 | 3.7 | 46.49 | 0.263 | 1.118 | 19.75 | 8.23 | 107.58 | 3.040 | 2.351 | 2 |
| 39 | 3.7 | 46.51 | 0.263 | 1.118 | 19.75 | 8.23 | 107.63 | 3.040 | 2.351 | 2 |
| 40 | 3.8 | 46.49 | 0.263 | 1.118 | 19.76 | 8.23 | 107.48 | 3.041 | 2.350 | 2 |
| 41 | 4.0 | 46.49 | 0.263 | 1.118 | 19.76 | 8.23 | 107.53 | 3.041 | 2.351 | 2 |
| 42 | 4.0 | 46.48 | 0.263 | 1.118 | 19.76 | 8.23 | 107.50 | 3.041 | 2.351 | 2 |
| 43 | 4.1 | 46.48 | 0.263 | 1.118 | 19.76 | 8.23 | 107.45 | 3.041 | 2.350 | 2 |
| 44 | 4.2 | 46.48 | 0.263 | 1.118 | 19.76 | 8.23 | 107.43 | 3.042 | 2.351 | 2 |
| 45 | 4.3 | 46.48 | 0.263 | 1.118 | 19.76 | 8.23 | 107.42 | 3.042 | 2.350 | 2 |
| 46 | 4.5 | 46.45 | 0.263 | 1.118 | 19.76 | 8.23 | 107.28 | 3.043 | 2.350 | 2 |
| 47 | 4.5 | 46.43 | 0.263 | 1.118 | 19.76 | 8.23 | 107.30 | 3.043 | 2.350 | 2 |
| 48 | 4.7 | 46.45 | 0.263 | 1.118 | 19.76 | 8.23 | 107.36 | 3.042 | 2.350 | 2 |
| 49 | 4.7 | 46.44 | 0.263 | 1.118 | 19.76 | 8.23 | 107.30 | 3.043 | 2.350 | 2 |
| 50 | 4.8 | 46.43 | 0.263 | 1.118 | 19.76 | 8.23 | 107.14 | 3.045 | 2.350 | 2 |
| Mean: | | 46.61 | 0.263 | 1.118 | 19.73 | 8.22 | 108.19 | 3.032 | 2.350 | |
| Stand.dev. | | 0.02 | 0.000 | 0.000 | 0.00 | 0.00 | 0.09 | 0.001 | 0.000 | |

Table 3.3 Surface Tension of high temperature Silk Solution Mix with 10% surfactant

| No. | Time | Gamma | Beta | R0 | Area | Volume | Theta | Height | Width | Opt |
|---|---|---|---|---|---|---|---|---|---|---|
| 1 | 0.0 | 39.83 | 0.275 | 1.059 | 17.45 | 7.04 | 117.75 | 2.737 | 2.231 | 2 |
| 2 | 0.4 | 39.73 | 0.276 | 1.059 | 17.53 | 7.05 | 116.61 | 2.759 | 2.232 | 2 |
| 3 | 0.9 | 39.60 | 0.277 | 1.058 | 17.59 | 7.07 | 115.46 | 2.779 | 2.230 | 2 |
| 4 | 1.4 | 0.00 | 0.000 | 0.000 | 0.00 | 0.00 | 0.00 | 0.000 | 0.000 | 0 Sides are too differ |
| 5 | 1.9 | 39.33 | 0.278 | 1.057 | 17.68 | 7.08 | 113.17 | 2.816 | 2.229 | 2 |
| 6 | 2.4 | 39.27 | 0.278 | 1.057 | 17.73 | 7.09 | 112.11 | 2.832 | 2.229 | 2 |
| 7 | 3.0 | 39.07 | 0.279 | 1.056 | 17.74 | 7.08 | 110.96 | 2.846 | 2.227 | 2 |
| 8 | 3.4 | 39.16 | 0.279 | 1.057 | 17.80 | 7.10 | 110.03 | 2.862 | 2.228 | 2 |
| 9 | 3.9 | 39.11 | 0.279 | 1.056 | 17.84 | 7.11 | 108.96 | 2.877 | 2.228 | 2 |
| 10 | 4.4 | 39.08 | 0.279 | 1.056 | 17.87 | 7.12 | 107.81 | 2.891 | 2.228 | 2 |
| 11 | 4.9 | 0.00 | 0.000 | 0.000 | 0.00 | 0.00 | 0.00 | 0.000 | 0.000 | 0 Error in profile |
| 12 | 5.4 | 38.98 | 0.280 | 1.056 | 17.94 | 7.13 | 105.43 | 2.921 | 2.227 | 2 |
| 13 | 5.9 | 38.96 | 0.280 | 1.055 | 17.98 | 7.13 | 103.73 | 2.941 | 2.226 | 2 |
| 14 | 6.4 | 38.94 | 0.280 | 1.055 | 18.03 | 7.13 | 101.75 | 2.964 | 2.225 | 2 |
| 15 | 7.0 | 38.93 | 0.280 | 1.055 | 18.07 | 7.14 | 99.67 | 2.987 | 2.225 | 2 |
| 16 | 7.5 | 38.92 | 0.280 | 1.054 | 18.12 | 7.14 | 97.29 | 3.012 | 2.223 | 2 |
| 17 | 8.0 | 38.94 | 0.279 | 1.054 | 18.18 | 7.14 | 94.20 | 3.044 | 2.223 | 2 |
| 18 | 8.4 | 0.00 | 0.000 | 0.000 | 0.00 | 0.00 | 0.00 | 0.000 | 0.000 | 0 Error in profile |
| 19 | 8.9 | 0.00 | 0.000 | 0.000 | 0.00 | 0.00 | 0.00 | 0.000 | 0.000 | 0 Error in profile |
| 20 | 9.5 | 1.26 | 4.182 | 0.733 | 1.53 | 0.18 | 32.45 | 0.276 | 1.288 | 7 |
| Mean: | | 36.82 | 0.523 | 1.036 | 16.82 | 6.67 | 102.96 | 2.722 | 2.169 | |
| Stand.dev. | | 2.37 | 0.244 | 0.020 | 1.02 | 0.43 | 5.01 | 0.165 | 0.059 | |

Compare the surface tension of high temperature silk solution with 60 minutes boiled silk from Table 3.4.and Table 3.5. Apparently, the surface tension of the high temperature silk solution is approach to 60 minutes boiled silk, but it has a higher viscosity.

Table 3.4 Surface Tension of Pure 60 Minutes Boiled Silk Solution

| No. | Time | Gamma | Beta | R0 | Area | Volume | Theta | Height | Width | Opt Messages |
|---|---|---|---|---|---|---|---|---|---|---|
| 1 | 0.0 | 45.22 | 0.249 | 1.073 | 17.64 | 7.06 | 118.23 | 2.767 | 2.248 | 2 |
| 2 | 0.1 | 44.98 | 0.251 | 1.074 | 17.71 | 7.09 | 117.52 | 2.780 | 2.251 | 2 |
| 3 | 0.2 | 44.77 | 0.252 | 1.074 | 17.77 | 7.12 | 116.80 | 2.792 | 2.252 | 2 |
| 4 | 0.3 | 44.65 | 0.253 | 1.075 | 17.84 | 7.15 | 115.93 | 2.806 | 2.254 | 2 |
| 5 | 0.4 | 44.42 | 0.254 | 1.075 | 17.88 | 7.17 | 115.21 | 2.816 | 2.255 | 2 |
| 6 | 0.4 | 44.39 | 0.255 | 1.075 | 17.91 | 7.18 | 114.99 | 2.821 | 2.256 | 2 |
| 7 | 0.6 | 44.47 | 0.255 | 1.076 | 17.92 | 7.19 | 115.12 | 2.821 | 2.258 | 2 |
| 8 | 0.7 | 44.38 | 0.255 | 1.076 | 17.94 | 7.20 | 114.82 | 2.826 | 2.258 | 2 |
| 9 | 0.8 | 44.24 | 0.256 | 1.076 | 17.97 | 7.21 | 114.42 | 2.832 | 2.258 | 2 |
| 10 | 0.9 | 44.24 | 0.256 | 1.076 | 17.98 | 7.22 | 114.30 | 2.834 | 2.259 | 2 |
| 11 | 0.9 | 44.25 | 0.256 | 1.076 | 17.99 | 7.23 | 114.28 | 2.835 | 2.259 | 2 |
| 12 | 1.1 | 44.15 | 0.257 | 1.076 | 18.01 | 7.23 | 113.97 | 2.840 | 2.259 | 2 |
| 13 | 1.1 | 44.09 | 0.257 | 1.076 | 18.02 | 7.24 | 113.75 | 2.843 | 2.259 | 2 |
| 14 | 1.3 | 44.07 | 0.257 | 1.076 | 18.03 | 7.24 | 113.63 | 2.845 | 2.260 | 2 |
| 15 | 1.3 | 44.05 | 0.257 | 1.077 | 18.04 | 7.25 | 113.53 | 2.847 | 2.261 | 2 |
| 16 | 1.4 | 44.00 | 0.258 | 1.077 | 18.05 | 7.25 | 113.41 | 2.849 | 2.260 | 2 |
| 17 | 1.6 | 43.96 | 0.258 | 1.077 | 18.06 | 7.25 | 113.22 | 2.851 | 2.261 | 2 |
| 18 | 1.6 | 43.96 | 0.258 | 1.077 | 18.07 | 7.26 | 113.19 | 2.852 | 2.261 | 2 |
| 19 | 1.7 | 43.93 | 0.258 | 1.077 | 18.07 | 7.26 | 113.10 | 2.854 | 2.261 | 2 |
| 20 | 1.8 | 43.89 | 0.258 | 1.077 | 18.08 | 7.26 | 112.96 | 2.856 | 2.261 | 2 |
| 21 | 1.9 | 43.86 | 0.259 | 1.077 | 18.09 | 7.27 | 112.82 | 2.857 | 2.261 | 2 |
| 22 | 2.0 | 43.84 | 0.259 | 1.077 | 18.09 | 7.27 | 112.79 | 2.858 | 2.261 | 2 |
| 23 | 2.1 | 43.83 | 0.259 | 1.077 | 18.10 | 7.27 | 112.67 | 2.860 | 2.262 | 2 |
| 24 | 2.2 | 43.81 | 0.259 | 1.077 | 18.10 | 7.27 | 112.63 | 2.861 | 2.261 | 2 |
| 25 | 2.3 | 43.78 | 0.259 | 1.077 | 18.11 | 7.28 | 112.52 | 2.862 | 2.261 | 2 |
| 26 | 2.4 | 43.79 | 0.259 | 1.077 | 18.11 | 7.28 | 112.47 | 2.863 | 2.262 | 2 |
| 27 | 2.6 | 43.76 | 0.259 | 1.077 | 18.12 | 7.28 | 112.41 | 2.864 | 2.261 | 2 |
| 28 | 2.6 | 43.74 | 0.260 | 1.077 | 18.12 | 7.29 | 112.33 | 2.866 | 2.262 | 2 |
| 29 | 2.8 | 43.72 | 0.260 | 1.077 | 18.13 | 7.29 | 112.22 | 2.867 | 2.262 | 2 |
| 30 | 2.8 | 43.71 | 0.260 | 1.077 | 18.13 | 7.29 | 112.20 | 2.868 | 2.262 | 2 |
| 31 | 2.9 | 43.70 | 0.260 | 1.077 | 18.14 | 7.29 | 112.14 | 2.869 | 2.262 | 2 |
| 32 | 3.1 | 43.68 | 0.260 | 1.077 | 18.14 | 7.29 | 112.10 | 2.869 | 2.262 | 2 |
| 33 | 3.1 | 43.67 | 0.260 | 1.077 | 18.15 | 7.30 | 112.00 | 2.870 | 2.263 | 2 |
| 34 | 3.3 | 43.64 | 0.260 | 1.077 | 18.15 | 7.30 | 111.94 | 2.871 | 2.262 | 2 |
| 35 | 3.3 | 43.65 | 0.260 | 1.077 | 18.15 | 7.30 | 111.92 | 2.872 | 2.262 | 2 |
| 36 | 3.4 | 43.64 | 0.260 | 1.077 | 18.16 | 7.30 | 111.84 | 2.873 | 2.263 | 2 |
| 37 | 3.5 | 43.64 | 0.260 | 1.077 | 18.16 | 7.30 | 111.78 | 2.873 | 2.263 | 2 |
| 38 | 3.6 | 43.62 | 0.260 | 1.077 | 18.16 | 7.30 | 111.78 | 2.874 | 2.263 | 2 |
| 39 | 3.8 | 43.61 | 0.260 | 1.077 | 18.17 | 7.30 | 111.73 | 2.875 | 2.263 | 2 |
| 40 | 3.8 | 43.59 | 0.260 | 1.077 | 18.17 | 7.31 | 111.68 | 2.876 | 2.263 | 2 |
| 41 | 4.0 | 43.58 | 0.261 | 1.077 | 18.17 | 7.31 | 111.62 | 2.876 | 2.263 | 2 |

| 42 | 4.0 | 43.57 | 0.261 | 1.077 | 18.17 | 7.31 | 111.57 | 2.877 | 2.264 | 2 |
| 43 | 4.1 | 43.56 | 0.261 | 1.077 | 18.18 | 7.31 | 111.54 | 2.878 | 2.263 | 2 |
| 44 | 4.3 | 43.54 | 0.261 | 1.077 | 18.18 | 7.31 | 111.49 | 2.879 | 2.263 | 2 |
| 45 | 4.3 | 43.55 | 0.261 | 1.077 | 18.19 | 7.31 | 111.44 | 2.879 | 2.264 | 2 |
| 46 | 4.4 | 43.52 | 0.261 | 1.077 | 18.19 | 7.31 | 111.37 | 2.880 | 2.263 | 2 |
| 47 | 4.5 | 43.52 | 0.261 | 1.077 | 18.19 | 7.31 | 111.35 | 2.880 | 2.264 | 2 |
| 48 | 4.7 | 43.52 | 0.261 | 1.077 | 18.19 | 7.32 | 111.32 | 2.881 | 2.264 | 2 |
| 49 | 4.8 | 43.50 | 0.261 | 1.077 | 18.19 | 7.32 | 111.30 | 2.881 | 2.263 | 2 |
| 50 | 4.8 | 43.49 | 0.261 | 1.077 | 18.20 | 7.32 | 111.25 | 2.882 | 2.264 | 2 |

==========================================================

| Mean: | | 43.91 | 0.258 | 1.077 | 18.07 | 7.26 | 113.01 | 2.854 | 2.261 | |
| Stand.dev. | | 0.06 | 0.000 | 0.000 | 0.02 | 0.01 | 0.24 | 0.004 | 0.000 | |

==========================================================

Table 3.5 Surface Tension of Pure 60 Minutes Boiled Silk Solution Mix with 10% surfactant

| No. Opt | Time Messages | Gamma | Beta | R0 | Area | Volume | Theta | Height | Width |
|---|---|---|---|---|---|---|---|---|---|
| 1 | 0.0 | 37.44 | 0.278 | 1.031 | 17.14 | 6.63 | 104.04 | 2.868 | 2.175 | 2 |
| 2 | 0.4 | 37.40 | 0.278 | 1.031 | 17.15 | 6.64 | 103.76 | 2.871 | 2.175 | 2 |
| 3 | 0.9 | 37.38 | 0.278 | 1.031 | 17.16 | 6.64 | 103.55 | 2.874 | 2.175 | 2 |
| 4 | 1.4 | 37.35 | 0.279 | 1.031 | 17.17 | 6.65 | 103.26 | 2.878 | 2.175 | 2 |
| 5 | 1.9 | 37.34 | 0.279 | 1.031 | 17.18 | 6.65 | 103.15 | 2.880 | 2.175 | 2 |
| 6 | 2.4 | 37.32 | 0.279 | 1.031 | 17.18 | 6.65 | 102.95 | 2.882 | 2.175 | 2 |
| 7 | 2.9 | 37.32 | 0.279 | 1.031 | 17.19 | 6.65 | 102.84 | 2.884 | 2.175 | 2 |
| 8 | 3.5 | 37.31 | 0.279 | 1.032 | 17.20 | 6.66 | 102.65 | 2.887 | 2.176 | 2 |
| 9 | 4.0 | 37.28 | 0.279 | 1.032 | 17.21 | 6.66 | 102.48 | 2.889 | 2.176 | 2 |
| 10 | 4.5 | 37.29 | 0.279 | 1.032 | 17.21 | 6.66 | 102.32 | 2.891 | 2.176 | 2 |
| 11 | 5.0 | 37.26 | 0.279 | 1.032 | 17.22 | 6.66 | 102.19 | 2.892 | 2.176 | 2 |
| 12 | 5.5 | 37.27 | 0.279 | 1.032 | 17.22 | 6.66 | 102.03 | 2.894 | 2.176 | 2 |
| 13 | 6.0 | 37.26 | 0.279 | 1.032 | 17.23 | 6.67 | 101.93 | 2.896 | 2.176 | 2 |
| 14 | 6.5 | 37.26 | 0.279 | 1.032 | 17.23 | 6.67 | 101.88 | 2.897 | 2.177 | 2 |
| 15 | 7.0 | 37.24 | 0.280 | 1.032 | 17.24 | 6.67 | 101.73 | 2.899 | 2.176 | 2 |
| 16 | 7.5 | 37.23 | 0.280 | 1.032 | 17.24 | 6.67 | 101.62 | 2.900 | 2.176 | 2 |
| 17 | 8.0 | 37.25 | 0.280 | 1.032 | 17.25 | 6.67 | 101.62 | 2.900 | 2.177 | 2 |
| 18 | 8.4 | 37.23 | 0.280 | 1.032 | 17.25 | 6.67 | 101.48 | 2.902 | 2.177 | 2 |
| 19 | 9.0 | 37.22 | 0.280 | 1.032 | 17.25 | 6.67 | 101.36 | 2.903 | 2.176 | 2 |
| 20 | 9.4 | 37.22 | 0.280 | 1.032 | 17.26 | 6.68 | 101.30 | 2.904 | 2.177 | 2 |
| Mean: | | 37.29 | 0.279 | 1.032 | 17.21 | 6.66 | 102.41 | 2.890 | 2.176 | |
| Stand.dev. | | 0.01 | 0.000 | 0.000 | 0.01 | 0.00 | 0.19 | 0.002 | 0.000 | |

3.3.4 Printable substrates for silk inks

The printable substrates using silk fibroin inks are limitless, simply depending on the available inkjet printers. The printable substrates include, but not limited to, the followings:

* Paper
* Glass and other insulators

- Silicon and other semiconductors
- Metals
- Cloth textiles
- Plastics

4 Inkjet printed silk patterns

We use the DMP-2800 printer to print some silk patterns, like dots, signal line, and 2D patterns, on both hydrophilic and hydrophobic substrates. The resolution of printing affects by viscosity and surface tension of the silk ink. Also the resolution of pattern depends on roughness of substrate and nozzle size. The DMP-2800 printer provides a 10pl size nozzle to make patterns, so one drop size is around 25μm and the width of a line is around 40um on the hydrophilic substrates. A signal layer line will give the interface between dots, and a 2D pattern presents interface between lines.

4.1 Parameter Setting for Silk Ink

4.1.1 Voltage

The voltage is function of drop size and drop velocity. So voltage setting depend on height level what you want the nozzle above your substrate and the drop size your want to print. But voltage level below 15 V, the silk ink will not come out due to the surface tension of silk ink. High Voltage setting gives you more volume of the drop. Figure 4.1 shows silk lines on silicon wafer under 15v, 20V and 25v voltage printing, and the width of silk lines are 65μm, 100μm, 110μm. Obviously, High voltage printing gives more width lines due to increasing the drop volume.

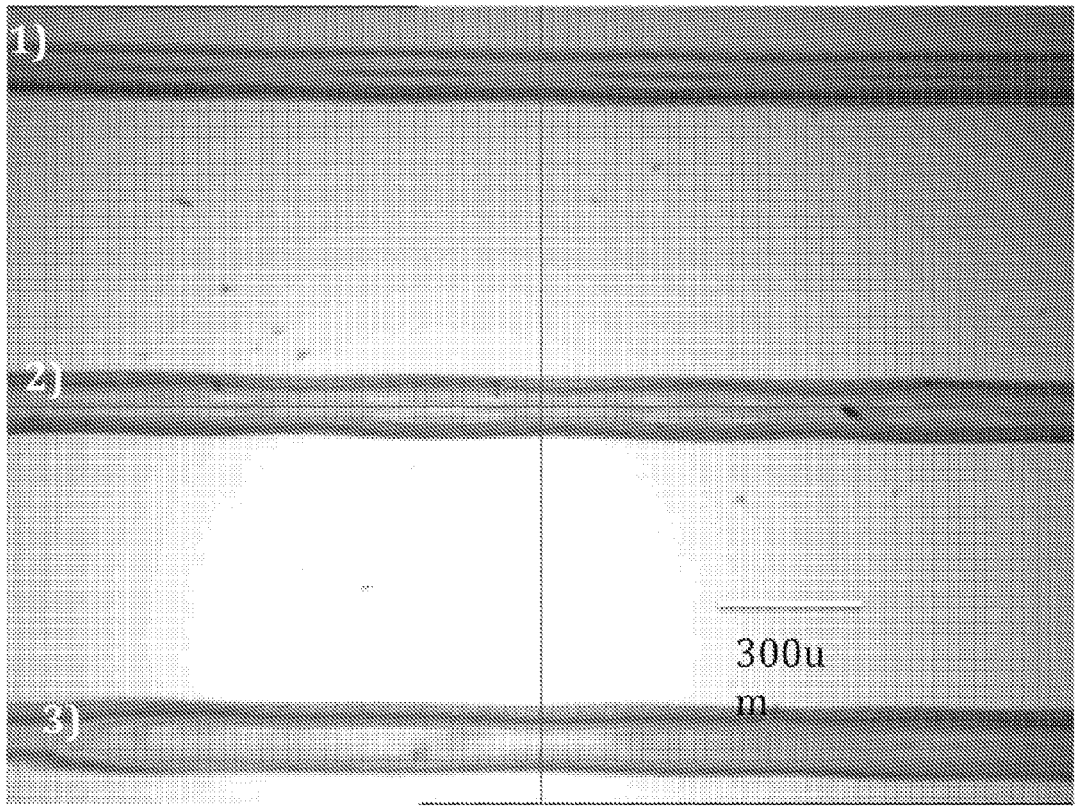

Figure 4.1: Silk Lines printed under different voltag:1) 15v voltage, 65um; 2) 20v voltage, 100um; 3) 25v voltage, 110um.

4.1.2 Waveform

After adding the surfactant to silk solution, the surface tension of the ink is about 36 dynes/cm. So we use the waveform which is developed by the Dimatix Company.

4.1.3 Cleaning Cycle

Before printing, we need a purging process that applies air pressure to outside of fluid bag to force fluid through entire fluid path and out all nozzles at nozzle, as shown in Figure 4.2. After purging process, it force air in the chamber out the nozzles, and make sure ink wet the nozzle to start printing.

During printing, blotting process is required to absorbent silk ink in close to nozzle plate. After blotting process, the excess silk ink which causes misdirected firing will be removed.

After printing, spitting process provides protect nozzle from clogging. Spitting designed to ejecting some drops ink from the chamber. It lets the fresh silk drops reach to the meniscus to replace the old one.

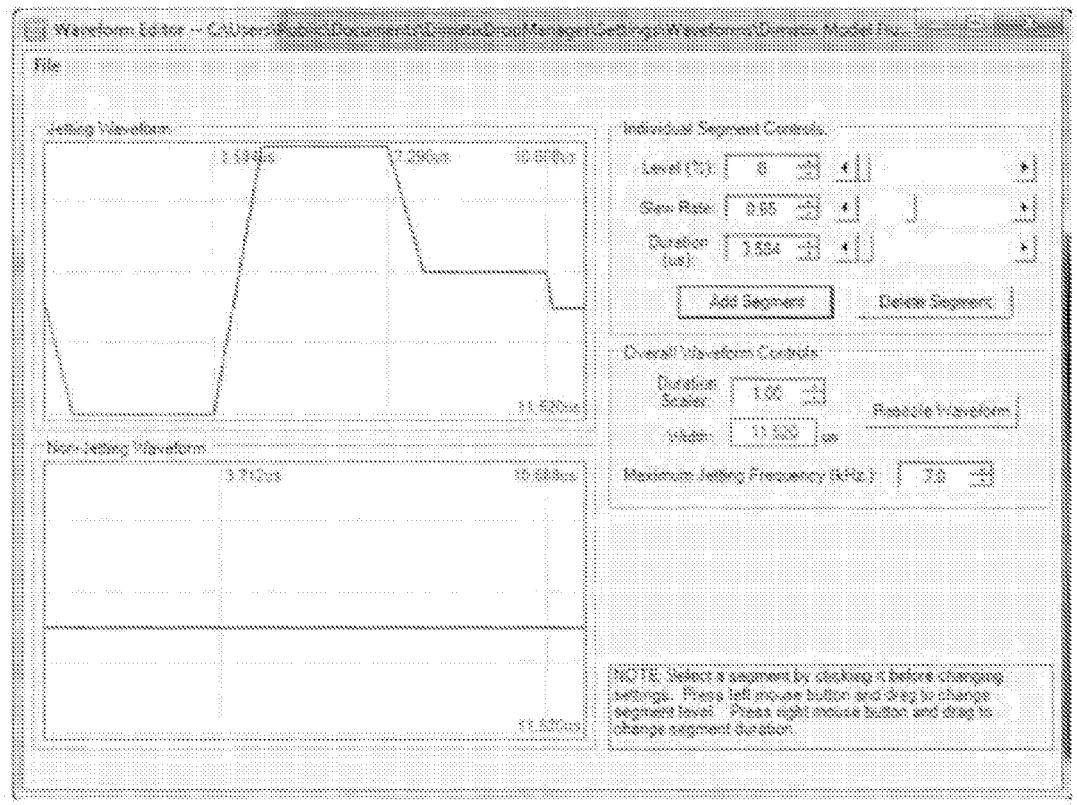

Figure 4.2: Waveform for silk ink printing.

4.1.4 Nozzle Number

The number of nozzle also affects the printing patterns. Figure 4.3 shows a silk line on the acrylic with 25v and one nozzle printing, and it gives 40μm width silk line. Figure 4.4 is silk line with 240 widths still under 25v printing. However, the width of the line become much more width than Figure 4.3, because it printing by 7 nozzles.

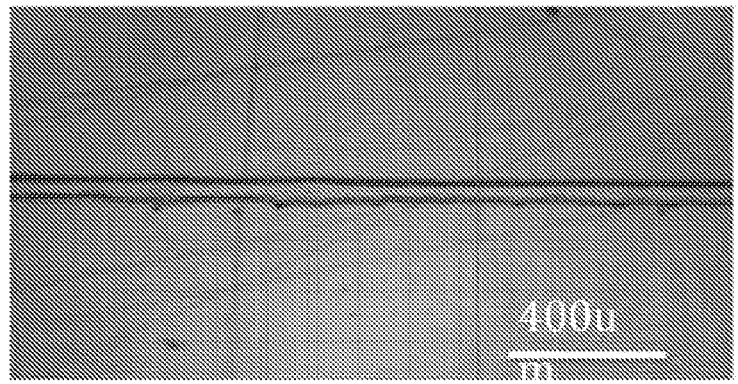

Figure 4.3: One Nozzle Printing (40μm line width).

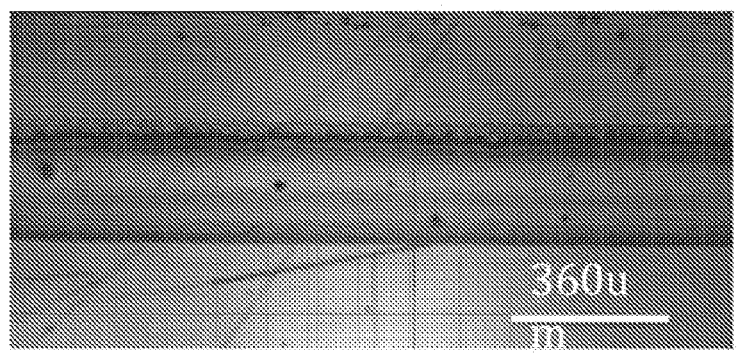

Figure 4.4: Multiple nozzles (n=7) Printing (240μm line width).

4.1.5 Silk Drops from Nozzle

Figure 4.5 is the drops from 10pL nozzles, and the voltage value set 23V, jetting frequency is 5 KHz. The uniform drops from nozzle performance stable. There are no misdirected nozzles which mean that silk solution jetting smooth without bubbles under the high frequency oscillate system. All of the sixteen nozzles work well last for 8 hours which means the high temperature silk will not clog the 20μm diameter nozzle.

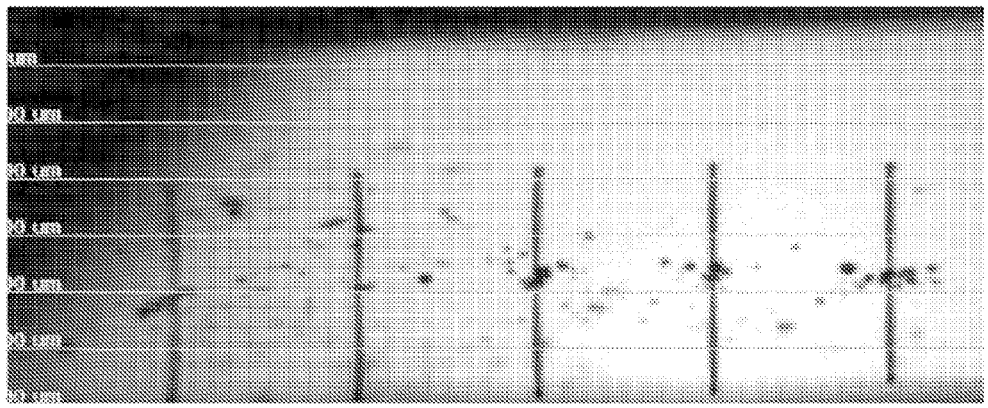
Figure 4.5: Silk drops.
4.2 Various silk patterns using directly inkjet printing technique
4.2.1 Dots
Figure 4.6 and Figure 4.7 show silk dots printed on silicon wafer and acrylic, respectively. We use 1 nozzle and 1 layer printing, the voltage value is 15v and jetting frequency is 1 KHz. The size of dots is 40μm on silicon wafer and 30μm on acrylic.
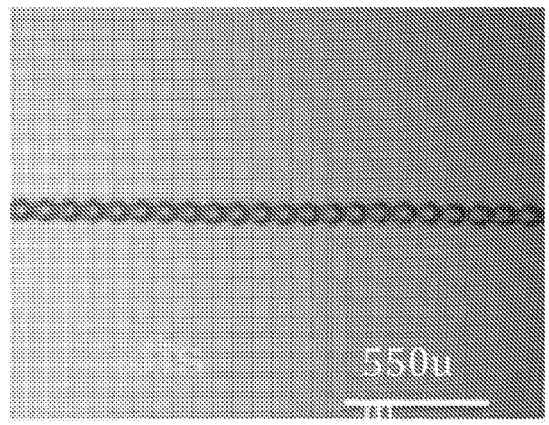
Figure 4.6: Silk dots (40μM) on silicon wafer.

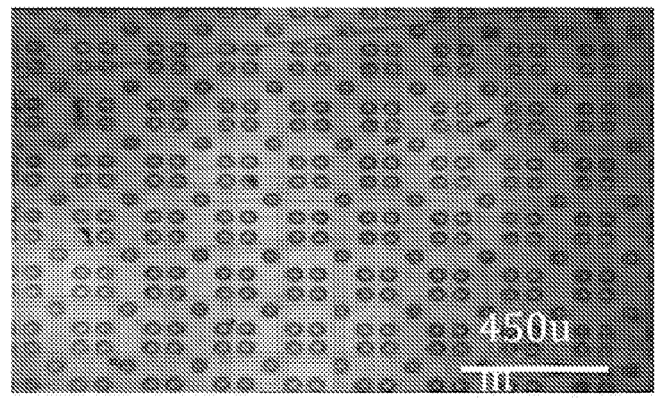

Figure 4.7: Silk dots (30 μm) on silicon acrylic.

4.2.2 Lines

4.2.2.1 Multiple layers printing

Figure 4.8 shows silk lines which are printed with one nozzle and 15v on the silicon wafer. And figure 4.9 shows the SEM picture of those one layer printing. One layer printing is clear without any interface between drops. Comparing one layer printing with three layers printing, one layer patterns are more uniform and the edge of line is cleaner. A rough edge shows on three layers printing (Figure 4.10), because the upper layer fluid causes capillary instability when the upper layers silk are printed. From the Figure 4.11, it indicates the first line is width than other 4 line, because the alignment of first line is not as good as other 4 lines. Figure 4.12 shows serious capillary instability in a twenty layers pattern, so multiply layer printing is just suitable for low resolution patterns.

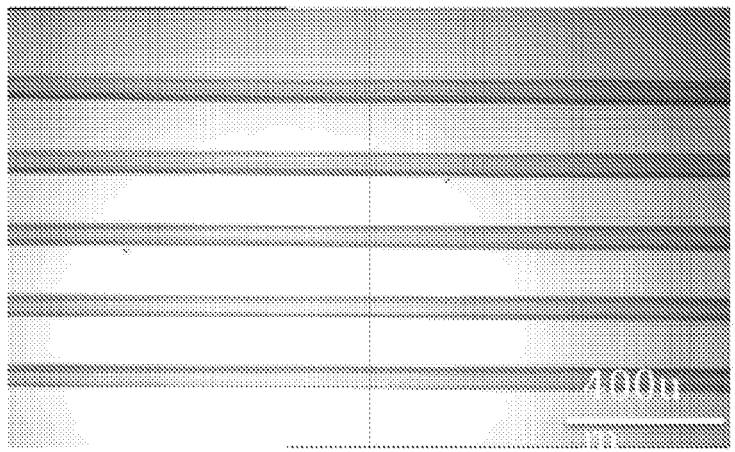
Figure 4.8: One layer silk pattern on silicon wafer.
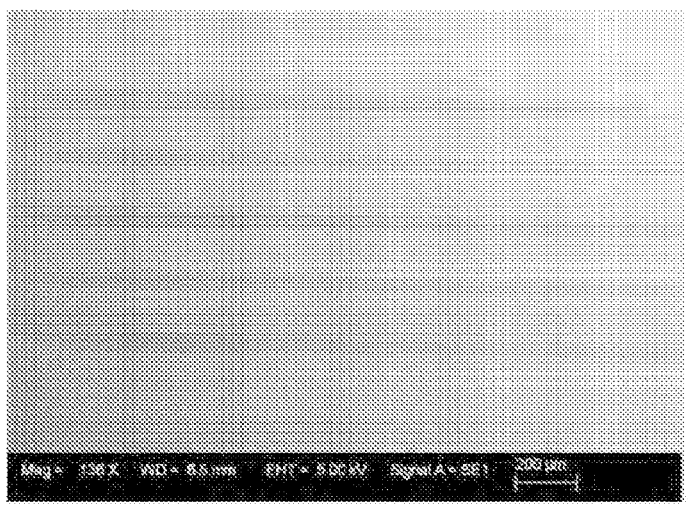
Figure 4.9: SEM photo of one layer lines.
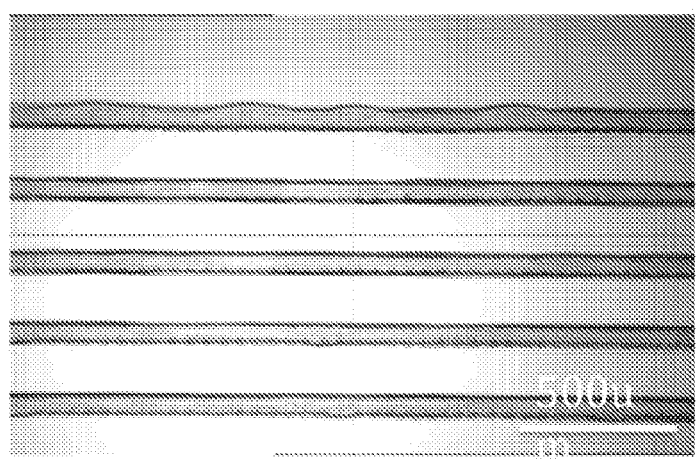

Figure 4.10: Three layers silk pattern on silicon wafer.

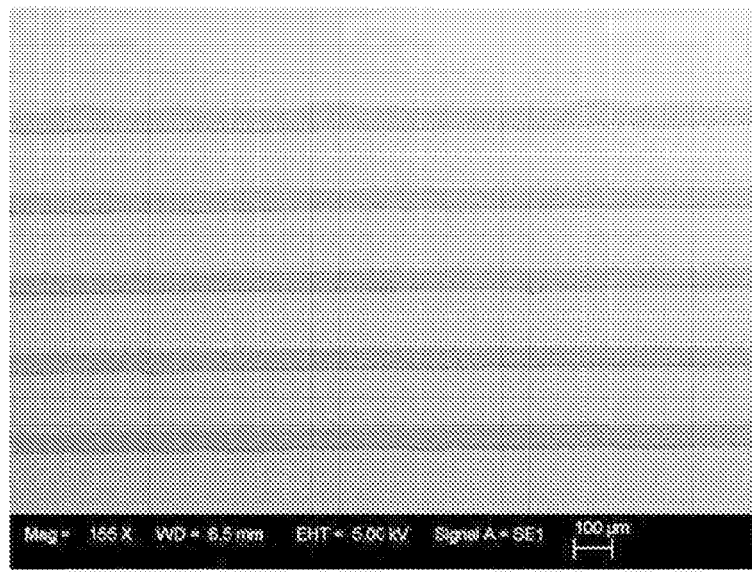

Figure 4.11: SEM photo of three layers lines.

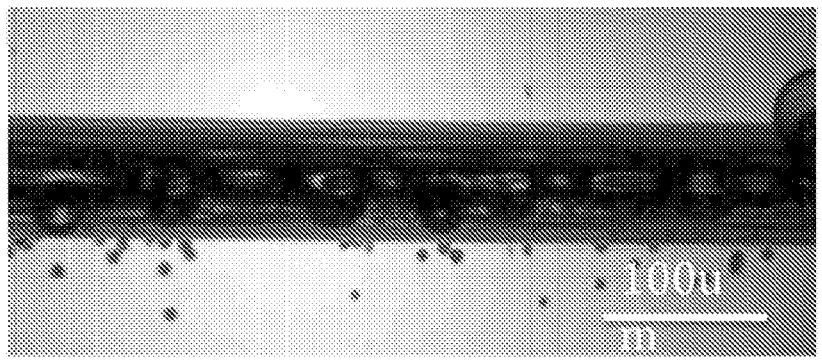

Figure 4.12: Twenty layers silk patterns on silicon wafer.

4.2.2.2 Cross lines printing

The method for printing multiple layers lines and cross lines is different. For multiple layers lines, the substrate is fixed during printing and the direction of printing among multiply layers lines is some. For the cross lines printing, the substrate is routed by 90 degree C after first layer printing, and then do the second layer printing. So the direction of the two layers is different. The Figure 4.13 - 4.15 indicates capillary instability between two layers, and the edge of pattern shows a clean gradual capillary instability process.
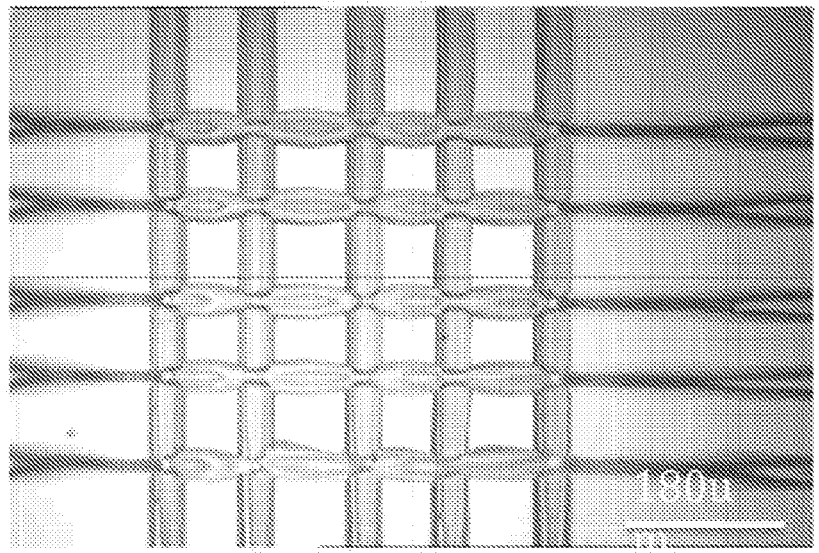
Figure 4.13: Cross silk line pattern.
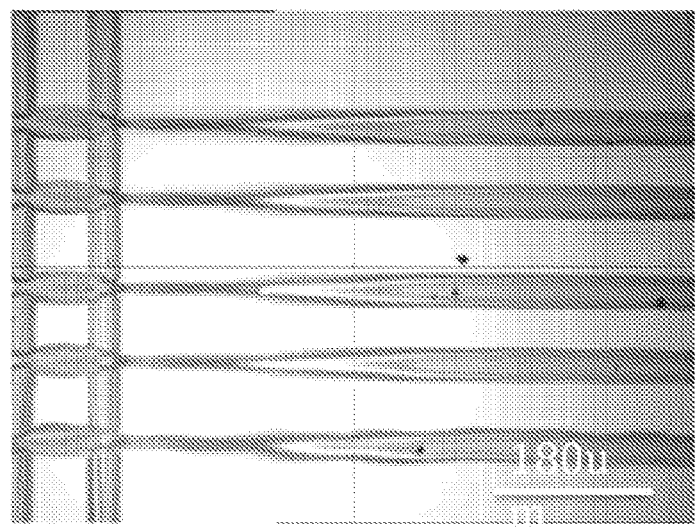
Figure 4.14: Cross silk line pattern (capillary instability).

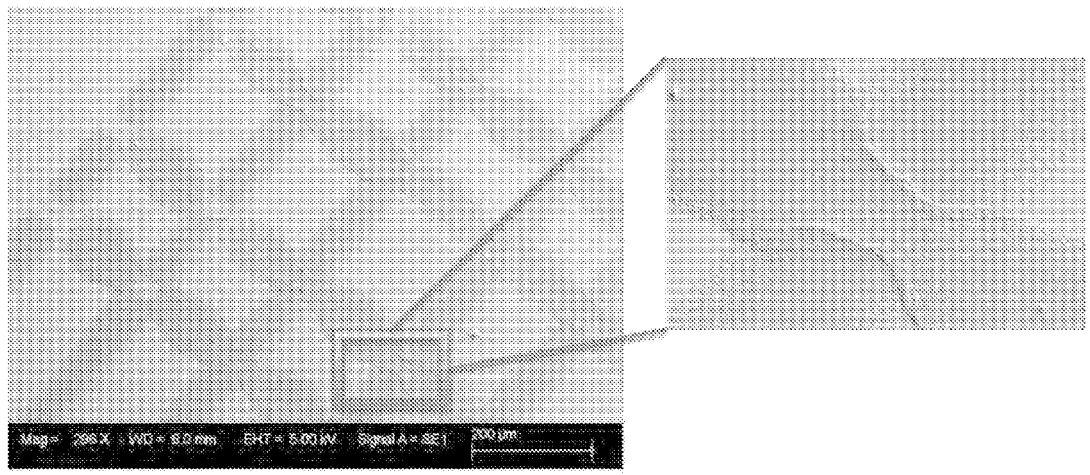

Figure 4.15: SEM photo of cross silk line pattern (capillary instability).

4.2.3 Two Dimension Printing

One layer square pattern shows interface between lines. From Figure 4.16, there is less than 1 μm width overlap between two lines. After applying laser point to the pattern, a diffraction grating patterns show on the wall due to the 1μm overlap, as shown in Figure 4.17. However, the overlap part of the pattern is disappeared after printing second layer pattern. So, the multiple layers give a smooth finish pattern (Figure 4.18 and 4.19).

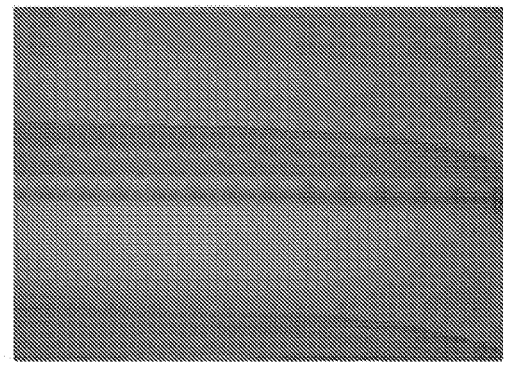

Figure 4.16: One layer 2D patterns.

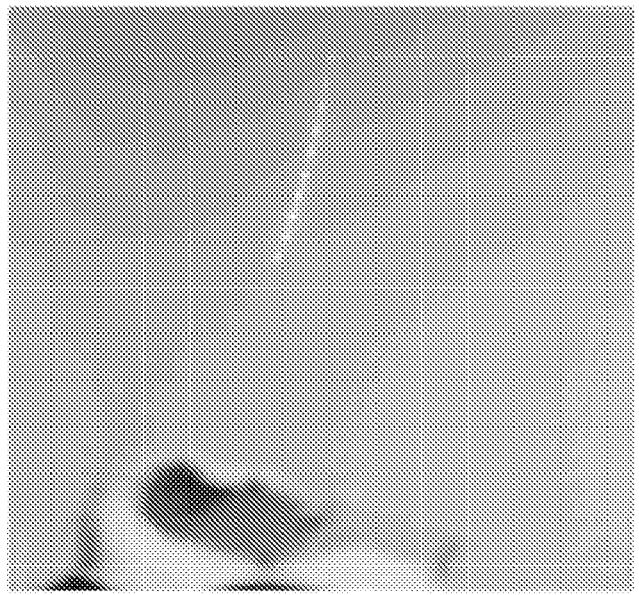
Figure 4.17: One layer 2D patterns showing diffraction grating patterns.
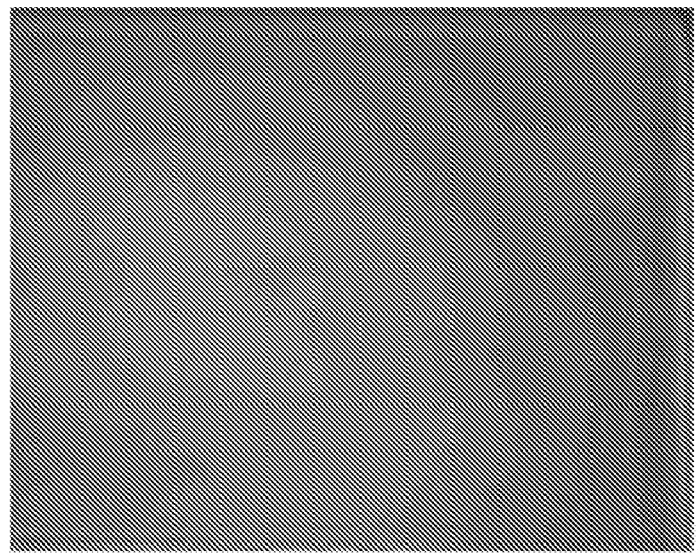
Figure 4.18: Multiple layers 2D patterns.

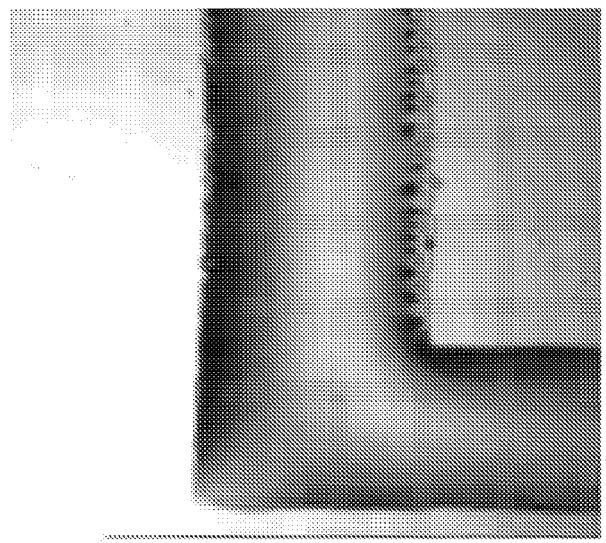

Figure 4.19: Multiple layers 2D patterns (zoom in view).

4.2.4 Silk patterns after alcohol annealing treatments

Silk film is easily dissolved in the water. However it will not dissolve after alcohol annealing due to the formation of β sheet. We try to use printer to make a β sheet pattern. So we put the printing pattern to do a 2 hours vacuum annealing. It turns out the patterns tend to spread out, as shown in Figure 4.20.

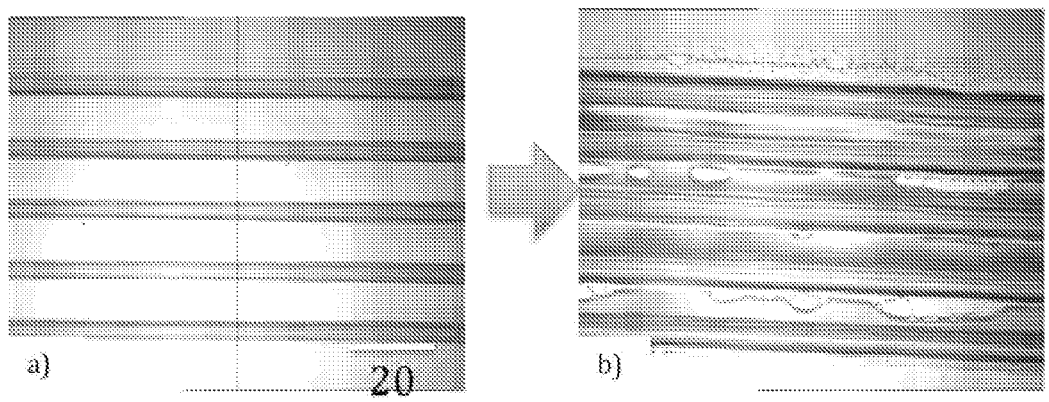

Figure 4.20: a) Silk Pattern before annealing; b) Silk Pattern after annealing.

4.3 Thickness of Silk pattern

Silk provides a biologically favorable environment allowing them to entrain various biological and chemical dopants and maintain their functionality. Mixing Different chemical solution with silk solution gives different viscosity and surface tension which are affect thickness of pattern. Obviously, the number of printing layer is another important element affects the thickness of pattern. Preparing three kinds of silk solution include food color silk, high refractive index silk and pure silk, and then print them with some number nozzles. Figure 4.21 - 4.23 shows the thickness of patterns are increased by the number printing layer. The thinnest pattern is less than 100nm created by one layer food color silk pattern. According to Figure 4.24 the thickest pattern is pure silk pattern due to highest percentage silk in the solution.

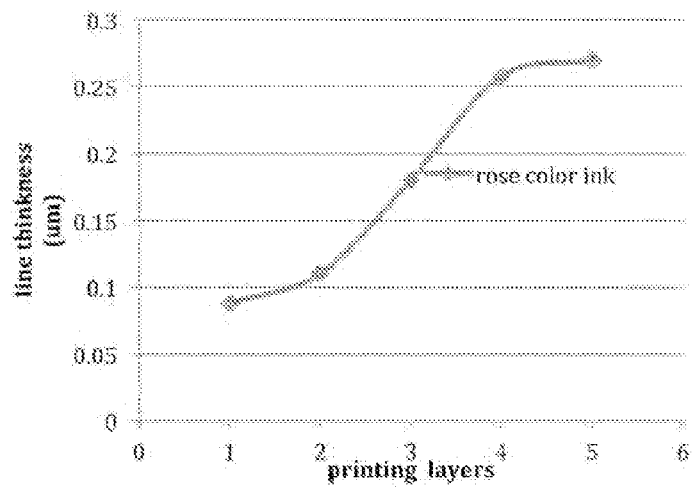

Figure 4.21: Printing layers vs. thickness of food color silk patterns.

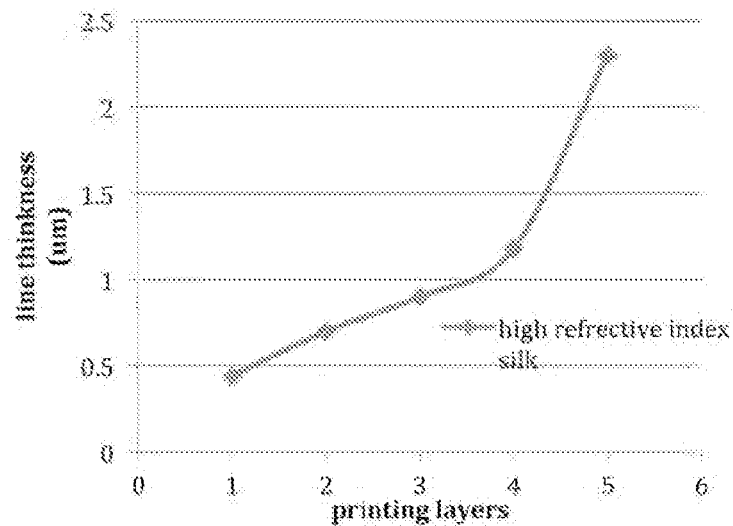
Figure 4.22: Printing layers vs. thickness of high refractive index silk patterns.
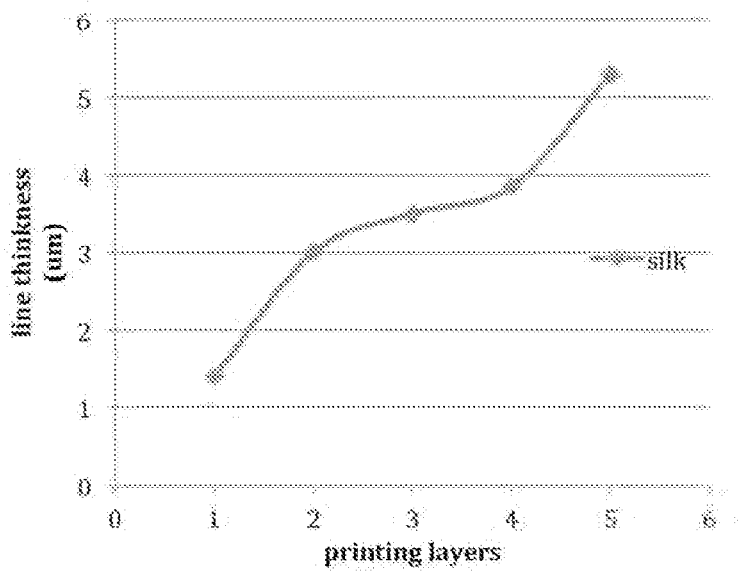
Figure 4.23: Printing layers vs. thickness of silk patterns.

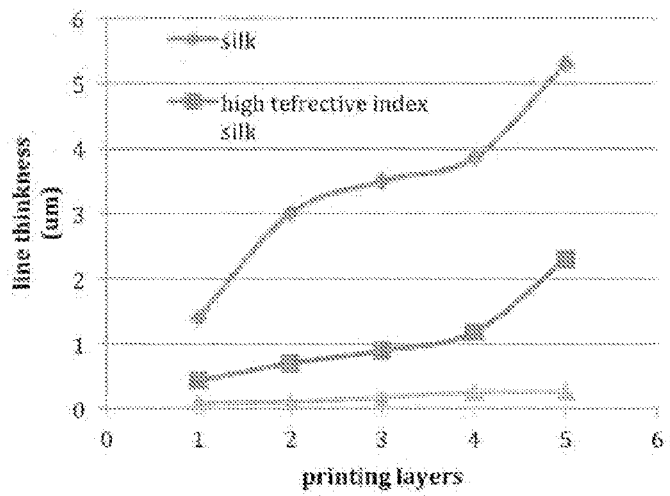

Figure 4.24: Comparison of printing layers vs. thickness of different silk inks.

4.4 Silk patterns on various substrates

The printable substrates for silk ink include paper, glass, silicon, metals, cloth textiles and plastics. Those substrates can be divided two groups which are hydrophobic substrate and hydrophilic substrate. The drop size on hydrophobic substrate is sight smaller due to high surface energy. The width of silk lines from Figure 4.8 is similar with the silk lines from Figure 4.25. However, the two patterns are supplied by different voltage. Silk patterns on silicon have slight large voltage value.

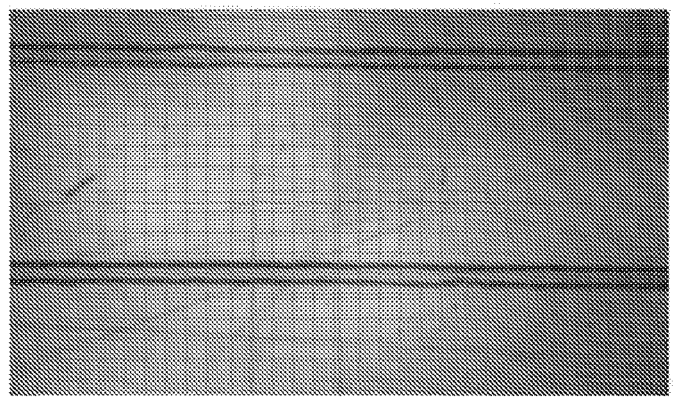

Figure 4.25: One layer silk patterns on acrylic.

5 Directly printing of functional silk devices using doped silk solution as the ink Silk fibroin has proved to be an effective material and matrix that can maintain the functionalities of dopants. Therefore, choosing the appropriate dopants (including both physical dopants - e.g. metallic nanoparticles, laser dyes, quantum dots and etc. - and biochemical dopants, e.g. cells, enzymes, bacterium and etc.) and mixing them into silk fibroin solution as the ink is a promising way to directly printing of functional devices using Dimatix DMP 2800 printer. In the following section, a series of functional silk devices (with different dopants) will be described as the proof of principle demonstrations.

5.1 Inkjet printing of gold nanoparticle doped silk patterns

As mentioned above, silk provides a biologically favorable environment allowing them to entrain various biological and chemical dopants and maintain their functionality. Proteins and enzymes haven been previously doped into various silk material formats, especially silk films. Recently, we have demonstrated gold nanoparticles doped silk films that resonantly absorb incident light and convert it to heat, which can be potentially used as a biocompatible thermal therapy for *in vivo* medical applications such as tumor and bacterial killing.

The preparation of gold nanoparticle silk ink consist of the production of the print grade silk fibroin solution and synthesis of gold nanoparticles, followed by a simple mixing of the two solution with a certain ratio that is determined by applications. Briefly, pre-cut *Bombyx mori* cocoon pieces are boiled in a 0.02 M $Na_2CO_3$ solution for 2 hours to remove sericin and boiled silk fibers are dried overnight and then are sidolved in a 9.3 M LiBr at 60 degree C for 4 hours. The lithium bromide salt is then removed from the silk solution through a water-based dialysis process. The gold nanoparticle solution is prepared by adding 20 mL 1% $Na_3C_6H_5O_7$ into 200 mL boiled 1.0 mM $HAuCl_4$, followed by continuously heating for 10 minutes until the solution has turned deep red. Then the gold nanoparticle solution is carefully added into the silk solution with gentle agitation for uniform dispersion and is ready for printing after being filtered against 0.2 micron filter.

Figure 5:
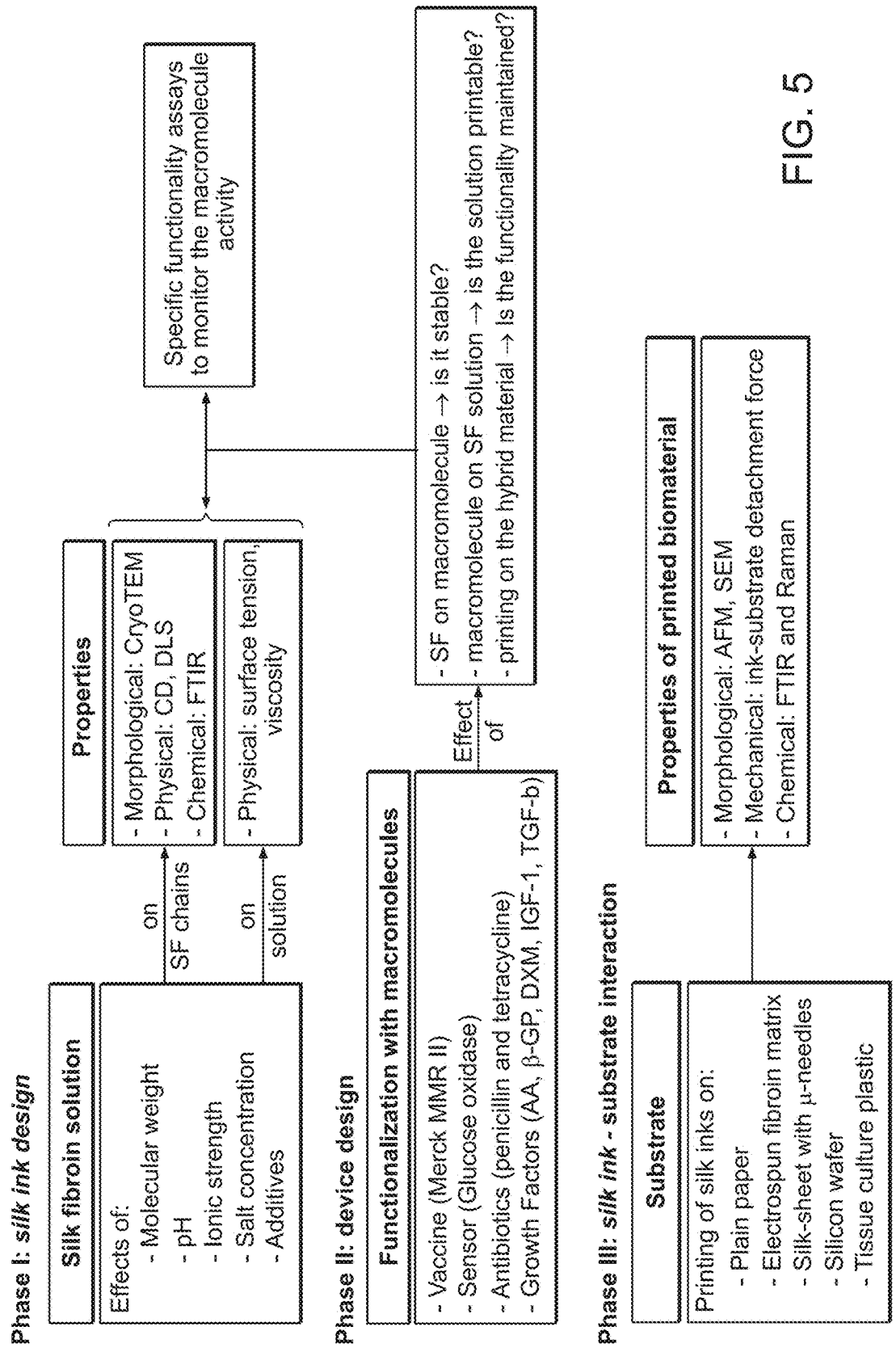
FIG. 5 shows an overview of biopolymer ink design, device design, and biopolymer ink-substrate interaction.

Table 5.1 gives the main parameters for printing and the printing result is showed in Figure 5.2.

The printed Au-NPs doped silk device showed enhanced plasmatic absorption of green light (figure 5.3), resulting in a temperature increase of ~ 15 degree s with an irradiance of ~ 0.25 W/cm$^2$. The heating effects could be further improved and optimized by adjusting the Au-NPs concentration and layers of the printed structures, which could be potentially used for light-mediated patterned heating treatments.

Table 5.1 Printing Permanents for Gold Nanoparticle Silk Ink

| | |
|---|---|
| Voltage | 25v |
| Nozzle Number | 4 |
| Drop Spacing | 25μm |
| Printing Layer | 5 |
| Firing Frequency | 2 KHz |

Figure 5.1: Gold nanoparticle doped silk ink.

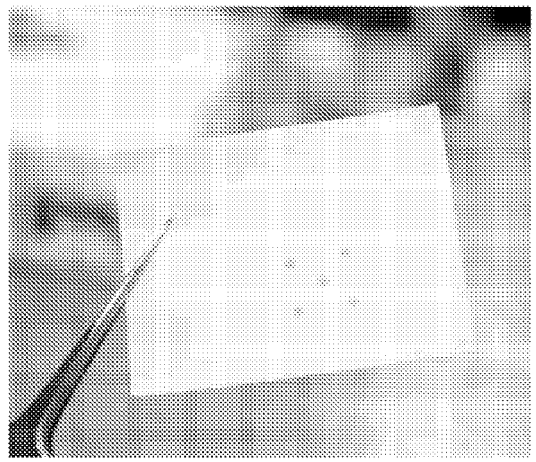

Figure 5.2: Gold nanoparticles doped silk dots patterns printed on paper.

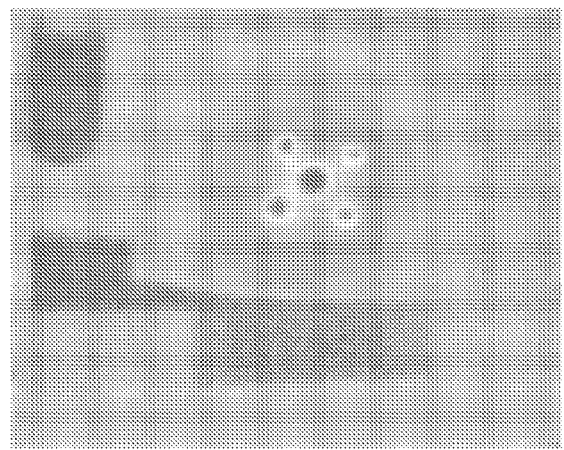

Figure 5.3: IR view of gold nanoparticles doped silk dots patterns exposed to green light radiation.

5.2 Inkjet printing of enzyme doped silk patterns

In addition to print gold nanoparticle doped silk, it is also possible to directly print enzyme-doped silk for biomedical applications such as enzyme-linked immunosorbent assay test (i.e. ELISA). ELISA is a widely used test to identify certain substance using antibodies and the colorimetric change as the sensing/diagnostic mechanism. Usually, the enzymes used in ELISA tests need to be stored at low temperature for maintaining the bioactivities. It has been proved that silk can help to maintain the functionalities of the doped enzyme at room temperatures without fridge-storage. Therefore, directly printing of enzyme doped silk patterns (in a precise way) holds great opportunities in such as rapid and low volume screening test, food allergens, and toxicology applications, as shown in Figure 5.4.

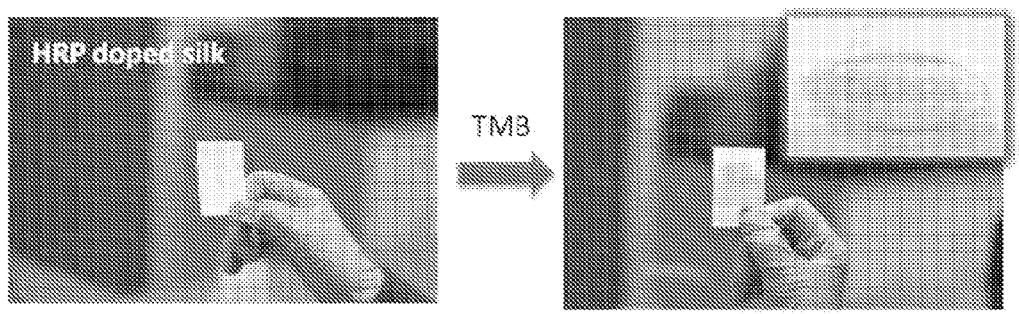

HRP: Horseradish peroxidase; TMB:3,3',5,5'-Tetramethylbenzidine

Figure 5.4: Printed HRP doped silk changes its color (to blue) when sprayed TMB solution.

5.3 Inkjet printing of antibiotics doped silk patterns

The use of antibiotics is important for effective infectious disease containment and curing. However, for most, if not all, of current antibiotics need to be maintained within a specific refrigeration temperature range due to their temperature sensitivity. Silk fibroin has been proven to be a biologically friendly protein polymer. Recently, researchers found that silk was capable of stabilizing labile antibiotics (in the form of films) even at temperatures up to 60 degree C over more than 6 months. We have been working on exploration of the possibilities of directly inkjet printing of antibiotics doped silk by mixing penicillin solution of various concentration levels with purified silk solution prepared as previously described. Compared to antibiotics doped silk films, directly printing of antibiotics doped silk has the advantages of precise control of the antibiotics distribution and potential multilayer and multi-drugs printing that may benefit more sophisticated cases where fine control and micro-manipulation of the antibiotic drug are needed.

To obtain a clear pattern on bacterial growth area, first we use method one try to print pattern before bacterial growth. The result shows that two clean square without any clean pattern in the Petri dish after 5 hours incubate, as shown in Figure 5.5.

Method one:

1) Culture 50ul bacterial on agar
2) Print 1 layers an arrow and "tufts" on bacterial, the drop gap 50um
3) Take 5 hours culture in 37 degree C incubator To improve the method, the pattern is printed after bacterial overnight growth (Method two). There is an arrow in the in the Petri dish after 9 hours incubate (Figure 5.6).

Method two:

1) Culture bacterial on agar
2) Take overnight culture in 37 degree C incubator
3) Print 2 layers an arrow and 25um drop gap on bacterial
4) Take 9 hours culture in 37 degree C incubator

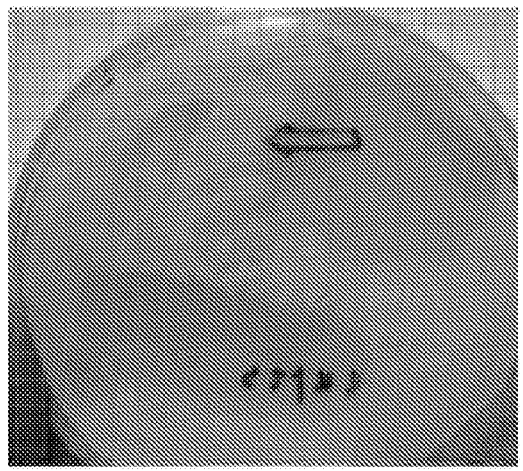

Figure 5.5: Two clean bacterial inhibition zones in bacterial growth petri dish.

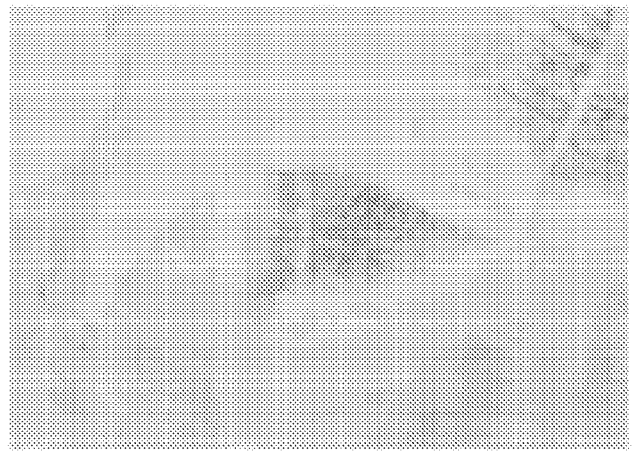

Figure 5.6: Bacterial growth inhibition zone (in the shape of an arrow).

5.4 Inkjet printing of colored silk patterns

In addition to biomedical applications (especially for implantable ones), silk has been used to construct edible food sensors [22] as a green and edible material that is extracted and purified from domesticated silkworm cocoons. Plain silk solution (i.e. non-doped silk solution) is a water-like highly transparent protein solution that is colorless.

Food coloring, alternatively called color additive, imparts color when added to food or drink, and is used widely both in commercial food production and in domestic cooking. We mix commercially available food dyes (considered as safe) with silk solution to make colored silk inks and try to directly inkjet print. And we try to print patterns on textile silk which carries a basic color (light yellow).

To get clear pattern on textile silk, it needs multiple layers printing, because the color of textile silk darker than a blank paper. After 7 layers printing, the pattern is clear and beautiful, as shown in Figure 5.7.

The color silk patterns remain its original pattern after 2 hours vacuum annealing. Also it is survival after dry cleaning process, as shown in Figure 5.8.

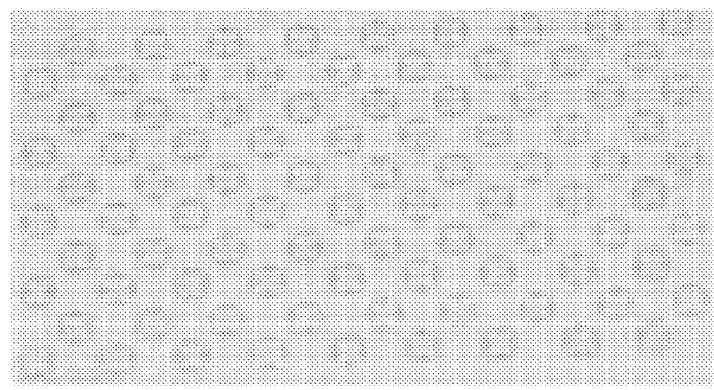

Figure 5.7: Single color silk patterns on silk textile.

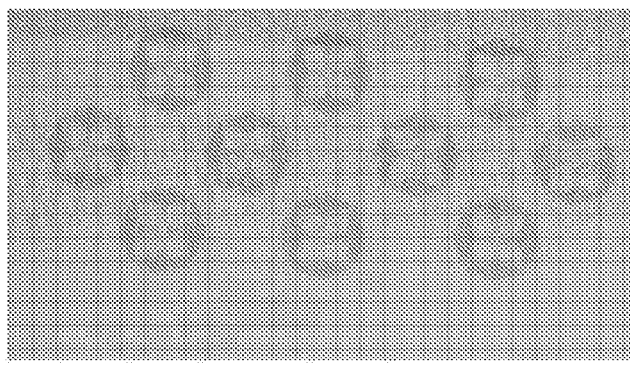

Figure 5.8: Single color silk patterns on silk textile after dry cleaning.

Multiple colors silk printing needs the alignment process, because the printer loads one cartridge with one color at one once, as shown in Figure 5.9. There are four steps alignments including multiple layers alignment, cartridge, voltage alignment and voltage alignment.

Multilayer alignment: one color for each layer printing;

Cartridge alignment: set drop offset before every layer printing;

Voltage alignment: different color inks have slight change in viscosity;

Nozzle alignment: using same nozzles for every layer printing (number of nozzles determines line width).

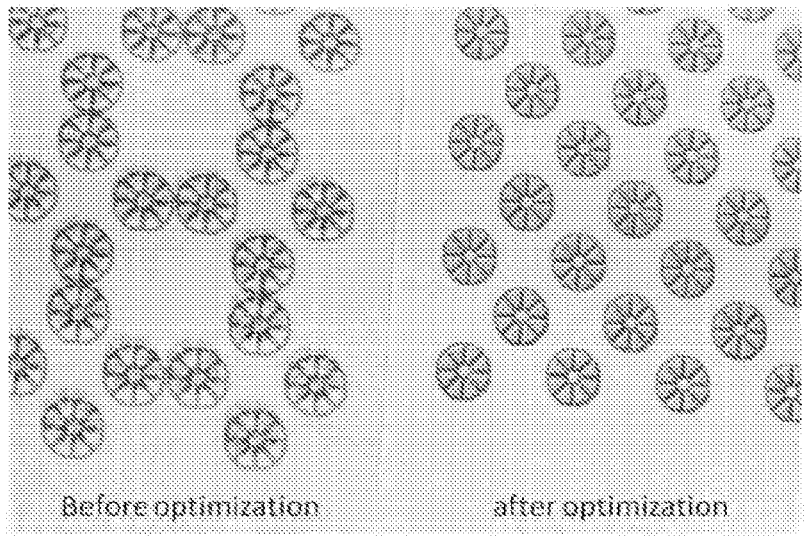
Figure 5.9: Multiple color silk patterns on silk textile before and after alignment optimization.

6 Conclusion

We have successfully demonstrated direct printing of silk fibroin protein based inks using a commercially available inkjet printer. Various types of silk inks have been prepared by choosing appropriate dopants and mixing with the purified silk fibroin solution, and printed successfully. A set of operating parameters have been tried and optimized for each individual silk ink (including gold nanoparticle silk ink, enzyme doped silk ink, high refractive index silk ink and antibacterial silk ink) to improve the performance for specific applications. Both single layer and multiple layers printing have been carried out and a resolution of 25 microns has been achieved.

Future work of silk ink printing would be focused on improving the silk ink properties – in terms of printing speed and resolution - to match to other inkjet printers in the marketing. More efforts should be put on improving the repeatability of the printing process, including avoiding the clogging within the nozzles when the silk ink gets dried, and the accuracy of step motor movement and alignment.

Another priority will be further studies of the effects of the nozzle jetting process on the properties of the silk ink, especially on the formation of silk beta sheet.

References

1. G.H. Altman, F. Diaz, C. Jakuba, T. Calabro, R.L. Horan, J. Chen, H. Lu, J. Richmond, D.L. Kaplan, "Silk-based biomaterials", Biomaterials 24 (2003) 401-416.
2. D.L. Kaplan, S.M> Mello, S. Arcidacono, S. Fossey, K. Senecal, W. Muller, "Protein based materials", BOston: Birkhauser, (1998) p.103-131.
3. D.L. Kaplan, W.W. Adams, B. Farmer, C. Viney, "Silk: biology, structure, properties and genetics." in the book of "Silk polymers: materials science and biotechnology". ACS Symp Ser (1994); 544:2-16.
4. D.L. Kaplan, S. Fossey, C. Viney, W. Muller, "Self-organization (assembly) in biosynthesis of silk fibers - a hierarchical problem." in the book of "Hierarchically structured materials" Materials Res Symp Proc (1992); 255:19-29.
5. R.L. Moy, A. Lee, A. Zakla, "Commonly used suture materials in skin surgery", American Family Physician, (1992); 44:2123-8.
6. C.M. Wen, S.T. Ye, L.X. Zhou, Y. Yu, "Silk-induced asthma in children: a report of 64 cases", Annals of Allergy, Asthma & Immunology, (1990); 65: 375-8.
7. E. Rossitch, D.E. Bullard, W.J. Oakes, "Delayed foreign-body reaction to silk sutures in pediatric neurosurgical patients", Child's Nervous System, (1987); 3: 375-8.
8. M. Dewair, X. Baur, K. Ziegler, "Use of immunoblot technique for detection of human IgE and IgG antibodies to individual silk proteins", Journal of Allergy and Clinical Immunology, (1985); 76: 537-42.
9. H. Sakabe, T. Miyamoto, Y. Noishiki, W.S. Ha, "In vivo blood compatibility of regenerated silk fibroin", Gen-I Gakkaishi, (1989); 45: 487-90.
10. M. Santin, A. Motta, G. Freddi, M. Cannas, "In vitro evaluation of the inflammatory potential of the silk fibroin", Journal of Biomedical Materials Research, (1999); 46: 382-9.
11. H. Peleg, U.N. Rao, L.J. Emrich, "A experimental comparison of suture materials for tracheal and bronchial anastomoses", The Journal of Thoracic and Cardiovascular Surgery, (1986); 34: 384-8.

12. H.J. Jin, J. Chen, V. Karageorgiou, G.H. Altman, D.L. Kaplan, "Human bone marrow stromal cell responses on electrospun silk fibroin mats", Biomaterials, (2004); 25 (6):1039-1047.
13. Y. Cao, B. Wang, "Biodegradation of silk biomaterials", International Journal of Molecular Sciences, (2009); 10: 1514-24.
14. C. Vepari, D.L. Kaplan, "Silk as a biomaterial", (2007); 32: 991-1007.
15. D.N. Rockwood, R.C. Preda, T. Yucel, X. Wang, M.L. Lovett, D.L. Kaplan, "Materials fabrication from *Bombyx mori* silk fibroin", Nature Protocol, (2011); 6 (10): 1612-31.
16. FUJIFILM Dimatix DMP 2800 printer user's manual.
17. A.H. Rida, "Conductive inkjet printed antennas on flexible low-cost paper-based substrates for RFID and WSN applications", Masters' thesis, Georgia Institute of Technology, May 2009.
18. G. Shaker, S. Safavi-Naeini, N. Sangary, M.M. Tentzeris, "Inkjet printing of ultrawideband (UWB) antennas on paper-based substrates", IEEE Antennas and Wireless Propagation Letters, Vol. 10, (2011); 111-114.
19. B. Derby, "Bioprinting: inkjet printing proteins and hybrid cell-containing materials and structures", Journal of Materials Chemistry, (2008), 18: 5717-21.
20. http://www.imaging.org/resources/Ieinkjet/part4.cfm
21. Jan Sumerel, unpublished observation
22. H. Tao, M.A. Brenckle, M. Yang, J. Zhang, M. Liu, S.M. Siebert, R.D. Averitt, M.S. Mannoor, M.C. McAlpine, J.A. Rogers, D.L. Kaplan, F.G. Omenetto, "Silk-based conformal, adhesive, edible food sensors", Advanced Materials, (2012).

What is claimed is:

1. A printable silk ink, comprising:
   an aqueous silk fibroin solution, substantially free of an organic solvent having
   a molecular weight of about 3.5 kD to about 350 kD; and
   a concentration of silk fibroin in a range of about 0.3 (wt/vol) % to at least about 10 (wt/vol) %;
   wherein when it is printed to a substrate, a droplet volume of about 0.1 pL to about 5 nL of the aqueous silk fibroin solution is characterized by
   a viscosity of about 1 centipoise to about 20 centipoise when viscosity is measured at room temperature; and
   a surface tension of about 15 dynes/cm and about 50 dynes/cm when measured at room temperature.

2. The printable silk ink of claim 1, having a pH value between 5-9.

3. The printable silk ink of claim 1, further comprising a viscosity-modifying agent, a surfactant, or combination thereof.

4. The printable silk ink of claim 3, wherein the viscosity-modifying agent is present at about 5-30 wt % of the aqueous unit composition.

5. The printable silk ink of claim 3, wherein the surfactant is present at about 0.1-10 wt % of the aqueous unit composition.

6. The printable silk ink of claim 1, further comprising an additive.

7. The printable silk ink of claim 1, further comprising a structural protein selected from the group consisting of: fibroins, actins, collagens, catenins, claudins, coilins, elastins, elaunins, extensins, fibrillins, lamins, laminins, keratins, tublins, viral structural proteins, zein proteins and any combinations thereof.

8. The printable silk ink of claim 7, wherein the structural protein is a low molecular weight structural protein selected from the group consisting of: low molecular weight actins, low molecular weight collagens, low molecular weight catenins, low molecular weight claudins, low molecular weight coilins, low molecular weight elastins, low molecular weight elaunins, low molecular weight extensins, low molecular weight fibrillins, low molecular weight lamins, low molecular weight laminins, low molecular weight keratins, low molecular weight tublins, low molecular weight viral structural proteins, and any combinations thereof.

9. The printable silk ink of claim 1, wherein the printable silk ink is substantially free of silk fibroin having a molecular weight over 200 kDa.

10. The printable silk ink of claim 1, wherein the droplet unit printed to the substrate, has a gel, semi-solid, or solid form and a diameter measured at its smallest cross-section of about 0.1 µm to about 250 µm.

11. The printable silk ink of claim 1, wherein the aqueous silk fibroin solution is characterized such that when it is printed to a substrate, a gel, semi-solid, or solid unit forms having a resolution about 50 dpi to about 20,000 dpi.

12. A printed array comprising:
 a substrate; and
 a plurality of dot units,
  wherein the plurality of dot units is in a gel form, a semi-solid form or a solid form,
 wherein
 dot units of the plurality of dot units were formed, jetted, printed and/or deposited from the printable silk ink of claim 1 upon the substrate, such that they form in a predetermined spatial pattern on a surface of the substrate.

13. The printed array of claim 12, wherein the printed array has a resolution of between about 50-20,000 dpi.

14. The printed array of claim 12, wherein the printed array forms substantially a two-dimensional (2D) structure having a predetermined spatial pattern of substantially even thickness.

15. The printed array of claim 12, wherein the printed array forms substantially a three-dimensional (3D) structure having a predetermined spatial pattern of varying thickness across the predetermined spatial pattern.

16. The printed array of claim 12, wherein the dot units of the plurality of dot units are about 0.1 µm to about 250 µm in diameter.

17. The printed array of claim 12, wherein the dot units of the plurality of dot units have a volume of about 0.1 pL to about 5 nL.

18. A method for printing a structure, the method comprising steps of:
 providing the printable silk ink of claim 1
 depositing the printable silk ink through a nozzle in liquid droplet units onto a substrate in a predetermined spatial pattern,
 wherein each of the liquid droplet units has a volume of about 0.1 pL to about 5 nL.

19. The method of claim 18, wherein the depositing step is or comprises a jetting velocity of about 7 m/sec to about 9 m/sec.

20. The method of claim 18, further comprising a step of piezoelectrically actuating the nozzle.

21. The method of claim 18, wherein the nozzle has a diameter in a range of 10 and 50 µm.

22. The method of claim 18, further comprising a step of applying at least one of (a) heat and (b) ultraviolet irradiation to the aqueous silk ink after depositing the aqueous silk ink onto the substrate.

23. The method of claim 18, wherein the aqueous silk ink further comprises a dopant.

24. The method of claim 23, wherein the dopant comprises a nanoparticle.

* * * * *